(12) United States Patent
Sun et al.

(10) Patent No.: US 12,338,246 B2
(45) Date of Patent: *Jun. 24, 2025

(54) PYRAZINE DERIVATIVE AND APPLICATION THEREOF IN INHIBITING SHP2

(71) Applicant: SUZHOU GENHOUSE PHARMACEUTICAL CO., LTD, Suzhou (CN)

(72) Inventors: Haifeng Sun, Suzhou (CN); Kuifeng Wang, Suzhou (CN); Tao Zhang, Suzhou (CN); Mengnan Ma, Suzhou (CN); Jinchang Lu, Suzhou (CN)

(73) Assignee: Suzhou Genhouse Pharmaceutical Co., Ltd., Suzhou (CN)

( * ) Notice: Subject to any disclaimer, the term of this patent is extended or adjusted under 35 U.S.C. 154(b) by 721 days.

This patent is subject to a terminal disclaimer.

(21) Appl. No.: 17/436,223

(22) PCT Filed: Mar. 2, 2020

(86) PCT No.: PCT/CN2020/077391
§ 371 (c)(1),
(2) Date: Sep. 3, 2021

(87) PCT Pub. No.: WO2020/177653
PCT Pub. Date: Sep. 10, 2020

(65) Prior Publication Data
US 2022/0127276 A1    Apr. 28, 2022

(30) Foreign Application Priority Data
Mar. 4, 2019   (CN) .................... 201910160960.7

(51) Int. Cl.
C07D 491/107 (2006.01)
C07D 519/00 (2006.01)

(52) U.S. Cl.
CPC ....... C07D 491/107 (2013.01); C07D 519/00 (2013.01)

(58) Field of Classification Search
CPC .................... C07D 491/107; C07D 519/00
USPC ........................................... 546/18
See application file for complete search history.

(56) References Cited

U.S. PATENT DOCUMENTS

| 10,077,276 | B2 | 9/2018 | Chen et al. |
| 10,287,266 | B2 | 5/2019 | Chen et al. |
| 10,590,090 | B2 | 3/2020 | Koltun et al. |
| 10,858,359 | B2 | 12/2020 | Ma et al. |
| 10,934,285 | B2 | 3/2021 | Chen et al. |
| 10,988,466 | B2 | 4/2021 | Ma et al. |
| 11,827,644 | B2 * | 11/2023 | Sun ............ A61P 9/12 |
| 2019/0343836 | A1 | 11/2019 | Alghalandis et al. |

FOREIGN PATENT DOCUMENTS

WO   WO-2015107494 A1 *  7/2015 ................ A61P 1/04

OTHER PUBLICATIONS

Chinese Office Action for CN Application No. 20191016090.7 mailed Mar. 16, 2021 (9 pages, English translation).
International Search Report for PCT/CN Application No. 2020/077391 mailed Sep. 10, 2020 (7 pages, English translation).
Chinese Search Report for CN Application No. 20191016090.7 mailed Mar. 8, 2021 (2 pages).

* cited by examiner

Primary Examiner — Kahsay Habte
(74) Attorney, Agent, or Firm — Womble Bond Dickinson (US) LLP

(57) ABSTRACT

The present invention relates to a pyrazine derivative, an application thereof in inhibiting SHP2, and a compound of formula (I) or pharmaceutically acceptable salts, esters, isomers, solvates, prodrugs or isotope labels thereof. The structure of the compound of formula (I) is as follows. The novel pyrazine derivative provided by the present invention has excellent inhibition of SHP2 activity and can be used to prevent and/or treat non-receptor protein tyrosine phosphatase-mediated or dependent diseases or disorders.

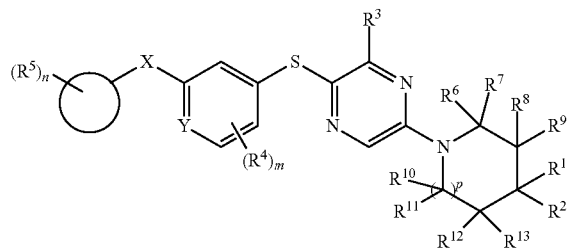

(I)

10 Claims, No Drawings

PYRAZINE DERIVATIVE AND APPLICATION THEREOF IN INHIBITING SHP2

CROSS-REFERENCE TO RELATED APPLICATIONS

This application is a National Stage Application of International Application PCT/CN2020/077391 which claims priority to CN 201910160960.7, and all the benefits accruing therefrom under 35 U.S.C. 371, the content of which is incorporated herein by reference in their entirety.

TECHNICAL FIELD

The present invention belongs to the field of medicine and relates to a pyrazine derivative, a preparation method thereof and application in medicine, more specifically, relates to a pyrazine derivative and its application as a protein tyrosine phosphatase 2 (SHP2) inhibitor in the prevention and/or treatment of diseases associated with abnormal SHP2 activities.

BACKGROUND TECHNOLOGY

Protein tyrosine phosphatase 2 (SHP2) belongs to the protein tyrosine phosphatase family, which is involved in the regulation of cell proliferation, survival, differentiation, migration and apoptosis. In recent years, more and more studies have shown that protein tyrosine phosphatases, such as SHP2, play an important role in tumors. In particular, with the increasing clarity of research on the role of SHP2 in tumors, studies have confirmed that inhibition of abnormal activation of SHP2 has become a feasible anti-tumor strategy.

Among the protein tyrosine phosphatase superfamily, SHP2 is the first bona fide proto-oncogene to be shown to play an important role in a variety of signaling pathways including metabolism, differentiation, proliferation, migration and survival. SHP2 regulates the Ras-mitogen-activated protein kinase, Janus kinase-signal transducer and transcriptional activator (JAK-STAT) or phosphoinositide 3-kinase-AKT and nuclear factor κB (NF-κB) signaling pathways; SHP2 also acts as a major regulator of the programmed cell death protein-1 (PD-1), B and T lymphocyte attenuator (BTLA) immune checkpoint signaling pathways and may be associated with tumor immunosuppression; in addition, SHP2 is rarely mutated in solid tumors, whereas it is overexpressed in head and neck cancer, non-small cell lung cancer, breast cancer, liver cancer, gastric cancer and thyroid cancer.

Recent studies have shown that combination use of SHP2 inhibitors and anaplastic lymphoma kinase (ALK) inhibitors can treat patients who are resistant to $1^{st}/2^{nd}$ generation ALK inhibitors and have not responded to the $3^{rd}$ generation ALK inhibitors. Combination use of SHP2 inhibitor and mitogen activated protein kinase kinase (MEK) or serine/threonine protein kinase (BRAF) inhibitors can treat patients with the KRAS or serine/threonine protein kinase (BRAF) mutations that are resistant to mitogen-activated protein kinase kinase or serine/threonine protein kinase inhibitors. SHP2 inhibitors can stimulate estrogen receptor a overexpression in triple negative breast cancer patients and combined with endocrine treatments is a potential treatment option for triple-negative breast cancer. SHP2 can also affect vascular smooth muscle cell proliferation, which is closely related to the development and progression of atherosclerosis. Therefore, SHP2 is a potential drug target with broad application prospects.

CONTENT OF THE INVENTION

Problems to be Solved by the Invention

As none of the drugs for protein tyrosine phosphatase have been marketed to date and compounds in the prior art have poor SHP2 inhibitory activity (e.g., WO2016/203406A1); the objective of the current invention is to provide a novel pyrazine derivative that has superior SHP2 inhibitory activity and can be used for the prevention and/or treatment of non-receptor protein tyrosine phosphatase-mediated or dependent diseases or disorders.

Plans Used to Solve the Problem

To solve the above technical problem, the present invention provides a compound of formula (I) or a pharmaceutically acceptable salt, ester, isomer, solvate, prodrug or isotope label thereof, said compound of formula (I) having the structure of:

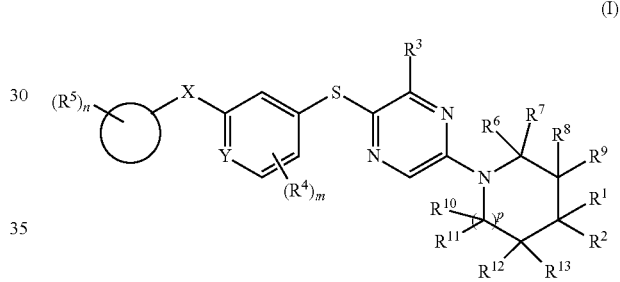

(I)

Wherein:
R1 and R2 are each the same or different, each independently selected from H, D, halogen, —CN, —COOH, —CHO, —OH, —NO2, a substituted or unsubstituted group of: —NH2, C1-C10 alkyl, C1-C10 alkylamino, C1-C10 alkoxy, C3-C12 cycloalkyl, C3-C12 cycloalkyloxy, 3-12 membered heterocyclyl, C6-C10 aryl, 5-10 membered heteroaryl; or 3-8 membered saturated or unsaturated cycloalkyl or heterocyclyl formed by R1 and R2, optionally, said 3-8 membered saturated or unsaturated cycloalkyl or heterocyclyl is substituted by 1-3 of —OH, —NH2, —CN, NO2, halogen, C1-C10 alkyl, C1-C10 alkoxy, C1-C10 alkylamino, C3-C12 cycloalkyl, C6-C10 aryl or 5-10 membered heteroaryl;
R3 is selected from H, D, —NH2;
X is selected from chemical bonds, —NH—, —CONH—;
Y is selected from N or CR0, wherein R0 is selected from H, D, —OH, —CN, halogen, C1-C10 alkyl, C1-C10 alkoxy, C3-C12 cycloalkylamino, C1-C10 alkylamino, C3-C12 cycloalkyl, 3-8 membered heterocyclyl, halogenated C1-C10 alkylamino, C6-C10 aryl or 5-10 membered heteroaryl, said heterocyclyl or heteroaryl optionally contains 1-4 heteroatoms, said heteroatoms are selected from S, O, N or NH;
Each R4 is the same or different, and each is independently selected from H, D, halogen, —CN, —COOH, —CHO, —OH, —NO2, —CONHR14, or —NHCOR15, a substituted or unsubstituted group of: —NH2, C1-C10 alkyl, C1-C10 alkylamino, C1-C10 alkoxy, C3-C12 cycloalkyl, 3-12 membered heterocyclyl, C6-C10 aryl, 5-10 membered heteroaryl; wherein R14 and R15 are each independently optionally selected from C1-C10 alkylamino, C3-C12 cycloalkyl, C6-C10 aryl, or 5-10 membered heteroaryl; said substitution is substituted by one or more of C1-C10 alkyl, halogen, —NH2, —CN, —COOH, —CHO, —OH, —NO2, C1-C10 alkoxy, C1-C10 alkylamino, C3-C12 cycloalkyl, C6-C10 aryl, 5-10 membered heteroaryl or 3-12 membered heterocyclyl, the above substituents are optionally substituted by 1-3 of C1-C10 alkyl, halogen, —NH2, —CN, —COOH, —CHO, —OH, —NO2, C1-C10 alkoxy, C1-C10 alkylamino, C3-C12 cycloalkyl;

is selected from C6-C10 aryl, 5-10 membered heteroaryl, C4-C12 cycloalkyl, 3-12 membered heterocyclyl, C6-C14 bridged cyclyl or spirocyclyl, C6-C14 bridged heterocyclyl or spiroheterocyclyl; wherein said 5-10 membered heteroaryl, 3-12 membered heterocyclyl, C6-C14 bridged heterocyclyl or spiroheterocyclyl contains 1-3 heteroatoms or groups optionally from N, NH, O, S, C(O), S(O);

Each R5 is the same or different, and each is independently selected from H, D, halogen, —CN, —COOH, —CHO, —OH, —NO2, a substituted or unsubstituted group of: C1-C10 alkyl, C1-C10 alkylamino, C1-C10 alkoxy, —NH2, C3-C12 cycloalkyl, 3-12 membered heterocyclyl, C6-C10 aryl, or 5-10 membered heteroaryl, said substitution is substituted with one or more of C1-C10 alkyl, C3-C12 cycloalkyl, 3-12 membered heterocyclyl, halogen, —NH2, —CN, —COOH, —CHO, —OH, —NO2, hydroxy-C1-C10-alkyl, C1-C10 alkoxy, C1-C10 alkylamino, 5-10 membered heteroaryl, C6-C10 aryl, or 3-12 membered heterocyclyl; or a 3-6 membered saturated or unsaturated ring formed by any two adjacent R5, optionally, said 3-6 membered saturated or unsaturated ring is substituted by 1-3 —OH, —NH2, —CN, halogen, C1-C10 alkyl, C1-C10 alkoxy, C3-C12 cycloalkylamino, C3-C12 alkylamino, C3-C12 cycloalkyl, halogenated C1-C10 alkylamino, C6-C10 aryl or 5-10 membered heteroaryl;

R6, R7, R8, R9, R10, R11, R12, R13 are independently selected from H, D, halogen, —CN, —COOH, —CHO, —OH, —NO2, a substituted or unsubstituted group of: —NH2, C1-C10 alkyl, C1-C10 alkylamino, C1-C10 alkoxy, C3-C12 cycloalkyl, C3-C12 cycloalkyloxy, 3-12 membered heterocyclyl, C6-C10 aryl, 5-10 membered heteroaryl, said substitution is selected from one or more of C1-C10 alkyl, C3-C12 cycloalkyl, 3-12 membered heterocyclyl, halogen, —NH2, —CN, —COOH, —CHO, —OH, —NO2, hydroxy-C1-C10 alkyl, C1-C10 alkoxy, C1-C10 alkylamino, 5-10 membered heteroaryl, or C6-C10 aryl.

m is 0, 1, 2, or 3;
n is 0, 1, 2, or 3;
p is 0, 1 or 2.

The present invention also provides a pharmaceutical composition, comprising a compound of formula (I) as described above or a pharmaceutically acceptable salt, ester, isomer, solvate, prodrug or isotope label thereof.

The present invention also provides a pharmaceutical preparation, comprising a compound of formula (I) as described above or a pharmaceutically acceptable salt, ester, isomer, solvate, prodrug or isotope label thereof or a pharmaceutical composition as described above, said preparation is any of, tablet, capsule, injection, granule, powder, suppository, pill, cream, paste, gel, dispersion, oral solution, inhaler, suspension, dry suspension, patch, or lotion.

The invention also provides a compound of formula (I) or a pharmaceutically acceptable salt, ester, isomer, solvate, prodrug or isotope label thereof as described above, or the above pharmaceutical composition, or a pharmaceutical preparation as described above, which is used in the prevention and treatment of non-receptor protein tyrosine phosphatase-mediated or dependent diseases or disorders.

The present invention also provides a compound of formula (I) or a pharmaceutically acceptable salt, ester, isomer, solvate, prodrug or isotope label thereof, or a pharmaceutical composition, or a pharmaceutical preparation described above for use in the prevention and/or treatment of non-receptor protein tyrosine phosphatase-mediated or dependent diseases or disorders.

The use of a compound of formula (I) or a pharmaceutically acceptable salt, ester, isomer, solvate, prodrug or isotope label thereof, as described above, or a pharmaceutical composition as described above, or a pharmaceutical preparation as described above in the manufacture of a medicament for the prevention and/or treatment of a non-receptor protein tyrosine phosphatase-mediated or dependent diseases or conditions.

The present invention also provides a method for prevention and/or treatment of non-receptor protein tyrosine phosphatase-mediated or dependent diseases or disorders, comprising the steps of: administration of a therapeutically effective amount of any one of the above described compound of formula (I) or a pharmaceutically acceptable salt, ester, isomer, solvate, prodrug or isotope label thereof, or the above-mentioned pharmaceutical composition, or the above-mentioned pharmaceutical preparation in patient in need thereof.

The present invention also provides a form of pharmaceutical combination comprising a compound of formula (I) described above or a pharmaceutically acceptable salt, ester, isomer, solvate, prodrug or isotope label thereof, or the aforementioned pharmaceutical combination, or the aforementioned pharmaceutical preparation, and at least one additional therapeutic agent.

Effects of the Invention

The novel pyrazine derivatives presented in this invention have superior SHP2 inhibitory activity, with significantly better SHP2 inhibitory activity than SHP2 inhibitors in the prior art (e.g., compound 96 in table 9 of WO2016/203406A1). The novel pyrazine derivatives presented herein are capable of being used in prevention and/or treatment of non-receptor tyrosine phosphatase-mediated or dependent diseases or disorders.

SPECIFIC EMBODIMENTS

First, the present invention provides a compound as shown in formula (I) or a pharmaceutically acceptable salt, ester, isomer, solvate, prodrug or isotope label thereof, said compound of formula (I) having the structure of:

(I)

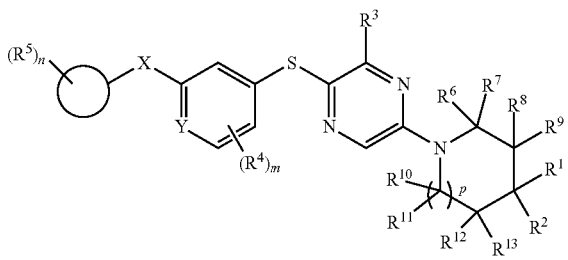

Wherein:
R1 and R2 are each the same or different, each independently selected from H, D, halogen, —CN, —COOH, —CHO, —OH, —NO2, a substituted or unsubstituted group of: —NH2, C1-C10 alkyl, C1-C10 alkylamino, C1-C10 alkoxy, C3-C12 cycloalkyl, C3-C12 cycloalkyloxy, 3-12 membered heterocyclyl, C6-C10 aryl, 5-10 membered heteroaryl; or 3-8 membered saturated or unsaturated cycloalkyl or heterocyclyl formed by R1 and R2, optionally, said 3-8 membered saturated or unsaturated cycloalkyl or heterocyclyl is substituted by 1-3 of —OH, —NH2, —CN, NO2, halogen, C1-C10 alkyl, C1-C10 alkoxy, C1-C10 alkylamino, C3-C12 cycloalkyl, C6-C10 aryl or 5-10 membered heteroaryl;

R3 is selected from H, D, —NH2;
X is selected from chemical bonds, —NH—, —CONH—;
Y is selected from N or CR0, wherein R0 is selected from H, D, —OH, —CN, halogen, C1-C10 alkyl, C1-C10 alkoxy, C3-C12 cycloalkylamino, C1-C10 alkylamino, C3-C12 cycloalkyl, 3-8 membered heterocyclyl, halogenated C1-C10 alkylamino, C6-C10 aryl or 5-10 membered heteroaryl, said heterocyclyl or heteroaryl optionally contains 1~4 heteroatoms, said heteroatoms are selected from S, O, N or NH;

Each R4 is the same or different, and each is independently selected from H, D, halogen, —CN, —COOH, —CHO, —OH, —NO2, —CONHR14, or —NH-COR15, a substituted or unsubstituted group of: —NH2, C1-C10 alkyl, C1-C10 alkylamino, C1-C10 alkoxy, C3-C12 cycloalkyl, 3-12 membered heterocyclyl, C6-C10 aryl, 5-10 membered heteroaryl; wherein R14 and R15 are each independently optionally selected from C1-C10 alkylamino, C3-C12 cycloalkyl, C6-C10 aryl, or 5-10 membered heteroaryl; said substitution is substituted by one or more of C1-C10 alkyl, halogen, —NH2, —CN, —COOH, —CHO, —OH, —NO2, C1-C10 alkoxy, C1-C10 alkylamino, C3-C12 cycloalkyl, C6-C10 aryl, 5-10 membered heteroaryl or 3-12 membered heterocyclyl, the above substituents are optionally substituted by 1-3 of C1-C10 alkyl, halogen, —NH2, —CN, —COOH, —CHO, —OH, —NO2, C1-C10 alkoxy, C1-C10 alkylamino, C3-C12 cycloalkyl;

is selected from C6-C10 aryl, 5-10 membered heteroaryl, C4-C12 cycloalkyl, 3-12 membered heterocyclyl, C6-C14 bridged cyclyl or spirocyclyl, C6-C14 bridged heterocyclyl or spiro heterocyclyl; wherein said 5-10 membered heteroaryl, 3-12 membered heterocyclyl, C6-C1 bridged cyclyl or spirocyclyl contains 1-3 heteroatoms or groups optionally from N, NH, O, S, C (O), S(O);

Each R5 is the same or different, and each is independently selected from H, D, halogen, —CN, —COOH, —CHO, —OH, —NO2, aminoacyl, a substituted or unsubstituted group of: C1-C10 alkyl, C1-C10 alkylamino, C1-C10 alkoxy, —NH2, C3-C12 cycloalkyl, 3-12 membered heterocyclyl, C6-C10 aryl, or 5-10 membered heteroaryl, said substitution is substituted with one or more of C1-C10 alkyl, C3-C12 cycloalkyl, 3-12 membered heterocyclyl, halogen, —NH2, —CN, —COOH, —CHO, —OH, —NO2, hydroxy-C1-C10-alkyl, C1-C10 alkoxy, C1-C10 alkylamino, 5-10 membered heteroaryl, C6-C10 aryl; or a 3-6 membered saturated or unsaturated ring formed by any two adjacent R5, optionally, said 3-6 membered saturated or unsaturated ring is substituted by 1-3 —OH, —NH2, —CN, halogen, C1-C10 alkyl, C1-C10 alkoxy, C3-C12 cycloalkylamino, C1-C10 alkylamino, C3-C12 cycloalkyl, halogenated C1-C10 alkylamino, C6-C10 aryl or 5-10 membered heteroaryl;

R6, R7, R8, R9, R10, R11, R12, R13 are independently selected from H, D, halogen, —CN, —COOH, —CHO, —OH, —NO2, a substituted or unsubstituted group of: —NH2, C1-C10 alkyl, C1-C10 alkylamino, C1-C10 alkoxy, C3-C12 cycloalkyl, C3-C12 cycloalkyloxy, 3-12 membered heterocyclyl, C6-C10 aryl, 5-10 membered heteroaryl, 3-12 membered heterocyclyl, said substitution is substituted by one or more of C1-C10 alkyl, C3-C12 cycloalkyl, 3-12 membered heterocyclyl, halogen, —NH2, —CN, —COOH, —CHO, —OH, —NO2, hydroxy-C1-C10 alkyl, C1-C10 alkoxy, C1-C10 alkylamino, 5-10 membered heteroaryl, or C6-C10 aryl.

m is 0, 1, 2, or 3;
n is 0, 1, 2, or 3;
p is 0, 1 or 2.

In order to describe the invention with better clarity, all the terms involved are defined as follows:

The term "halogen" refers to, alone or in combination, fluorine, chlorine, bromine or iodine, in particular fluorine, chlorine or bromine.

The term "C1-C10 alkyl" alone or in combination means a saturated straight or branched alkyl containing 1-10, in particular 1-6 carbon atoms, including methyl, ethyl, propyl, isopropyl, butyl, sec-butyl, isobutyl, tert-butyl, n-pentyl, 2-pentyl, 3-pentyl, 2-methyl-2-butyl, 3-methyl-2-butyl, 3-methyl-1-butyl, 2-methyl-1-butyl, n-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl and the like. Preferably, the "C1-C10 alkyl" is any one of methyl, ethyl, n-propyl, isopropyl, and tert-butyl. Similarly, the term "C1-6 alkyl" alone or in combination means a saturated straight or branched alkyl containing 1-6 carbon atoms, including methyl, ethyl, propyl, isopropyl, and the like.

The term "C1-C10 alkoxy" represents C1-C10 alkyl-O— alone or in combination, wherein "C1-C10 alkyl" means as defined above, which includes (but not limited to) methoxy (—OCH3), ethoxy (—OCH2CH3), n-propoxy (—OCH2CH2CH3), isopropoxy (—OCH(CH3)2), n-butoxy (—OCH2CH2CH2CH3), sec-butoxy (—OCH (CH3) CH2CH3), isobutoxy (—OCH2CH (CH3)2), tert-butoxy (—OC (CH3)3), n-pentyloxy (—OCH2CH2CH2CH2CH3), neopentyloxy (—OCH2C(CH3)3) and so on.

The term "C3-C12 cycloalkyl" refers to a saturated or partially unsaturated monocyclic or polycyclic cycloalkyl having 3 to 12, in particular 3-8 carbon atoms, alone or in combination, including cyclopropyl, cyclobutyl, cyclopentyl, cyclohexyl, cycloheptyl and the like.

The term "C3-C12 cycloalkyloxy" refers to C3-C12 cycloalkyl-O—, alone or in combination, wherein C3-C12 cycloalkyl is as defined above.

The term "3-12 membered heterocyclyl" refers to a saturated or partially unsaturated monocyclic ring or polycyclic heterocyclic group containing 3-12, in particular 5-12, more particularly 5-7 carbon atoms and heteroatoms or heteroatom containing groups, said heteroatoms or heteroatom containing groups are selected from N, NH, O, C(O), S(O)m (where m is 0, 1 or 2); said 3-12 membered heterocyclic groups include aziridinyl, azetidinyl, oxetanyl, pyrrolidinyl, tetrahydrofuranyl, tetrahydrothiophenyl, piperidinyl, morpholinyl, piperazinyl, thiomorpholinyl, tetrahydropyranyl, 1,1-dioxothiomorpholinyl, butyrolactamyl, valerolactamyl, caprolactamyl, butyrolactone, valerolactone, caprolactone, succinimide or

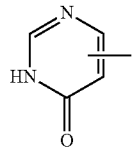

etc., preferably, said 3-12 membered heterocyclic group includes butyrolactamyl, pyrrolidinyl, succinimide or

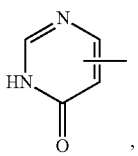

more preferably, said 3-12 membered heterocyclic group is

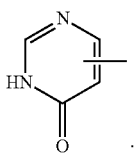

The term "aryl" means any stable 6-10 membered monocyclic or bicyclic aromatics, including phenyl, naphthyl, tetrahydronaphthyl, 2,3-dihydroindenyl or biphenyl, and the like. The hydrogen on the "aryl" is independently and optionally substituted with one or more substituents described in the present invention.

The term "heteroaryl" refers to an aromatic ring where carbon atoms in the ring are replaced by at least one heteroatom selected from sulfur, oxygen, or nitrogen. The aromatic ring may be 5-7 membered monocyclic ring or 7-12 bicyclics. In the present invention, the number of heteroatoms in the heteroaryl is preferably 1, 2, 3 or 4, such as thienyl, pyridyl, pyrimidinyl, pyrazinyl, pyridazinyl, pyridin-2 (1H)-keto, pyridine-4 (1H)-keto, pyrrolyl, pyrazolyl, thiazolyl, 1,2,3-triazolyl, 1,2,4-triazolyl, imidazolyl, tetrazolyl, isothiazolyl, oxazolyl, isoxazolyl, thiadiazolyl, oxadiazolyl, naphthyl, benzothienyl, indolyl, benzimidazolyl, benzothiazolyl, benzofuranyl, quinolinyl, isoquinolinyl, quinazolinyl, indazolyl, indolo[1,2-a]pyrazinyl, 4,7-diazaindole, pyrazolopyrimidinyl, imidazopyrimidinyl, oxazolopyrimidinyl, isoxazolopyrimidinyl, imidazopyrazinyl, pyrazolopyrazine, pyrrolopyrazinyl, furanopyrazinyl, thienopyrazinyl, pyridopyrimidinone, benzoxazolyl or benzothiazolyl, etc. The hydrogen atom on the "heteroaryl" is independently and optionally substituted with one or more substituents described in the present invention.

The term "C6-10 aryl" means aryl with 6 to 10 carbon atoms, where aryl is defined as above.

The term "5-10-membered heteroaryl" refers to a heteroaryl ring having 5 to 10 carbon atoms and heteroatoms, wherein the heteroaryl ring is as defined above.

The term "3-8 membered saturated or unsaturated cycloalkyl or heterocyclyl" means a saturated or partially unsaturated monocyclic ring or fused cyclocycloalkyl having 3-8, in particular 3-6, and more particularly 5-6 carbon atoms, including cyclopropyl, cyclobutyl, cyclopentyl, cyclohexyl, cycloheptyl, etc.; or a heterocyclic group having 3-8, in particular 3-6, more particularly 5-6 carbon atoms and heteroatoms or heteroatomic groups, and said heteroatoms or heteroatomic groups are selected from N, NH, O, S(O)m (where m is 0, 1, 2); e.g. aziridinyl, azetidinyl, oxetanyl, pyrrolidinyl, tetrahydrofuranyl, tetrahydrothiophenyl, piperidinyl, morpholinyl, piperazinyl, thiomorpholinyl, tetrahydropyranyl, 1,1-dioxothiomorpholinyl and the like.

The term "—CONH—" refers to —C(=O)—NH—, more specifically C(=O) is attached to

or NH is attached to

preferably C(=O) is attached to

The term "amino" means, alone or in combination, a primary amino (—NH2), secondary amino (—NH—) or tertiary amino group

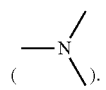

The term "C1-C10 alkylamino", alone or in combination, represents an amino group as defined above, wherein the hydrogen atom of the amino group is substituted by at least one C1-C10 alkyl, wherein "C1-C10 alkyl" is as defined above, and accordingly, "C1-C10 alkylamino" includes methylamino, ethylamino, propylamino, isopropylamino, n-butylamino, isobutylamino, 2-butylamino, tert-butylamino, n-pentylamino, 2-pentylamino, 3-pentylamino, 2-methyl-2-butylamino, 3-methyl-2-butylamino, 3-methyl-1-butylamino, 2-methyl-1-butylamino, n-hexylamino, 2-hexylamino, 3-hexylamino, 2-methyl-2-pentylamino, 3-methyl-2-pentylamino, 4-methyl-2-pentylamino, 3-methyl-3-pentylamino, 2-methyl-3-pentylamino, 2,3-dimethyl-2-butylamino, 3,3-dimethyl-2-butylamino and the like. Especially, "C1-C10 alkylamino" is methylamino, ethylamino, isopropylamino, tert-butylamino, and the like.

The term "C3-C12 cycloalkylamino" means, alone or in combination, an amino group as defined above, wherein the hydrogen atom of the amino group is substituted by at least one C3-C12 cycloalkyl, "C3-C12 cycloalkyl" is as defined above.

The term "isomer" encompasses all isomeric forms including enantiomers, diastereomers, tautomers and geometric isomers (including cis-trans isomers). Therefore, mixtures of individual stereochemical isomers or enantiomers, diastereomers, tautomers or geometric isomers (or cis-trans isomers) of the compounds designed in the present invention are all within the scope of the invention.

The term "pharmaceutically acceptable salts" means that the compounds of the present invention exist in the form of their pharmaceutically acceptable salts, including acid addition salts and base addition salts. S. M. Berge described pharmaceutically acceptable salts in J. Pharmaceutical Sciences (Vol. 66: pages 1-19, 1977). In the present invention, a pharmaceutically acceptable non-toxic acid addition salt means a salt formed by the compounds in the present invention with organic or inorganic acids, such organic or inorganic acids including but not limited to hydrochloric acid, sulfuric acid, hydrobromic acid, hydroiodic acid, phosphoric acid, nitric acid, perchloric acid, acetic acid, oxalic acid, maleic acid, fumaric acid, tartaric acid, benzenesulfonic acid, methanesulfonic acid, salicylic acid, succinic acid, citric acid, lactic acid, propionic acid, benzoic acid, p-toluenesulfonic acid, malic acid, etc. A pharmaceutically acceptable non-toxic base addition salt means a salt formed by the compounds of the present invention with an organic or inorganic base, including but not limited to alkali metal salts such as lithium, sodium or potassium salts; alkaline earth metal salts such as calcium or magnesium salts; organic base salts, such as ammonium salts or N+ (C1-6 alkyl)$_4$ salts formed by association with an organic base containing an N group, preferably lithium hydroxide, sodium hydroxide, potassium hydroxide, sodium carbonate, sodium bicarbonate, potassium carbonate, potassium bicarbonate, magnesium carbonate, calcium carbonate, ammonia, triethylamine, tetrabutylammonium hydroxide and the like.

The term "solvate" refers to a conjugate formed by one or more solvent molecules with the compound of the present invention. Solvate-forming solvents include, but are not limited to, water, methanol, ethanol, isopropanol, ethyl acetate, tetrahydrofuran, N, N-dimethylformamide, dimethylsulfoxide, and the like. A "Pharmaceutically acceptable salt" can be synthesized by general chemical methods.

The term "ester" refers to organic esters, including monoesters, diesters, triesters, and more commonly polyesters.

The term "prodrug" refers to chemical derivatives of the compound in the present invention that can be converted into the compound represented by the general formula I by chemical reactions in vivo.

The term "isotopic derivative" refers to an isotopic derivative obtained by replacing the hydrogen atom in the general formula (I) with 1-6 deuterium atoms (D), or an isotopic derivative obtained by replacing the carbon atom in the general formula (I) with 1-3 carbon 14 (14C) atoms.

The terms used in the present invention are defined as above. Those skilled in the art can understand the above terms in combination with the prior art, and the following further describes the terms based on the contents of the present invention and the definition of the terms.

In a preferred embodiment, said compound in formula (I) has the following structure as shown in formula (I-1):

(I-1)

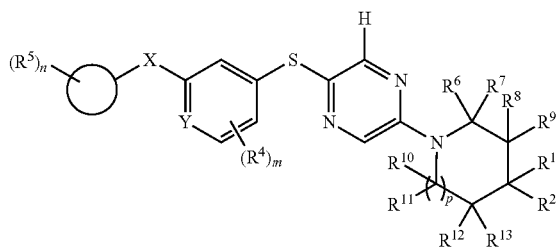

Wherein, R1, R2, R4, R5, R6, R7, R8, R9, R10, R11, R12, R13, X, Y, m, n, p and

are defined as shown in the definitions of the groups in the above compound of formula (I).

In a preferred embodiment, said compound in formula (I) has the following structure as shown in formula (I-2):

(I-2)

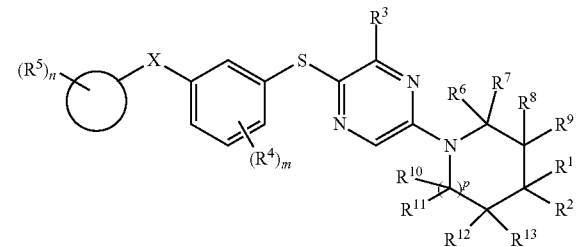

Wherein, R1, R2, R3, R4, R5, R6, R7, R8, R9, R10, R11, R12, R13, X, m, n, p and

are defined as shown in the definitions of the groups in the above compound in formula (I).

In a preferred embodiment, R1 and R2 in the above compounds are each the same or different, and each of them is independently selected from H, D, halogen, —CN, —COOH, —CHO, —OH, —NO2, substituted or unsubstituted groups of: —NH2, C1-C10 alkyl, C1-C10 alkylamino, C1-C10 alkoxy, C3-C12 cycloalkyl, C3-C12 cycloalkoxy, 3-12 membered heterocyclyl, C6-C10 aryl, 5-10-membered heteroaryl; wherein said substituted —NH2, C1-C10 alkyl, C1-C10 alkylamino, C1-C10 alkoxy, C3-C12 cycloalkyl, C3-C12 cycloalkoxy, 3-12-membered heterocyclyl, C6-C10 aryl, 5-10-membered heteroaryl, 3-12-membered heterocyclyl are substituted by one or more of C1-C10 alkyl, C1-C10 alkylamino, halogen, —NH2, —CN, —NO2, —OH, hydroxy substituted C1-C10 alkylamino, C1-C10 alkoxy, C3-C8 alkylamino, C3-C12 cycloalkyl, 5-10 membered heteroaryl, C6-C10 aryl, and 5-10 membered heterocyclyl; said heterocyclyl or heteroaryl optionally contains 1-4 heteroatoms or heteroatom-containing groups, said heteroatoms or heteroatom-containing groups are selected from S, O, N, or C(O); or 3-8 membered saturated or unsaturated cycloalkyl or heterocyclyl formed by R1 and R2, optionally, said 3-8 membered saturated or unsaturated cycloalkyl or heterocyclyl is substituted by 1-3 —OH, —NH2, —CN, NO2, halogen, C1-C10 alkyl, C1-C10 alkoxy, C1-C10 alkylamino, C3-C12 cycloalkyl, C6-C10 aryl or 5-10 membered heteroaryl; wherein said saturated or unsaturated cycloalkyl or heterocyclyl is optionally a carbocyclic ring or a heterocyclyl containing 1-3 heteroatoms or groups selected from N, NH, O, S, C(O), S(O).

In a more preferred embodiment, R1 and R2 in the above compound form a 5-6-membered heterocyclic group, said heterocyclic group containing 1-3 heteroatoms selected from N, NH, O, and S, and optionally, said 5-6-membered heterocyclic group is substituted by 1-3 halogen, —OH, —NH2, C1-C10 alkylamino, C1-C10 alkyl, or C1-C10 alkoxy.

In a preferred embodiment, the

○ in the above compound is selected from C6-C10 aryl, 5-10 membered heteroaryl, or 3-12 membered heterocyclyl; wherein said 5-10 membered heteroaryl or 3-12 membered heterocyclyl contains 1-3 heteroatoms or groups from N, NH, O, S, C(O), S (O).

In a preferred embodiment, said compound in formula (I) has the following structure as shown in formula (I-3):

(I-3)

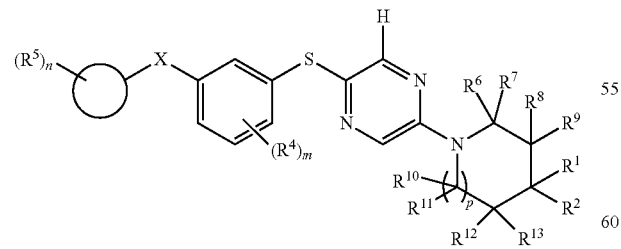

Wherein R1 and R2 form a 5-6-membered heterocyclyl, said heterocyclyl contains 1-3 heteroatoms selected from N, NH, O, and S, optionally, said 5-6-membered heterocyclyl is substituted by 1-3 —OH, —NH2, C1-C6 alkyl, or C1-C6 alkoxy;

○ is selected from C6-C10 aryl or 5-10 membered heteroaryl; wherein said 5-10 membered heteroaryl contains 1-3 heteroatoms or groups optionally selected from N, NH, O, S, C(O), S(O).

In a preferred embodiment, R4 in the above compounds are each the same or different, and are independently selected from H, D, —NH2, halogen, —CN, —COOH, —CHO, —OH, —NO2, C1-C10 alkyl, C1-C10 alkoxy, C3-C12 cycloalkyl, 3-12 membered heterocyclyl, C6-C10 aryl, or 5-10 membered heteroaryl.

In a preferred embodiment, R5 in the above compounds are each the same or different, and are independently selected from H, D, halogen, —CN, —COOH, —CHO, —OH, —NO2, C1-C10 alkyl, C1-C10 alkylamino, C1-C10 alkoxy, —NH2, C3-C12 cycloalkyl, 3-12 membered heterocyclyl, C6-C10 aryl or 5-10 membered heteroaryl; or a 3-6 membered saturated or unsaturated ring formed by any two adjacent R5, optionally, said 3-6 membered saturated or unsaturated ring group is substituted by 1-3 —OH, —NH2, —CN, halogen, C1-C10 alkyl, C1-C10 alkoxy, C3-C12 cycloalkylamino, C1-C10 alkylamino, C3-C12 cycloalkyl, halogenated C1-C10 alkylamino, C6-C10 aryl or 5-10 membered heteroaryl.

In a preferred embodiment, each R5 in the above compounds is the same or different, each independently selected from H, D, halogen, C1-C6 alkyl, C1-C6 alkylamino, C1-C6 alkoxy, —NH2; or two adjacent R5 can form a 5-6-membered saturated ring group, optionally, said 5-6-membered saturated ring group is substituted with 1-2 —OH, —NH2, —CN, halogen, C1-C6 alkyl, C1-C6 alkoxy, C3-C6 cycloalkylamino, C1-C6 alkylamino, C3-C6 cycloalkyl, halogenated C1-C6 alkylamino, C6-C10 aryl, or 5-6-membered heteroaryl.

In a preferred embodiment, R1 and R2 in the above compounds form a 3-6 membered saturated or unsaturated ring group, optionally, said 3-6 membered saturated or unsaturated cycloalkyl or heterocyclyl is substituted by 1-3 —OH, —NH2, —CN, NO2, halogen, C1-C10 alkyl, C1-C10 alkoxy, C3-C12 cycloalkyl, C6-C10 aryl or 5-10 membered heteroaryl;

R3 is selected from H;

X is selected from chemical bond, —NH—, —CONH—;

Y is selected from CR0, wherein R0 is optionally selected from H, D, —OH, —CN, halogen, C1-C10 alkyl, C1-C10 alkoxy, C3-C12 cycloalkylamino, C1-C10 alkylamino, C3-C12 cycloalkyl, or halogenated C1-C10 alkylamino;

Each R4 is the same or different, and each is independently selected from H, D, —NH2, halogen, —CN, —COOH, —CHO, —OH, —NO2, a substituted or unsubstituted group of: C1-C10 alkyl, C1-C10 alkylamino, C1-C10 alkoxy, C3-C12 cycloalkyl, 3-12 membered heterocyclyl, C6-C10 aryl, or 5-10 membered heteroaryl; preferably, said 3-12 membered heterocyclyl is any of aziridinyl, azetidinyl, oxetanyl, pyrrolidinyl, tetrahydrofuranyl, tetrahydrothiophenyl, piperidinyl, morpholinyl, piperazinyl, thiomorpholinyl, tetrahydropyranyl, 1,1-dioxothiomorpholinyl, butyrolactamyl, valerolactamyl, caprolactamyl, butyrolactone, valerolactone, caprolactone, succinimide or

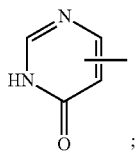

more preferably, said 3-12 membered heterocyclyl is any of butyrolactamyl, pyrrolidinyl, succinimide or

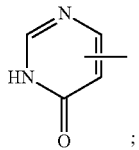

is selected from C6-C10 aryl, 5-10 membered heteroaryl, 3-12 membered heterocyclyl, wherein said 5-10 membered heteroaryl and 3-12 membered heterocyclyl contain 1-3 heteroatoms or groups selected from any of N, NH, O, S, C(O).

Each R5 is the same or different, and each is independently selected from H, D, halogen, —CN, —COOH, —CHO, —OH, —NO2, a substituted or unsubstituted group of: C1-C6 alkyl, C1-C6 alkylamino, C1-C6 alkoxy, —NH2, C3-C6 cycloalkyl, 3-6 membered heterocyclyl, C6-C10 aryl or 5-10 membered heteroaryl, or a 5-6 membered saturated ring formed by any adjacent two of R5, optionally, said 5-6 membered saturated ring is substituted by 1-3 of —OH, —NH2, —CN, halogen, C1-C6 alkyl, C1-C6 alkoxy, C3-C6 cycloalkylamino, C1-C6 alkylamino, C3-C6 cycloalkyl, halogenated C1-C6 alkylamino, C6-C10 aryl or 5-10 membered heteroaryl;

R6, R7, R8, R9, R10, R11, R12, R13 are independently selected from H, D, halogen, —CN, —COOH, —CHO, —OH, —NO2, —NH2, C1-C10 alkyl, C1-C10 alkylamino, C1-C10 alkoxy, C3-C12 cycloalkyl, C3-C12 cycloalkoxy, 3-12 membered heterocyclyl, C6-C10 aryl, 5-10 membered heteroaryl, 3-12 membered heterocyclyl;

m is 1 or 2;
n is 1 or 2 or 3;
p is 0 or 1.

In a more preferred embodiment, R1 and R2 in the above compounds form a 5-6 membered saturated ring group, preferably cyclohexane, cyclopentane, tetrahydrofuran ring, tetrahydropyrrole ring, tetrahydrothiophene ring, tetrahydropyran ring; optionally, said 5-6 membered saturated ring group is substituted by 1-3 —OH, —NH2, —CN, NO2, halogen, methyl, methoxy;

R3 is selected from H;
X is selected from chemical bonds, —NH—, —CONH—;
Y is selected from CR0, wherein R0 is optionally selected from H, halogen, C1-C6 alkyl, or C1-C6 alkoxy;
Each R4 is the same or different, and is independently selected from H, —NH2, halogen, —CN, C1-C6 alkyl, C1-C6 alkylamino, or C1-C6 alkoxy;

is selected from C6-C10 aryl, 5-10 membered heteroaryl, 5-12 membered heterocyclyl, preferably C6-C10 aryl, 5-9 membered heteroaryl; wherein said 5-6 membered heteroaryl, 5-12 membered heterocyclyl contains 1-3 heteroatoms or groups optionally from N, NH, O, S, C(O);

Each R5 is the same or different, each is independently selected from H, halogen, —CN, —COOH, —CHO, —OH, —NO2, C1-C6 alkyl, C1-C6 alkoxy, —NH2, or a 5-6 membered saturated ring formed by any two adjacent R5, optionally, said 5-6 membered saturated ring is substituted by 1-3 —OH, —NH2, —CN, halogen, C1-C6 alkyl, C1-C6 alkoxy;

R6, R7, R8, R9, R10, R11, R12, R13 are independently selected from H, halogen, —CN, —COOH, —CHO, —OH, —NO2, —NH2, C1-C6 alkyl, or C1-C6 alkoxy;

m is 1 or 2;
n is 1 or 2;
p is 0 or 1.

In a more preferred embodiment, R1 and R2 of the above compounds form a cyclopentane, a tetrahydrofuran ring, a tetrahydropyrrole ring, and a tetrahydrothiophene ring; said cyclopentane, tetrahydrofuran ring, tetrahydropyrrole ring, tetrahydrothiophene ring is substituted by 1-3 —OH, —NH2, halogen, methyl, or methoxy;

R3 is selected from H;
X is selected from chemical bonds, —NH—, —CONH—;
Y is selected from CR0, wherein R0 is optionally selected from H, halogen, C1-C6 alkyl, or C1-C6 alkoxy;
Each R4 is the same or different and is independently selected from H, halogen, C1-C6 alkyl, or C1-C6 alkoxy;

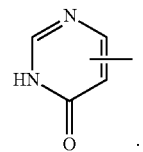

is selected from phenyl, naphthyl, 5-10 membered heteroaryl or 5-12 membered heterocyclyl; wherein said 5-6 membered heteroaryl contains 1-3 optionally selected from N, NH, O, S, heteroatoms; Preferably, said 5-6 membered heteroaryl ring is selected from thienyl, pyridyl, pyrimidinyl, pyrazinyl, pyridazinyl, pyrrolyl, pyrazolyl, thiazolyl, 1,2,3-triazolyl, 1,2,4-triazolyl, imidazolyl, tetrazolyl, isothiazolyl, oxazolyl, isoxazolyl, thiadiazolyl, oxadiazolyl, benzothienyl, indolyl, benzimidazolyl, benzothiazolyl, benzofuranyl, quinolinyl, isoquinolinyl, quinazolinyl, indazolyl, indolo[1,2-a]pyrazinyl, 4,7-diazaindole, pyrazolopyrimidinyl, imidazopyrimidinyl, oxazolopyrimidinyl, isoxazolopyrimidinyl, imidazopyrazinyl, pyrazolopyrazine, pyrrolopyrazinyl, furanopyrazinyl, thienopyrazinyl, pyridopyrimidinone, benzoxazolyl or benzothiazolyl; said 5-12-membered heterocyclyl is selected from any one of butyrolactamyl, pyrrolidinyl, succinimide group or Each R5 is the same or different, and each is independently selected from H, halogen, —CONH2, —COOH, —CN, C1-C6 alkyl, hydroxy-substituted C1-C6 alkyl, amino-substituted C1-C6 alkyl, C1-C6 alkoxy, —NH2, or any two adjacent R5 forming a cyclohexane or cyclopentane;

R6, R7, R8, R9, R10, R11, R12, R13 are all H;
m is 1;
n is 1 or 2 or 3;
p is 1.

In a preferred embodiment, said compound of formula (I) has the structure shown in formula (I-4).

(I-4)

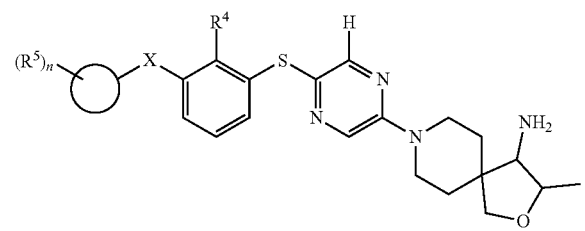

(I-4)

X is selected from chemical bonds, —NH—, —CONH—;
R4 is selected from H, D, halogen, —CN, —COOH, —CHO, —OH, —NO2, —CONHR14 or —NH-COR15, a substituted or unsubstituted group of: —NH2, C1-C10 alkyl, C1-C10 alkylamino, C1-C10 alkoxy, C3-C12 cycloalkyl, 3-12 membered heterocyclyl, C6-C10 aryl, 5-10 membered heteroaryl; wherein R14 and R15 are each independently and optionally selected from C1-C10 alkylamino, C3-C12 cycloalkyl, C6-C10 aryl, or 5-10 membered heteroaryl; said substitution is one or more substituents selected from C1-C10 alkyl, halogen, —NH2, —CN, —COOH, —CHO, —OH, —NO2, C1-C10 alkoxy, C1-C10 alkylamino, C3-C12 cycloalkyl, C6-C10 aryl, 5-10 membered heteroaryl, or 3-12 membered heterocyclyl, the above substituents are optionally substituted with 1-3 C1-C10 alkyl, halogen, —NH2, —CN, —COOH, —CHO, —OH, —NO2, C1-C10 alkoxy, C1-C10 alkylamino, C3-C12 cycloalkyl.

is selected from C6-C10 aryl, 5-10 membered heteroaryl, C4-C12 cycloalkyl, 3-12 membered heterocyclyl, C6-C14 bridged cyclyl or spirocyclyl, C6-C14 bridged heterocyclyl or spiro heterocyclyl; wherein said 5-10 membered heteroaryl, 3-12 membered heterocyclyl, C6-C14 bridged heterocyclyl or spiro heterocyclyl contains 1-3 heteroatoms or groups optionally from N, NH, O, S, C(O), S(O);

Each R5 is the same or different, and each is independently selected from H, D, halogen, —CN, —COOH, —CHO, —OH, —NO2, aminoacyl, a substituted or unsubstituted group of: C1-C10 alkyl, C1-C10 alkylamino, C1-C10 alkoxy, —NH2, C3-C12 cycloalkyl, 3-12 membered heterocyclyl, C6-C10 aryl, or 5-10 membered heteroaryl, said substitution is substituted with one or more of C1-C10 alkyl, C3-C12 cycloalkyl, 3-12 membered heterocyclyl, halogen, —NH2, —CN, —COOH, —CHO, —OH, —NO2, hydroxy-C1-C10-alkyl, C1-C10 alkoxy, C1-C10 alkylamino, 5-10 membered heteroaryl, C6-C10 aryl or 3-12 membered heterocyclyl; or a 3-6 membered saturated or unsaturated ring formed by any two adjacent R5, optionally, said 3-6 membered saturated or unsaturated ring is substituted by 1-3 —OH, —NH2, —CN, halogen, C1-C10 alkyl, C1-C10 alkoxy, C3-C12 cycloalkylamino, C1-C10 alkylamino, C3-C12 cycloalkyl, halogenated C1-C10 alkylamino, C6-C10 aryl or 5-10 membered heteroaryl;

n is 0, 1, 2, or 3;

In a preferred embodiment, R4 is selected from H, D, halogen, —CN;

is selected from phenyl, naphthyl, 5-10-membered heteroaryl or 3-12-membered heterocyclyl;
wherein said 5-10-membered heteroaryl, 3-12-membered heterocyclyl contains 1-3 heteroatoms or groups selected from any of N, NH, O, S, C(O), Preferably, said 5-10 membered heteroaryl ring is selected from thienyl, pyridyl, pyrimidinyl, pyrazinyl, pyridazinyl, pyrrolyl, pyrazolyl, thiazolyl, 1,2,3-triazolyl, 1,2,4-triazolyl, imidazolyl, tetrazolyl, isothiazolyl, oxazolyl, isoxazolyl, thiadiazolyl, oxadiazolyl, benzothienyl, indolyl, benzimidazolyl, benzothiazolyl, benzofuranyl, quinolinyl, isoquinolinyl, quinazolinyl, indazolyl, indolo[1,2-a]pyrazinyl, 4,7-diazaindole, pyrazolopyrimidinyl, imidazopyrimidinyl, oxazolopyrimidinyl, isoxazolopyrimidinyl, imidazopyrazinyl, pyrazolopyrazine, pyrrolopyrazinyl, furanopyrazinyl, thienopyrazinyl, pyridopyrimidinone, benzoxazolyl or benzothiazolyl; said 3-12 membered heterocyclyl is any of aziridinyl, azetidinyl, oxetanyl, pyrrolidinyl, tetrahydrofuranyl, tetrahydrothiophenyl, piperidinyl, morpholinyl, piperazinyl, thiomorpholinyl, tetrahydropyranyl, 1,1-dioxothiomorpholinyl, butyrolactamyl, valerolactamyl, caprolactamyl, butyrolactone, valerolactone, caprolactone, succinimide or

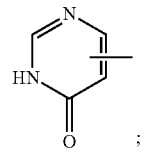

more preferably, said 3-12 membered heterocyclyl is selected from any of butyrolactamyl, pyrrolidinyl, succinimide or

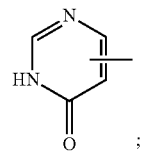

Each R5 is the same or different, and each is independently selected from H, D, halogen, —CN, —COOH, —CHO, —OH, —NO2, aminoacyl, a substituted or unsubstituted group of: C1-C10 alkyl, C1-C10 alkylamino, C1-C10 alkoxy, —NH2, said substitution is substituted with one or more of C1-C10 alkyl, halogen, —NH2, —CN, —OH, —NO2; or a 3-6 membered saturated or unsaturated ring formed by any two adjacent R5, optionally, said 3-6 membered saturated or unsaturated ring is substituted by 1-3 —OH, —NH2, —CN, halogen, C1-C10 alkyl, C1-C10 alkoxy.

In a more preferred embodiment, the structure shown in formula (I-4) has the substituted methyl and amino groups on the tetrahydrofuran ring flipped to the same side. In a more preferred embodiment, said compound of formula (I) is selected from:

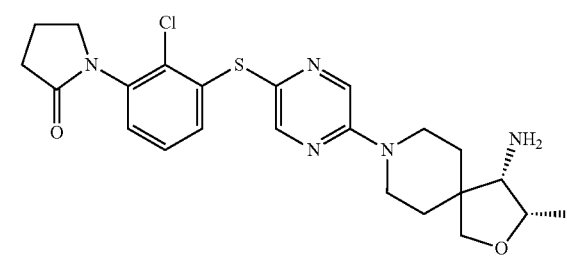

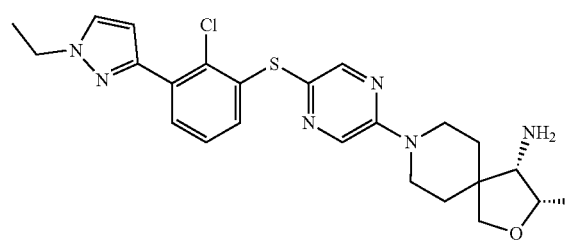

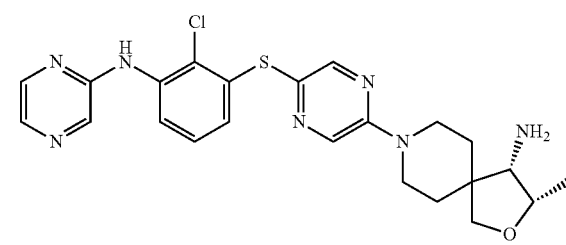

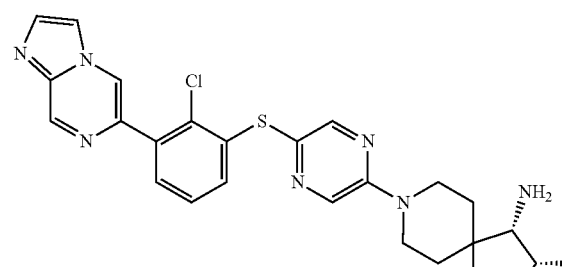

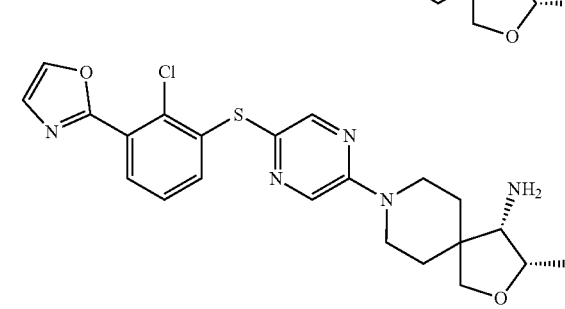

-continued

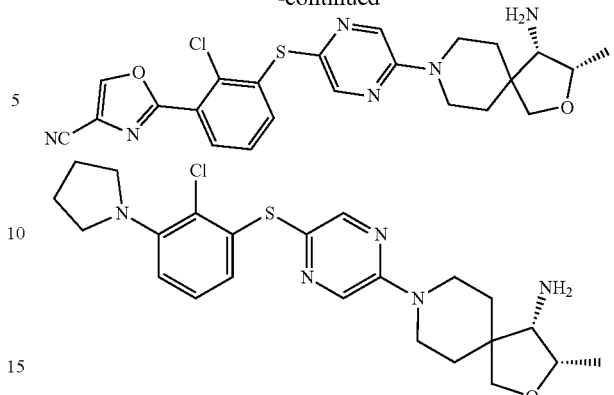

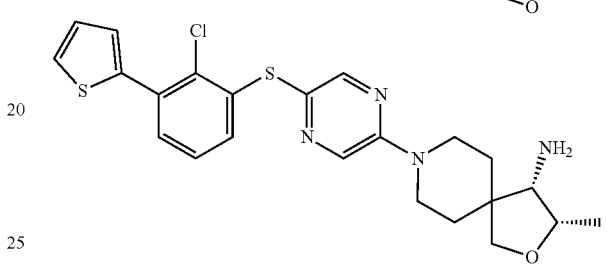

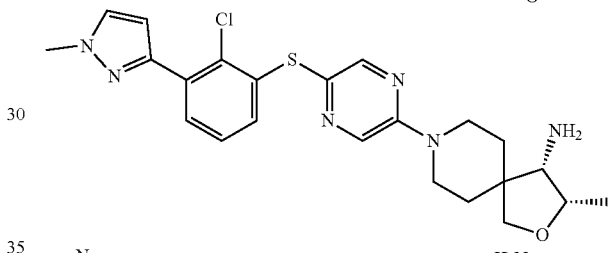

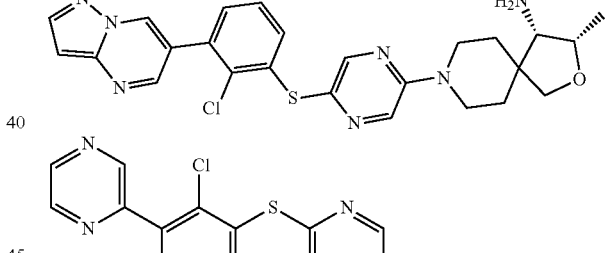

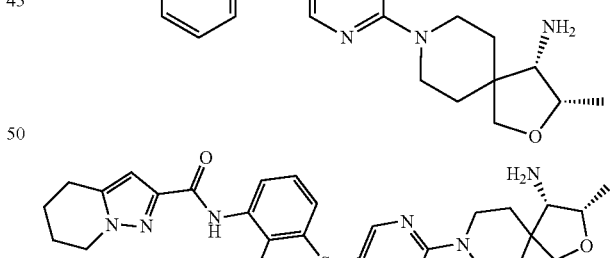

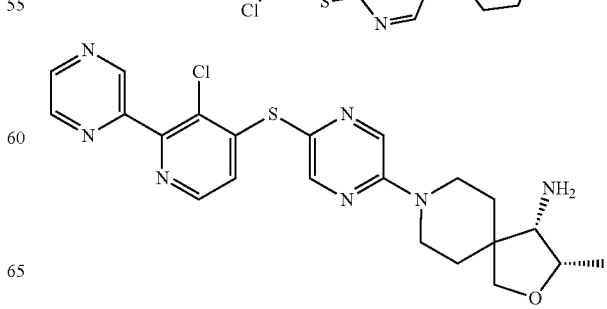

-continued
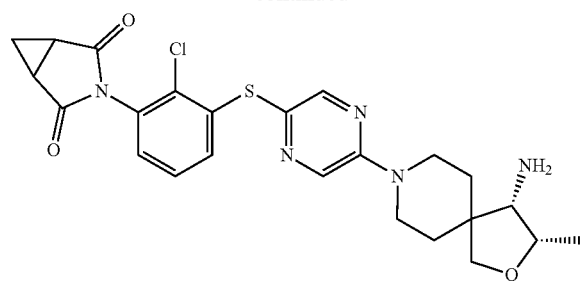
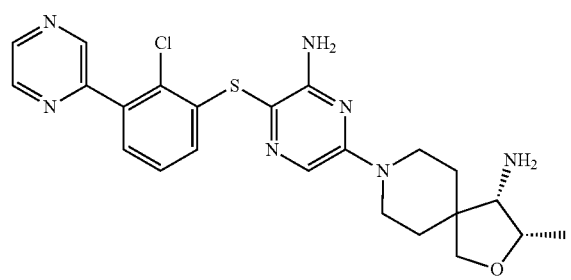
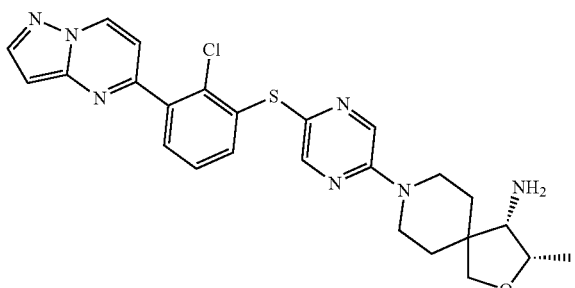
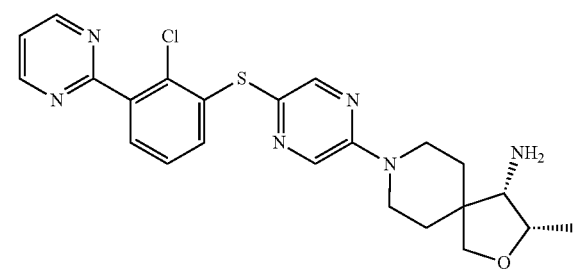
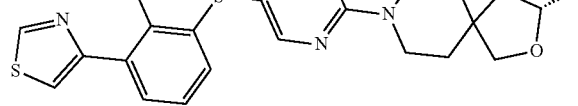
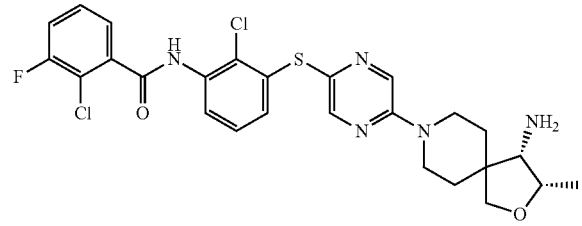
-continued
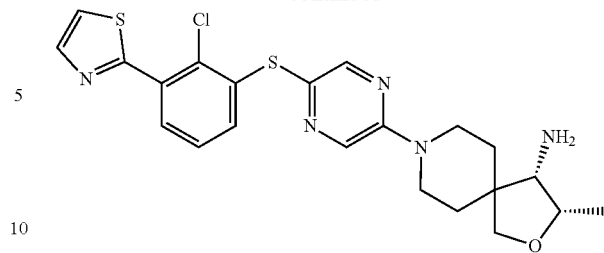
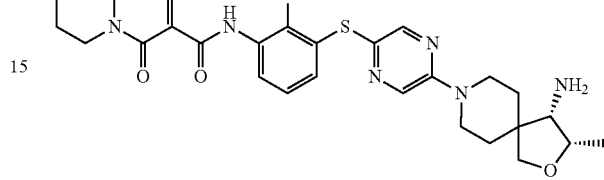
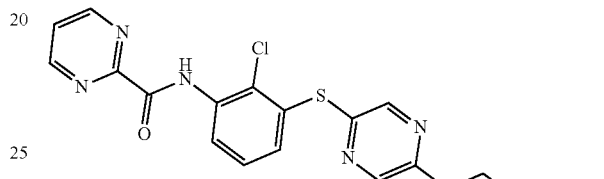
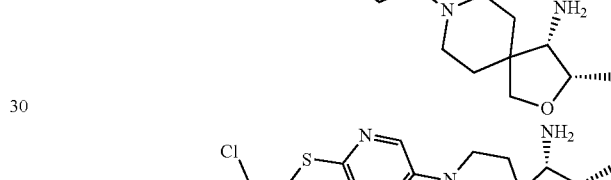
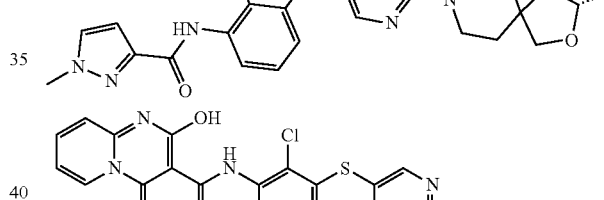
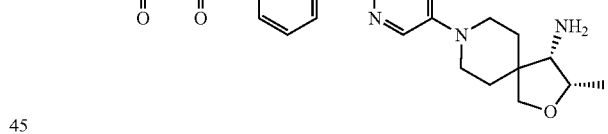
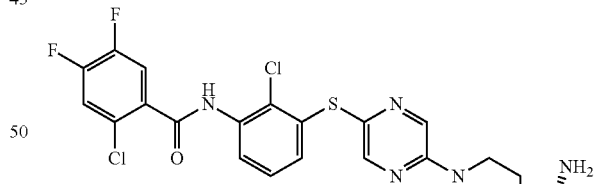
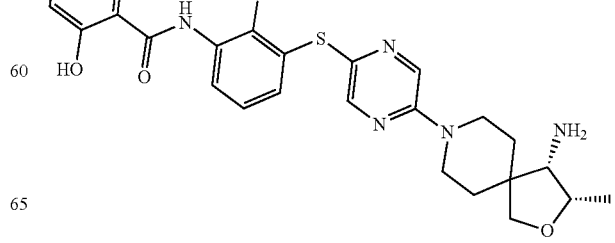

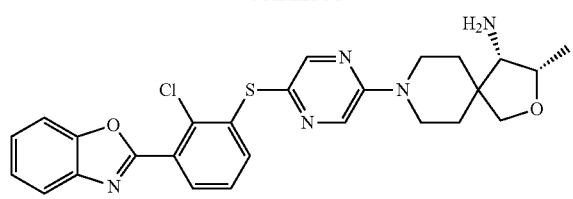
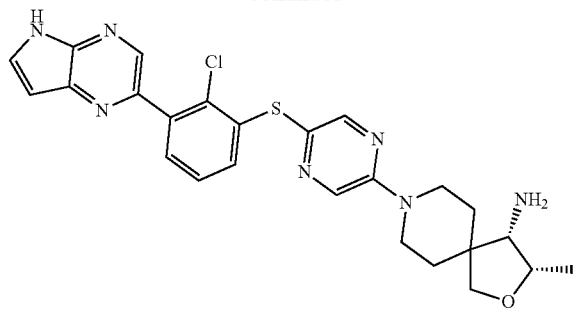
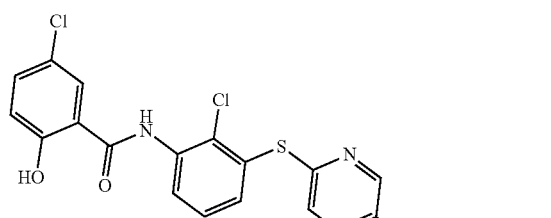
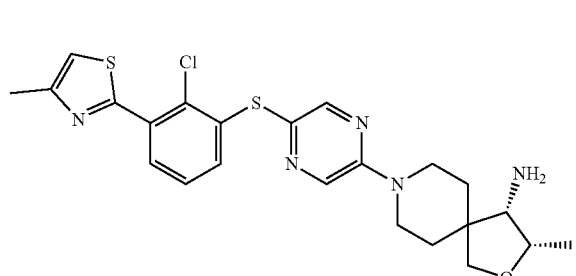
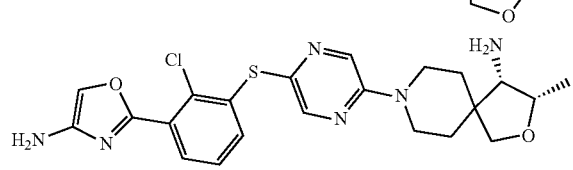
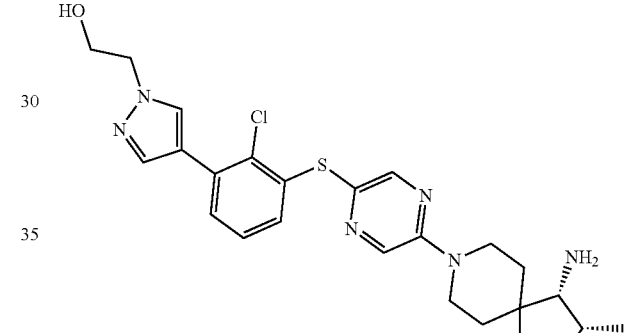
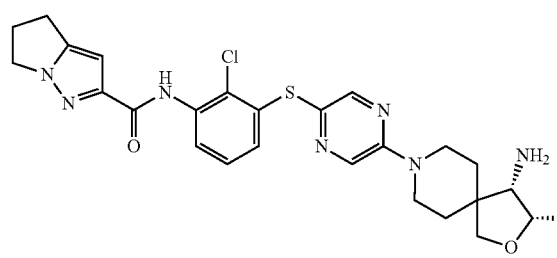
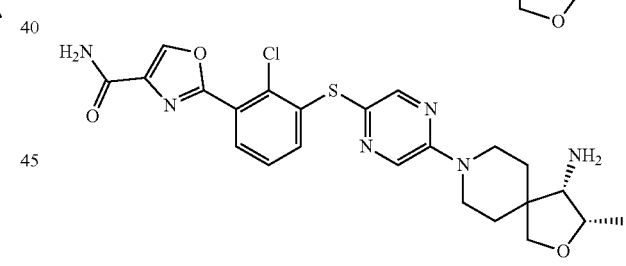
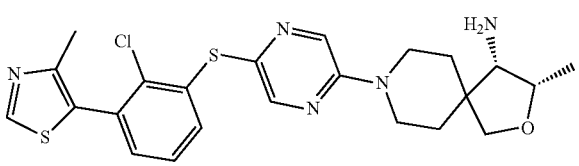
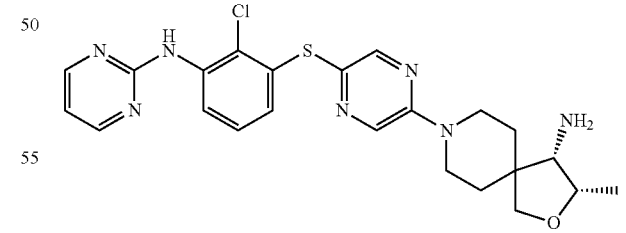
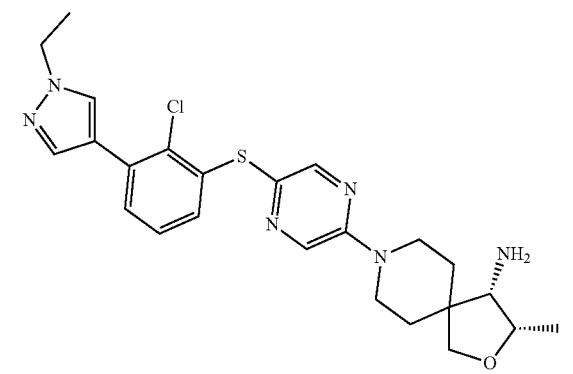
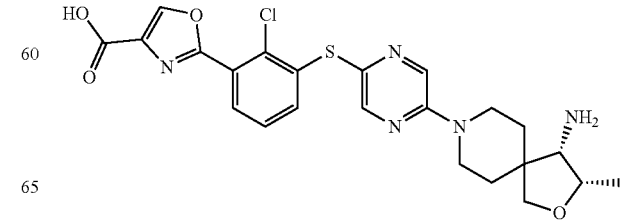
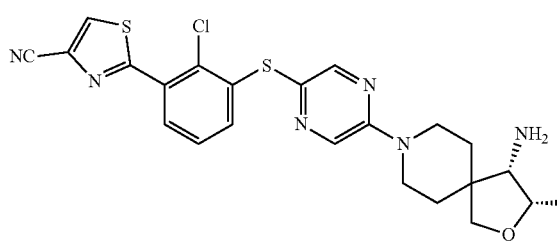

-continued

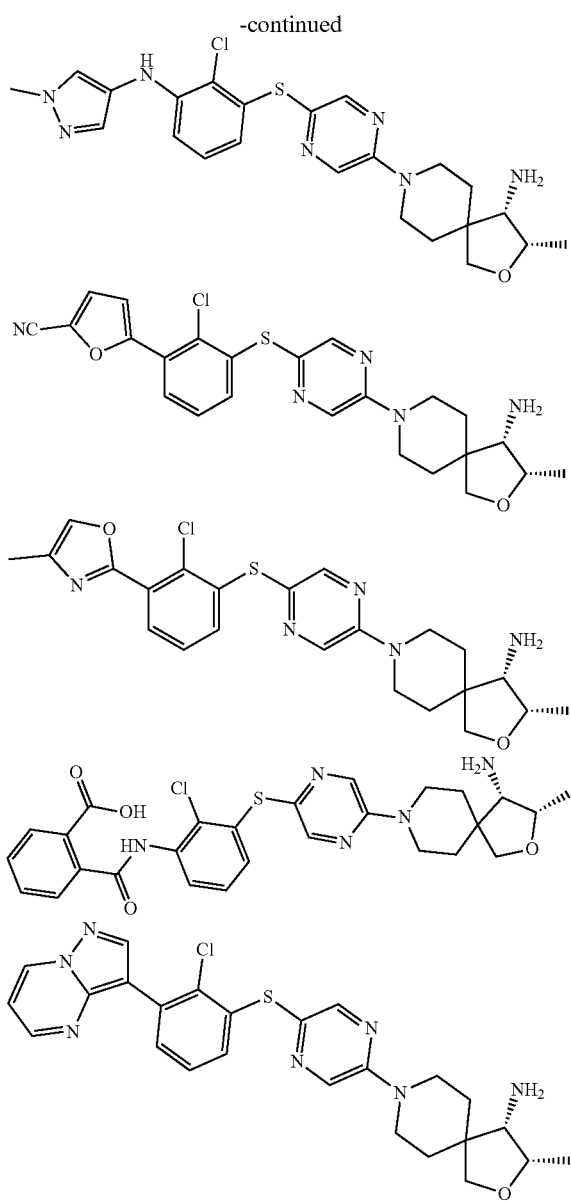

The present invention also provides a pharmaceutical composition, comprising one of the compounds of formula (I) described above or a pharmaceutically acceptable salt, ester, isomer, solvate, prodrug or isotope label thereof.

In some embodiments of the present invention, the above said pharmaceutical composition further comprises a pharmaceutically acceptable carrier.

In a more preferred embodiment, the above said pharmaceutical composition further includes:
A pharmaceutically acceptable carrier;
Adjuvants, and/or
Excipients The present invention also provides a method for preparing the above said pharmaceutical composition, which comprises the compound of formula (I) or a pharmaceutically acceptable salt, ester, isomer, solvate, prodrug or isotope label thereof with pharmaceutically acceptable carriers, adjuvants (such as diluents) and/or excipients.

The present invention also provides a pharmaceutical preparation, comprising one of the compounds of formula (I) described above or a pharmaceutically acceptable salt, ester, isomer, solvate, prodrug or isotope label thereof, or a pharmaceutical composition, said preparation can be in a form suitable for oral administration, such as tablets, sugar coated lozenges, lozenges, water or oil suspensions, dispersible powders or granules, wakaba leaves, hard or soft capsules or syrups. Oral compositions may be prepared according to any method known in the art for preparing pharmaceutical compositions, and such compositions may contain one or more ingredients selected from: sweeteners, flavor modifiers, colorants and preservatives, to provide a pleasing and palatable pharmaceutical preparation. Tablets contain the active ingredients and non-toxic pharmaceutically acceptable excipients suitable for the preparation of tablets for mixing. These excipients may be inert excipients, granulating and disintegrating agents, and lubricants. These tablets may be uncoated or may be coated by known techniques to mask the taste of the drug or delay disintegration and absorption in the gastrointestinal tract, thereby providing a sustained release over a longer period of time. For example, water-soluble taste-masking substances may be used.

Oral preparations may also be prepared in soft gelatin capsules in which the active ingredient is mixed with an inert solid diluent, or in which the active ingredient is mixed with a water-soluble carrier.

Aqueous suspension contains active substance and excipients suitable for aqueous suspension preparation. Such excipients are suspending agents; dispersing or wetting agents may be a naturally occurring phospholipid. The aqueous suspension may also contain one or more preservatives, one or more colorants, one or more flavoring agents, and one or more sweeteners.

Oil suspensions may be formulated by suspending the active ingredient in a vegetable or mineral oil. Oil suspensions may contain thickening agents, and the above sweeteners and flavoring agents may be added to provide a palatable formulation, and these compositions may be preserved by the addition of antioxidants.

By adding water, dispersible powders and granules suitable for use in the preparation of aqueous suspensions can provide active ingredients and dispersing or wetting agents, suspending agents or one or more preservatives, suitable dispersing or wetting agents for mixing and suspending agents can illustrate the above examples. Other excipients such as sweeteners, flavors and colorants can also be intervened, and these compositions are preserved by the addition of antioxidants such as ascorbic acid.

The pharmaceutical composition of the present invention may also be in the form of an oil-in-water emulsion. The oil phase may be a vegetable or mineral oil or a mixture thereof. A suitable emulsifier may be a naturally occurring phospholipid. Available sweeteners. Such formulations may also contain demulcents, preservatives, colorants, and antioxidants.

The pharmaceutical preparation of the present invention may be in the form of a sterile injectable aqueous solution, and acceptable vehicles or solvents that may also be used are water, Glico's solution, and isotonic sodium chloride solution. The sterile injectable preparation may be a sterile injectable oil-in-water microemulsion in which the active ingredient is dissolved in the oil phase, and the injection solution or microemulsion may be injected into the bloodstream of the patient through local large-scale injection. Alternatively, solutions and microemulsions are preferably administered in a manner that maintains a constant circulating concentration of a compound of the invention. To maintain this constant concentration, a continuous intravenous drug delivery device may be used, an example of which is the Deltec CADD-PLUS™ 5400 intravenous injection pump.

The pharmaceutical preparation of the present invention may be in the form of a sterile injectable water or oil suspension for intramuscular and subcutaneous administration. This suspension may be formulated according to the known arts using those suitable dispersing or wetting agents and suspending agents described above. The sterile injectable preparation may also be a sterile injectable solution or suspension prepared in a parenteral non-toxic diluent or a collective preparation of the preparations. In addition, a sterile fixed oil can be conveniently used as a solvent or suspension medium. In addition, fatty acids can also be prepared for injection.

The compounds of the invention may be administered in the form of suppositories for rectal administration. These pharmaceutical compositions can be prepared by mixing the drug with a suitable non-irritating excipient that is solid at ordinary temperatures but liquid in the rectum because it will dissolve in the rectum to release the drug.

As is well known to those skilled in the art, the dose of a drug depends on a variety of factors, including but not limited to the following: the activity of the specific compounds used, or the age of the patient, or the weight of the patient, or the health status of the patient, or the diet of the patient, time of administration, mode of administration, rate of excretion, combination of drugs, etc.; in addition, the optimal treatment method such as the mode of treatment, the daily dosage of the general compound (I) or the types of pharmaceutically acceptable salt can be verified according to the conventional treatment regimens.

The present invention also provides the above-mentioned compound of formula (I) or a pharmaceutically acceptable salt, ester, isomer, solvate, prodrug or isotope label thereof, or the pharmaceutical composition, or the pharmaceutical preparation as described above for use in the prevention and treatment of non-receptor protein tyrosine phosphatase (SHP2, Src Homolgy-2 phosphatase)-mediated or dependent diseases or conditions.

The present invention also provides the above-mentioned compound of formula (I) or a pharmaceutically acceptable salt, ester, isomer, solvate, prodrug or isotope label thereof, or the above described pharmaceutical composition, or the pharmaceutical preparation described above for use in the prevention and/or treatment of non-receptor protein tyrosine phosphatase-mediated or dependent diseases or conditions.

The present invention also provides the above described compound of formula (I) or a pharmaceutically acceptable salt, ester, isomer, solvate, prodrug or isotope label thereof, or the above described pharmaceutical composition, or the pharmaceutical preparation described above in the manufacture of a medicament for the prevention and/or treatment of non-receptor protein tyrosine phosphatase-mediated or dependent diseases or conditions.

Wherein, the non-receptor protein tyrosine phosphatase-mediated or dependent diseases or disorders are selected from cancer, central nervous system defects, cardiovascular system defects, hematological system defects, immune or inflammatory diseases, infectious diseases, metabolic defects, neurological defects, mental impairments and reproductive defects. Wherein, said cancer may be breast cancer, endometrial cancer, head and neck cancer, skin cancer, lung cancer, liver cancer, leukemia, ovarian cancer, cervical cancer, prostate cancer, bile duct cancer, esophageal cancer, pancreatic cancer, colorectal cancer, glioma, leiomyoma, fallopian tube tumor, kidney cancer, myeloma, bone cancer, and thyroid cancer. Said central nervous system defects may be alcoholism or migraine; said cardiovascular system defects may be aortic aneurysm, susceptible myocardial infarction, aortic valve sclerosis, cardiovascular disease, coronary artery disease, hypertension; said hematological system defects may be deep vein thrombosis; said immune and inflammatory diseases may be arthritis, multiple sclerosis, liver cirrhosis; said infectious diseases may be hepatitis B, chronic hepatitis, osteopenia, osteoporosis; said neurological defects may be Alzheimer's disease, Parkinson's disease, migraine, vertigo; said mental defects may be anorexia nervosa, attention deficit with hyperactivity disorder, dementia, severe depressive disorder, psychosis; said reproductive defects may be menarche age, endometriosis, infertility and the like.

The present invention also provides a method for preventing and/or treating non-receptor protein tyrosine phosphatase-mediated or dependent diseases or disorders, comprising the steps of: administration of a therapeutically effective amount of any one of the above described compound of formula (I) or a pharmaceutically acceptable salt, ester, isomer, solvate, prodrug or isotope label thereof, or the above-mentioned pharmaceutical composition, or the above-mentioned pharmaceutical preparation to a patient in need thereof.

The term "therapeutically effective amount" refers to the dose of a pharmaceutically active ingredient capable of inducing a biological or medical response in a cell, tissue, organ, or organism (e.g., a patient).

The term "administration" refers to the process of the application of an active pharmaceutical ingredient (such as the compound of the present invention) or a pharmaceutical composition containing an active pharmaceutical active ingredient (such as a pharmaceutical composition of the present invention) to patients or their cells, tissues, organs, biological fluids, etc. in order to bring the active pharmaceutical ingredient or pharmaceutical composition into contact with the patients or their cells, tissues, organs, biological fluids, etc. Common modes of administration include (but are not limited to) oral administration, subcutaneous administration, intramuscular administration, subperitoneal administration, ocular administration, nasal administration, sublingual administration, rectal administration, and vaginal administration.

The term "in need" refers to the judgment of a doctor or other caregiver about a patient's need or to benefit from a preventive and/or therapeutic procedure based on various factors in the doctor's or caregiver's area of expertise.

The term "patient" (or subjects) refers to a human or non-human animal (such as a mammal).

The present invention also provides a form of pharmaceutical combination, which comprises any of the above described compound of formula (I) or a pharmaceutically acceptable salt, ester, isomer, solvate, prodrug or isotope label thereof, or the aforementioned pharmaceutical composition, or the aforementioned pharmaceutical preparation, and at least one additional therapeutic agent for the prevention and/or treatment of non-receptor protein tyrosine phosphatase-mediated or dependent diseases or disorders.

The compound of formula (I) or its pharmaceutically acceptable salt, ester, isomer, solvate, prodrug or isotope label of the present invention, or the aforementioned pharmaceutical composition, or the aforementioned pharmaceutical preparation can be used in combination with the following, but not limited to, compounds or antibodies, or to be used for antibody conjugation as drugs.

The present invention also provides a method for preparing a compound of formula (I) or a pharmaceutically acceptable salt, ester, isomer, solvate, prodrug or isotope label thereof; a few of the typical synthesis routes are described below for the compound of formula (I) to further describe the technical scheme of the invention, which can be seen in combination with the reaction routes shown below:

(1) Compound Ic is obtained by reactions of the compound Ia and Ib under basic conditions, wherein, A in Ib is halogen, preferably chlorine, bromine or iodine, and X is a chemical bond.

(2) Compound Ic is deprotected to obtain compound Id;

(3) Compound If is obtained by reactions of the compounds Id and Ie, wherein B in compound Ie is halogen, preferably chlorine, bromine or iodine;

(4) Compound (I) is obtained by reactions of the compounds If and Ig under basic conditions.

The synthesis route of the reaction is as follows:

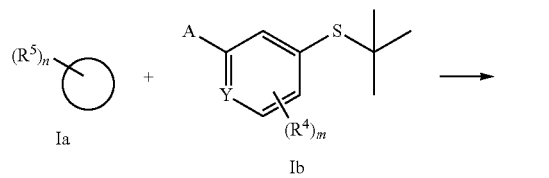

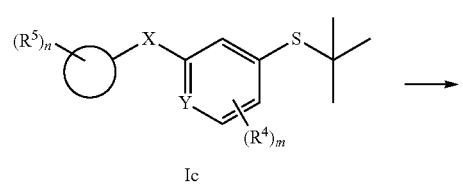

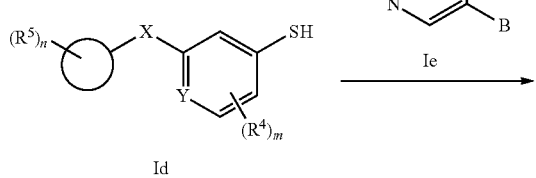

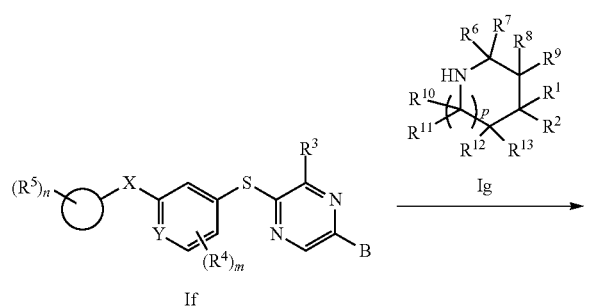

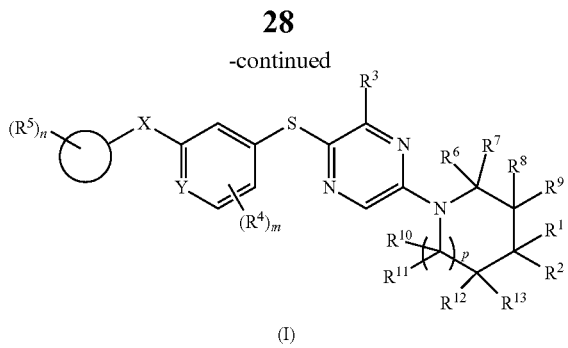

In a preferred embodiment, in step (1), the catalyst is cuprous iodide and a base, and the base is preferably sodium hydroxide, potassium hydroxide, potassium carbonate, sodium carbonate, sodium methoxide, sodium ethoxide, sodium tert-butoxide, potassium tert-butoxide or lithium tert-butoxide.

In a preferred embodiment, in step (2), the catalyst for the deprotection reaction is protonic acid or Lewis acid, preferably aluminum trichloride.

In a preferred embodiment, in step (3), the reaction catalyst is an organic or inorganic base, wherein the inorganic base is preferably sodium hydroxide, potassium hydroxide, potassium carbonate, sodium carbonate, and the organic base is preferably triethylamine, diethylamine, diisopropylamine or N, N-diisopropylethylamine.

In a preferred embodiment, in step (4), the reaction catalyst is an organic or inorganic base, wherein the inorganic base is preferably sodium hydroxide, potassium hydroxide, potassium carbonate, sodium carbonate, and the organic base is preferably triethylamine, diethylamine, diisopropylamine or N, N-diisopropylethylamine.

The present invention also provides another method for compound Ic preparation, where Ic is obtained from compounds Ia1 and compound Ib reactions. The reaction catalyst is a coupling reaction catalyst, preferably tetrakis (triphenylphosphine) palladium. The reaction route is:

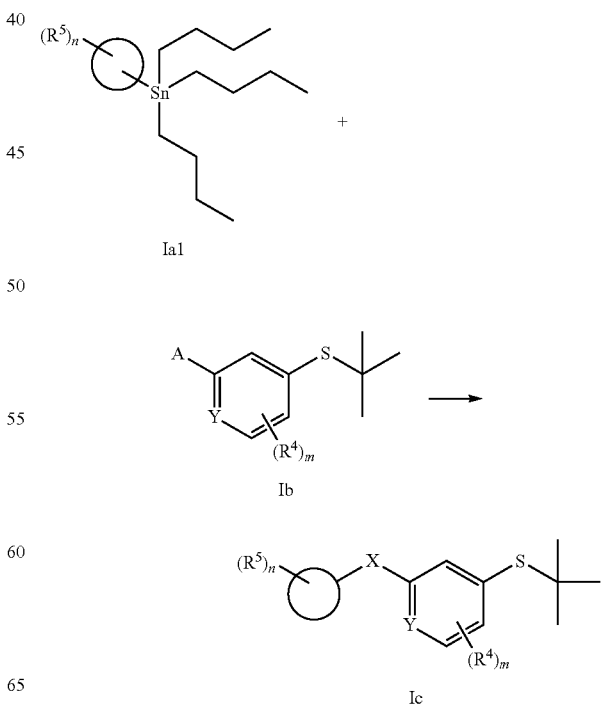

The invention also provides another synthesis method for the compound (I), including
(1) Compound Ih reacts with compound Ii to obtain compound Ij, wherein, A in compound Ii is halogen, preferably chlorine, bromine or iodine;
(2) Compound Ij reacts with compound Ik to obtain compound Il, and X in compound Il is —CONH—;
(3) Compound Il reacts with compound Ig to obtain compound (I).

In a preferred embodiment, in step (1), the catalyst for the reaction is an organic base or an inorganic base, wherein the inorganic base is preferably sodium hydroxide, potassium hydroxide, potassium carbonate, sodium carbonate, cesium carbonate, and the organic base is preferably triethylamine, diethylamine, diisopropylamine or N, N-diisopropylethylamine.

In a preferred embodiment, in step (2), the catalyst for the reaction is thionyl chloride and/or an organic base, wherein the organic base is preferably triethylamine, diethylamine, diisopropylamine, or N, N-diisopropylethylamine, pyridine or 4-dimethylaminopyridine.

In a preferred embodiment, in step (2), the catalyst for the reaction is an organic base, wherein it is preferably triethylamine, diethylamine, diisopropylamine, N, N-diisopropylethylamine, pyridine or 4-dimethylaminopyridine.

The synthesis route for the reaction is:

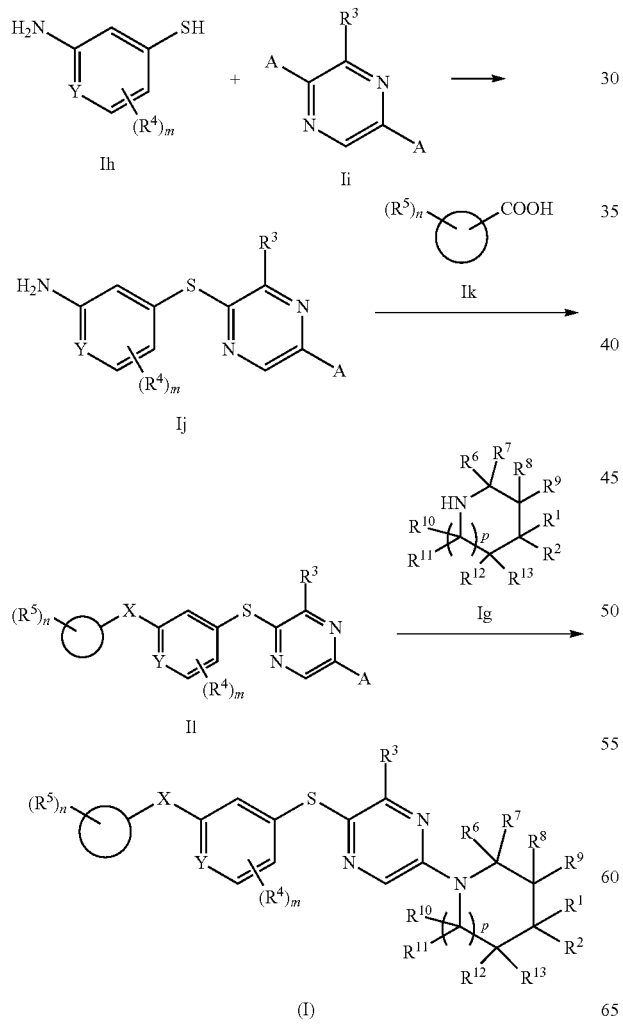

The following embodiments may further describe the present invention, however, they are not to be used to restrict the scope of this invention.

Example 1

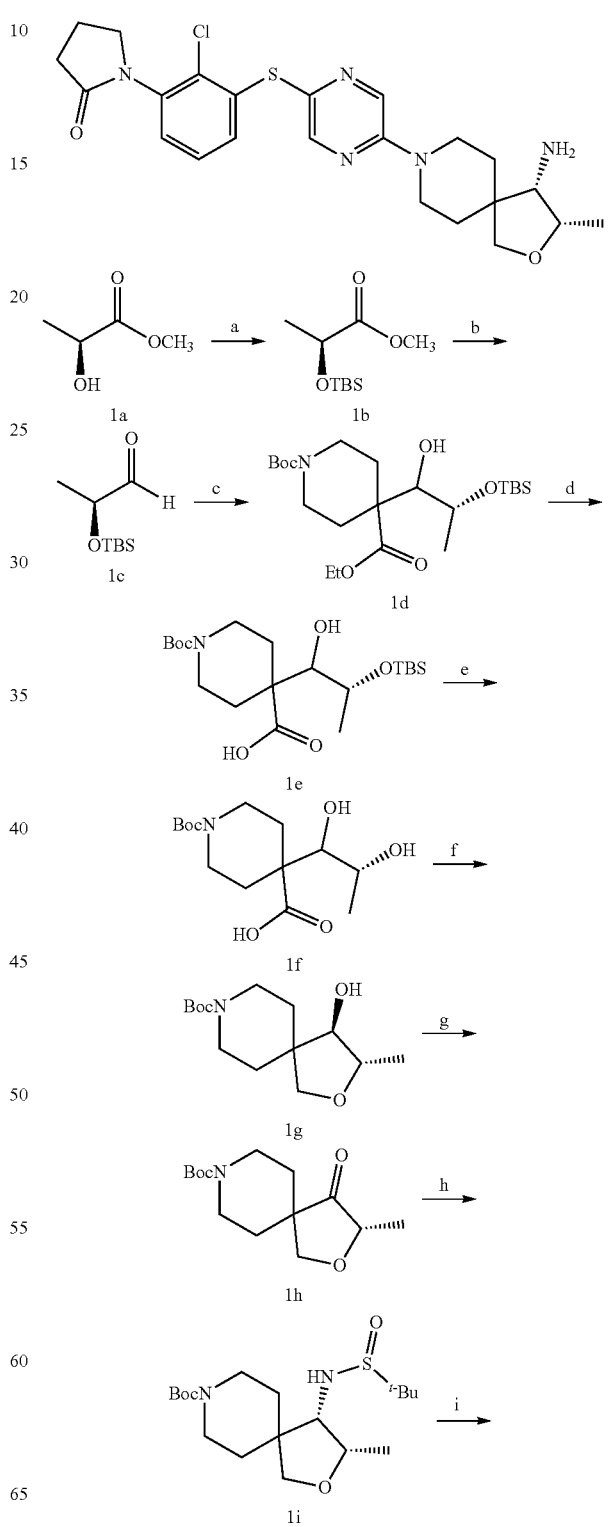

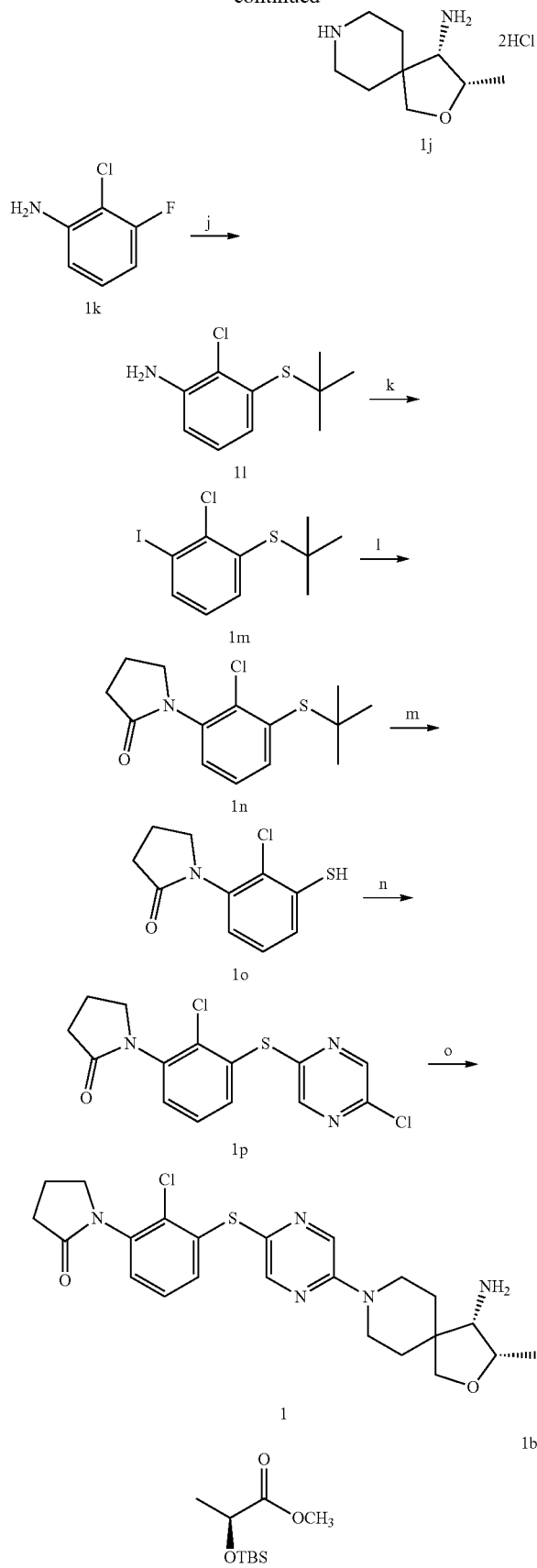

Imidazole (102 g, 1.5 mol) was added to a solution of 1a (104 g, 1.0 mol) in dichloromethane (600 mL), followed by dropwise addition of dichloromethane (200 mL) solution of tert-butyldimethylsilane (165 g, 1.1 mol) in an ice-water bath, reacted at room temperature for 16 hours. The reaction solution was diluted with dichloromethane, washed 3 times with water, and the organic phase was dried with anhydrous sodium sulfate. The desiccant was filtered and the filtrate was concentrated to obtain crude 1b (237 g, yield 100%), which was used directly in the next step.

$^1$H NMR (CDCl3, 400 MHz): δ 4.32 (q, J=8.0 Hz, 1H), 3.71 (s, 3H), 1.39 (d, J=8.0 Hz 3H), 0.89 (s, 9H), 0.09 (s, 3H), 0.06 (s, 3H).

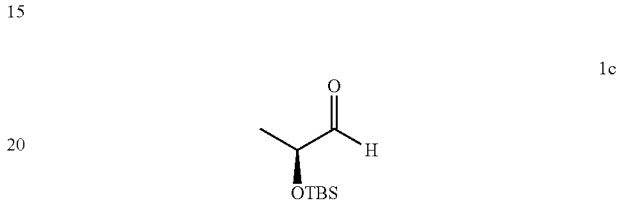

Diisobutylaluminum hydride (367 mL, 0.55 mol, 1.5 M toluene solution) was added dropwise to a solution of 1b (120 g, 0.55 mol) in dichloromethane (600 mL) in an ice-water bath, reacted for 16 hours. Methanol (100 mL) was added dropwise to quench the reaction, diatomite was added and stirred well. After filtration, the filtrate was diluted with dichloromethane, washed 3 times with water, and the organic phase was dried with anhydrous sodium sulfate. The desiccant was filtered, and the filtrate was concentrated, and the residue was purified by silica gel column (petroleum ether/ethyl acetate=10/1 eluent) to obtain 1c (56 g, yield 54%).

$^1$H NMR (CDCl3, 400 MHz): δ 9.61 (s, 1H), 4.08 (q, J=8.0 Hz, 1H), 1.27 (d, J=8.0 Hz 3H), 0.91 (s, 9H), 0.10 (s, 3H), 0.09 (s, 3H).

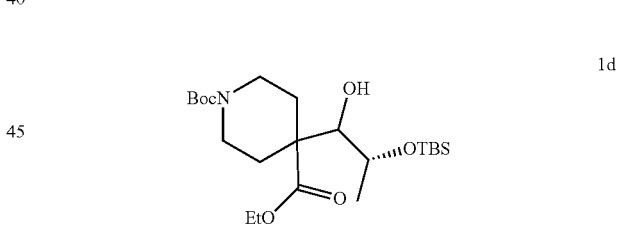

Under nitrogen protection, diisopropylamine (23.4 mL, 166 mmol) was dissolved in anhydrous tetrahydrofuran (220 mL), cooled to −20° C., and n-butyllithium (64 mL, 160 mmol, 2.5 M n-hexane solution) was added dropwise, after reacting for 1 hour, a solution of ethyl N-tert-butoxycarbonyl-4-piperidinecarboxylate (27.5 g, 107 mmol) in anhydrous tetrahydrofuran (50 mL) was added dropwise, the temperature was raised to 0° C. and reacted for 1 hour, added 1c (20.5 mL, 102 mmol), reacted at 0° C. for 3 hours. The reaction was quenched with 5% sodium bicarbonate solution, extracted 3 times with ethyl acetate, and the organic phase was dried with anhydrous sodium sulfate. Filtered and concentrated under reduced pressure, and the residue was purified with silica gel column (petroleum ether/ethyl acetate=2/1) to obtain 1d (32.6 g, yield 72%).

MS m/z [M+H]$^+$: 446.7.

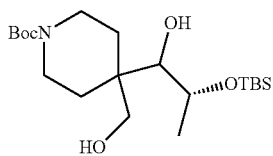

1e

Lithium borohydride (2.3 g, 107 mmol) was added in batches to a 1d (31.7 g, 71 mmol) solution of tetrahydrofuran (600 mL) under an ice water bath. After the addition, the reaction was carried out for 16 hours at room temperature. The reaction was cooled to 0° C. in an ice-water bath, saturated sodium bicarbonate solution was added to quench the reaction, the mixture was extracted 3 times with ethyl acetate, and the organic phase was dried with anhydrous sodium sulfate. The desiccant was filtered, and the filtrate was concentrated to obtain crude 1e (30.2 g, yield 100%), which was used directly in the next step.

MS m/z [M+H]+: 404.5, [M−H]−: 402.4

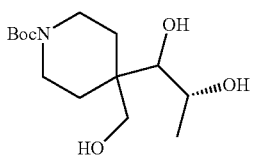

1f 1e (59.0 g, 146 mmol) was dissolved in tetrahydrofuran (600 mL), tetrabutylammonium fluoride (35 g, 109 mmol) was added and stirred for 16 hours at room temperature. The reaction solution was quenched with saturated sodium bicarbonate solution and partitioned with ethyl acetate, the aqueous phase was extracted until no product. The organic phases were combined and washed with saturated brine. The organic phase was dried with anhydrous sodium sulfate, the desiccant was filtered, and the filtrate was concentrated under reduced pressure, and 1f (24 g, 57% yield) was obtained by column chromatography.

$^1$H NMR (CDCl3, 400 MHz): δ 3.94-4.00 (m, 1H), 3.65-3.81 (m, 5H), 3.07-3.15 (m, 2H), 1.60-1.71 (m, 4H), 1.45 (s, 9H), 1.33 (d, J=4.0 Hz, 3H). MS m/z [M+H]+: 290.3, [M−H]−: 288.3.

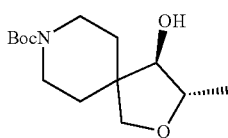

1g

Sodium hydrogen (2.3 g, 57.44 mmol) was added to tetrahydrofuran (80 mL), the temperature was reduced to −15° C., tetrahydrofuran (50 mL) solution of 1f (8.3 g, 28.72 mmol) was added dropwise, followed by the addition of tetrahydrofuran (15 mL) solution of p-toluenesulfonyl chloride (1.72 g, 9 mmol), reacted for 16 hours. The reaction solution was cooled to −15° C., and a saturated ammonium chloride solution was added dropwise until no air bubbles were produced, partitioned with ethyl acetate, and the aqueous phase was extracted until no product, the organic phases were combined and washed with saturated brine. The organic phase was dried with anhydrous sodium sulfate, the desiccant was filtered, the filtrate was concentrated under reduced pressure, and 1g (5 g, yield 64%) was obtained by column chromatography.

$^1$H NMR (CDCl3, 400 MHz): δ 4.08-4.14 (m, 1H), 3.01-3.80 (m, 7H), 1.68-1.81 (m, 4H), 1.46 (s, 9H), 1.26 (d, J=8.0 Hz, 3H).

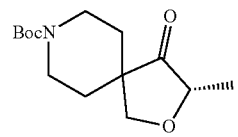

1h 1g (13.5 g, 49.7 mmol) was added to dichloromethane (160 mL), and Dess-Martin periodinane (42 g, 99 mmol) was added in batches at −10° C. and reacted at 0° C. for 16 hours. Ether (500 mL) was added and a large amount of solid was precipitated, filtered, washed once with ether (100 mL), the filtrate was washed once with saturated sodium bicarbonate solution followed by saturated sodium thiosulfate solution, and the organic phase was dried over anhydrous sodium sulfate. The desiccant was filtered, the filtrate was concentrated under reduced pressure, and was separated by column chromatography to obtain 1 h (5.5 g, yield 41%).

$^1$H NMR (CDCl3, 400 MHz): δ 4.19 (d, J=8.0 Hz, 1H), 3.83-3.92 (m, 4H), 2.96-3.16 (m, 2H), 1.55-1.79 (m, 4H), 1.46 (s, 9H), 1.32 (d, J=8.0 Hz, 3H).

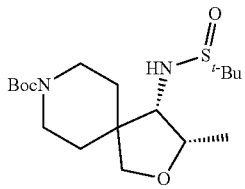

1i 1h (20.0 g, 274.3 mmol) and R-(+)-tert-butylsulfinamide (33.2 g, 274.3 mmol) were dissolved in tetrahydrofuran (350 mL) solution, tetraethyl titanate (67.7 g, 297 mmol) was added, displaced with nitrogen, reacted at 100° C. for 20 hours. After cooling to −25° C., methanol (30 mL) was added, and lithium borohydride (5.97 g, 274.3 mmol) was added in batches. Reacted at −10° C. for 45 minutes after the addition. A saturated ammonium chloride solution was added at −10° C., a large amount of solids were precipitated, filtered with suction, the filter cake was washed with ethyl acetate, and the filtrate was partitioned, the aqueous phase was extracted with ethyl acetate again until no product, the organic phase was washed once with saturated brine, dried with sodium sulfate, the desiccant was filtered, and the organic phase was concentrated under reduced pressure, and 1i (12.4 g, yield 59%) was obtained by column chromatography.

$^1$H NMR (CDCl3, 400 MHz): δ 4.15-4.19 (m, 1H), 3.63-3.88 (m, 4H), 3.30-3.44 (m, 2H), 2.92 (s, 1H), 1.80 (s, 2H), 1.60 (s, 2H), 1.44 (s, 9H), 1.25 (s, 9H), 1.20 (d, J=8.0 Hz, 3H). LCMS m/z [M+H]+: 375.3, [M−H]−: 373.5.

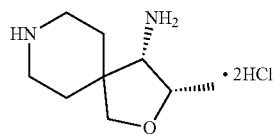

1j

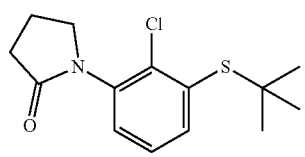

1n 1i (12.0 g, 32.1 mmol) was dissolved in methanol (150 mL), a solution of HCl in dioxane (15 mL, 4 M) was added, the temperature was raised to 40° C., the reaction was stirred and reacted for 1 hour, stopped the reaction. The reaction solution was cooled to room temperature, concentrated under reduced pressure to obtain 1j (7.85 g, yield 100%).

$^1$H NMR (DMSO, 400 MHz): δ 9.25 (br, 2H), 8.38 (br, 3H), 4.20-4.23 (m, 1H), 3.81 (d, J=8.0 Hz, 1H), 3.62 (d, J=8.0 Hz, 1H), 3.46 (br, 1H), 3.14-3.23 (m, 2H), 2.84-2.92 (m, 2H), 1.69-2.01 (m, 4H), 1.22 (d, J=8.0 Hz, 3H). LCMS m/z [M+H]+: 171.2.

Cuprous iodide (5.84 mg, 0.03 mmol) and potassium carbonate (169.6 mg, 1.2 mmol) were added to toluene (4 mL), displaced with nitrogen, followed by N, N'-dimethylethylenediamine (5.4 mg, 0.06 mmol), 1m (200 mg, 0.61 mmol), and 2-pyrrolidone (64.7 mg, 0.76 mmol), and refluxed for 16 hours. Extracted with ethyl acetate, washed with water, dried with sodium sulfate, filtered, and the organic phase was concentrated under reduced pressure, and solid in was obtained with column chromatography (6.1 mg, yield 71.8%).

$^1$H NMR (DMSO, 400 MHz): δ 7.67 (d, J=8.0 Hz, 1H), 7.46-7.42 (m, 2H), 3.70-3.67 (m, 2H), 2.44-2.40 (t, J=8.0 Hz, 2H), 2.16-2.13 (t, J=8.0 Hz, 2H), 1.33 (s, 9H). LCMS m/z [M+H]+: 284.7.

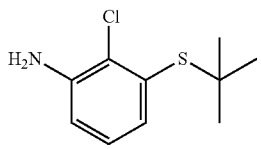

1l 1k (50 g, 0.3448 mol) was dissolved in N, N-dimethylformamide (500 mL), tert-butyl mercaptan (87 g, 0.9374 mol) and cesium carbonate (224 g, 0.6696 mol) were added, under nitrogen protection, the temperature was raised to 120° C. and reacted for 24 hours. The reaction mixture was diluted with ethyl acetate and quenched with water. The organic phase was separated and washed five times with saturated brine, dried with sodium sulfate, the desiccant was filtered, the organic phase was concentrated under reduced pressure to obtain oily product 1l, and the product was directly used in the next step without purification.

1o

Aluminum trichloride (424 mg, 3.3 mmol) was added to anhydrous dichloromethane (20 mL) and stirred for 10 minutes, 1n (300 mg, 1 mmol) was added, and the reaction solution was poured into ice water after 3 hours, extracted with dichloromethane, dried with sodium sulfate, filtered, and the organic phase was concentrated under reduced pressure to obtain oily product 1o (182 mg, yield 80%).

LCMS m/z [M+H]+: 228.4

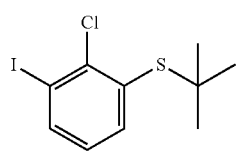

1m

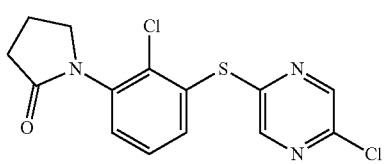

1p 1l (1 g, 4.65 mmol) was added to concentrated hydrochloric acid (2 mL), an aqueous solution (10 mL) of sodium nitrite (0.25 g, 5.26 mmol) was added dropwise at −5° C., stirred for 30 minutes, an aqueous solution (10 mL) of potassium iodide (1.08 g, 9.3 mmol) was added dropwise at −5° C. The reaction was stopped after 10 minutes, ethyl acetate was added, washed with water, dried with sodium sulfate, filtered, and the organic phase was concentrated under reduced pressure, and 1m was obtained by column chromatography (1 g, yield 66.7%).

1o (286 mg, 1.26 mmol) was dissolved in isopropanol (5 mL), then dichloropyrazine (376 mg, 2.5 mmol) and diisopropylamine (323 mg, 2.5 mmol) were added, displaced with nitrogen, reacted overnight at 80° C. After cooling, it was concentrated and subjected to column chromatography to obtain yellow oily product 1p (400 mg). LCMS m/z [M+H]+: 340.3.

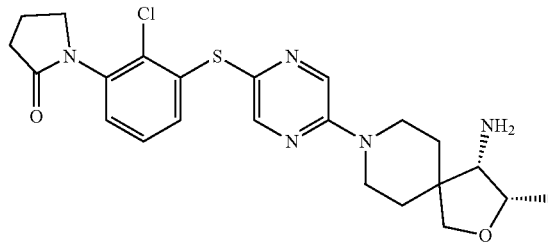

1p (413 mg, 1.22 mmol), 1j (417 mg, 2.5 mmol), and N,N-diisopropylethylamine (317 mg, 2.5 mmol) were dissolved in N-methylpyrrolidone (5 mL). Displaced with nitrogen, reacted at 100° C. overnight, trifluoroacetate was directly prepared by spin-drying the solvent, neutralized with sodium bicarbonate, extracted with dichloromethane, dried and concentrated, and lyophilized to obtain the target product 1 (115 mg, 20% yield in steps n and o).

$^1$H NMR (DMSO, 400 MHz): δ 8.45 (s, 1H), 8.27 (s, 1H), 7.30-7.22 (m, 2H), 6.82 (d, J=8.0 Hz, 1H), 4.09-4.06 (m, 1H), 3.89 (m, 2H), 3.69-3.67 (m, 3H), 3.50-3.48 (m, 2H), 2.92-2.91 (m, 1H), 2.43 (d, J=8.0 Hz, 2H), 2.15 (m, 2H), 1.77 (m, 1H), 1.66 (m, 1H), 1.57-1.54 (m, 3H), 1.09 (d, J=4.0 Hz, 3H). MS m/z [M+H]+: 474.7.

Example 2

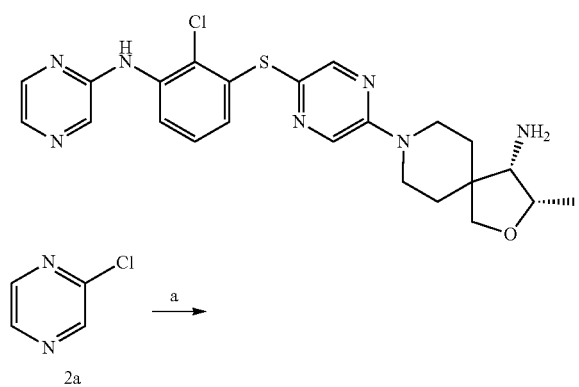

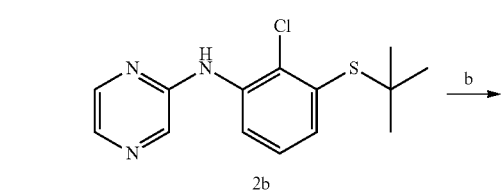

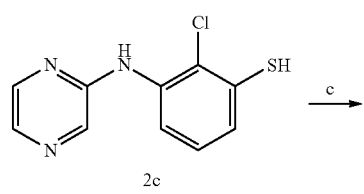

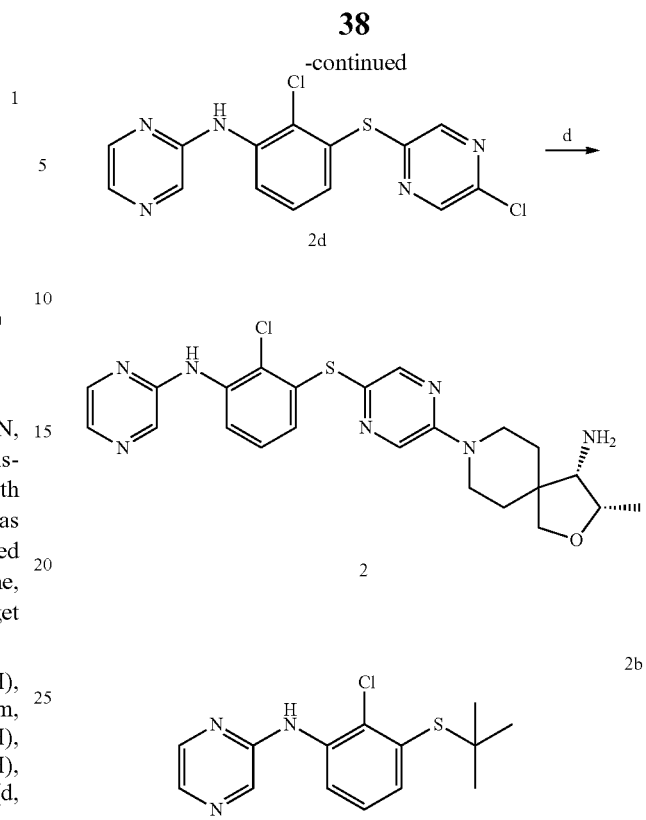

2a (1 g, 4.65 mmol) and 1l (0.64 g, 5.58 mmol) were dissolved in toluene (10 mL), then sodium tert-butoxide (0.63 g, 6.51 mmol) and 4,5-bis(diphenylphosphino)-9,9-dimethylxanthene (28 mg) were added, displaced with nitrogen 3 times, tris (dibenzylidene-indenylacetone) dipalladium (39 mg) was added, reacted at 120° C. for 1 hour. After cooling to 20° C., water and ethyl acetate were added and partitioned. The aqueous phase was extracted twice with ethyl acetate, dried with sodium sulfate, filtered, the organic phase was concentrated under reduced pressure and 2b was obtained by column chromatography (660 mg, yield 48.5%).

$^1$H NMR (CDCl$_3$, 400 MHz): δ 8.34 (d, J=8.0 Hz, 1H), 8.29 (s, 1H), 8.20 (d, J=4.0 Hz, 1H), 8.09 (d, J=4.0 Hz, 1H), 7.37 (d, J=8.0 Hz, 1H), 7.26-7.30 (m, 1H), 7.19 (s, 1H), 1.38 (s, 9H). LCMS m/z [M+H]$^+$: 294.1.

2b (0.44 g) was dissolved in concentrated hydrochloric acid (22 mL), reacted at 50° C. for 2 hours. After cooling to 20° C., the reaction was quenched by sodium bicarbonate to neutrality, the aqueous phase was extracted three times with ethyl acetate, dried with sodium sulfate, filtered the desiccant, concentrated under reduced pressure and separated by column chromatography to obtain 2c (193 mg, yield 54.2%).

LCMS m/z [M+H]+: 238.0, [M−H]−: 236.0.

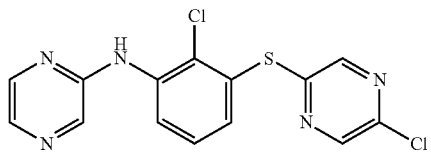

2c (160 mg, 0.675 mmol) was dissolved in acetonitrile (2 mL), then 2,5-dichloropyrazine (201 mg, 1.35 mmol) and potassium carbonate (279 mg, 2.025 mmol) were added, and increased the temperature to 80° C. and reacted for 2 hours. The reaction was cooled to 20° C. and filtered with suction, the filtrate was concentrated dry under reduced pressure, 2d was obtained by column chromatography (62 mg, yield 26.3%).

$^1$H NMR (DMSO, 400 MHz): δ 9.06 (s, 1H), 8.67 (d, J=4.0 Hz, 1H), 8.42 (d, J=4.0 Hz, 1H), 8.40 (d, J=4.0 Hz, 1H), 8.08-8.11 (m, 2H), 8.01 (d, J=4.0 Hz, 1H), 7.40-7.43 (m, 2H). LCMS m/z [M+H]+: 350.0, [M−H]−: 348.0.

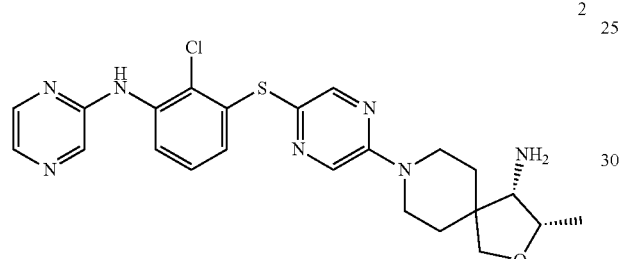

2d (462 mg, 1.83 mmol), 1j (622 mg, 3.66 mmol), N,N-diisopropylethylamine (944 mg, 7.32 mmol), and N-methylpyrrolidone (10 mL) were added to a reaction flask, reacted at 120° C. overnight. Concentrated with an oil pump, and the crude product was directly prepared, concentrated to obtain the target product 2 (150 mg, yield 23%).

$^1$H NMR (DMSO, 400 MHz): δ 8.97 (s, 1H), 8.43 (d, J=4.0 Hz, 1H), 8.39 (d, J=2.0 Hz, 1H), 8.26 (d, J=4.0 Hz, 1H), 8.09 (dd, J1=4.0 Hz, J2=2.0 Hz, 1H), 7.98 (d, J=2.0 Hz, 1H), 7.76 (dd, J1=4.0 Hz, J2=2.0 Hz, 1H), 7.19 (t, J=8.0 Hz, 1H), 6.59 (dd, J1=4.0 Hz, J2=2.0 Hz, 1H), 4.04-4.10 (m, 1H), 3.85-3.93 (m, 2H), 3.67 (d, J=8.0 Hz, 1H), 3.48 (d, J=8.0 Hz, 1H), 3.38-3.46 (m, 2H), 2.91 (d, J=2.0 Hz, 1H), 1.41-1.79 (m, 6H), 1.08 (d, J=2.0 Hz, 3H). MS m/z [M+H]+: 484.2.

Example 3

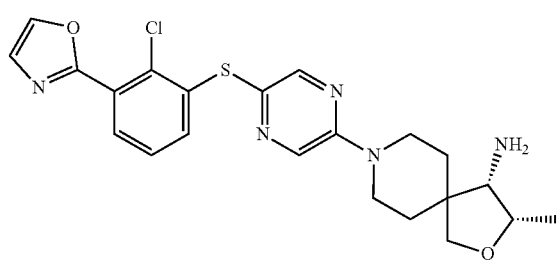

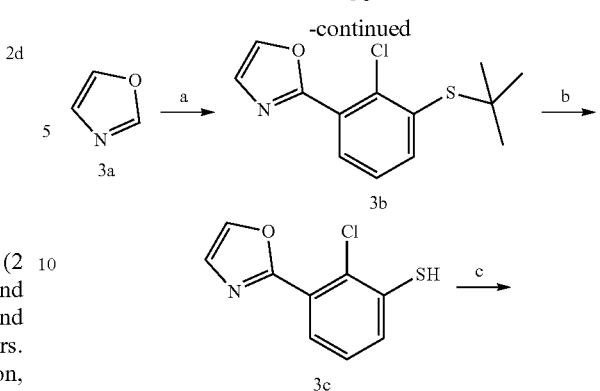

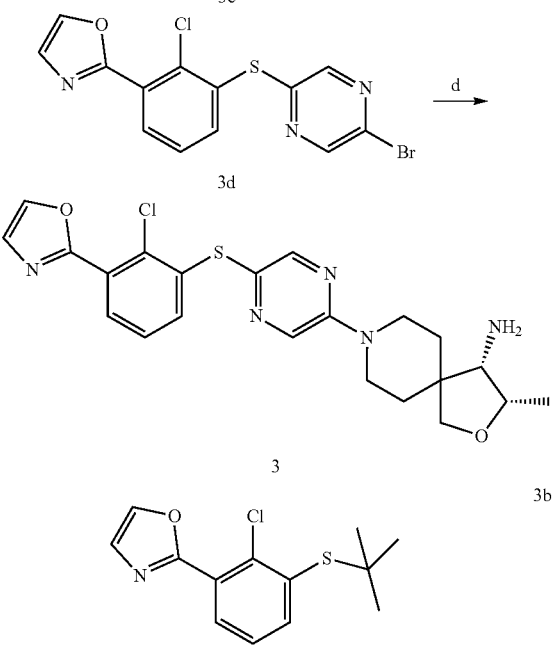

3a (530 mg, 7.68 mmol) was added to N, N-dimethylformamide (50 mL), followed by 1m (5 g, 15.36 mmol), lithium tert-butoxide (1.23 g, 15.36 mmol), and cuprous iodide (146 mg, 0.768 mmol) were added, placed into a preheated oil bath at 140° C., reacted for 20 minutes, cooled to room temperature, water was added, extracted with ethyl acetate, dried with sodium sulfate, filtered the desiccant, concentrated under reduced pressure, passed through a column to obtain 3b (980 mg, yield 49%).

$^1$H NMR (CDCl3, 400 MHz): δ 7.92 (dd, J=8.0 Hz, 1H), 7.81 (s, 1H), 7.78 (dd, J=8.0 Hz, 1H), 7.36-7.32 (m, 2H), 1.38 (s, 9H).

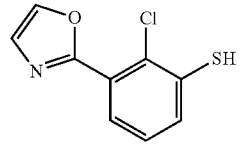

3b (1.6 g, 5.99 mmol) was dissolved in toluene (32 mL), anhydrous aluminum trichloride (3.2 g, 23.97 mmol) was added, and the reaction was stirred for 1 hour at room temperature under nitrogen protection. Quenched with ice water, extracted and partitioned with ethyl acetate, dried over sodium sulfate, the desiccant was filtered, concentrated dry under reduced pressure to obtain crude 3c (2.1 g, yield 100%), which was used directly in the next reaction step.

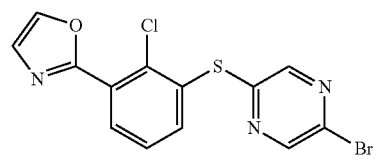

3d 2,5-dibromopyrazine (2.77 g, 11.94 mmol) was added to isopropanol (30 mL), protected with nitrogen, raised temperature to 88° C. and stirred, (3c/isopropanol/N, N-diisopropylethylamine) (1.26 g, 5.97 mmol/15 mL/1.5 g, 11.94 mmol) was slowly added dropwise, and continued for 1 hour. The temperature was reduced and the reaction was filtered, rinsed with ethyl acetate, washed with water, dried over sodium sulfate, the desiccant was filtered, and the filtrate was concentrated and dried under reduced pressure, and purified by column to obtain 3d (380 mg, yield 17.3%).

$^1$H NMR (CDCl3, 400 MHz): δ 8.45 (s, 1H), 8.14 (s, 1H), 8.07 (d, J=8.0 Hz, 1H), 7.81 (s, 1H), 7.76 (d, J=8.0 Hz, 1H), 7.43 (t, J=8.0 Hz, 1H), 7.34 (d, J=4.0 Hz, 1H).

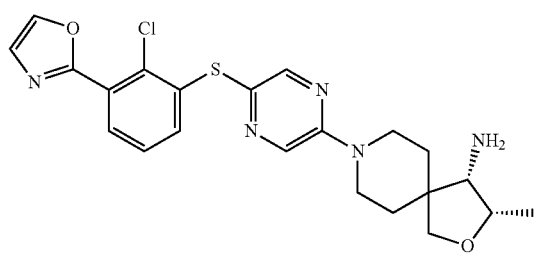

3

3d (727 mg, 1.9375 mmol), 1j (1.1 g, 3.947 mmol), and potassium phosphate (1.4 g, 6.6 mmol) were added to isopropanol (50 mL), displaced with nitrogen, and stirred for 16 hours at 95° C. Concentrated under reduced pressure, dichloromethane and water were added and partitioned, extracted twice with dichloromethane, dried over sodium sulfate, the desiccant was filtered, and the filtrate was concentrated dry under reduced pressure, and purified by column to obtain target product 3 (300 mg, yield 48%)

$^1$H NMR (DMSO, 400 MHz): δ 8.44 (s, 1H), 8.32 (s, 1H), 8.28 (s, 1H), 7.71 (d, J=8.0 Hz, 1H), 7.46 (s, 1H), 7.36 (t, J=8.0 Hz, 1H), 6.98 (d, J=8.0 Hz, 1H), 4.04 (m, 1H), 3.87 (m, 2H), 3.67 (d, J=8.0 Hz, 1H), 3.49-3.32 (m, 3H), 2.90 (d, J=8.0 Hz, 1H), 1.74-1.43 (m, 6H), 1.07 (d, J=8.0 Hz, 3H). LCMS m/z [M+H+]: 458.3.

Example 4

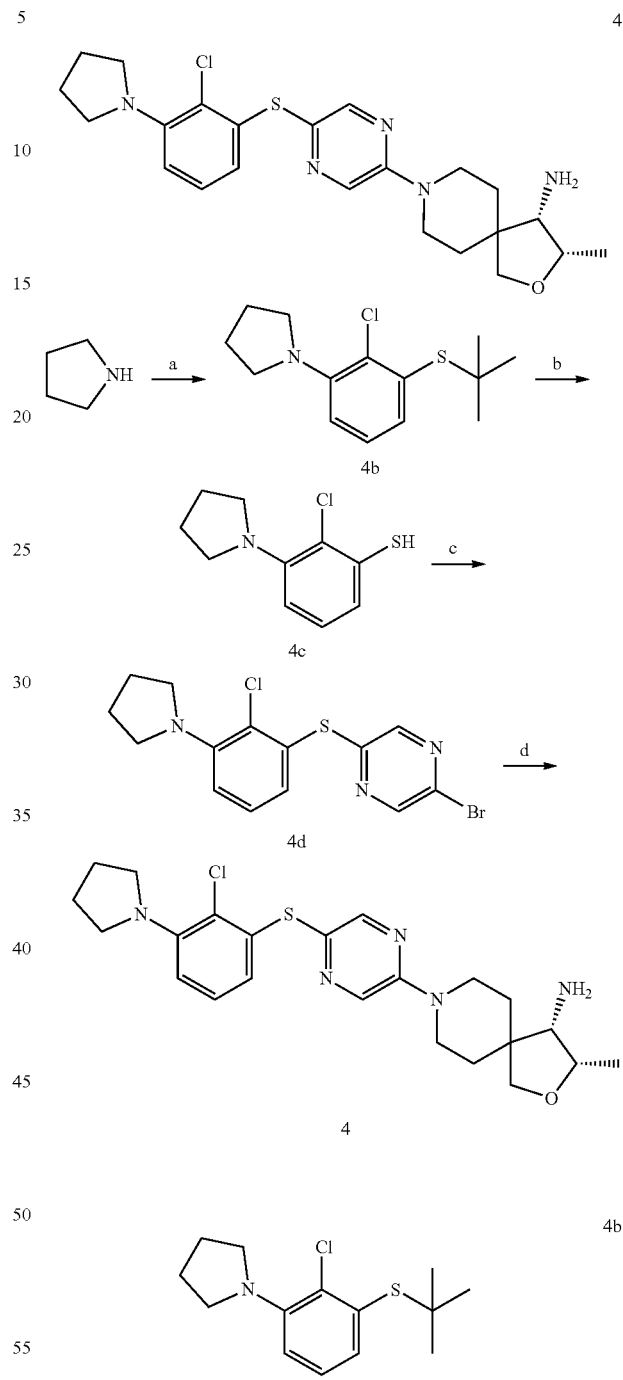

4a (22 mg, 0.31 mmol) was added to xylene (2 mL), followed by 1m (100 mg, 0.31 mmol), 2-dicyclohexylphosphino-2', 6'-diisopropoxy-1, 1'-biphenyl (10 mg, 0.031 mmol), potassium tert-butoxide (103 mg, 0.93 mmol), and chlorine (2-dicyclohexylphosphino-2', 6'-diI-propoxy-1, biphenyl) [2-(2-aminoethylphenyl)] palladium (II)-methyl tert-butyl ether (10 mg, 0.031 mmol), the temperature was raised to 120° C. and reacted for 18 hours, concentrated and passed through a column to obtain 4b (41 mg, 50% yield).

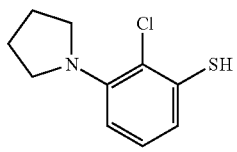

4c was obtained using the synthesis methods of 3c.

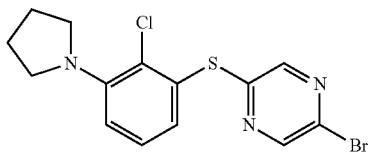

4d was obtained using the synthesis methods of 3d.
¹H NMR (CDCl3, 400 MHz): δ 8.45 (s, 1H), 7.95 (s, 1H), 7.18 (m, 2H), 7.01 (m, 1H), 3.39 (m, 4H), 1.96 (m, 4H).

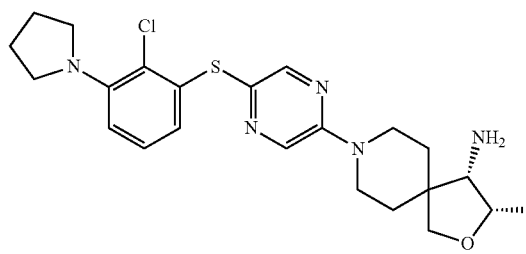

Target product 4 was obtained using the synthesis methods of 3.
¹H NMR (DMSO, 400 MHz): δ 8.40 (s, 1H), 8.19 (s, 1H), 7.02 (t, J=8.0 Hz, 1H), 6.78 (d, J=8.0 Hz, 1H), 6.26 (d, J=8.0 Hz, 1H), 4.09 (m, 1H), 3.88 (m, 2H), 3.68 (d, J=8.0 Hz, 1H), 3.49-3.26 (m, 7H), 2.92 (d, J=4.0 Hz, 1H), 2.10 (br s, 2H), 1.84 (m, 4H), 1.74-1.43 (m, 4H), 1.06 (d, J=8.0 Hz, 3H). LCMS m/z [M+H⁺]: 460.3.

Example 5

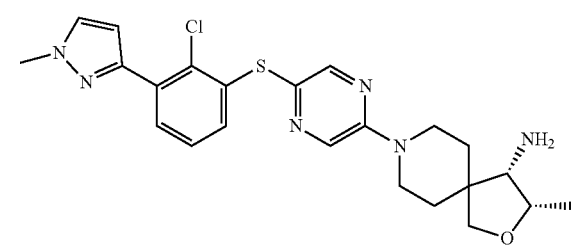

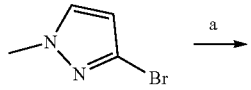

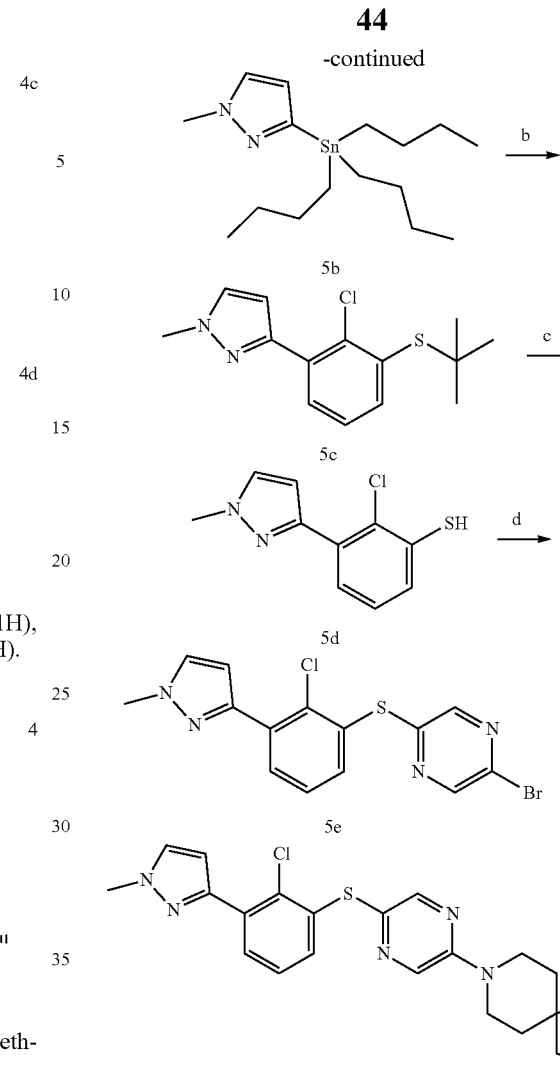

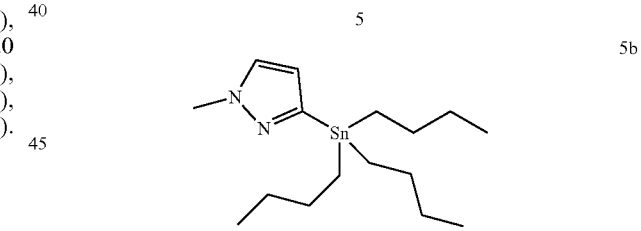

5a (1 g, 6.25 mmol) was added to toluene (16 mL), followed by hexa-n-butylditin (3.61 g, 6.25 mmol), tetrakis(triphenylphosphine) palladium (358 mg, 0.312 mmol), the temperature was raised to 115° C. and reacted for 4.5 hours, concentrated through a column to obtain 5b (489 mg, yield 21%).

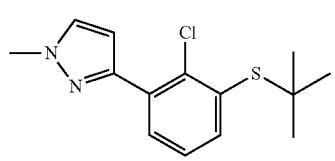

5b (389 mg, 1.046 mmol) was added to xylene (16 mL), followed by 1m (340 mg, 1.046 mmol) and tetrakis(triphenylphosphine) palladium (60 mg, 0.0522 mmol), and the temperature was raised to 155° C. and reacted for 2 hours, concentrated and passed through a column to obtain 5c (216 mg, yield 74%).

5d 5c (100 mg, 0.3571 mmol) was dissolved in toluene (3.4 mL), anhydrous aluminum trichloride (218 mg, 1.428 mmol) was added, stirred at room temperature for 1 hour under nitrogen protection, quenched with ice water, extracted with ethyl acetate and partitioned, washed with water, dried over sodium sulfate, the desiccant was filtered, and the filtrate was concentrated and dried under reduced pressure to obtain crude 5d.

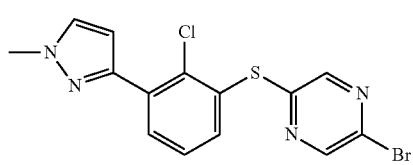
5e 2,5-dibromopyrazine (195 mg, 0.7142 mmol) was dissolved in isopropanol (3 mL), the temperature was raised to 88° C. under nitrogen protection, a mixture of 5d (0.3571 mmol)/isopropanol (1.6 mL)/N, N-diisopropylethylamine (106 mg, 0.7142 mmol) were added slowly dropwise in 0.5 hours, and stirred at 88° C. for 16 hours. Cooled down, extracted with ethyl acetate, dried over sodium sulfate, the desiccant was filtered, the filtrate was concentrated and dried under reduced pressure, and purified by column to obtain 5e (58 mg, yield 43%).

¹H NMR (CDCl3, 400 MHz): δ 8.45 (s, 1H), 8.03 (s, 1H), 7.90 (d, J=8.0 Hz, 1H), 7.66 (d, J=8.0 Hz, 1H), 7.42 (s, 1H), 7.36 (t, J=8.0 Hz, 1H), 6.74 (d, J=4.0 Hz, 1H), 3.98 (s, 3H).

5

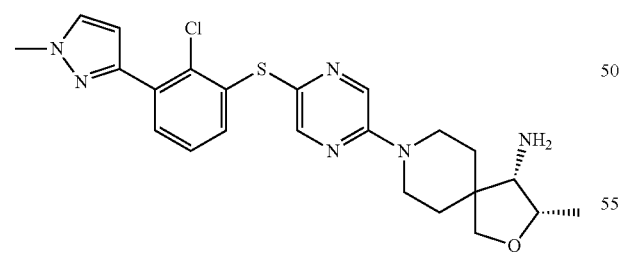

5e (500 mg, 1.316 mmol), 1j (1.1 g, 3.947 mmol), and potassium phosphate (1.4 g, 6.6 mmol) were added to isopropanol (50 mL), displaced with nitrogen, the temperature was raised to 95° C. and stirred for 16 hours. Concentrated, added water, extracted twice with dichloromethane, dried over sodium sulfate, the desiccant was filtered, the filtrate was concentrated and dried under reduced pressure, crystallized from ethyl acetate to obtain the target product 5 (300 mg, yield 48%).

¹H NMR (DMSO, 400 MHz): δ 8.45 (d, J=4.0 Hz, 1H), 8.27 (d, J=4.0 Hz, 1H), 7.79 (s, 1H), 7.50 (d, J=8.0 Hz, 1H), 7.23 (t, J=8.0 Hz 1H), 6.80 (d, J=8.0 Hz, 1H), 6.66 (d, J=4.0 Hz, 1H), 4.07 (m, 1H), 3.90 (m, 5H), 3.67 (d, J=8.0 Hz, 1H), 3.46 (d, J=8.0 Hz, 1H), 3.39 (m, 2H), 2.90 (d, J=4.0 Hz, 1H), 1.77-1.41 (m, 6H), 1.07 (d, J=8.0 Hz, 3H). LCMS m/z [M+H+]: 471.3.

Example 6

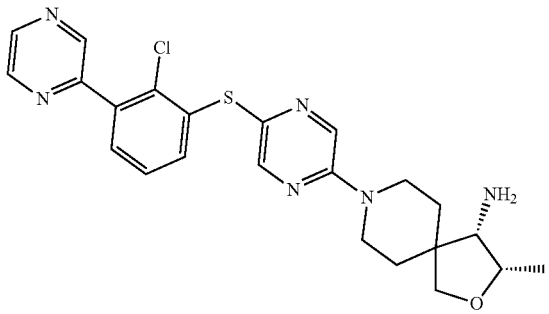
6

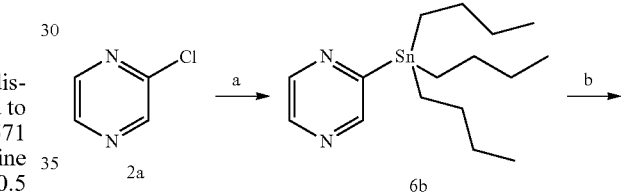

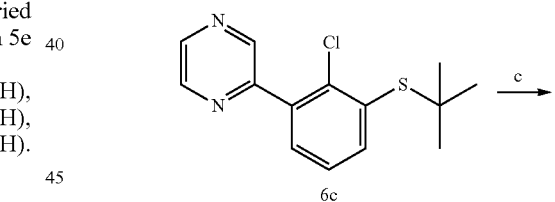

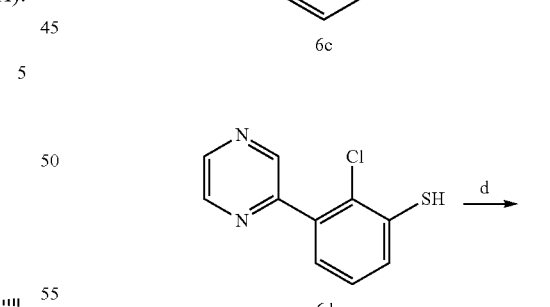

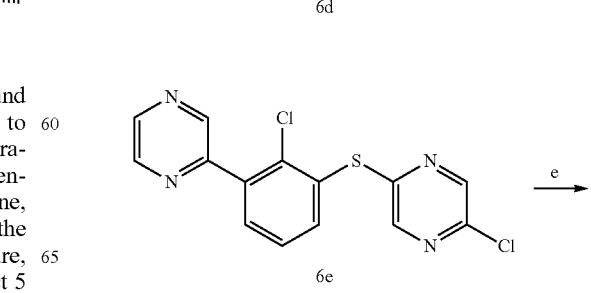

-continued

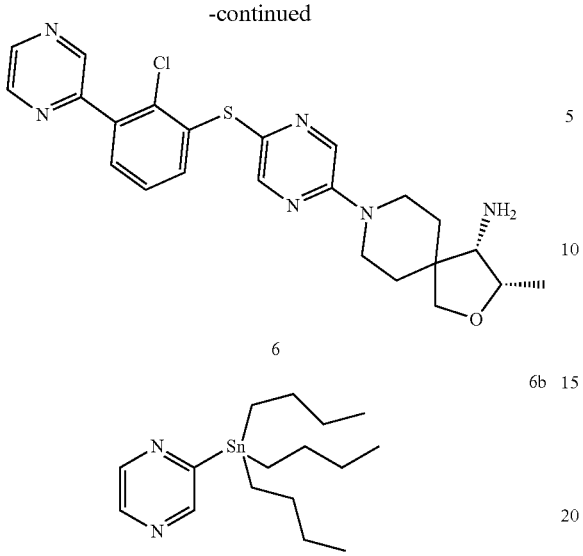

6

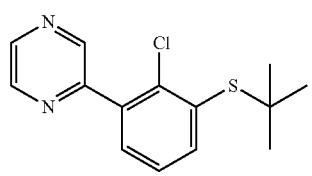

6b

Diisopropylamine (4.65 g, 46 mmol) was dissolved in tetrahydrofuran (50 mL), n-butyllithium (18.4 mL, 46 mmol) was added under an ice-water bath, reacted for 15 minutes in an ice-water bath, N-butyltin hydrogen (13.35 g, 46 mmol) was added dropwise, continued to react for 20 minutes, cooled to −78° C., 2a (5 g, 44 mmol, in 100 mL THF) was slowly added dropwise, reacted at −78° C. for 4 hours, the temperature was raised to −40° C., the reaction was quenched by adding dropwise aqueous solution of potassium fluoride, extracted with ethyl acetate, dried over sodium sulfate, the desiccant was filtered, and the filtrate was concentrated and dried under reduced pressure, and passed through a column to obtain 6b (7.4 g, yield 46%).

$^{1}$H NMR (CDCl3, 400 MHz): δ 8.71-8.73 (m, 1H), 8.57 (d, J=4.0 Hz 1H), 8.36-8.40 (m, 1H), 1.54-1.62 (m, 6H), 1.30-1.39 (m, 6H), 1.16-1.20 (m, 6H), 0.90 (t, J=8.0 Hz 9H).

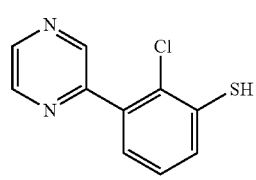

6c 6b (6.8 g, 18.4 mmol) and 1 m (5 g, 15.3 mmol) were dissolved in xylene (50 mL), tetrakis (triphenylphosphine) palladium (1.78 g, 1.3 mmol), displaced with nitrogen, and the temperature was raised to 150° C. and reacted for 6 hours, after cooling, the solvent was spin-dried and passed through a column to obtain 6c (4.2 g, yield 99%).

6d 6c (500 mg, 1.8 mmol) was dissolved in toluene (5 mL), and then aluminum trichloride (957 mg, 7.2 mmol) was added in batches in an ice-water bath, reacted at room temperature for 1 hour. The reaction was quenched with water, extracted with ethyl acetate, dried over sodium sulfate, the desiccant was filtered, and the filtrate was concentrated and dried under reduced pressure to obtain 6d, which was used directly in the next reaction step.

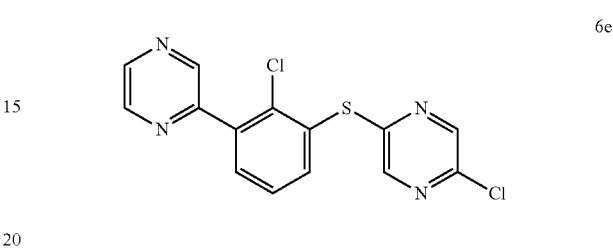

6e 6d (280 mg, 1.26 mmol), dichloropyrazine (376 mg, 2.5 mmol), and diisopropylamine (323 mg, 2.5 mmol) were added to isopropanol (5 mL), displaced with nitrogen 3 times, the temperature was raised to 80° C. and reacted for 16 hours. After cooling, the solvent was spin-dried, and passed through a column to obtain 6e (400 mg, yield 95%).

$^{1}$H NMR (CDCl3, 400 MHz): δ 8.95 (s, 1H), 8.71-8.72 (m, 1H), 8.61 (d, J=4.0 Hz 1H), 8.40 (s, 1H), 8.18 (s, 1H), 7.78-7.80 (m, 1H), 7.68-7.70 (m, 1H), 7.47-7.51 (m, 1H).

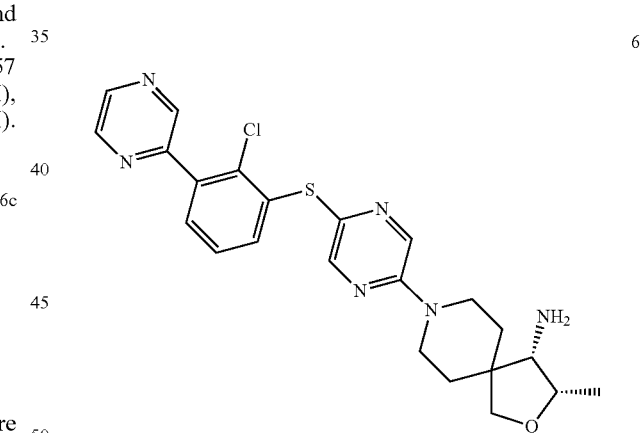

6

6e (410 mg, 1.22 mmol) was dissolved in N-methylpyrrolidone (10 mL), and then 1j (417 mg, 2.5 mmol) and diisopropylamine (317 mg, 2.5 mmol) were added. Displaced with nitrogen three times and the temperature was raised to 100° C. and reacted for 16 hours. The target product 6 was prepared directly by spin-drying the solvent and lyophilization (120 mg, yield 21%).

$^{1}$H NMR (DMSO, 400 MHz): δ 8.92 (s, 1H), 8.79-8.80 (m, 1H), 8.71-8.72 (d, J=4.0 Hz 1H), 8.46 (s, 1H), 8.30 (s, 1H), 7.36-7.43 (m, 2H), 7.00-7.02 (m, 1H), 4.06-4.09 (m, 1H), 3.89-3.91 (m, 2H), 3.69 (d, J=12.0 Hz 1H), 3.40-3.53 (m, 3H), 2.92 (d, J=4.0 Hz 1H), 1.75-1.80 (m, 1H), 1.63-1.69 (m, 1H), 1.48-1.57 (m, 2H), 1.41 (s, 2H), 1.09 (d, J=8.0 Hz 3H). MS m/z [M+H]+: 469.4.

Example 7

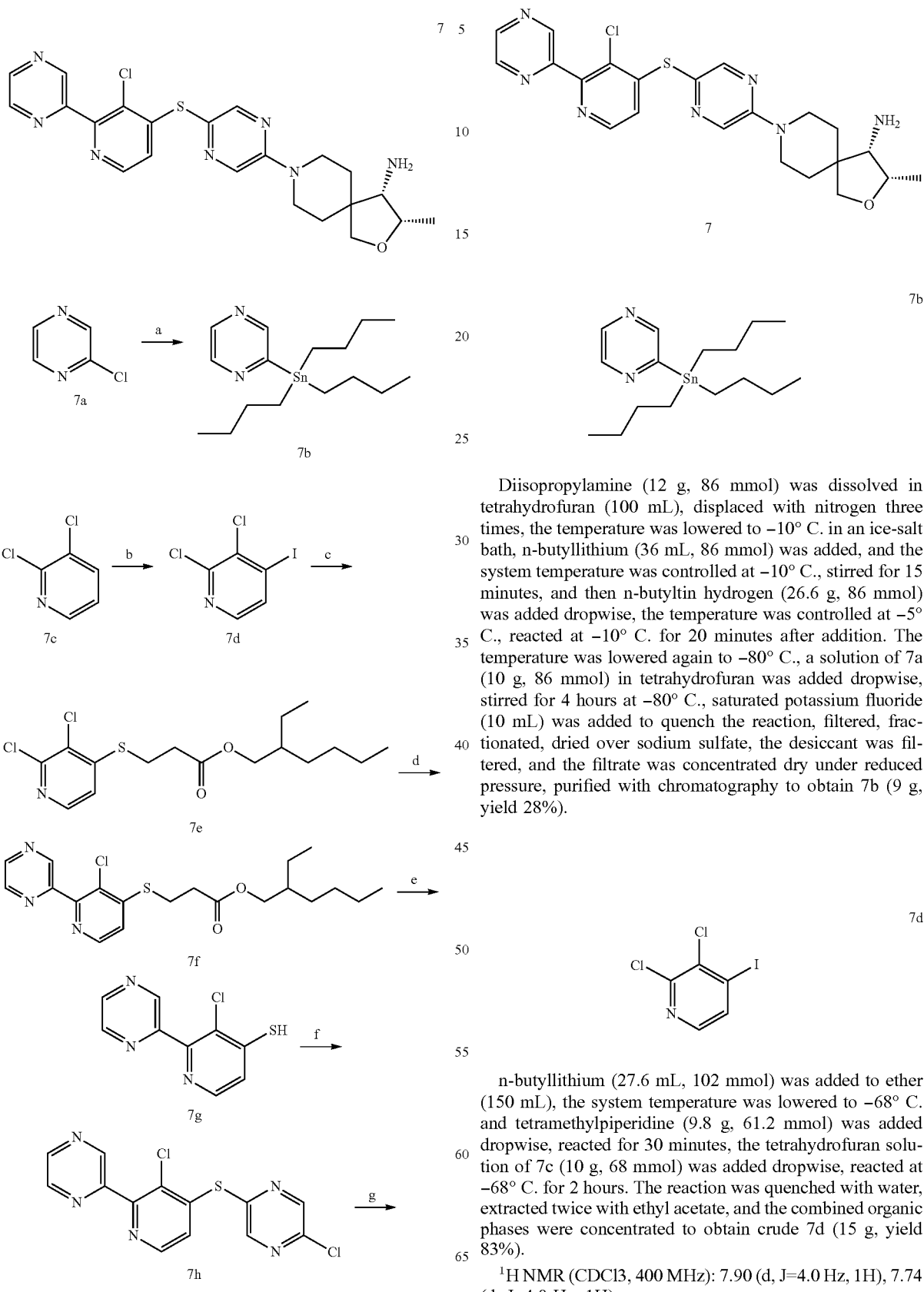

Diisopropylamine (12 g, 86 mmol) was dissolved in tetrahydrofuran (100 mL), displaced with nitrogen three times, the temperature was lowered to −10° C. in an ice-salt bath, n-butyllithium (36 mL, 86 mmol) was added, and the system temperature was controlled at −10° C., stirred for 15 minutes, and then n-butyltin hydrogen (26.6 g, 86 mmol) was added dropwise, the temperature was controlled at −5° C., reacted at −10° C. for 20 minutes after addition. The temperature was lowered again to −80° C., a solution of 7a (10 g, 86 mmol) in tetrahydrofuran was added dropwise, stirred for 4 hours at −80° C., saturated potassium fluoride (10 mL) was added to quench the reaction, filtered, fractionated, dried over sodium sulfate, the desiccant was filtered, and the filtrate was concentrated dry under reduced pressure, purified with chromatography to obtain 7b (9 g, yield 28%).

n-butyllithium (27.6 mL, 102 mmol) was added to ether (150 mL), the system temperature was lowered to −68° C. and tetramethylpiperidine (9.8 g, 61.2 mmol) was added dropwise, reacted for 30 minutes, the tetrahydrofuran solution of 7c (10 g, 68 mmol) was added dropwise, reacted at −68° C. for 2 hours. The reaction was quenched with water, extracted twice with ethyl acetate, and the combined organic phases were concentrated to obtain crude 7d (15 g, yield 83%).

$^1$H NMR (CDCl3, 400 MHz): 7.90 (d, J=4.0 Hz, 1H), 7.74 (d, J=4.0 Hz, 1H).

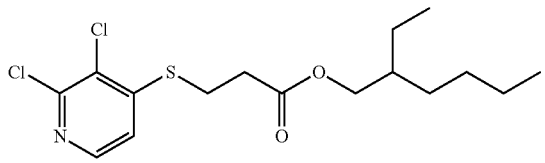

7d (10.08 g, 36.9 mmol) was dissolved in dioxane, and then 3-mercaptopropionic acid-2-ethylhexyl ester (10.46 g, 47.9 mmol) and 4,5-bisdiphenylphosphine-9,9-dimethyl-xanthene (0.533 g, 0.92 mmol), N, N-diisopropylethylamine (14.31 g, 110 mmol), tris (dibenzylideneacetone) dipalladium (0) (0.422 g, 0.46 mmol) were added, displaced with nitrogen three times, and the system temperature was raised to 108° C., reacted for 2 hours, concentrated under reduced pressure, and purified by column chromatography to obtain 7e (10 g, yield 74%).

$^1$H NMR (CDCl3, 400 MHz): δ 8.14 (s, J=8.0 Hz, 1H), 7.02 (d, J=4.0 Hz, 1H), 4.04-4.05 (m, 2H), 3.27 (t, J=8.0 Hz 2H), 2.74 (t, J=8.0 Hz 2H), 1.53-1.60 (m, 1H), 1.24-1.41 (m, 8H), 0.86-0.90 (m 6H).

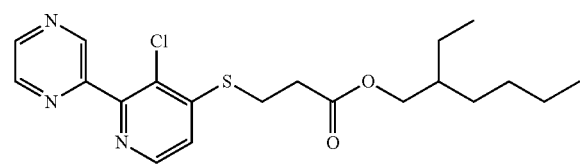

7b (6.50 g, 17.5 mmol) and 7e (5.30 g, 14.5 mmol) were dissolved in xylene, then cuprous iodide (0.21 g, 1.10 mmol) and tetrakis(triphenylphosphine) palladium (3.30 g, 1.09 mmol) were added, displaced with nitrogen three times, and the temperature was raised to 158° C., reacted for 8 hours. The temperature was lowered to 120° C., and the reaction was continued for 16 hours. The reaction was quenched with water, extracted 2 times with ethyl acetate, dried over sodium sulfate, concentrated under reduced pressure, and purified by column chromatography to obtain 7f (1.5 g, yield 25.4%).

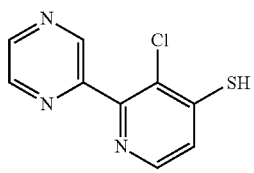

7f (1.54 g, 0.1 mmol) was dissolved in tetrahydrofuran, the system temperature was lowered to −68° C., a tetrahydrofuran solution of potassium tert-butoxide (1.27 g, 0.2 mmol) was added dropwise, and the temperature was brought to room temperature naturally overnight. A 5% potassium carbonate (20 mL) aqueous solution was added and extracted twice with ethyl acetate, a 5% potassium carbonate (20 mL) aqueous solution was added to the organic phase and stirred for 10 minutes. The liquid phases were separated, the aqueous phases were combined, adjusted the pH to 3 with 2N hydrochloric acid, and extracted twice with ethyl acetate. The organic phases were combined, washed once with saturated brine, dried over sodium sulfate, and concentrated under reduced pressure to obtain 7g (800 mg, yield 95%).

$^1$H NMR (CDCl3, 400 MHz): δ 9.11 (s, 1H), 8.74-8.75 (m, 1H), 8.68 (s, 1H), 7.71 (d, J=8.0 Hz, 1H), 7.05 (d, J=4.0 Hz, 1H).

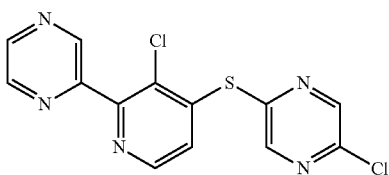

7g (800 mg, 3.6 mmol) was dissolved in acetonitrile (3 mL), then 2,5-dichloropyrazine (1.69 g, 7.2 mmol) and potassium carbonate (990 mg, 7.2 mmol) were added, displaced with nitrogen 3 times, and the system temperature was raised to 85° C., reacted for 16 hours. Dichloromethane was added to the reaction system, filtered and concentrated under reduced pressure to obtain 7h (630 mg, yield 46%).

$^1$H NMR (CDCl3, 400 MHz): δ 9.01 (d, J=1.6 Hz, 1H), 8.74-8.75 (m, 1H), 8.71 (d, J=1.6 Hz, 1H), 8.67 (d, J=2.4 Hz, 1H), 8.62 (d, J=1.6 Hz, 1H), 8.34 (d, J=4.8 Hz, 1H), 7.36 (d, J=1.6 Hz, 1H).

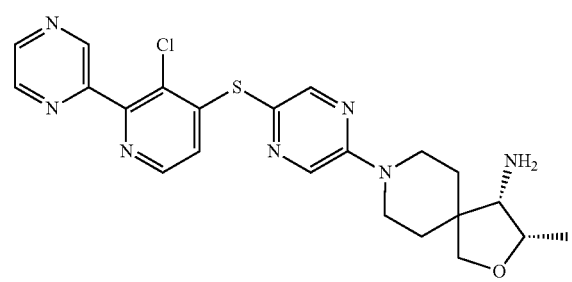

7h (400 mg, 1.05 mmol) and 1j (529 mg, 1.88 mmol) were dissolved in isopropanol (10 mL), then potassium phosphate (1.8 g, 8.49 mmol) was added, displaced with nitrogen 3 times, and the system temperature was raised to 88° C., reacted for 16 hours. Filtered and concentrated to obtain product 7 (81 mg, 16.3% yield).

$^1$H NMR ((CD3)2SO, 400 MHz): δ 9.01 (s, 1H), 8.83 (s, 1H), 8.77 (s, 1H), 8.39 (s, 1H), 8.36 (d, J=4.8 Hz, 1H), 8.25 (s, 1H), 7.40 (d, J=4.8 Hz, 1H), 4.04-4.07 (m, 1H), 3.89 (m, 2H), 3.67 (d, J=8.4 Hz, 1H), 3.47-3.49 (m, 3H), 2.91 (d, J=4.0 Hz, 1H), 1.50-1.78 (m, 6H), 1.06 (d, J=4.0 Hz, 3H). LCMS m/z [M+H+]: 470.3.

Example 8

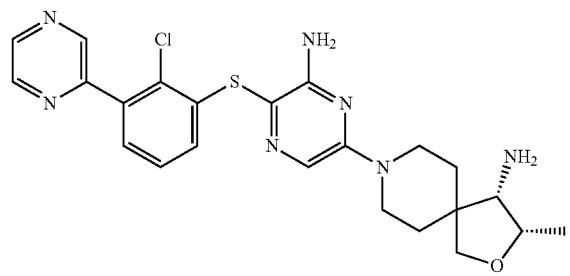

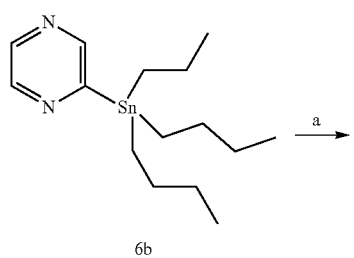

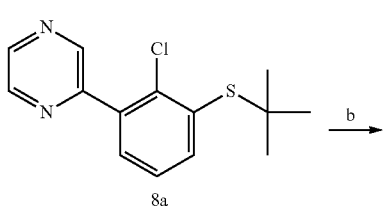

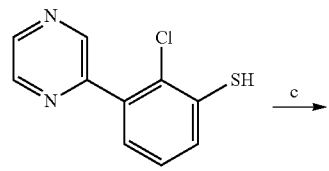

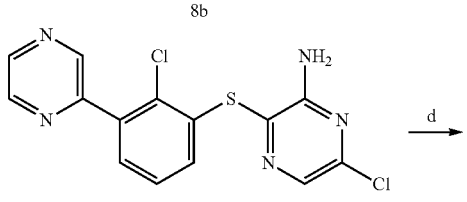

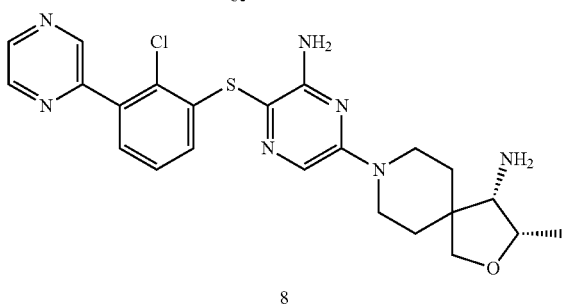

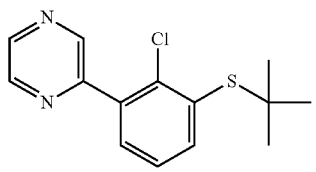

8a was synthesized according to the method of 6c synthesis.

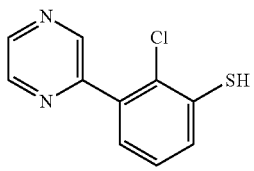

8b was synthesized according to the synthesis method of 6d.

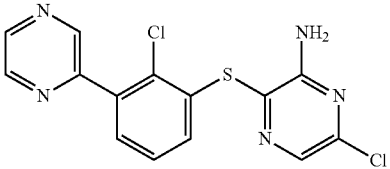

8b (1.6 g, 7.2 mmol) was dissolved in dioxane (60 mL), and then 2-amino-3-bromo-5-chloropyrazine (1.25 g, 7.2 mmol), potassium phosphate (1.9 g, 10.8 mmol), and 1,10-o-phenanthroline (216 mg, 1.44 mmol) were added, displaced with nitrogen 3 times, and finally cuprous iodide (228 mg, 1.44 mmol) was added, displaced with nitrogen 3 times. The temperature was raised to 100° C. and the reaction was refluxed overnight. After cooling to room temperature, it was directly concentrated through a column to obtain 8c (624 mg, yield 25%).

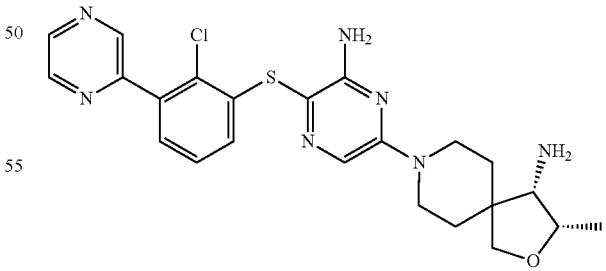

8 was synthesized according to the synthesis method of 7.
$^1$H NMR (DMSO, 400 MHz): δ 8.88 (s, 1H), 8.77 (s, 1H), 8.25 (s, 1H), 7.69 (s, 1H), 7.34 (m, 2H), 6.73 (m, 1H), 6.17 (br s, 2H), 4.04 (m, 1H), 3.83 (m, 2H), 3.67 (d, J=8.0 Hz, 1H), 3.49 (d, J=8.0 Hz, 1H), 3.34-3.27 (m, 2H), 2.90 (d, J=4.0 Hz, 1H), 1.74-1.43 (m, 6H), 1.06 (d, J=8.0 Hz, 3H). LCMS m/z [M+H$^+$]: 484.1.

Example 9

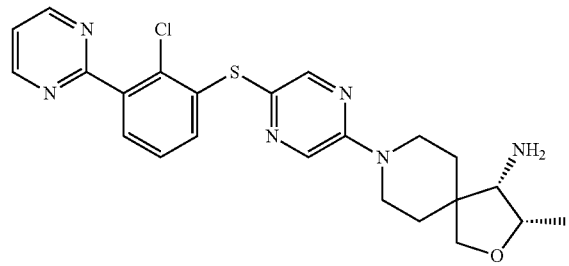

9

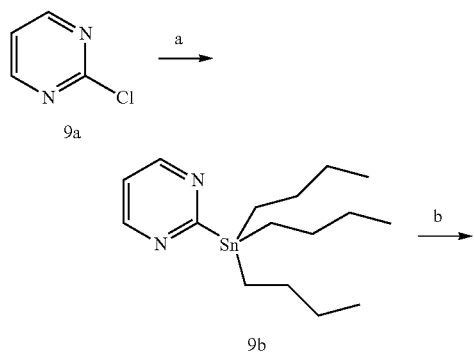

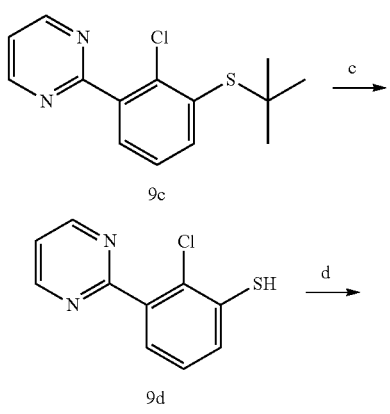

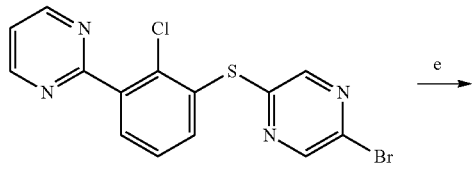

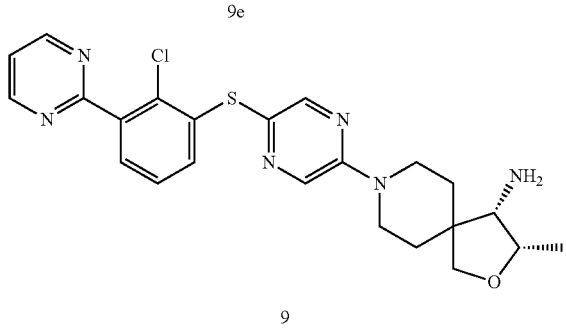

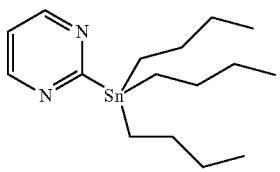

9b

The temperature was lowered to 0° C., and lithium diisopropylamide solution (64 mL, 0.064 mol, 1 mol/L) was added dropwise to tetrahydrofuran (100 mL). Tributyltin hydrogen (18.6 g, 0.064 mol) was added dropwise at a controlled temperature of −5° C. After addition, reacted for 20 minutes while maintaining temperature, the reaction was cooled to −78° C., 9a (7.0 g, 0.061 mol) was added in three batches, reacted for 2 hours while maintaining temperature, the temperature was raised to room temperature, ammonium chloride was added to quench the reaction, extracted with ethyl acetate, dried over sodium sulfate, and the desiccant was filtered, concentrated dry under reduced pressure, purified by chromatography to obtain 9b (0.486 g, yield 2.1%).

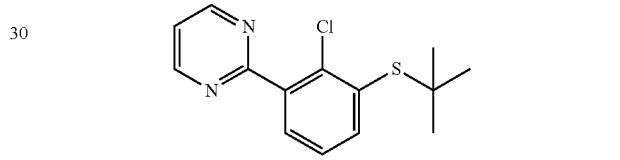

9c 9b (70 mg, 0.189 mmol) was dissolved in xylene (2 mL), then 1m (65 mg, 0.1986 mmol), tetrakis(triphenylphosphine) palladium (22 mg, 0.0189 mmol), and cuprous iodide (10 mg, 0.0189 mmol) were added, reacted at 125° C. for 2 hours, the temperature was lowered to room temperature, and concentrated through a column to obtain 9c (30 mg, yield 57%).

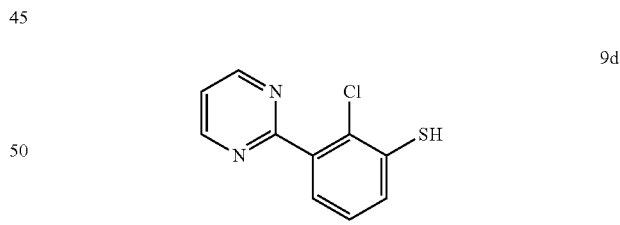

9d 9d was synthesized according to the synthesis method of 6d.

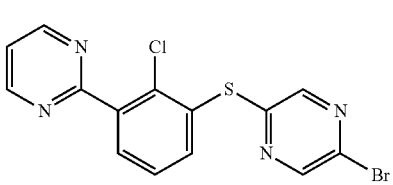

9e 9e was synthesized according to the synthesis method of 8c.

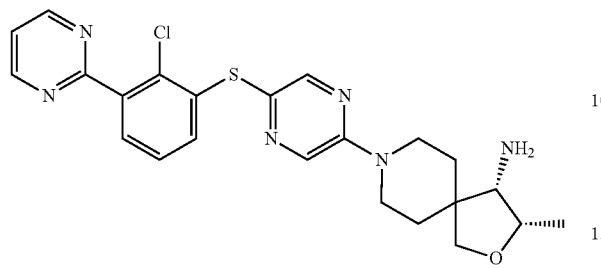

9 was synthesized according to the synthesis method of 8.

¹H NMR (DMSO, 400 MHz): δ 8.96 (d, J=4.0 Hz, 2H), 8.45 (s, 1H), 8.28 (s, 1H), 7.55 (m, 1H), 7.43 (d, J=4.0 Hz 1H), 7.33 (t, J=8.0 Hz, 1H), 6.95 (d, J=8.0 Hz, 1H), 4.05 (m, 1H), 3.88 (m, 2H), 3.65 (d, J=8.0 Hz, 1H), 3.48 (d, J=8.0 Hz, 1H), 3.34 (m, 2H), 2.87 (d, J=4.0 Hz, 1H), 1.77-1.41 (m, 6H), 1.07 (d, J=8.0 Hz, 3H). LCMS m/z [M+H⁺]: 469.2.

Example 10

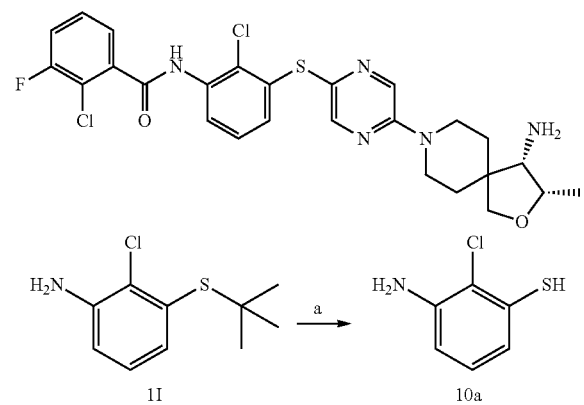

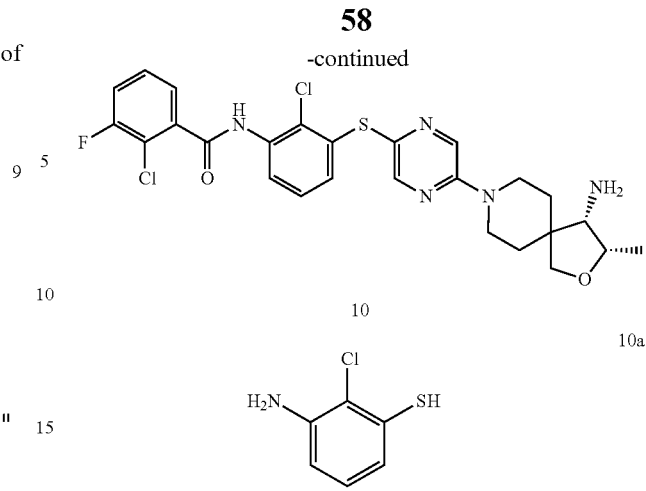

11 (20.0 g, 93 mmol) was dissolved in concentrated hydrochloric acid (750 mL), the temperature was raised to 55° C. and reacted for 24 hours. Concentrated under reduced pressure to 150 mL, cooled to room temperature, filtered, and dried to obtain 10a (10.0 g, yield 67%).

¹H NMR (DMSO, 400 MHz): δ 6.84 (t, J=8.0 Hz, 1H), 6.66 (dd, J1=8.0 Hz, J2=4.0 Hz, 1H), 6.53 (dd, J1=8.0 Hz, J2=4.0 Hz, 1H), 5.37 (br, 2H), 5.30 (br, 1H).

MS m/z [M−H]−: 157.9

10a (0.66 g, 3.4 mmol) was dissolved in dimethyl sulfoxide (10 mL), then 2,5-dichloropyrazine (0.5 g, 3.4 mmol) and cesium carbonate (2.2 g, 6.7 mmol) were added, the temperature was raised to 80° C. and reacted for 6 hours. Cooled down to room temperature, extracted with ethyl acetate, washed 3 times with water, dried with sodium sulfate, and the desiccant was filtered, concentrated dry under reduced pressure, and purified by column chromatography to obtain 10b (0.39 g, yield 42%).

MS m/z [M−H]−: 270.1

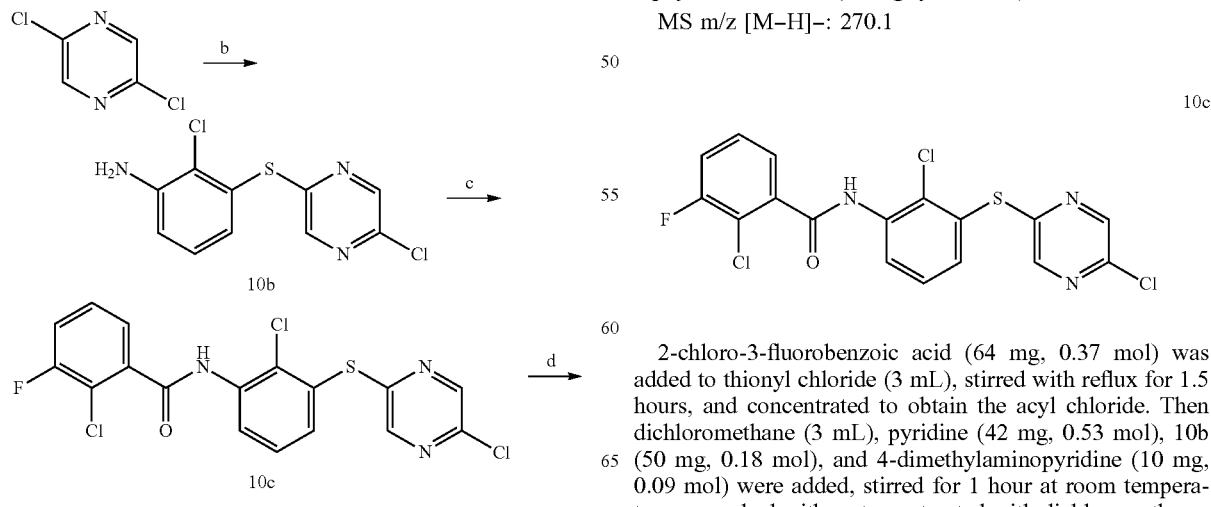

2-chloro-3-fluorobenzoic acid (64 mg, 0.37 mol) was added to thionyl chloride (3 mL), stirred with reflux for 1.5 hours, and concentrated to obtain the acyl chloride. Then dichloromethane (3 mL), pyridine (42 mg, 0.53 mol), 10b (50 mg, 0.18 mol), and 4-dimethylaminopyridine (10 mg, 0.09 mol) were added, stirred for 1 hour at room temperature, quenched with water, extracted with dichloromethane, dried and concentrated to obtain crude product 10c, which was directly used in the next step.

LCMS m/z [M+H]+: 429.0, [M−H]−: 427.0

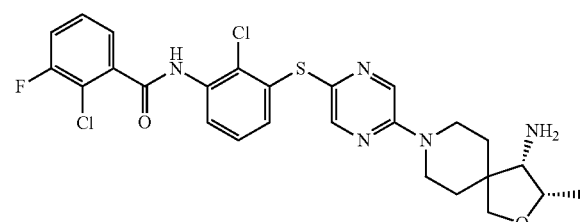

10c (430 mg, 1 mol) and 1j (187 mg, 1.2 mol) were dissolved in N-methylpyrrolidone (10 mL), and then N,N-diisopropylethylamine (645 mg, 5 mol) was added, the temperature was raised to 120° C. and stirred overnight, concentrated with an oil pump and the crude product was directly prepared. 10C was obtained (260 mg, yield 46%).

$^1$H NMR (DMSO, 400 MHz): δ 10.41 (s, 1H), 8.44 (s, 1H), 8.27 (s, 1H), 7.48-7.69 (m, 4H), 7.28 (t, J=8.0 Hz, 1H), 6.79 (d, J=8.0 Hz, 1H), 4.04-4.10 (m, 1H), 3.88-3.90 (m, 2H), 3.67 (d, J=8.0 Hz, 1H), 3.48 (d, J=8.0 Hz, 1H), 3.38-3.43 (m, 2H), 2.91 (d, J=4.0 Hz, 1H), 1.52-1.77 (m, 6H), 1.08 (d, J=4.0 Hz, 3H). MS m/z [M+H]+: 562.1.

Example 11

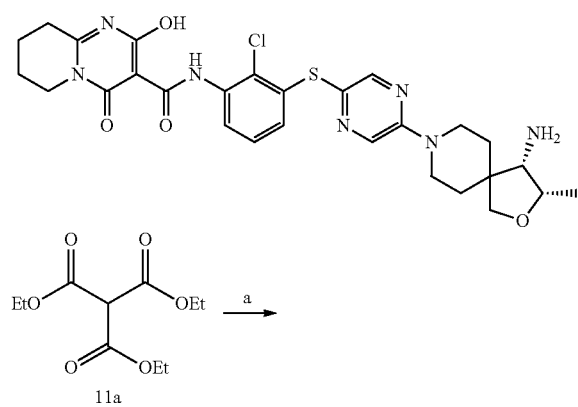

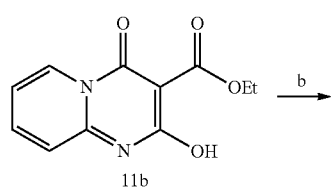

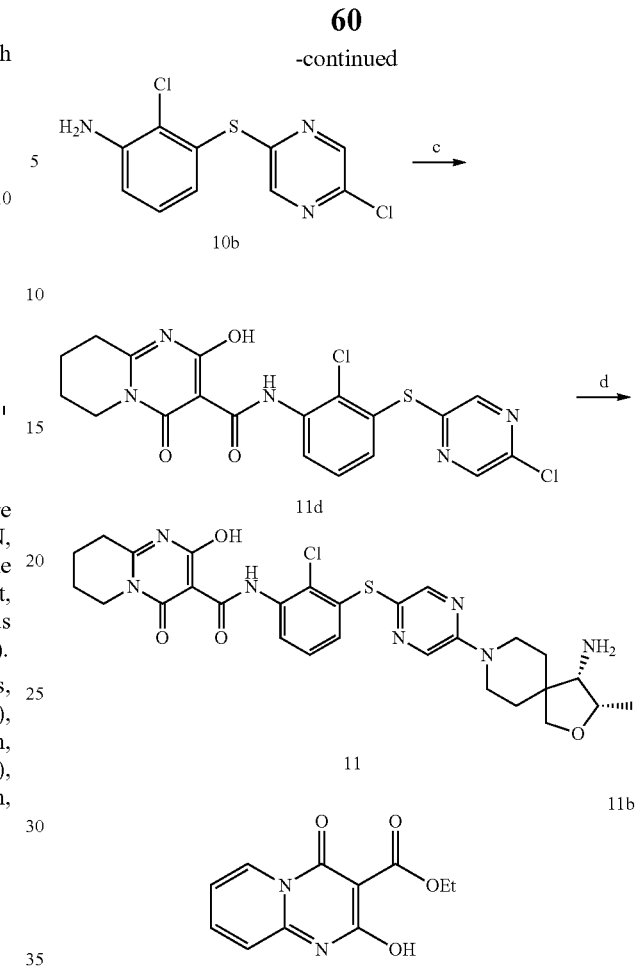

2-aminopyridine (10.0 g, 0.1 mol) and 11a (49.0 g, 0.2 mol) were dissolved in xylene (100 mL), heated to 130° C. and reacted for 16 hours, cooled to room temperature, filtered, and the filter cake was washed with methanol 3 times, dried to obtain 11b (3.80 g, yield 15%).

$^1$H NMR (DMSO, 400 MHz): δ 12.45 (br, 1H), 8.89 (d, J=8.0 Hz, 1H), 8.16 (t, J=8.0 Hz, 1H), 7.34-7.38 (m, 2H), 4.12 (q, J=8.0 Hz, 2H), 1.21 (t, J=8.0 Hz, 3H). MS m/z [M+H]+: 235.5, [M−H]−: 233.2

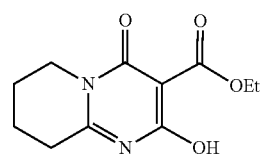

Under nitrogen protection, 11b (2.00 g, 8.5 mmol) and palladium on carbon (0.2 g) were dissolved with methanol (20 mL), displaced with hydrogen, and reacted at normal pressure and temperature for 3 hours, filtered and concentrated under reduced pressure to obtain 11c (1.77 g, yield 87%).

$^1$H NMR (DMSO, 400 MHz): δ 12.29 (br, 1H), 4.06 (q, J=8.0 Hz, 2H), 3.64 (t, J=8.0 Hz, 2H), 2.76 (t, J=8.0 Hz, 2H), 1.71-1.83 (m, 4H), 1.17 (t, J=8.0 Hz, 3H). MS m/z [M+H]+: 239.2, [M−H]−: 237.2.

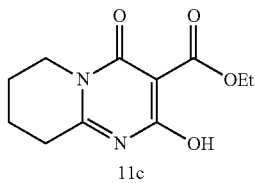

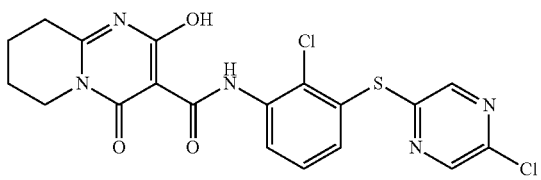

11c (275 mg, 1.1 mmol) and 10b (271 mg, 1.0 mmol) were dissolved in chlorobenzene (6 mL), heated to 130° C. and reacted for 5 hours, cooled to room temperature, filtered, and dried to obtain 11d (260 mg, yield 56%).

$^1$H NMR (DMSO, 400 MHz): δ 14.74 (s, 1H), 12.31 (s, 1H), 8.66 (d, J=4.0 Hz, 1H), 8.48 (br, 1H), 8.44 (s, 1H), 7.47-7.51 (m, 2H), 3.84 (br, 2H), 2.88 (t, J=8.0 Hz, 2H), 1.78-1.90 (m, 4H). MS m/z [M−H]−: 462.3.

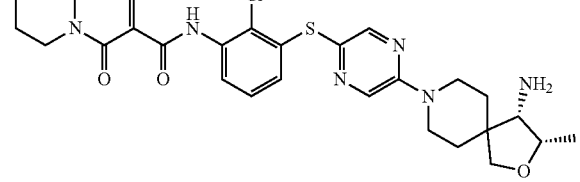

11d (200 mg, 0.43 mmol), 1j (190 mg, 0.79 mmol), and potassium phosphate (0.34 mg, 1.6 mol) were added to N-methylpyrrolidone (8 mL), the temperature was raised to 120° C. and stirred for 16 hours. The reaction solution was cooled to room temperature and purified by reverse-phase preparative column to obtain 11 (43 mg, yield 17%).

$^1$H NMR (DMSO, 400 MHz): δ 12.8 (br, 1H), 8.41 (s, 1H), 8.30 (br, 1H), 8.23 (s, 1H), 7.17 (s, 1H), 6.58 (d, J=8.0 Hz, 1H), 5.50 (br, 3H), 3.50-4.10 (m, 9H), 2.99 (d, J=4.0 Hz, 1H), 2.73 (s, 2H), 1.52-1.85 (m, 8H), 1.09 (d, J=8.0 Hz, 3H). MS m/z [M+H]+: 598.6.

Example 12

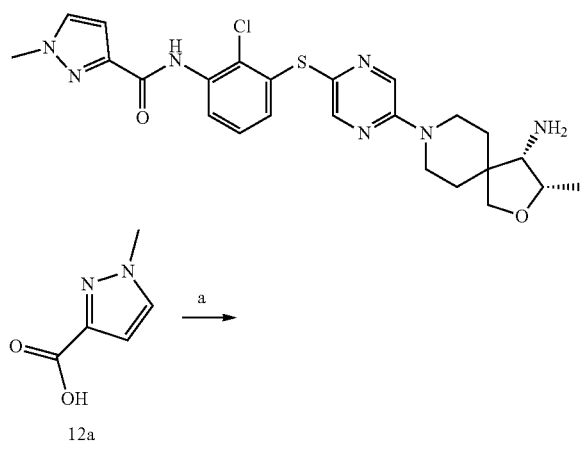

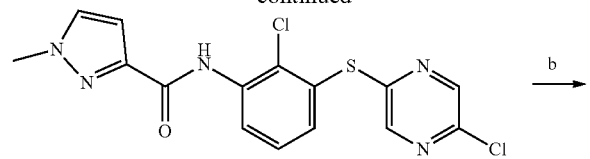

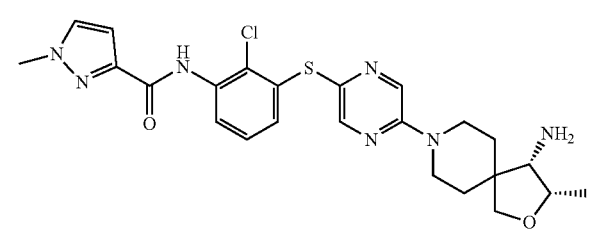

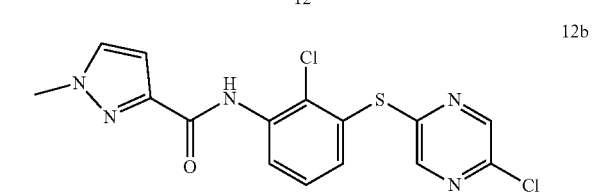

12a (279 mg, 2.2 mol) was added to thionyl chloride (5 mL), stirred at reflux for 1.5 hours, and concentrated to obtain acyl chloride. Dichloromethane (5 mL), pyridine (262 mg, 3.32 mol), 10b (300 mg, 1.1 mol), and 4-dimethylaminopyridine (68 mg, 0.55 mol) were added to the acyl chloride, stirred at room temperature for 1 hour. The reaction was quenched with water, extracted with dichloromethane, dried and concentrated, a white solid 12b (250 mg, yield 59%) was obtained by column chromatography.

LCMS m/z [M+H]+: 379.9

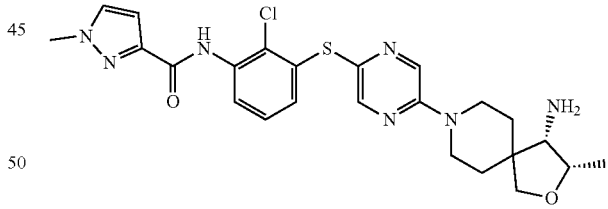

12b (250 mg, 0.66 mol) was dissolved in N-methylpyrrolidone (5 mL), then 1j (224 mg, 1.2 mol) and N, N-diisopropylethylamine (340 mg, 2.64 mol) were added, stirred overnight at 120° C., concentrated under reduced pressure, and the crude product was directly prepared to obtain off-white solid 12 (140 mg, yield 41%).

$^1$H NMR (DMSO, 400 MHz): δ 9.59 (s, 1H), 8.44 (s, 1H), 8.26 (s, 1H), 7.90-7.93 (m, 2H), 7.26 (t, J=8.0 Hz, 1H), 6.79 (d, J=4.0 Hz, 1H), 6.69 (d, J=8.0 Hz, 1H), 4.06-4.08 (m, 1H), 3.98 (s, 3H), 3.85-3.93 (m, 2H), 3.67 (d, J=8.0 Hz, 1H), 3.48 (d, J=8.0 Hz, 1H), 3.38-3.46 (m, 2H), 2.91 (d, J=4.0 Hz, 1H), 1.24-1.76 (m, 6H), 1.08 (d, J=4.0 Hz, 3H). MS m/z [M+H]+: 514.2.

Example 13

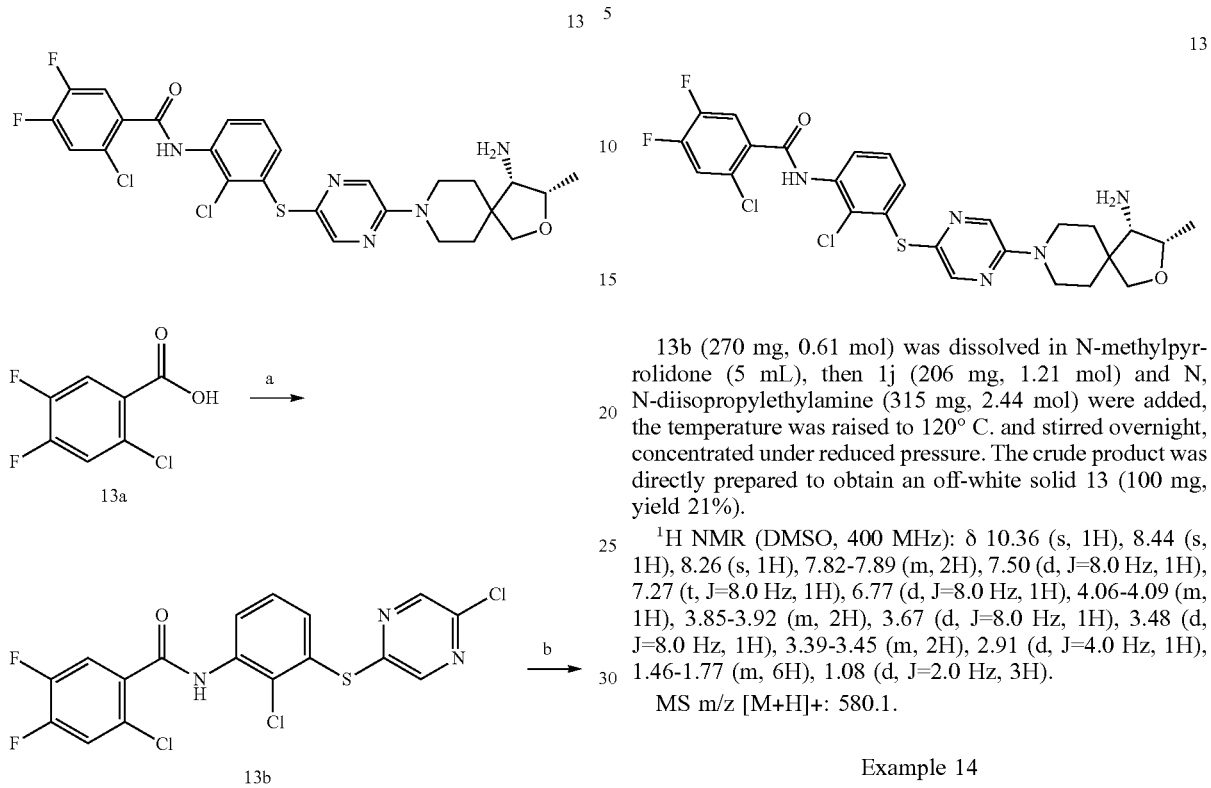

2-chloro-4,5-difluorobenzoic acid (425 mg, 2.2 mol) was added to thionyl chloride (5 mL), stirred at reflux for 1.5 hours, and concentrated under reduced pressure to obtain the acyl chloride. Dichloromethane (5 mL), pyridine (262 mg, 3.32 mol), 4-dimethylaminopyridine (68 mg, 0.55 mol), and 10b (300 mg, 1.1 mol) were added to the acyl chloride, stirred for 1 hour at room temperature, quenched with water, extracted with dichloromethane, dried over sodium sulfate, the desiccant was filtered, concentrated dry under reduced pressure, and a white solid 13b (270 mg, yield 54.9%) was obtained by column chromatography.

LCMS m/z [M+H]+: 446.0, [M−H]−: 444.0

13b (270 mg, 0.61 mol) was dissolved in N-methylpyrrolidone (5 mL), then 1j (206 mg, 1.21 mol) and N,N-diisopropylethylamine (315 mg, 2.44 mol) were added, the temperature was raised to 120° C. and stirred overnight, concentrated under reduced pressure. The crude product was directly prepared to obtain an off-white solid 13 (100 mg, yield 21%).

$^1$H NMR (DMSO, 400 MHz): δ 10.36 (s, 1H), 8.44 (s, 1H), 8.26 (s, 1H), 7.82-7.89 (m, 2H), 7.50 (d, J=8.0 Hz, 1H), 7.27 (t, J=8.0 Hz, 1H), 6.77 (d, J=8.0 Hz, 1H), 4.06-4.09 (m, 1H), 3.85-3.92 (m, 2H), 3.67 (d, J=8.0 Hz, 1H), 3.48 (d, J=8.0 Hz, 1H), 3.39-3.45 (m, 2H), 2.91 (d, J=4.0 Hz, 1H), 1.46-1.77 (m, 6H), 1.08 (d, J=2.0 Hz, 3H).

MS m/z [M+H]+: 580.1.

Example 14

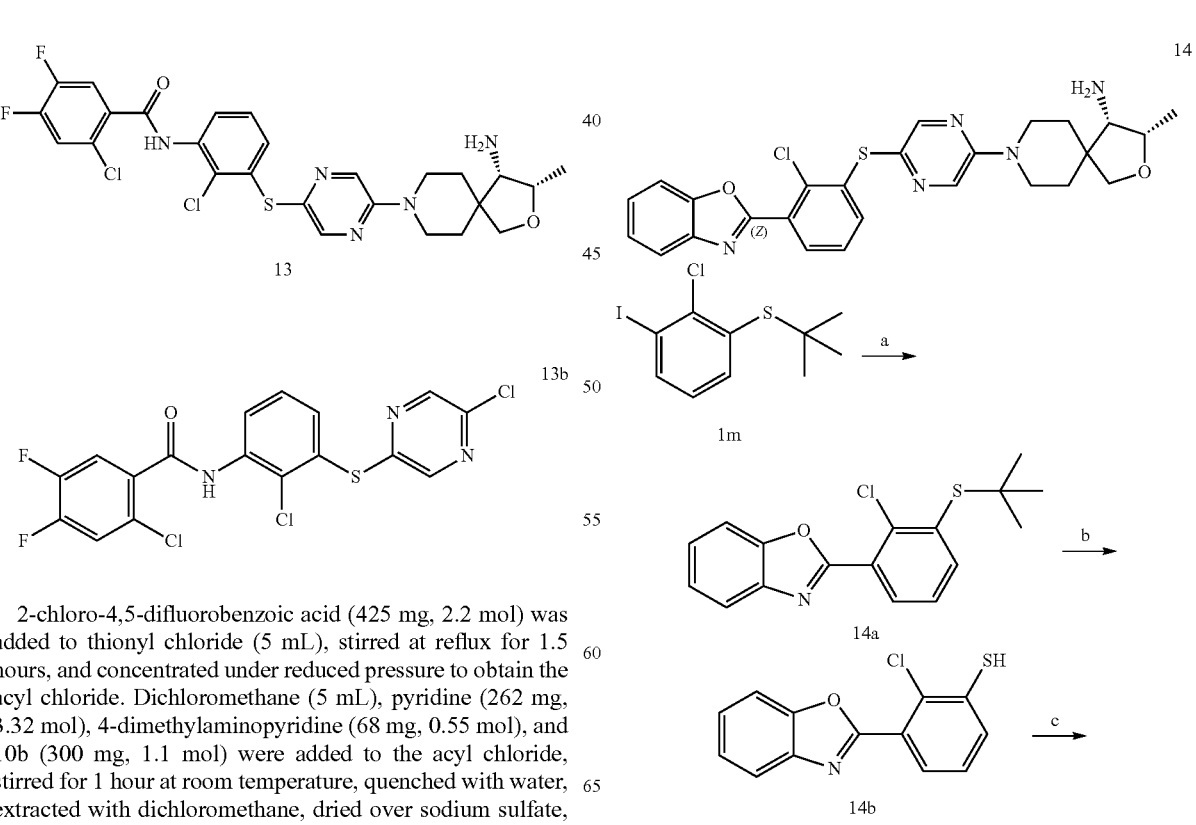

-continued

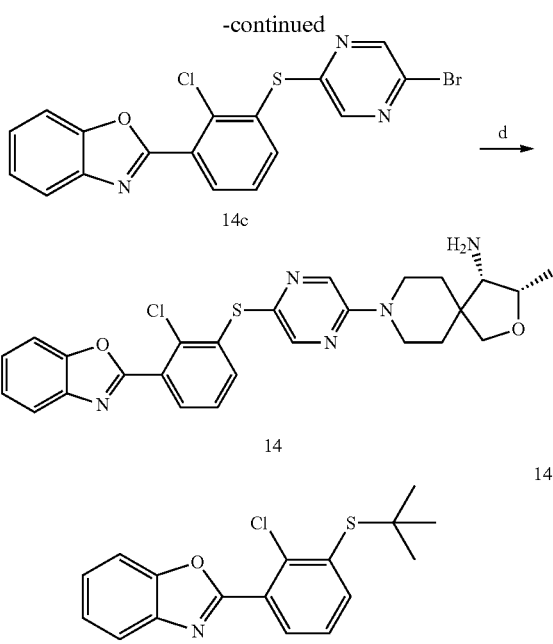

14c

14

14a

The compound benzoxazole (575 mg, 4.82 mmol), lithium tert-butoxide (772 mg, 9.64 mmol), and cuprous iodide (91.8 mg, 0.482 mmol) were added to a 100 mL three-necked flask, 1m (2 g, 7.225 mmol) was added, dissolved in N,N-dimethylformamide (15 mL), heated to 150° C. under nitrogen protection, and stirred for 1.5 h. The reaction solution was cooled to room temperature, 50 mL of water was added, extracted with ethyl acetate, washed the organic phase 3 times with water and then dried, concentrated, and passed through a column to obtain 14a (300 mg, yield: 20%).

$^1$H NMR (CDCl$_3$, 400 MHz): δ 8.03-8.05 (d, J=8.0 Hz 1H), 7.83-7.86 (m, 2H), 7.61-7.64 (m, 1H), 7.37-7.41 (m, 3H), 1.39 (s, 9H).

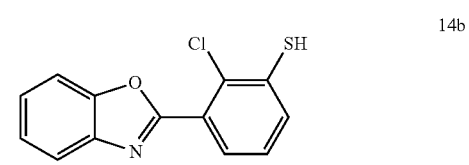 [SMILES: Sc1cccc(-c2nc3ccccc3o2)c1Cl]

14b 14a (100 mg, 0.315 mmol) and anhydrous aluminum trichloride (167.8 mg, 1.26 mmol) were added to a 50 mL three-necked flask, toluene (3 mL) was added, and stirred at room temperature for 15 h. After adding 20 mL of water, extracted with ethyl acetate, the organic phase was dried and spin-dried to obtain 14b. It was used directly in the next step.

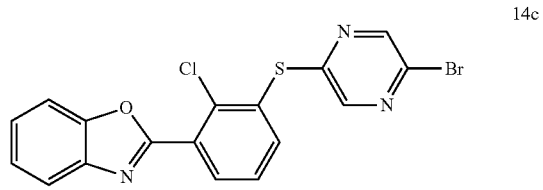 [SMILES: Clc1c(Sc2cnc(Br)cn2)cccc1-c1nc2ccccc2o1]

14c 2,5-dibromopyrazine (3 g, 13.2 mmol) was added to a 50 mL three-necked flask, isopropanol (15 mL) was added, the temperature was raised and stirred to 60° C., 14b (580 mg, 2.20 mmol) and N, N-diisopropylethylamine (568.6 mg, 4.40 mmol) were added dropwise and the reaction was stirred overnight. After extraction with water and ethyl acetate, the organic phase was dried, concentrated, and passed through a column to obtain 14c (230 mg, yield: 25%).

$^1$H NMR (CDCl$_3$, 400 MHz): δ 8.46 (s, 1H), 8.18-8.22 (m, 2H), δ 7.82-7.86 (m, 2H), δ 7.61-7.63 (m, 1H), δ 7.46-7.50 (t, 1H), δ 7.39-7.42 (m, 2H).

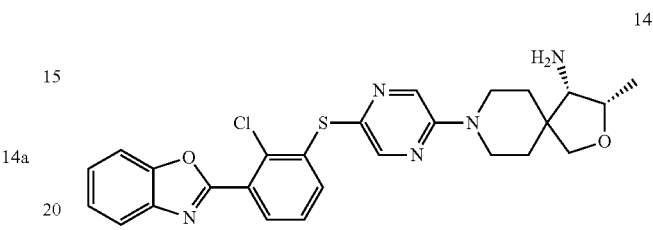

14

14d (230 mg, 0.55 mmol), isopropanol (10 mL), 1j (173 mg, 0.71 mmol), and potassium phosphate (700 mg, 3.3 mmol) were added to a 50 mL three-necked flask and the reaction was heated to 95° C., stirred for 18 hours. The reaction solution was cooled to room temperature, 30 mL of water was added, extracted with dichloromethane, and the organic phase was concentrated. The crude product was passed through a column to obtain 14 (30 mg, yield 11%).

$^1$H NMR (CDCl$_3$, 400 MHz): δ 8.29-8.31 (d, J=8.0 Hz 2H), 7.87-7.88 (d, J=4.0 Hz 1H), 7.80-7.82 (d, J=8.0 Hz 1H), 7.70-7.72 (d, J=8.0 Hz 1H), 7.43-7.50 (m, 2H), δ 7.35-7.38 (t, 1H), 7.10-7.12 (d, J=8.0 Hz 1H), 4.22-4.25 (m, 1H), 4.22-4.25 (m, 1H), 4.05-4.13 (m, 2H), 3.87-3.89 (d, J=8.0 Hz 1H), 3.71-3.73 (d, J=8.0 Hz 1H), 3.36-3.44 (m, 2H), 3.01-3.03 (d, J=8.0 Hz 1H), 1.69-1.85 (m, 5H), 1.21-1.23 (d, J=8.0 Hz 3H). MS m/z [M−H$^+$]: 508.04.

Example 15

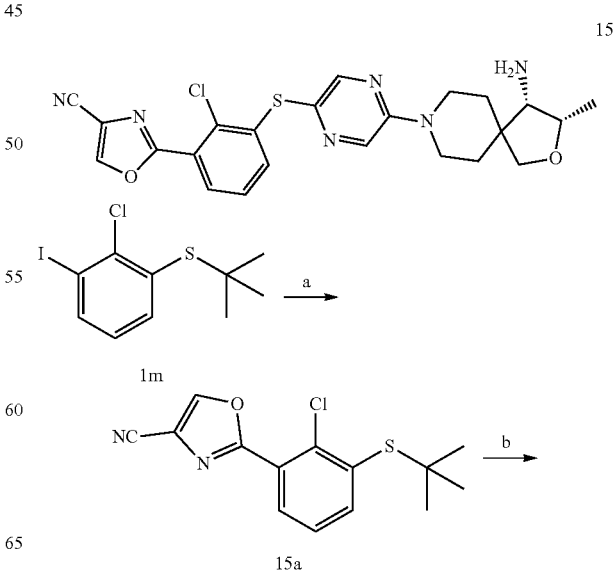

15

1m

15a

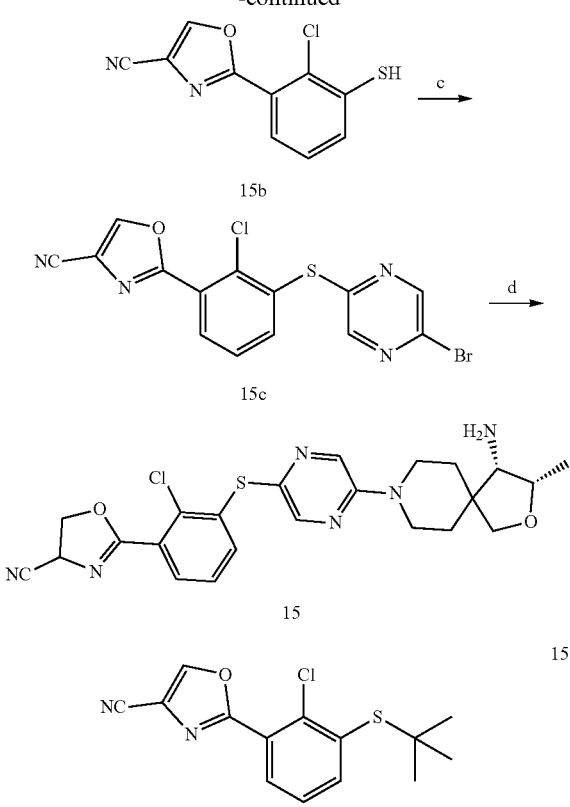

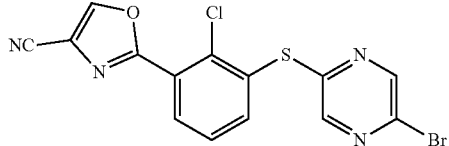

2,5-dibromopyrazine (3.0 g, 12.9 mmol) was added to a 50 mL three-necked flask, isopropanol (15 mL) was added, temperature was raised and stirred to 60° C., 15b (509 mg, 2.15 mmol) and N, N-diisopropylethylamine (556 mg, 4.3 mmol) were added dropwise, stirred and reacted overnight, after adding 30 mL of water, it was extracted with ethyl acetate, the organic phase was dried, concentrated, and passed through a column to obtain 15c (220 mg, yield: 25%).

$^1$H NMR (CDCl$_3$, 400 MHz): δ 8.49 (s, 1H), δ 8.36 (s, 1H), 8.24 (s, 1H), 8.09-8.11 (d, J=8.0 Hz 1H), 7.87-7.89 (d, J=8.0 Hz 1H), 7.49-7.53 (t, 1H).

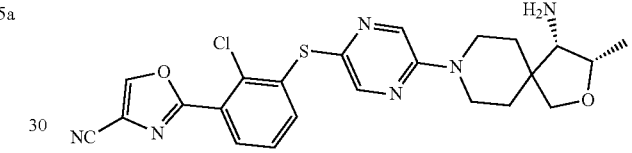

The compound 4-oxazolecarbonitrile (1.0 g, 10.63 mmol), palladium acetate (2.86 g, 12.8 mmol), 2-dicyclohexylphosphino-2',6'-dimethoxy-biphenyl (218 mg, 0.53 mmol), 1,8-diazabicycloundec-7-ene (3.24 g, 21.26 mmol) were added to a 100 mL three-necked flask, 1m (3.50 g, 12.8 mmol) was added, dissolved in N,N-dimethylformamide, heated to 130° C. under nitrogen protection and stirred for 48 h. The reaction solution was cooled to room temperature, 50 mL of water was added, extracted with dichloromethane, the organic phase was washed three times with water, concentrated and passed through a column to obtain 15a (630 mg, yield 20%).

$^1$H NMR (CDCl$_3$, 400 MHz): δ 8.31 (s, 1H), 7.88-7.90 (d, J=8.0 Hz 1H), 7.83-7.85 (d, J=8.0 Hz 1H), 7.35-7.39 (t, 1H), 1.36 (s, 9H).

15a (630 mg, 2.15 mmol) and anhydrous aluminum trichloride (1.20 g, 8.61 mmol) were added to a 50 mL three-necked flask, toluene (8 mL) was added, stirred at room temperature for 5 h. After adding 20 mL of water, it was extracted with ethyl acetate, and the organic phase was dried and spin-dried to obtain 15b. It was used directly in the next step.

15c (220 mg, 0.56 mmol), isopropanol (10 mL), 1j (176 mg, 0.71 mmol), and potassium phosphate (700 mg, 3.3 mmol) were added to a 50 mL three-necked flask and heated to 95° C., stirred and reacted for 18 hours, the reaction solution was cooled to room temperature, 30 mL of water was added, extracted with dichloromethane, concentrated and passed through a column to obtain 15 (16 mg, yield 6%).

$^1$H NMR (CDCl$_3$, 400 MHz): δ 8.34 (s, 1H), δ 8.30 (s, 1H), 8.24 (s, 1H), 7.77-7.79 (d, J=8.0 Hz 1H), 7.25-7.29 (t, 1H), 7.15-7.17 (d, J=8.0 Hz 1H), 4.20-4.26 (m, 1H), 3.93-4.03 (m, 2H), 3.85-3.87 (d, J=8.0 Hz 1H), 3.72-3.75 (d, J=12.0 Hz 1H), 3.50-3.57 (m, 1H), 3.40-3.46 (m, 1H), 3.04-3.05 (d, J=4.0 Hz 1H), 1.90-1.94 (m, 1H), 1.71-1.82 (m, 3H), 1.52 (s, 2H), 1.27-1.29 (d, J=8.0 Hz 3H). MS m/z [M−H$^+$]: 483.4.

Example 16

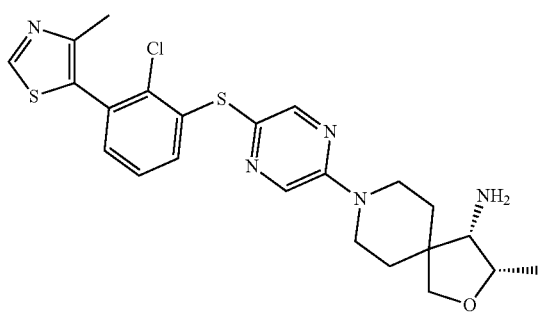

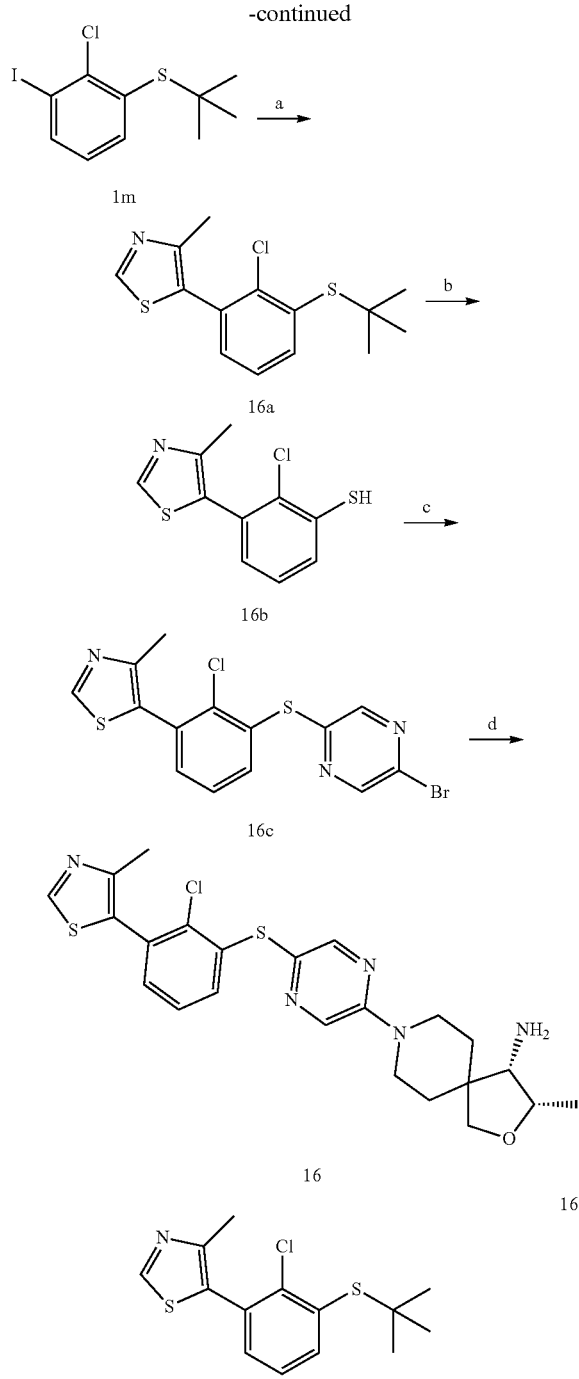

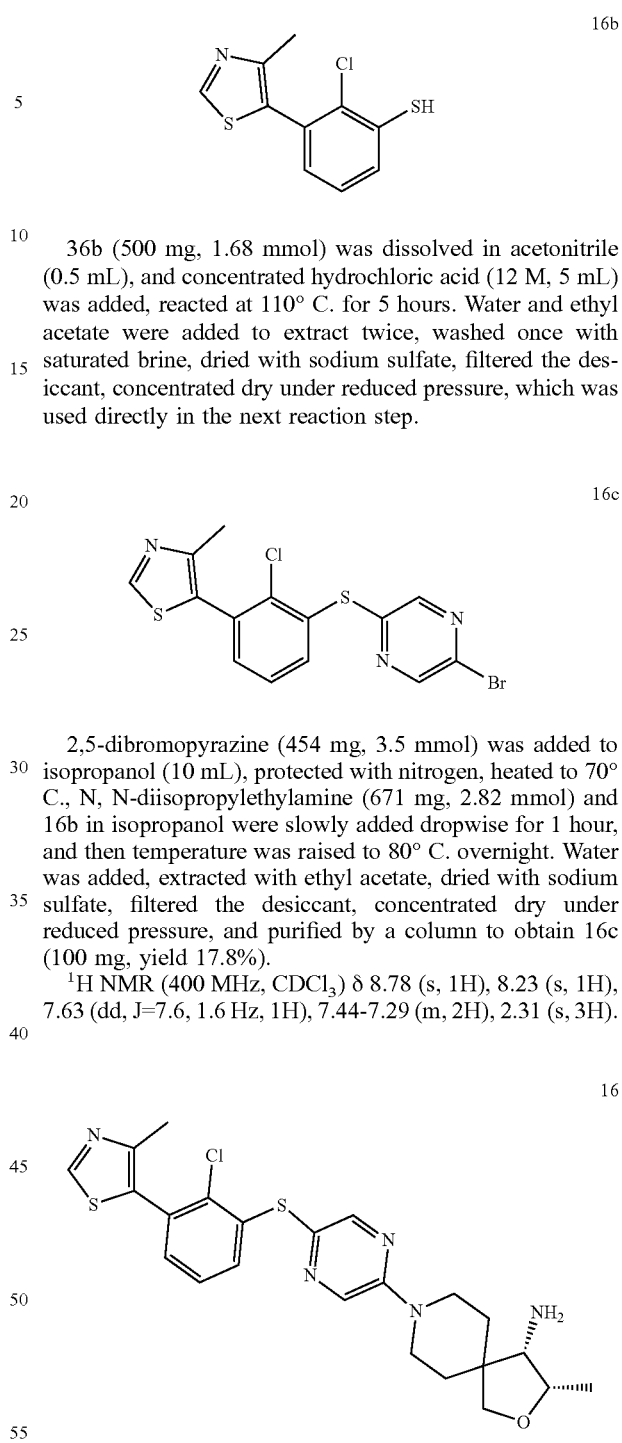

36b (500 mg, 1.68 mmol) was dissolved in acetonitrile (0.5 mL), and concentrated hydrochloric acid (12 M, 5 mL) was added, reacted at 110° C. for 5 hours. Water and ethyl acetate were added to extract twice, washed once with saturated brine, dried with sodium sulfate, filtered the desiccant, concentrated dry under reduced pressure, which was used directly in the next reaction step.

2,5-dibromopyrazine (454 mg, 3.5 mmol) was added to isopropanol (10 mL), protected with nitrogen, heated to 70° C., N, N-diisopropylethylamine (671 mg, 2.82 mmol) and 16b in isopropanol were slowly added dropwise for 1 hour, and then temperature was raised to 80° C. overnight. Water was added, extracted with ethyl acetate, dried with sodium sulfate, filtered the desiccant, concentrated dry under reduced pressure, and purified by a column to obtain 16c (100 mg, yield 17.8%).

$^1$H NMR (400 MHz, CDCl$_3$) δ 8.78 (s, 1H), 8.23 (s, 1H), 7.63 (dd, J=7.6, 1.6 Hz, 1H), 7.44-7.29 (m, 2H), 2.31 (s, 3H).

Compound 16c (100 mg, 0.25 mmol) was added to a 100 mL single-mouth flask, then 1j (61 mg, 0.25 mmol) and N,N-dimethylformamide (2 mL) were added, followed by potassium phosphate (318 mg, 1.5 mmol), heated to 110° C., and reacted for 2 hours. 20 mL of water was added, extracted twice with ethyl acetate, washed three times with saturated brine, the organic phase was dried with sodium sulfate, spin-dried, and the plate was scraped (twice) to obtain 16 (35 mg, yield 28%).

$^1$H NMR (400 MHz, CDCl$_3$) δ 8.78 (s, 1H), 8.24 (dd, J=21.5, 1.1 Hz, 2H), 7.20-7.10 (m, 2H), 7.03-6.95 (m, 1H), 4-methylthiazole (455 mg, 4.6 mmol), 1,4-dioxane (10 mL), 1m (1.25 g, 13.8 mmol), 2-(dicyclohexylphosphino) biphenyl (262 mg, 0.76 mmol), and cesium carbonate (2.42 g, 7.6 mmol) were added to a 100 mL single-mouth flask. The reaction was carried out overnight at 110° C. For post-treatment, first the reaction solution was cooled to room temperature, 50 mL of water was added, extracted three times with ethyl acetate, the organic phases were combined, washed once with saturated aqueous sodium chloride solution, dried with anhydrous sodium sulfate, and purified by column to obtain 16a (500 mg, Yield: 44%).

$^1$H NMR (400 MHz, CDCl$_3$) δ 7.77 (s, 1H), 7.72 (dd, J=7.6, 1.6 Hz, 1H), 7.35 (dd, J=7.6, 1.6 Hz, 1H), 7.28 (t, J=7.6 Hz, 1H), 2.31 (s, 3H), 1.37 (s, 9H).

4.25-4.14 (m, 1H), 4.02-3.88 (m, 2H), 3.83 (d, J=8.8 Hz, 1H), 3.70 (d, J=8.8 Hz, 1H), 3.53-3.31 (m, J=22.8, 13.0, 9.2, 3.5 Hz, 2H), 3.00 (t, J=15.4 Hz, 1H), 2.33 (s, 3H), 1.97-1.73 (m, 4H), 1.26 (s, 3H). LCMS m/z [M+H⁺]: 488.4.

Example 17

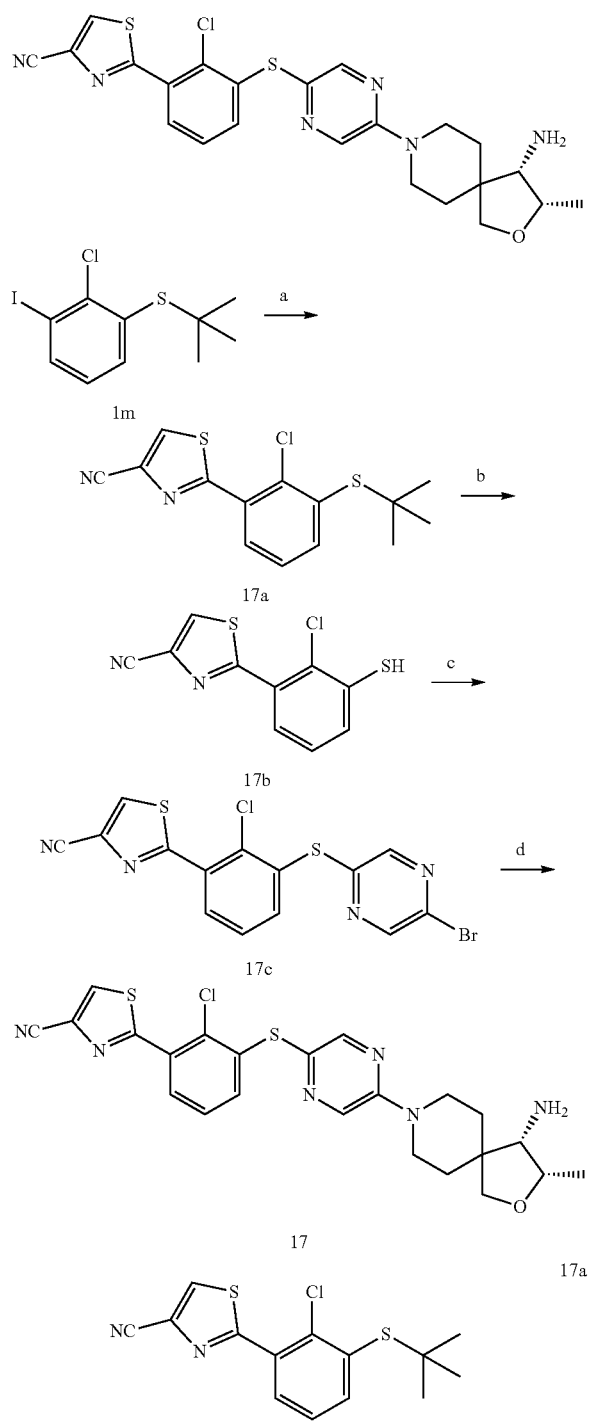

4-cyanothiazole (600 mg, 5.5 mmol), 1,4-dioxane (30 mL), 1m (1.5 g, 4.6 mmol), 2-(dicyclohexylphosphino) biphenyl (300 mg, 0.92 mmol), and cesium carbonate (3.0 g, 9.2 mmol) were added to a 100 mL single-mouth flask. Reacted at 110° C. for 5 hours. For post-treatment, the reaction solution was first cooled to room temperature, 50 mL of water was added, extracted three times with ethyl acetate, the organic phases were combined, washed once with saturated sodium chloride aqueous solution, dried with anhydrous sodium sulfate, and purified by column to obtain 17a (630 mg, Yield: 44%).

¹H NMR (400 MHz, CDCl₃) δ 8.90 (s, 1H), 7.82 (dd, J=7.6, 1.6 Hz, 1H), 7.51 (dd, J=7.6, 1.6 Hz, 1H), 7.37 (t, J=7.6 Hz, 1H), 1.38 (s, 9H).

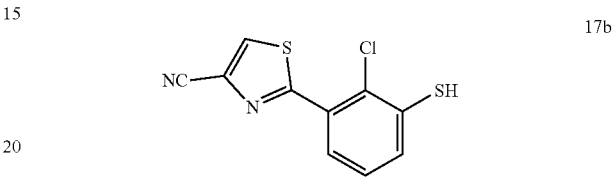

17b (630 mg, 2.0 mmol) was dissolved in toluene (20 mL), anhydrous aluminum trichloride was added, and reacted at room temperature for 5 hours. Water and ethyl acetate were added to extract twice, washed with saturated brine once, dried with sodium sulfate, filtered the desiccant, concentrated under reduced pressure to dryness, which was used directly in the next reaction step.

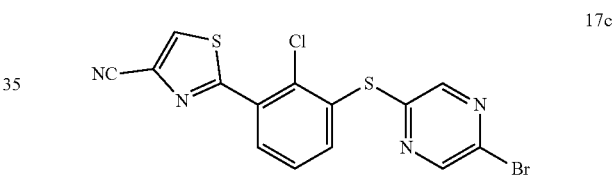

2,5-dibromopyrazine (387 mg, 3.0 mmol) and N,N-diisopropylethylamine (571 mg, 2.4 mmol) were added to acetonitrile (5 mL), protected with nitrogen, and an acetonitrile solution of 17b was added continuously dropwise for 1 hour, and reacted at room temperature for 1 hour. Water was added, extracted with ethyl acetate, dried with sodium sulfate, the desiccant was filtered, concentrated under reduced pressure to dryness, and 17c was obtained by column purification (70 mg, yield 14.3%).

¹H NMR (400 MHz, CDCl₃) δ 8.95 (s, 1H), 8.50 (d, J=1.2 Hz, 1H), 8.24 (d, J=1.2 Hz, 1H), 7.82 (dd, J=7.6, 1.6 Hz, 1H), 7.64 (dd, J=7.6, 1.6 Hz, 1H), 7.49 (t, J=7.6 Hz, 1H).

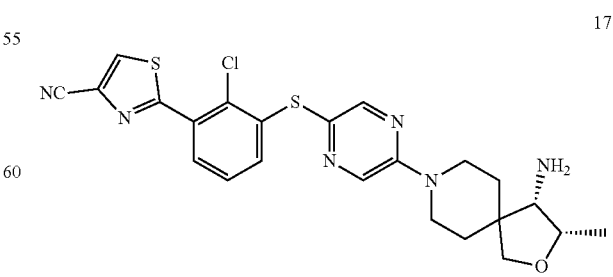

Compound 17d (70 mg, 0.17 mmol) was added to a 100 mL single-mouth flask, followed by 1j (42 mg, 0.17 mmol), N, N-dimethylformamide (2 mL), and then potassium phosphate (216 mg, 1.0 mmol), heated to 80° C., reacted for 2 hours. 20 mL of water was added, extracted twice with ethyl acetate, washed three times with saturated brine, the organic phase was dried with sodium sulfate, spin-dried, and beat (petroleum ether:ethyl acetate=30:1) to obtain 17 (56 mg, yield 66.0%).

$^1$H NMR (400 MHz, CDCl$_3$) δ 8.91 (s, 1H), 8.28 (d, J=1.2 Hz, 1H), 8.21 (d, J=1.2 Hz, 1H), 7.34 (dd, J=7.6, 1.2 Hz, 1H), 7.23 (d, J=7.6 Hz, 1H), 7.10 (dd, J=8.0, 1.2 Hz, 1H), 4.23-4.14 (m, 1H), 4.00-3.88 (m, 2H), 3.82 (d, J=8.8 Hz, 1H), 3.70 (d, J=8.8 Hz, 1H), 3.55-3.34 (m, 2H), 3.01 (d, J=4.6 Hz, 1H), 1.94-1.85 (m, 1H), 1.80-1.69 (m, 3H), 1.25 (s, 3H). MS m/z [M+H]$^+$: 499.4.

Example 18

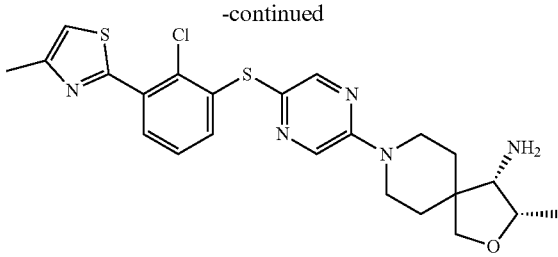

18

1m

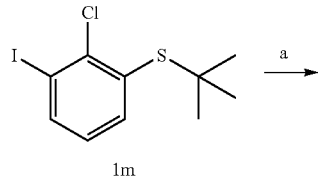

18a

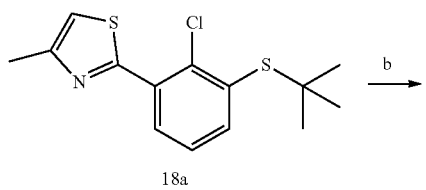

18b

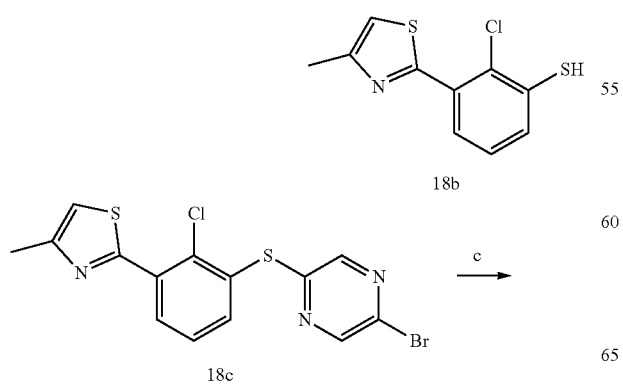

18c

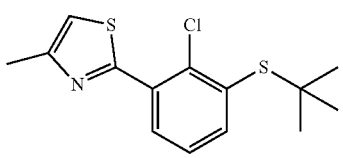

18a 4-methylthiazole (1.1 g, 11.0 mmol), N, N-dimethylformamide (20 mL), 1m (3.0 g, 9.2 mmol), copper trifluoroacetate (531 mg, 1.84 mmol), and lithium tert-butoxide (1.48 g, 18.4 mmol) were added to a 100 mL single-mouth flask. Reacted overnight at 130° C. under nitrogen. For post-treatment, the reaction solution was first cooled to room temperature, 50 mL of water was added, extracted three times with ethyl acetate, the organic phases were combined, washed once with saturated sodium chloride solution, dried with anhydrous sodium sulfate, and purified by column to obtain 18a (1.0 g, Yield: 36.6%).

$^1$H NMR (400 MHz, CDCl$_3$) δ 8.14 (dd, J=8.0, 1.6 Hz, 1H), 7.71 (dd, J=7.6, 1.6 Hz, 1H), 7.31 (dd, J=9.6, 6.0 Hz, 1H), 7.05 (s, 1H), 2.53 (s, 3H), 1.36 (s, 9H).

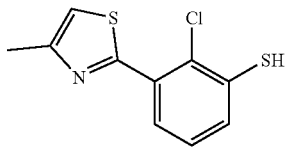

18b 18a (1.0 g, 3.3 mmol) was dissolved in toluene (30 mL), anhydrous aluminum trichloride was added, and reacted at room temperature for 5 hours. Water and ethyl acetate were added to extract twice, washed with saturated brine once, dried with sodium sulfate, the desiccant was filtered, concentrated under reduced pressure to dryness, and it was used directly in the next reaction step.

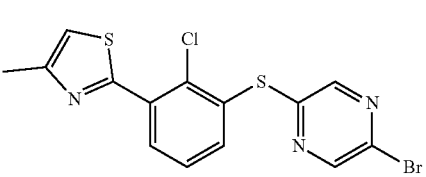

18c 2,5-dibromopyrazine (2.38 g, 10 mmol) and N, N-diisopropylethylamine (1.0 g, 8.0 mmol) were added to acetonitrile (20 mL), protected by nitrogen, and 18b in acetonitrile was slowly added dropwise for 1 hour, and then reacted at room temperature for 5 hours. Water was added, extracted with ethyl acetate, dried with sodium sulfate, the desiccant was filtered, concentrated under reduced pressure to dryness, and purified by column to obtain 18c (100 mg, yield 6.3%).

$^1$H NMR (400 MHz, CDCl$_3$) δ 8.45 (d, J=1.2 Hz, 1H), 8.29 (dd, J=8.0, 1.6 Hz, 1H), 8.09 (d, J=1.2 Hz, 1H), 7.73 (dd, J=7.6, 1.6 Hz, 1H), 7.42 (t, J=7.6 Hz, 1H), 7.08 (s, 1H), 2.54 (s, 3H).

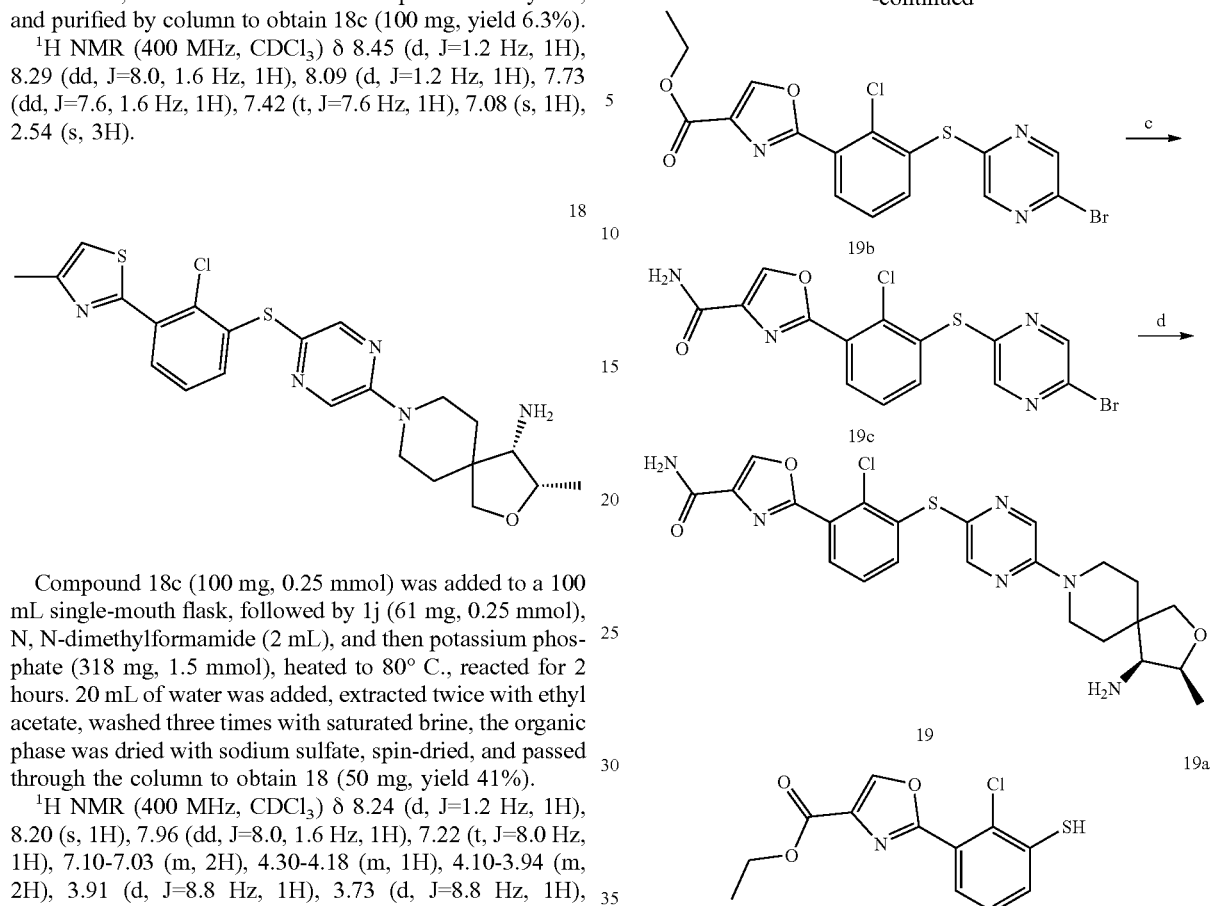

Compound 18c (100 mg, 0.25 mmol) was added to a 100 mL single-mouth flask, followed by 1j (61 mg, 0.25 mmol), N, N-dimethylformamide (2 mL), and then potassium phosphate (318 mg, 1.5 mmol), heated to 80° C., reacted for 2 hours. 20 mL of water was added, extracted twice with ethyl acetate, washed three times with saturated brine, the organic phase was dried with sodium sulfate, spin-dried, and passed through the column to obtain 18 (50 mg, yield 41%).

$^1$H NMR (400 MHz, CDCl$_3$) δ 8.24 (d, J=1.2 Hz, 1H), 8.20 (s, 1H), 7.96 (dd, J=8.0, 1.6 Hz, 1H), 7.22 (t, J=8.0 Hz, 1H), 7.10-7.03 (m, 2H), 4.30-4.18 (m, 1H), 4.10-3.94 (m, 2H), 3.91 (d, J=8.8 Hz, 1H), 3.73 (d, J=8.8 Hz, 1H), 3.45-3.23 (m, 2H), 3.12 (d, J=4.0 Hz, 1H), 2.54 (s, 3H), 1.96 (d, J=9.6 Hz, 1H), 1.87-1.74 (m, 3H), 1.32 (d, J=6.4 Hz, 3H). MS m/z [M+H]$^+$: 488.3.

Example 19

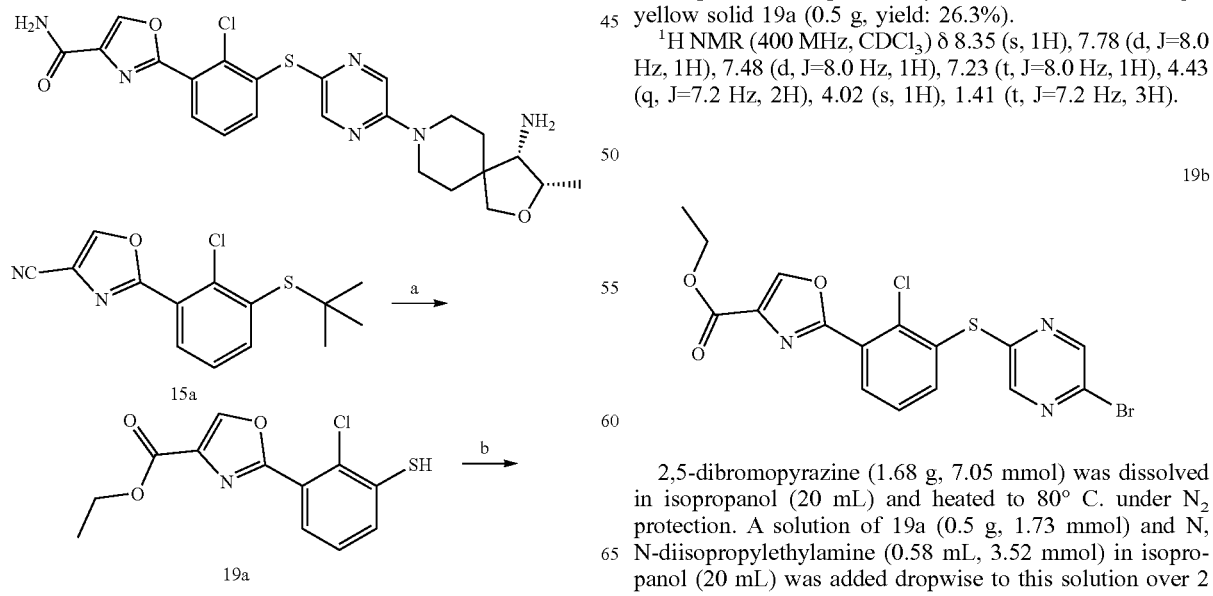

Sulfuric acid (13 mL) was slowly added to the ethanol (30 mL) solution of 15a (2.0 g, 6.83 mmol) and heated and refluxed. After the reaction was completed, the reaction was cooled to room temperature, diluted with ethyl acetate (100 mL), and extracted with water. The organic phase was dried with anhydrous sodium sulfate and concentrated and the crude product was purified by column to obtain the light yellow solid 19a (0.5 g, yield: 26.3%).

$^1$H NMR (400 MHz, CDCl$_3$) δ 8.35 (s, 1H), 7.78 (d, J=8.0 Hz, 1H), 7.48 (d, J=8.0 Hz, 1H), 7.23 (t, J=8.0 Hz, 1H), 4.43 (q, J=7.2 Hz, 2H), 4.02 (s, 1H), 1.41 (t, J=7.2 Hz, 3H).

2,5-dibromopyrazine (1.68 g, 7.05 mmol) was dissolved in isopropanol (20 mL) and heated to 80° C. under N$_2$ protection. A solution of 19a (0.5 g, 1.73 mmol) and N, N-diisopropylethylamine (0.58 mL, 3.52 mmol) in isopropanol (20 mL) was added dropwise to this solution over 2 hours. After the addition was completed, reacted for 1 hour.

Then the reaction mixture was concentrated and purified by column to obtain the white solid 19b (0.229 g, yield 29.5%).

¹H NMR (400 MHz, CDCl₃) δ 8.45 (d, J=1.2 Hz, 1H), 8.36 (s, 1H), 8.16 (d, J=1.2 Hz, 1H), 8.10 (dd, J=8.0, 1.6 Hz, 1H), 7.80 (dd, J=7.6, 1.6 Hz, 1H), 7.44 (t, J=7.6 Hz, 1H), 4.44 (q, J=7.2 Hz, 2H), 1.41 (t, J=7.2 Hz, 3H).

Ammonia (3 mL, 28% aqueous solution) was added to a solution of 19b (229 mg, 0.52 mmol) in tetrahydrofuran/methanol (2.0 mL/3.0 mL) and stirred at room temperature for 2 days. After the reaction was completed, the reaction mixture was diluted with water, the precipitate was filtered and dried to obtain 19c (128 mg, yield: 92%).

¹H NMR (400 MHz, CDCl₃) δ 8.46 (s, 1H), 8.36 (s, 1H), 8.17 (s, 1H), 8.05 (d, J=8.0 Hz, 1H), 7.81 (d, J=7.6 Hz, 1H), 7.46 (t, J=8.0 Hz, 1H).

19c (128 mg, 0.31 mmol), 1j (0.083 g, 0.342 mmol) and potassium phosphate (0.396 g, 1.86 mmol) were added to dry N, N-dimethylformamide (5 mL) and stirred at 50° C. under nitrogen overnight. After the completion of the reaction, the reaction mixture was concentrated under reduced pressure, diluted with water and extracted with ethyl acetate. The organic phase was dried, concentrated, and purified by scraping the plate to obtain 19 (70 mg, yield: 44.8%).

¹H NMR (400 MHz, MeOD-d₄) δ 8.58 (s, 1H), 8.34 (d, J=14.4 Hz, 2H), 7.84 (dd, J=7.6, 1.2 Hz, 1H), 7.37 (t, J=8.0 Hz, 1H), 7.16 (dd, J=8.0, 1.2 Hz, 1H), 4.37-4.19 (m, 3H), 4.00 (d, J=8.8 Hz, 1H), 3.87 (d, J=8.8 Hz, 1H), 3.43-3.24 (m, 3H), 2.00 (s, 1H), 1.95-1.83 (m, 3H), 1.80-1.71 (m, 1H), 1.34-132 (m, 4H). LC-MS [M+H]⁺: m/z=501.2.

Example 20

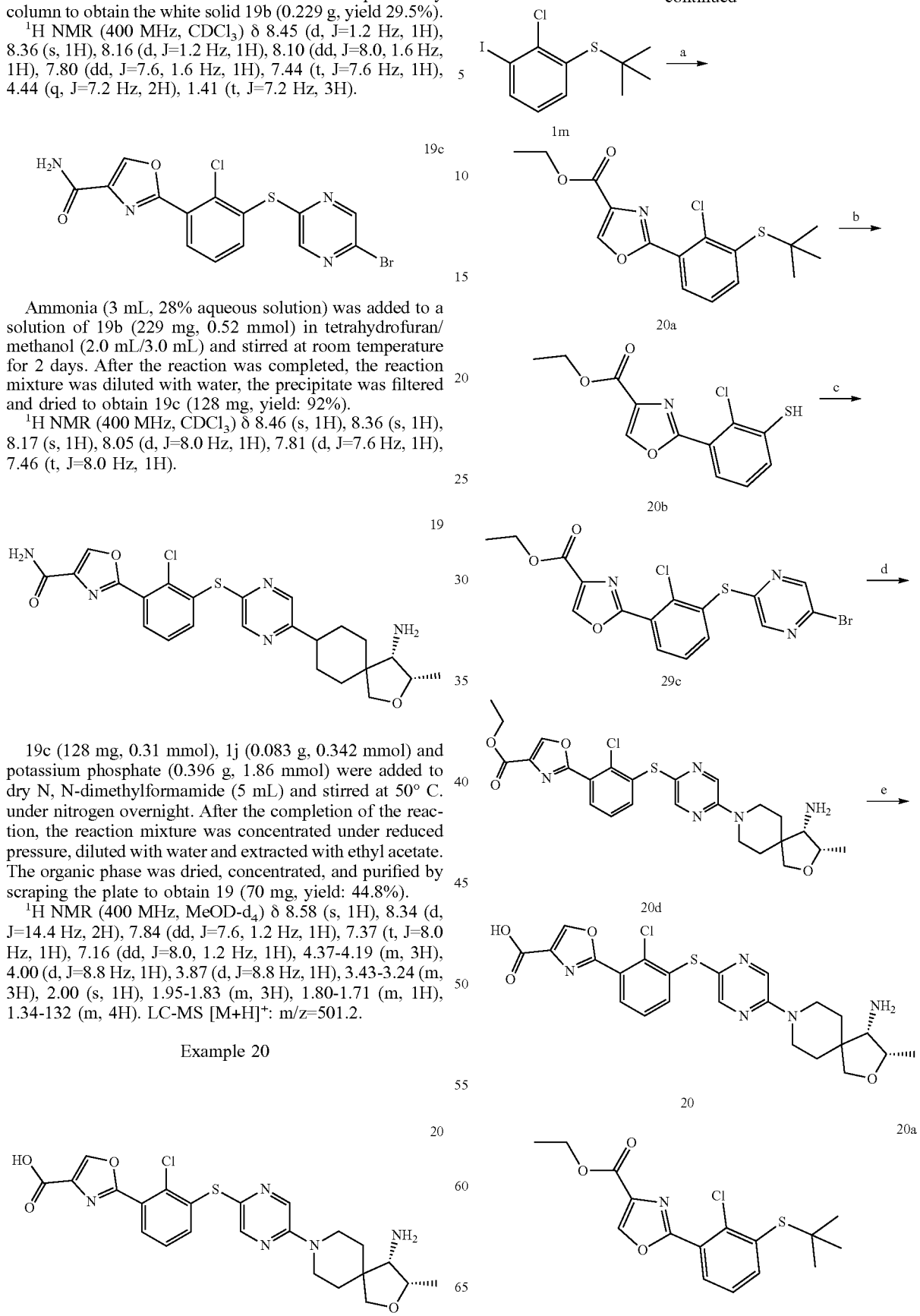

Ethyl 4-oxazolecarboxylate (1.0 g, 7.08 mmol), 1m (2.3 g, 7.08 mmol), palladium acetate (0.079 g, 0.35 mmol), 2-(dicyclohexylphosphino)biphenyl (0.25 g, 0.71 mmol) and cesium carbonate (4.65 g, 14.17 mmol) were added to 25 mL of 1,4-dioxane solution, heated and reacted at 110° C. overnight under nitrogen protection. The reaction mixture was filtered through diatomite. The filtrate was concentrated under reduced pressure and purified by column chromatography to obtain a brown-yellow solid 20a (1.0 g, 41.4%).

$^1$H NMR (400 MHz, CDCl$_3$)$^1$H NMR (400 MHz, CDCl$_3$) δ 8.36 (s, 1H), 7.93 (dd, J=7.6, 1.6 Hz, 1H), 7.81 (dd, J=7.6, 1.6 Hz, 1H), 7.33 (t, J=7.6 Hz, 1H), 4.43 (q, J=7.2 Hz, 2H), 1.41 (t, J=7.2 Hz, 3H), 1.36 (s, 9H).

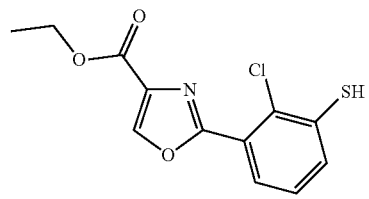

20b

Aluminum trichloride (1.57 g, 11.78 mmol) was slowly added to a solution of 20a (1.0 g, 2.95 mmol) in toluene (30 mL) at 0° C., and the reaction mixture was stirred at room temperature under nitrogen protection for 4 hours. After the reaction was completed, the reaction was quenched with ice water, and extracted with ethyl acetate. The organic phase was washed with saline, and dried over anhydrous sodium sulfate, the organic phase was concentrated under reduced pressure to obtain 20b. It can be directly used in the next reaction step without further purification.

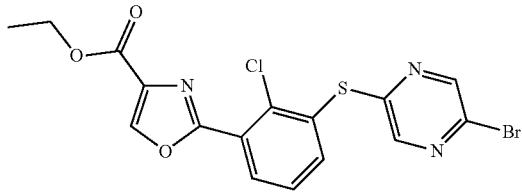

20c 2,5-dibromopyrazine (6.72 g, 28.2 mmol) was dissolved in isopropanol (20 mL), heated to 80° C. under nitrogen protection. A solution of 20b (2.0 g, 6.92 mmol) and N,N-diisopropylethylamine (2.328 mL, 14.08 mmol) in isopropanol (20 mL) was added dropwise to this solution over 2 hours and continued the reaction for 1 hour. After the completion of the reaction, the reaction mixture was concentrated and purified to obtain the white solid 20c (0.950 g, yield: 30.6%).

$^1$H NMR (400 MHz, CDCl$_3$) δ 8.45 (d, J=1.6 Hz, 1H), 8.36 (s, 1H), 8.16 (d, J=1.6 Hz, 1H), 8.10 (dd, J=8.0, 1.6 Hz, 1H), 7.80 (dd, J=7.6, 1.6 Hz, 1H), 7.44 (t, J=7.6 Hz, 1H), 4.44 (q, J=7.2 Hz, 2H), 1.41 (t, J=7.2 Hz, 3H).

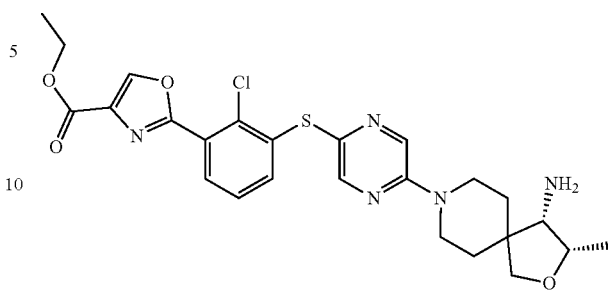

20d 20c (215 mg, 0.49 mmol), 1j (0.12 g, 0.49 mmol) and potassium phosphate (0.57 g, 2.71 mmol) were added to dry N,N-dimethylformamide (10 mL), reacted overnight at 80° C. under nitrogen protection. After the completion of the reaction, the reaction mixture was concentrated under reduced pressure, diluted with water and extracted with ethyl acetate. The organic phase was dried, concentrated and purified by scraping the plate to obtain 20d (108 mg, yield: 45%).

$^1$H NMR (400 MHz, CDCl$_3$) δ 8.35 (s, 1H), 8.24 (d, J=1.2 Hz, 1H), 8.18 (d, J=1.2 Hz, 1H), 7.79 (dd, J=7.6, 1.6 Hz, 1H), 7.20 (t, J=8.0 Hz, 1H), 7.09 (dd, J=8.0, 1.6 Hz, 1H), 4.42 (q, J=7.2 Hz, 2H), 4.21-4.18 (m, 1H), 4.02-3.91 (m, 2H), 3.84 (d, J=8.8 Hz, 1H), 3.70 (d, J=8.8 Hz, 1H), 3.47-3.29 (m, 2H), 3.05 (d, J=4.4 Hz, 1H), 1.94-1.70 (m, 4H), 1.40 (t, J=7.2 Hz, 3H), 1.26 (d, J=6.4 Hz 3H).

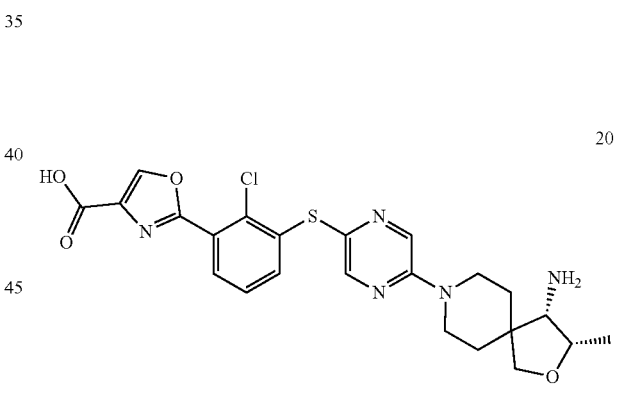

20

20d (0.1g, 0.189 mmol) and lithium hydroxide (0.032 g, 0.76 mmol) were added to a mixture of methanol/water (0.5 mL/2.0 mL) and reacted at room temperature for 4 hours. After the completion of the reaction, the reaction mixture was diluted with water (2 mL), and the pH was adjusted to 7 with 1N hydrochloric acid. The solid was filtered, washed with water, and then washed with a small amount of cold methanol/dichloromethane (1/20) solution, the solid was dried to obtain 20 (76 mg, yield: 80%).

$^1$H NMR (400 MHz, MeOD-d$_4$) δ 8.29-8.27 (m, 3H), 7.78 (d, J=7.6 Hz, 1H), 7.29 (t, J=8.0 Hz, 1H), 7.05 (d, J=8.0 Hz, 1H), 4.29-4.23 (m, 1H), 4.13-4.06 (m, 2H), 3.89 (d, J=8.8 Hz, 1H), 3.75 (d, J=8.8 Hz, 1H), 3.4-3.36 (m, 2H), 3.05 (d, J=4.8 Hz, 1H), 1.91-1.69 (m, 4H), 1.39-1.30 (m, 2H), 1.25 (d, J=6.4 Hz, 3H). LC-MS [M+H]$^+$: m/z=502.1.

Example 21

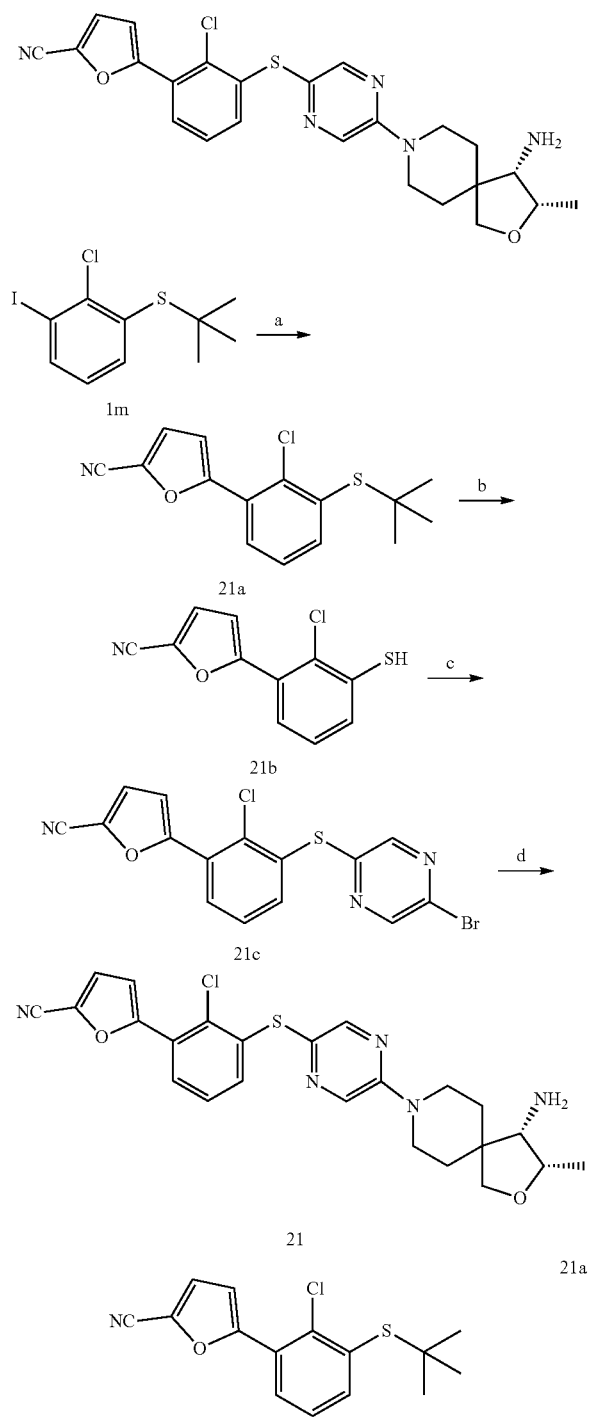

2-cyanofuran (1 mL), N, N-dimethylformamide (10 mL), 1m (1.0 g, 3.1 mmol), palladium acetate (67 mg, 0.3 mmol), 2-(dicyclohexylphosphino)biphenyl (210 mg, 0.6 mmol), and cesium carbonate (1.98 g, 6.1 mmol) were added to a 100 mL single-mouth bottle. Reacted at 110° C. for 5 hours. For post-treatment, the reaction solution was first cooled to room temperature, 50 mL of water was added, extracted three times with ethyl acetate, the organic phases were combined, washed once with saturated aqueous sodium chloride solution, dried with anhydrous sodium sulfate, and purified by column to obtain 21a (500 mg, yield: 59%).

$^1$H NMR (400 MHz, CDCl$_3$) δ 8.90 (s, 1H), 7.82 (dd, J=7.6, 1.6 Hz, 1H), 7.51 (dd, J=7.6, 1.6 Hz, 1H), 7.37 (t, J=7.6 Hz, 1H), 1.38 (s, 9H).

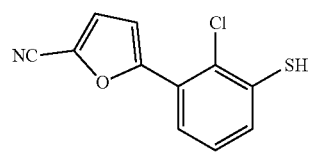

21a (500 mg, 2.1 mmol) was dissolved in toluene (30 mL), anhydrous aluminum chloride (1.7 g, 12.8 mmol) was added, and reacted at room temperature for 3 hours. Water and ethyl acetate were added to extract twice, washed once with saturated brine, dried with sodium sulfate, filtered and concentrated under reduced pressure to obtain 21b, which was used directly in the next reaction step.

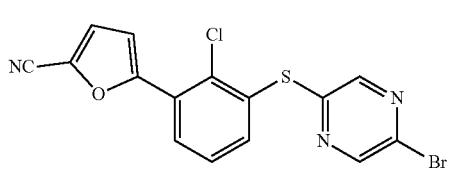

2,5-dibromopyrazine (1.6 g, 6.7 mmol) and N, N-diisopropylethylamine (670 mg, 5.4 mmol) were added to acetonitrile (20 mL), protected with nitrogen, and a solution of 21b in acetonitrile was slowly added dropwise for about 1 hour, then reacted at room temperature for 5 hours. Water was added slowly, extracted with ethyl acetate, dried over sodium sulfate, filtered and concentrated under reduced pressure, and purified to obtain 21c (180 mg, yield 21%).

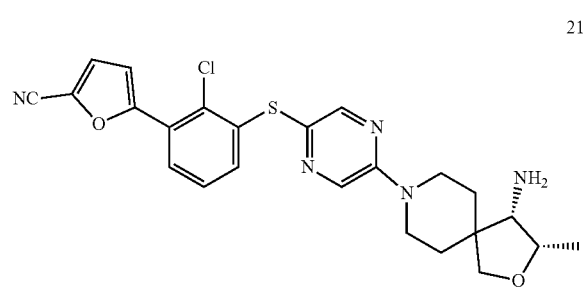 [SMILES: C[C@@H]1OCC2(CCN(c3cnc(Sc4cccc(-c5ccc(C#N)o5)c4Cl)cn3)CC2)[C@@H]1N]

Compound 21c (180 mg, 0.45 mmol) was added to a 100 mL single-mouth flask, followed by 1j (110 mg, 0.45 mmol), N, N-dimethylformamide (5 mL), and then potassium phosphate (572 mg, 2.7 mmol), heated to 80° C., and reacted for 2 hours. 20 mL of water was added, extracted twice with ethyl acetate, washed three times with saturated brine, and the organic phase was dried with sodium sulfate, concentrated and purified to obtain 21 (40 mg, yield 18%).

$^1$H NMR (400 MHz, CDCl$_3$) δ 8.25 (s, 1H), 8.20 (s, 1H), 7.66 (d, J=7.6 Hz, 1H), 7.22 (d, J=10.4 Hz, 3H), 6.98 (d, J=8.0 Hz, 1H), 4.26-4.13 (m, 1H), 4.01-3.87 (m, 2H), 3.82

(d, J=8.8 Hz, 1H), 3.70 (d, J=8.8 Hz, 1H), 3.57-3.30 (m, 2H), 3.00 (d, J=4.4 Hz, 1H), 1.97-1.82 (m, 1H), 1.80-1.64 (m, 3H), 1.24 (s, 3H). MS m/z [M+H]⁺: 482.2.

Example 22

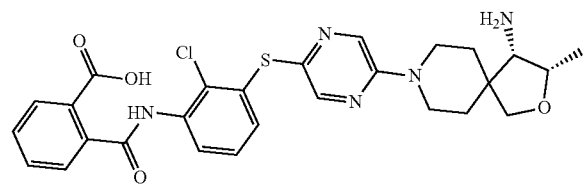

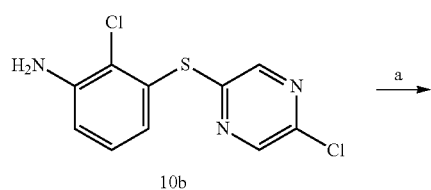

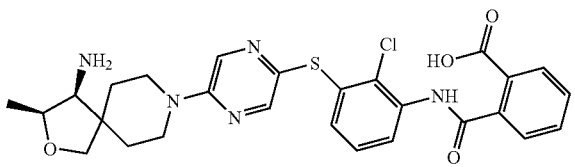

22a (250 mg, 0.6 mmol), potassium phosphate (764 mg, 3.6 mmol) and 1j (145 mg, 0.6 mmol) were added to 10 mL of N, N-dimethylformamide, heated to 80° C. and reacted for 5 hours, water was added, extracted with ethyl acetate, dried over sodium sulfate, filtered, concentrated under reduced pressure, and purified to obtain 22 (30 mg, yield: 9.1%).

¹H NMR (DMSO, 400 MHz): 8.25 (s, 1H), 7.79-7.63 (m, 3H), 7.50-7.40 (m, 2H), 7.20 (t, J=8.0 Hz, 1H), 6.70 (d, J=8.0 Hz, 1H), 4.17-4.10 (m, 1H), 4.08-3.97 (m, 2H), 3.81-3.76 (d, J=8.8 Hz, 1H), 3.60-3.56 (d, J=8.8 Hz, 1H), 3.25-3.22 (m, 1H), 3.17-3.14 (m, 1H), 1.77-1.48 (m, 4H), 1.15 (d, J=6.4 Hz, 3H). MS m/z [M+H]⁺: 554.2.

Example 23

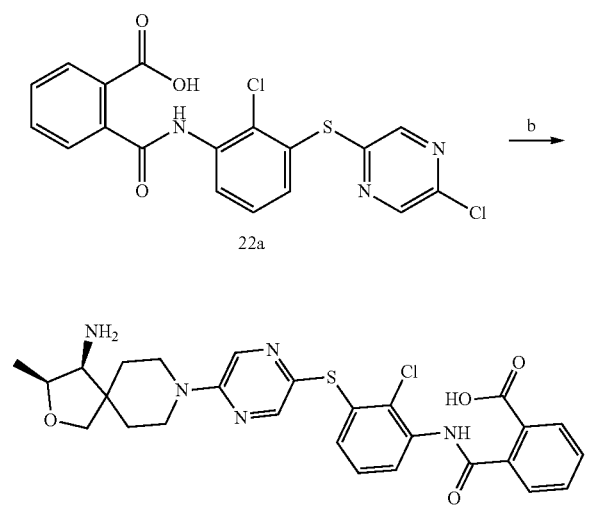

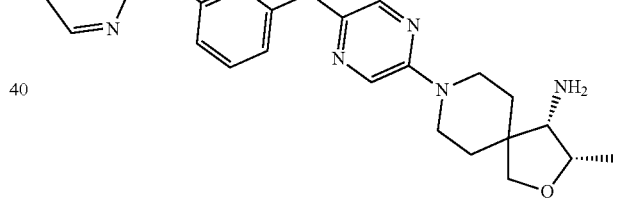

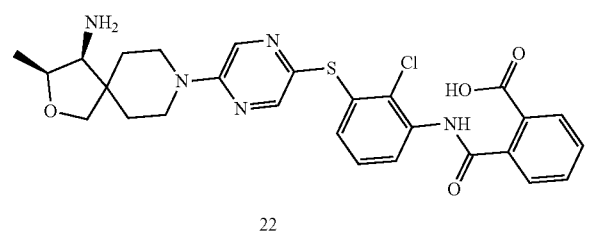

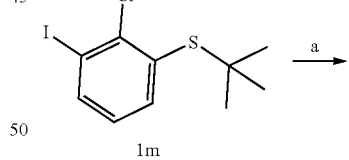

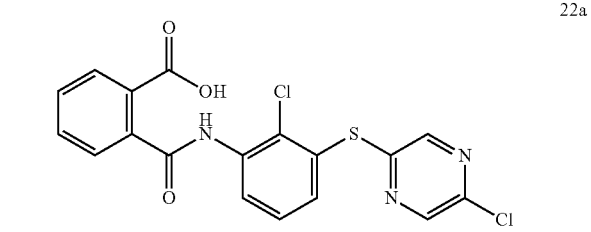

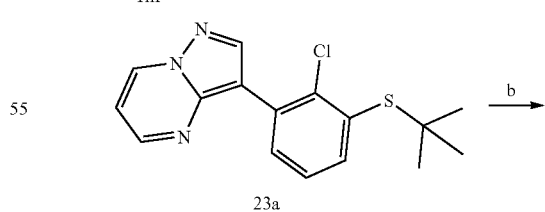

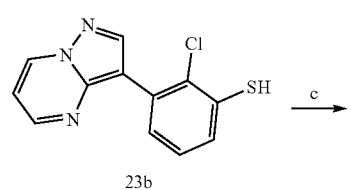

10b (200 mg, 0.74 mmol) and phthalic anhydride (180 mg, 1.2 mmol) were added to acetic acid (2 mL) and reacted at 140° C. for 5 hours in a sealed tube. Water was added, extracted with ethyl acetate, dried with sodium sulfate, filtered, concentrated to dryness under reduced pressure, and purified to obtain 22a (250 mg, yield 80.6%).

¹H NMR (400 MHz, CDCl₃) δ 8.40 (s, 1H), 8.17 (s, 1H), 8.02-7.93 (m, 2H), 7.85-7.77 (m, 3H), 7.48 (m, 2H).

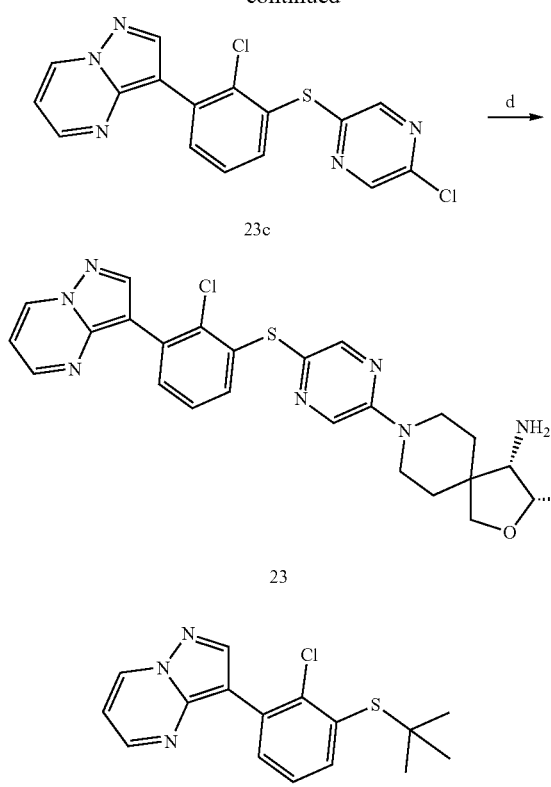

Pyrazolo[1,5-A]pyrimidine (547 mg, 4.6 mmol), N,N-dimethylformamide (8 mL), 1m (1.5 g, 4.6 mmol), palladium acetate (103 mg, 0.46 mmol), lithium chloride (190 mg, 4.6 mmol), and potassium carbonate (640 mg, 4.6 mmol) were added to a 30 mL sealed tube. The reaction was carried out at 120° C. for 5 hours under nitrogen protection. For post-treatment, the reaction solution was first cooled to room temperature, and 50 mL of water was added. It was extracted three times with ethyl acetate, the organic phases were combined, washed once with saturated aqueous sodium chloride solution, dried over anhydrous sodium sulfate, and purified to obtain a solid 23a (400 mg, yield: 25.6%).

$^1$H NMR (400 MHz, CDCl$_3$): δ 8.73 (dd, J=7.2, 1.6 Hz, 1H), 8.55 (d, J=2.4 Hz, 2H), 7.81 (dd, J=7.6, 1.6 Hz, 1H), 7.65 (dd, J=7.6, 1.6 Hz, 1H), 7.33 (t, J=7.8 Hz, 1H), 6.88 (dd, J=7.2, 4.0 Hz, 1H), 1.38 (s, 9H).

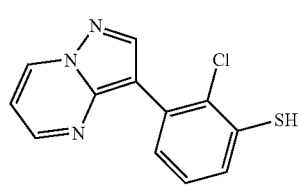

23a (400 mg, 1.3 mmol) was dissolved in toluene (10 mL), anhydrous aluminum chloride (335 mg, 2.52 mmol) was added, and reacted at room temperature for 3 hours. Water and ethyl acetate were added to extract twice, washed with saturated brine once, dried with sodium sulfate, the desiccant was filtered and concentrated to dryness under reduced pressure to obtain 23b. It was used directly in the next reaction step.

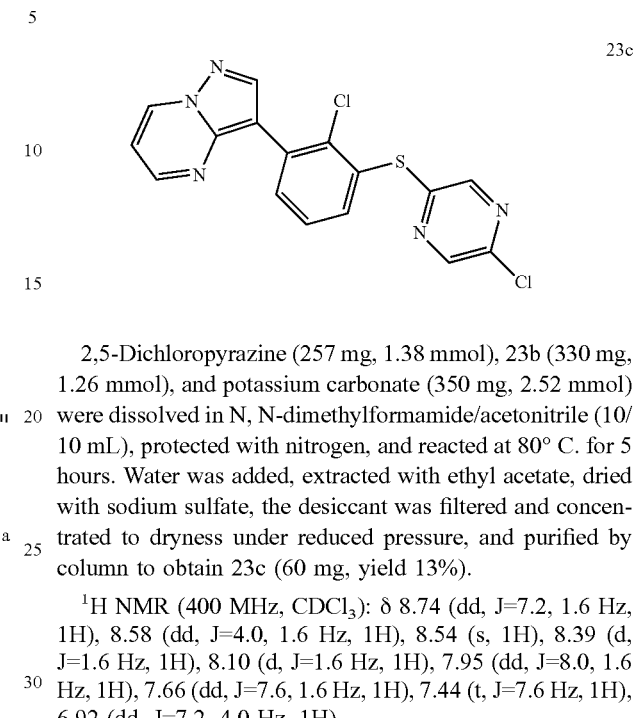

2,5-Dichloropyrazine (257 mg, 1.38 mmol), 23b (330 mg, 1.26 mmol), and potassium carbonate (350 mg, 2.52 mmol) were dissolved in N,N-dimethylformamide/acetonitrile (10/10 mL), protected with nitrogen, and reacted at 80° C. for 5 hours. Water was added, extracted with ethyl acetate, dried with sodium sulfate, the desiccant was filtered and concentrated to dryness under reduced pressure, and purified by column to obtain 23c (60 mg, yield 13%).

$^1$H NMR (400 MHz, CDCl$_3$): δ 8.74 (dd, J=7.2, 1.6 Hz, 1H), 8.58 (dd, J=4.0, 1.6 Hz, 1H), 8.54 (s, 1H), 8.39 (d, J=1.6 Hz, 1H), 8.10 (d, J=1.6 Hz, 1H), 7.95 (dd, J=8.0, 1.6 Hz, 1H), 7.66 (dd, J=7.6, 1.6 Hz, 1H), 7.44 (t, J=7.6 Hz, 1H), 6.92 (dd, J=7.2, 4.0 Hz, 1H).

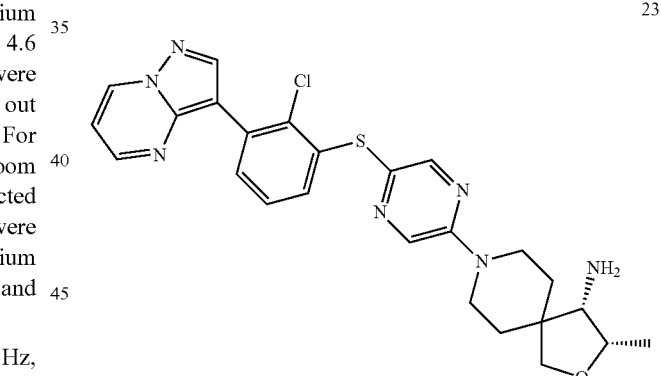

Compound 23c (60 mg, 0.16 mmol) was added to a 100 mL single-mouth flask, followed by 1j (110 mg, 0.16 mmol), N,N-dimethylformamide (5 mL), and then potassium phosphate (203 mg, 0.96 mmol), heated to 80° C. and reacted for 2 hours. 20 mL of water was added, extracted twice with ethyl acetate, the organic phase was washed three times with saturated brine, dried with sodium sulfate, concentrated and purified by column chromatography to obtain 23 (20 mg, yield 24.5%).

$^1$H NMR (400 MHz, CDCl$_3$): δ 8.73 (dd, J=7.2, 1.6 Hz, 1H), 8.57-8.49 (m, 2H), 8.21 (d, J=11.6 Hz, 2H), 7.62 (dd, J=7.6, 1.6 Hz, 1H), 7.22 (t, J=7.6 Hz, 1H), 6.99 (dd, J=8.0, 1.2 Hz, 1H), 6.88 (dd, J=7.2, 4.0 Hz, 1H), 4.29-4.21 (m, 1H), 4.15-3.91 (m, 3H), 3.74 (d, J=9.0 Hz, 1H), 3.36-3.20 (m, 2H), 2.04-1.96 (m, 1H), 1.90-1.75 (m, 3H), 1.37 (d, J=6.4 Hz, 3H). MS m/z [M+H]$^+$: 508.3

Example 24

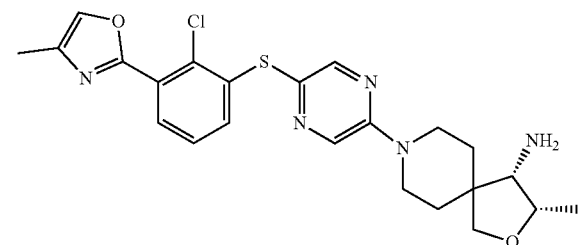

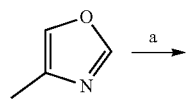

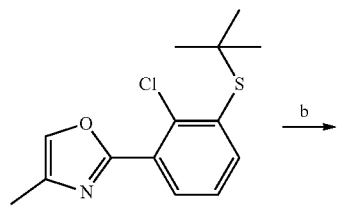

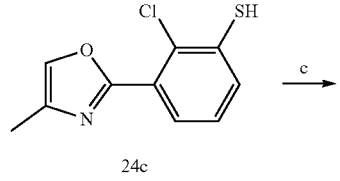

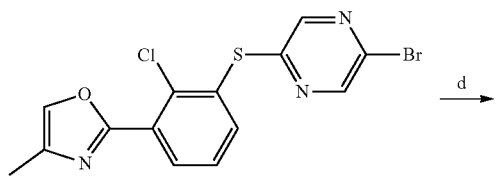

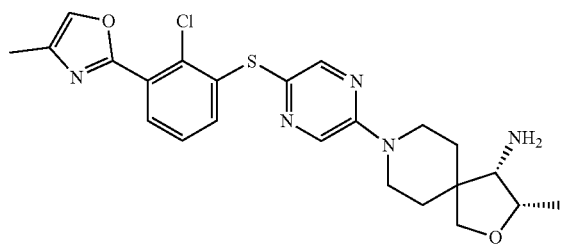

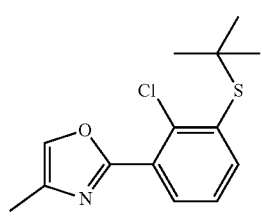

24a (1.0 g, 12.0 mmol) was added to N—N dimethylformamide (24 mL), followed by 1m (5.9 g, 18.0 mmol), cuprous iodide (457 mg, 2.4 mmol), and lithium tert-butoxide (1.15 g, 14.4 mmol). Under nitrogen protection, the temperature was raised to 145° C. and stirred for 3 hours. The reaction was cooled to room temperature, saturated aqueous ammonium chloride solution was added, extracted and partitioned with ethyl acetate, washed with saturated aqueous salt solution once, dried with anhydrous sodium sulfate, the desiccant was filtered, concentrated under reduced pressure, and passed through the column to obtain 24b (2.3 g, yield 67%).

$^1$H NMR (400 MHz, CDCl$_3$) δ 7.87 (d, J=4.0 Hz, 1H), 7.75 (d, J=4.0 Hz, 1H), 7.51 (s, 1H), 7.30 (t, J=8.0 Hz, 1H), 2.27 (s, 3H), 1.36 (s, 9H).

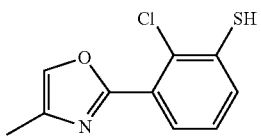

24b (2.0 g, 7.1 mmol) was dissolved in toluene (40 mL), anhydrous aluminum trichloride (5.68 g, 42.6 mmol) was added, protected with nitrogen, and the reaction was stirred at room temperature for 3 hours. The reaction was quenched with ice water, extracted with ethyl acetate and partitioned, dried over anhydrous sodium sulfate, the desiccant was filtered and concentrated to dryness under reduced pressure to obtain crude product 24c, which was used in the next reaction directly.

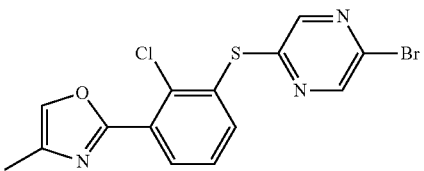

2,5-dibromopyrazine (5.06 g, 21.3 mmol) and N, N-diisopropylethylamine (1.84 mL, 14.2 mmol) were dissolved in isopropanol (50 mL), under nitrogen protection, the temperature was raised to 70° C., a solution of 24c (1.6 g, 7.1 mmol) in isopropanol (15 mL) was slowly added dropwise for 1 hour, the temperature was raised to 80° C. and stirred for 16 hours. The reaction was cooled to room temperature, extracted with ethyl acetate, dried over anhydrous sodium sulfate, the desiccant was filtered, concentrated under reduced pressure, and purified by column to obtain 24d (600 mg, yield 22%).

$^1$H NMR (CDCl$_3$, 400 MHz): δ 8.42 (s, 1H), 8.10 (s, 1H), 8.02 (d, J=8.0 Hz, 1H), 7.74 (d, J=8.0 Hz, 1H), 7.51 (s, 1H), 7.39 (t, J=8.0 Hz, 1H), 2.26 (s, 3H).

24

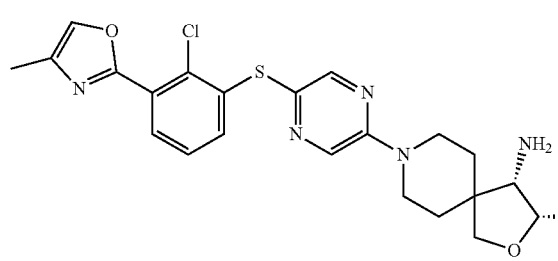

24d (600 mg, 1.57 mmol), 1j (495 mg, 2.04 mmol), and potassium phosphate (2.0 g, 9.41 mmol) were added to isopropanol (20 mL), displaced with nitrogen, and the temperature was raised to 95° C. and stirred for 36 hours. The reaction was cooled to room temperature, extracted with dichloromethane, dried with anhydrous sodium sulfate, the desiccant was filtered, and concentrated under reduced pressure to obtain the target product 24 (349 mg, yield 47%).

$^1$H NMR (400 MHz, CDCl$_3$): δ 8.21 (s, 1H), 8.15 (s, 1H), 7.69 (d, J=8.0 Hz, 1H), 7.48 (s, 1H), 7.15 (t, J=8.0 Hz, 1H), 7.01 (d, J=8.0 Hz, 1H), 4.13-4.17 (m, 1H), 3.84-3.94 (m, 2H), 3.77 (d, J=8.8 Hz, 1H), 3.65 (d, J=8.8 Hz, 1H), 3.40-3.47 (m, 1H), 3.30-3.36 (m, 1H), 2.96 (d, J=4.8 Hz, 1H), 2.24 (s, 3H), 1.81-1.88 (m, 1H), 1.62-1.75 (m, 3H), 1.19-1.21 (m, 5H). LCMS m/z [M+H$^+$]: 472.2.

Example 25

25

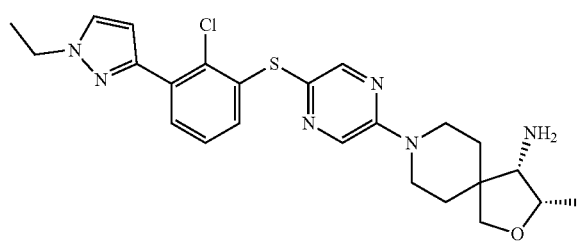

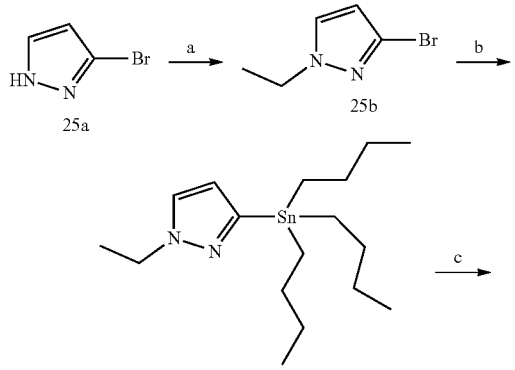

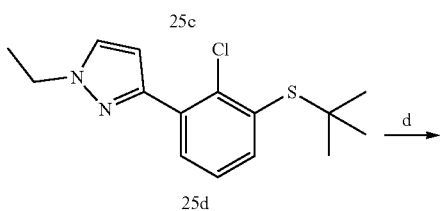

-continued

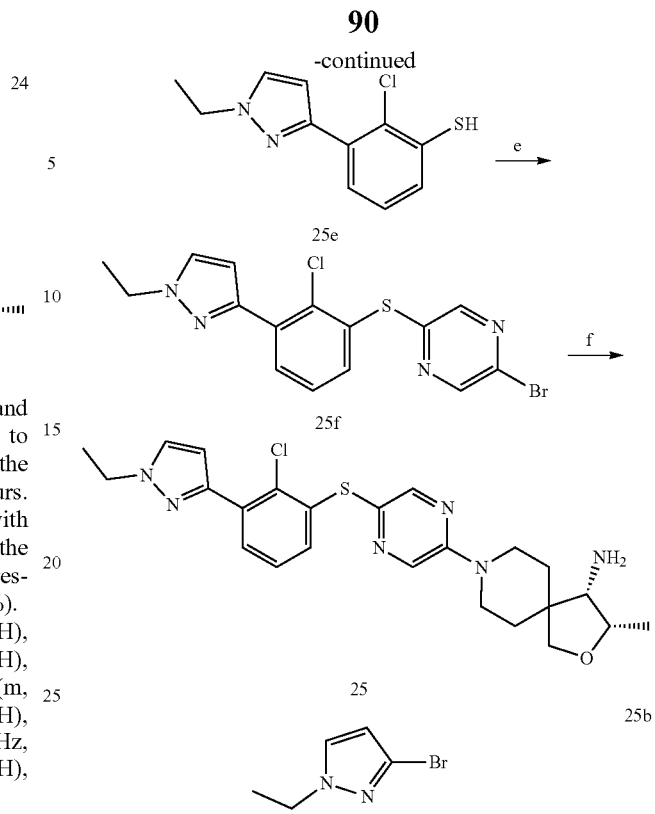

25a (4.8 g, 32.66 mmol) was added to N—N dimethylformamide (160 mL), sodium hydrogen (1.96 g, 48.99 mmol) was added in batches under ice water bath, stirred for 30 minutes, then added iodoethane (8.15 g, 52.26 mmol), reacted at room temperature for 3 hours. The reaction was quenched by adding saturated ammonium chloride aqueous solution under ice water bath, extracted with ethyl acetate, dried over anhydrous sodium sulfate, the desiccant was filtered and concentrated under reduced pressure to obtain 25b (4.3 g, yield 75%).

$^1$H NMR (400 MHz, CDCl$_3$) δ 7.25 (m, 1H), 6.19 (m, 1H), 4.08 (m, 2H), 1.41 (m, 3H).

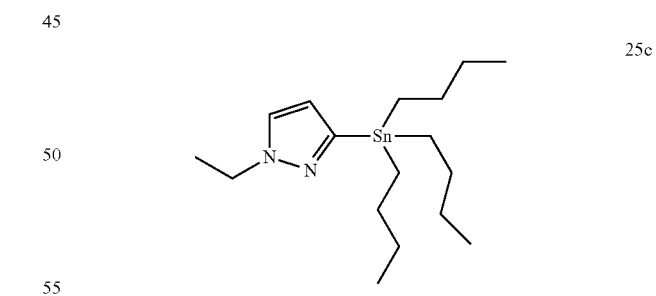

25b (4.3 g, 24.56 mmol) was added to toluene (125 mL), followed by tetrakis(triphenylphosphine) palladium (1.42 g, 1.23 mmol), hexa-n-butyl ditin (14.25 g, 24.56 mmol). Under nitrogen protection, the temperature was raised to 110° C. and reacted for 16 hours. The reaction was cooled to room temperature, concentrated under reduced pressure, and passed through a column to obtain 25c (2.6 g, yield 27%).

$^1$H NMR (400 MHz, CDCl$_3$) δ 7.46 (d, J=2.0 Hz, 1H), 6.30 (d, J=2.0 Hz, 1H), 4.24 (m, 2H), 1.58 (m, 6H), 1.47 (m, 3H), 1.32 (m, 6H), 1.07 (m, 6H), 0.89 (m, 9H).

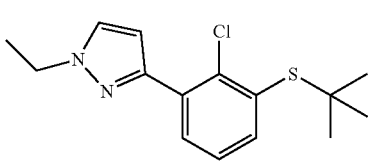
25d 25c (2.5 g, 6.49 mmol) was added to xylene (65 mL), followed by 1m (1.8 g, 6.49 mmol), tetrakis(triphenylphosphine) palladium (376 mg, 0.33 mmol), and heated to 155° C. under nitrogen protection and reacted for 2 hours. The reaction was cooled to room temperature, concentrated under reduced pressure, and passed through column to obtain 25d (1.65 g, yield 85%).

$^1$H NMR (400 MHz, CDCl$_3$) δ 7.76 (dd, J=6.0, 1.6 Hz, 1H), 7.62 (dd, J=7.6, 2.0 Hz, 1H), 7.44 (d, J=2.4 Hz, 1H), 7.26 (m, 1H), 6.73 (d, J=2.4 Hz, 1H), 4.22 (m, 2H), 1.53 (m, 3H), 1.35 (s, 9H).

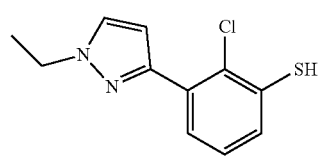
25e 25d (1.55 g, 5.26 mmol) was dissolved in toluene (50 mL), anhydrous aluminum trichloride (2.8 g, 21.03 mmol) was added under ice water bath, protected by nitrogen, stirred the reaction for 4 hours at room temperature. Quenched with ice water, extracted with ethyl acetate and partitioned, dried with anhydrous sodium sulfate, the desiccant was filtered and concentrated under reduced pressure to obtain crude product 25e (1.25 g, yield 100%), which was used directly in the next reaction step.

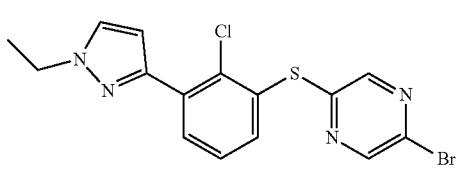
25f 2,5-dibromopyrazine (5 g, 21.03 mmol) was dissolved in isopropanol (10 mL), heated to 65° C. under nitrogen protection, and a mixture of 25e (1.25 g, 5.26 mmol)/isopropanol (10 mL)/N, N-diisopropylethylamine (1.36 g, 10.52 mmol) was slowly added dropwise for 1 hour, and continued stirring for 1 hour at 65° C. The reaction was cooled to room temperature, concentrated under reduced pressure, and purified by column to obtain 25f (500 mg, yield 25%).

$^1$H NMR (400 MHz, CDCl$_3$) δ 8.44 (s, 1H), 8.01 (s, 1H), 7.91 (m, 1H), 7.64 (d, J=6.4 Hz, 1H), 7.45 (d, J=2.0 Hz, 1H), 7.35 (t, J=7.6 Hz, 1H), 6.73 (d, J=2.1 Hz, 1H), 4.23 (m, 2H), 1.53 (m, 3H).

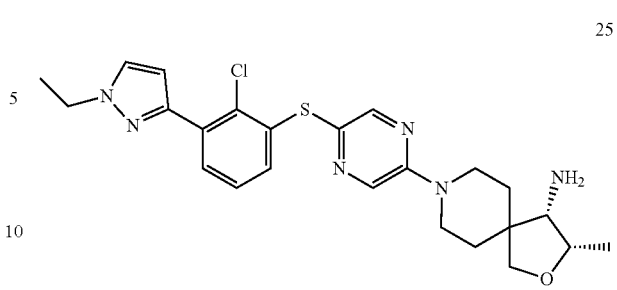
25

25f (450 mg, 1.14 mmol), 1j (360 mg, 1.48 mmol), and potassium phosphate (1.45 g, 6.85 mmol) were added to isopropanol (12 mL) and stirred at 95° C. for 48 hours under nitrogen protection. Concentrated under reduced pressure to obtain the target product 25 (200 mg, yield 36%).

$^1$H NMR (400 MHz, CDCl$_3$) δ 8.18 (d, J=16.9 Hz, 2H), 7.59 (d, J=7.4 Hz, 1H), 7.44 (d, J=1.3 Hz, 1H), 7.13 (t, J=7.8 Hz, 1H), 6.94 (d, J=7.6 Hz, 1H), 6.72 (d, J=1.4 Hz, 1H), 4.27-4.09 (m, 3H), 3.88 (m, 2H), 3.72 (m, 2H), 3.40 (m, 2H), 2.96 (m, 1H), 1.84 (m, 1H), 1.69 (m, 3H), 1.51 (m, 4H), 1.21 (d, J=6.3 Hz, 3H). LCMS m/z [M+H]$^+$: 485.2.

Example 26

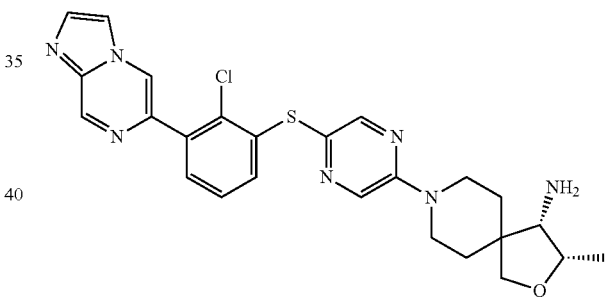
26

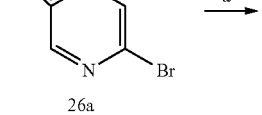
26a

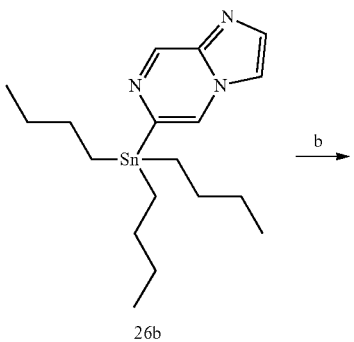
26b

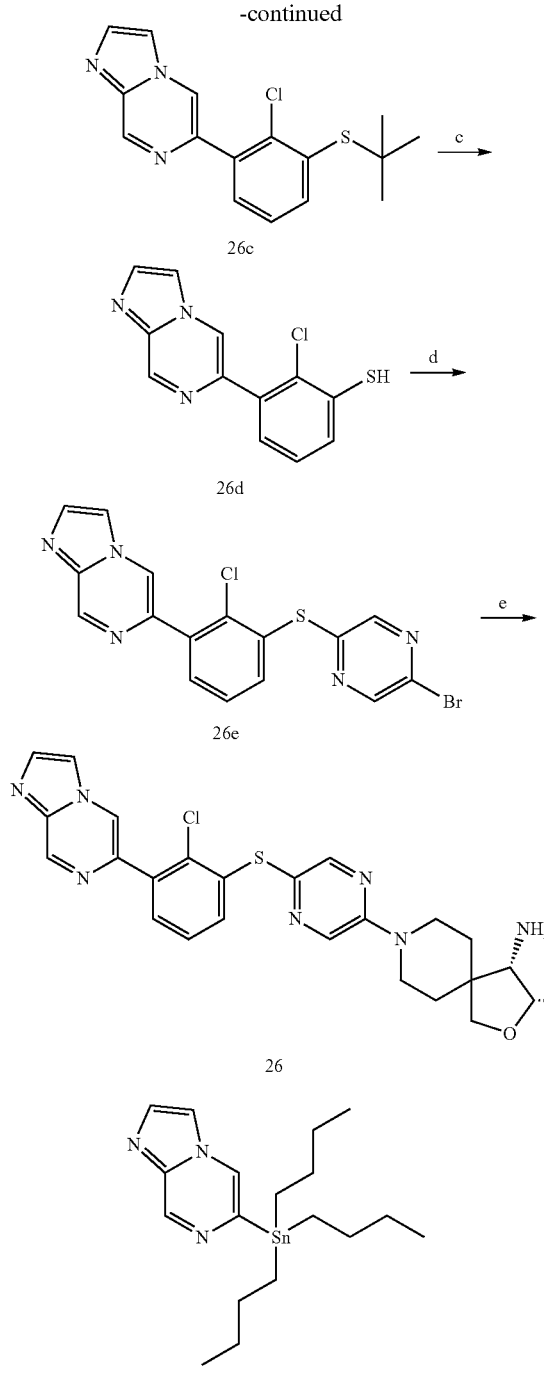

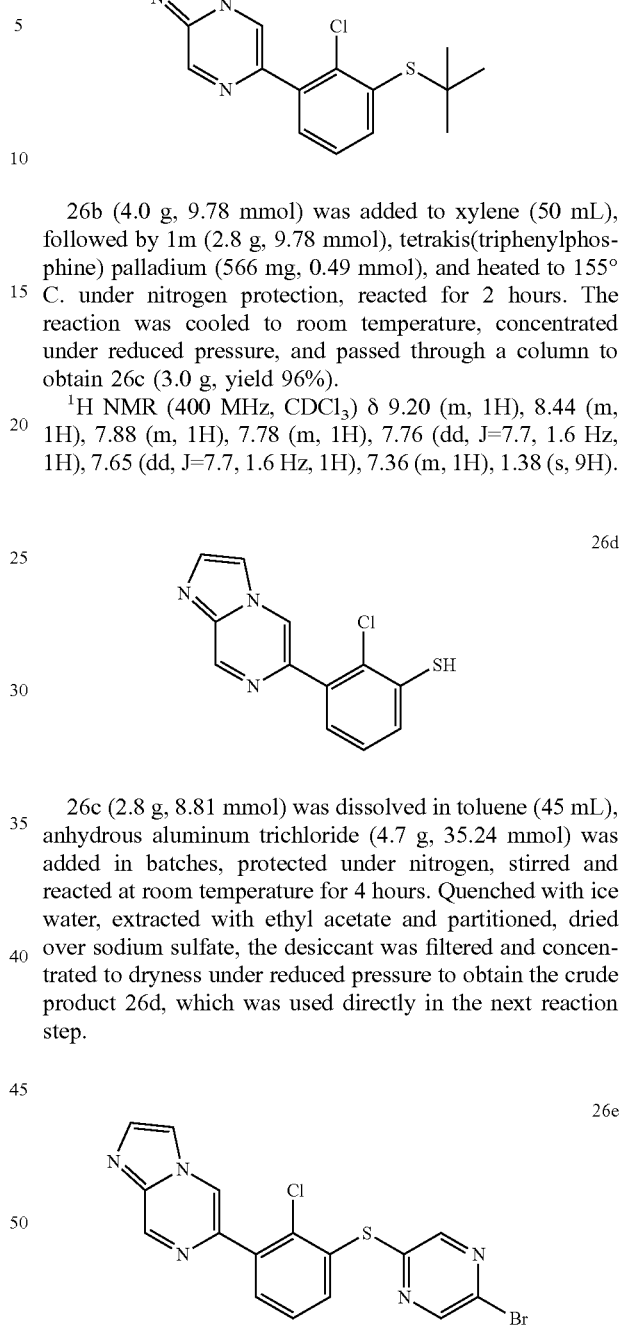

26b (4.0 g, 9.78 mmol) was added to xylene (50 mL), followed by 1m (2.8 g, 9.78 mmol), tetrakis(triphenylphosphine) palladium (566 mg, 0.49 mmol), and heated to 155° C. under nitrogen protection, reacted for 2 hours. The reaction was cooled to room temperature, concentrated under reduced pressure, and passed through a column to obtain 26c (3.0 g, yield 96%).

$^1$H NMR (400 MHz, CDCl$_3$) δ 9.20 (m, 1H), 8.44 (m, 1H), 7.88 (m, 1H), 7.78 (m, 1H), 7.76 (dd, J=7.7, 1.6 Hz, 1H), 7.65 (dd, J=7.7, 1.6 Hz, 1H), 7.36 (m, 1H), 1.38 (s, 9H).

26c (2.8 g, 8.81 mmol) was dissolved in toluene (45 mL), anhydrous aluminum trichloride (4.7 g, 35.24 mmol) was added in batches, protected under nitrogen, stirred and reacted at room temperature for 4 hours. Quenched with ice water, extracted with ethyl acetate and partitioned, dried over sodium sulfate, the desiccant was filtered and concentrated to dryness under reduced pressure to obtain the crude product 26d, which was used directly in the next reaction step.

26a (5.0 g, 25.25 mmol) was added to 1,4-dioxane (150 mL), followed by sodium carbonate (8.0 g, 75.75 mmol), tris(dibenzylideneacetone) dipalladium (1.16 g, 1.26 mmol), 2-dicyclohexylphosphino-2′, 6′-dimethoxy-biphenyl (1.04 g, 2.53 mmol), and hexa-n-butyl ditin (17.6 g, 30.30 mmol). Under the protection of nitrogen, the temperature was raised to 110° C. and reacted for 16 hours. The reaction was cooled to room temperature, concentrated under reduced pressure and passed through a column to obtain 26b (4.05 g, yield 39%).

$^1$H NMR (400 MHz, CDCl$_3$) δ 9.25 (brs, 1H), 7.99 (d, J=2.0 Hz, 1H), 7.75 (brs, 1H), 7.62 (s, 1H), 1.58 (m, 6H), 1.36 (m, 6H), 1.19 (m, 6H), 0.91 (m, 9H).

2,5-dibromopyrazine (8.4 g, 35.24 mmol) was dissolved in isopropanol (60 mL), under nitrogen protection, the temperature was raised to 65° C., and a mixture solution of 26d (2.2 g, 8.81 mmol)/isopropanol (15 mL)/N, N-diisopropylethylamine (2.27 g, 17.62 mmol) was slowly added dropwise for 1 hour, and continued stirring for 1 hour at 65° C. The reaction was cooled to room temperature, concentrated to dryness under reduced pressure and purified by column to obtain 26e (700 mg, yield 20%).

$^1$H NMR (400 MHz, CDCl$_3$) δ 9.20 (s, 1H), 8.48 (m, 2H), 8.14 (d, J=1.3 Hz, 1H), 7.88 (brs, 1H), 7.76 (m, 3H), 7.47 (t, J=7.6 Hz, 1H).

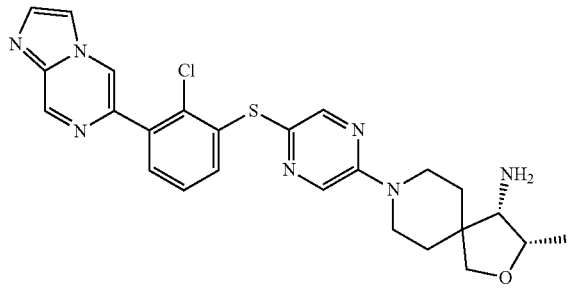

26e (700 mg, 1.67 mmol), 1j (528 mg, 2.17 mmol), and potassium phosphate (2.13 g, 10.02 mmol) were added to isopropanol (36 mL), displaced with nitrogen, the temperature was raised to 95° C. and stirred for 20 hours. The reaction was cooled to room temperature and concentrated under reduced pressure, the target product 26 (310 mg, yield 36%) was obtained.

$^1$H NMR (400 MHz, CDCl$_3$) δ 9.09 (s, 1H), 8.39 (s, 1H), 8.15 (d, J=21.3 Hz, 2H), 7.76 (d, J=17.1 Hz, 2H), 7.36 (d, J=7.3 Hz, 1H), 7.14 (t, J=7.8 Hz, 1H), 6.94 (d, J=7.7 Hz, 1H), 4.12 (m, 1H), 3.84 (m, 2H), 3.74 (m, 1H), 3.62 (m, 1H), 3.36 (m, 2H), 2.93 (m, 1H), 1.86-1.77 (m, 1H), 1.64 (m, 4H), 1.16 (d, J=6.3 Hz, 3H). LCMS m/z [M+H]$^+$: 508.2.

Example 27

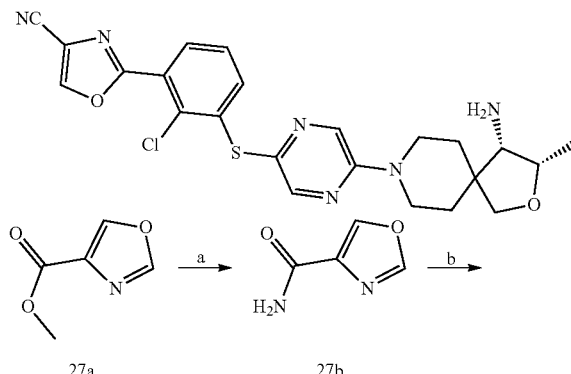
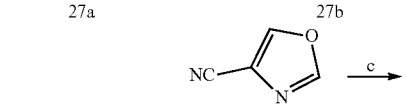
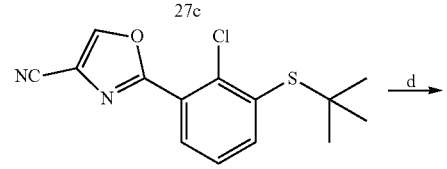
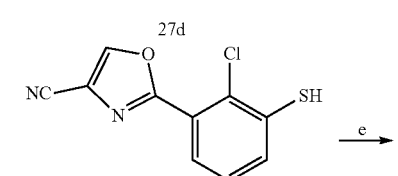

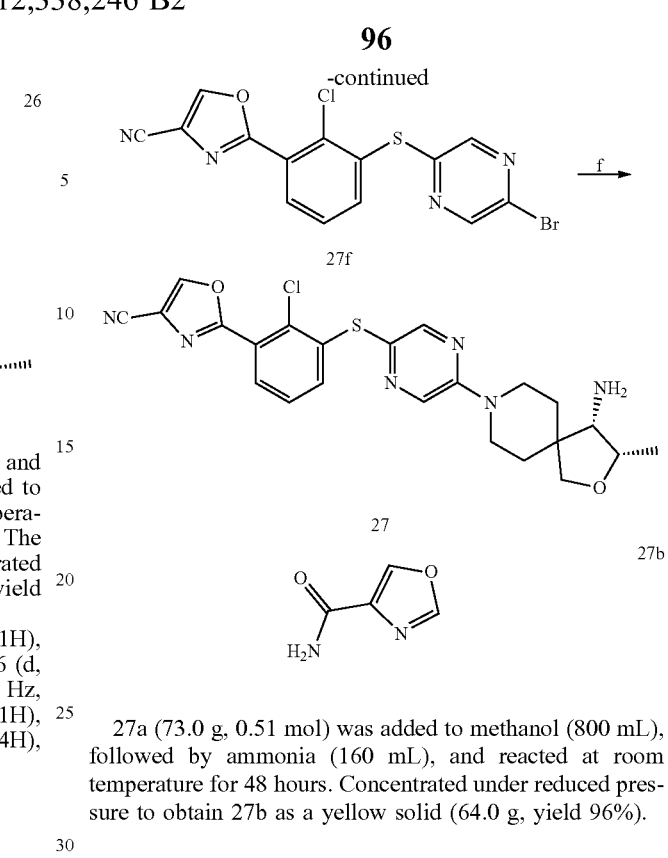

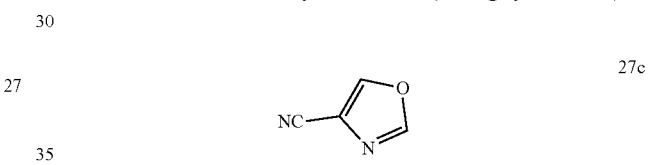

27a (73.0 g, 0.51 mol) was added to methanol (800 mL), followed by ammonia (160 mL), and reacted at room temperature for 48 hours. Concentrated under reduced pressure to obtain 27b as a yellow solid (64.0 g, yield 96%).

27b (56.0 g, 0.5 mol) was added to tetrahydrofuran (700 mL), followed by pyridine (79.1 g), TFFA (136.5 g) was slowly added dropwise under an ice-water bath, and then stirred at room temperature for 3 hours. Ethyl acetate was added, washed once each with water, diluted hydrochloric acid and saturated brine, the organic phase was dried with anhydrous sodium sulfate, the desiccant was filtered, the filtrate was concentrated under reduced pressure, and obtained 27c (34.0 g, yield 72%) by column chromatography.

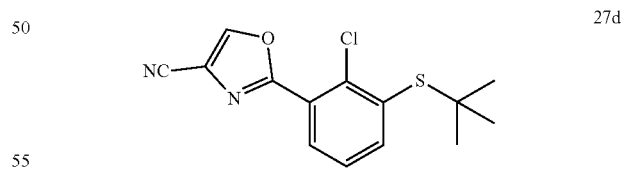

27c (30 g, 0.318 mol) was added to dioxane (50 mL), followed by 1m (104 g, 0.318 mol), palladium acetate (6.92 g, 0.0318 mol), 2-(dicyclohexylphosphino)biphenyl (11.14 g, 0.0318 mol), cesium carbonate (209.3 g, 0.637 mol), heated to 110° C. and stirred for 16 hours under nitrogen protection. The reaction was cooled to room temperature, concentrated under reduced pressure and passed through a column to obtain 27d (15 g, yield 15.9%).

$^1$H NMR (400 MHz, CDCl$_3$) δ 8.35 (s, 1H), 7.95-7.88 (m, 2H), 7.41 (t, J=8.0 Hz, 1H), 1.41 (s, 9H).

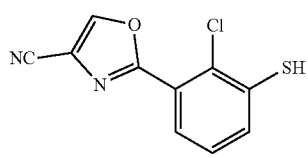

27d (10.0 g, 34.13 mmol) was dissolved in toluene (150 mL), anhydrous aluminum trichloride (27.3 g, 204.78 mmol) was added, protected with nitrogen, and stirred at room temperature to react for 4 hours. Quenched with ice water, extracted with ethyl acetate and partitioned, dried over anhydrous sodium sulfate, the desiccant was filtered, and concentrated under reduced pressure to obtain crude product 27e, which was used directly in the next reaction step.

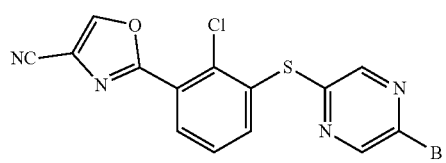

2,5-dibromopyrazine (20.3 g, 85.33 mmol) and 27d (8.0 g, 34.13 mmol) were added to acetonitrile (150 mL), followed by N, N-diisopropylethylamine (8.82 g, 68.26 mmol), protected with nitrogen, and stirred at room temperature for 2 hours. Concentrated under reduced pressure and purified by column to obtain 27e (2.5 g, two-step yield 18.0%).

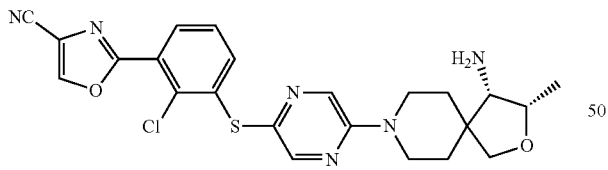

27e (2.5 g, 6.35 mmol), 1j (1.85 g, 7.62 mmol), and potassium phosphate (8.09 g, 38.10 mmol) were added to N—N dimethylformamide (50 mL) and stirred at 70° C. under nitrogen protection for 4 hours. Water was added and the solid was precipitated, filtered to obtain the solid, and passed through the column to obtain the target product 27 (1.1 g, yield 37%).

$^1$H NMR (400 MHz, CDCl$_3$) δ 8.34 (s, 1H), 8.31 (m, 1H), 8.24 (m, 1H), 7.80-7.78 (m, 1H), 7.27 (d, J=8.0 Hz, 1H), 7.19-7.17 (m, 1H), 4.27-4.21 (m, 1H), 3.98-3.97 (m, 2H), 3.84 (d, J=4.0 Hz, 1H), 3.74 (d, J=8.0 Hz, 1H), 3.55-3.44 (m, 2H), 3.04 (d, J=4.0 Hz, 1H), 1.95-1.74 (m, 6H), 1.30 (s, 5H). LCMS m/z [M+H$^+$]: 483.2.

Example 28

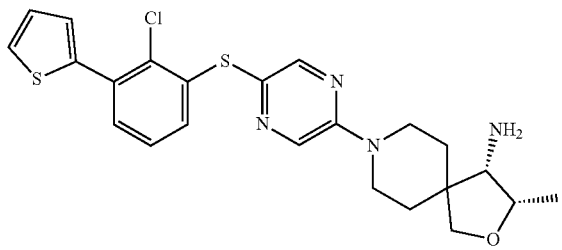

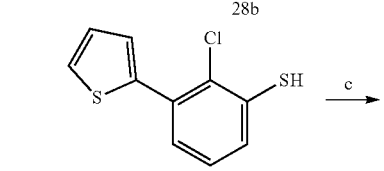

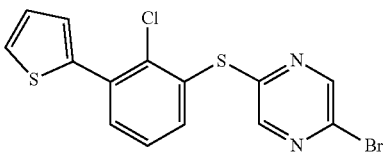

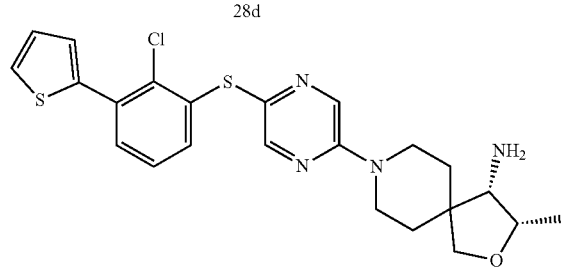

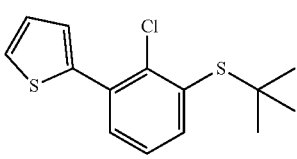

28a (3.87g, 45.92 mmol) was added to N—N dimethylformamide (50 mL), followed by 1m (3.0 g, 9.18 mmol), palladium acetate (207 mg, 0.92 mmol), 2-(dicyclohexylphosphino)biphenyl (644 mg, 1.84 mmol), and cesium carbonate (5.97 g, 18.36 mmol), under the protection of nitrogen, the temperature was raised to 110° C. and reacted for 16 hours. The reaction was cooled to room temperature, water was added, extracted with ethyl acetate, the organic phase was washed twice with saturated brine, dried with anhydrous sodium sulfate, the desiccant was filtered, concentrated under reduced pressure and passed through the column to obtain 28b (1.8 g, yield 69%).

¹H NMR (400 MHz, CDCl₃) δ 7.69 (d, J=8.0 Hz, 1H), 7.55 (d, J=8.0 Hz, 1H), 7.45 (d, J=4.0 Hz, 1H), 7.40 (d, J=4.0 Hz, 1H), 7.29 (t, J=4.0 Hz, 1H), 7.15 (t, J=4.0 Hz, 1H), 1.43 (s, 9H).

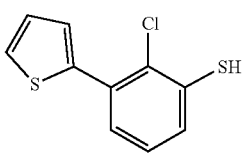

28c 28b (1.2 g, 4.23 mmol) was dissolved in toluene (50 mL), anhydrous aluminum trichloride (3.4 g, 25.35 mmol) was added, protected with nitrogen, and stirred the reaction at room temperature for 3 hours. Quenched with ice water, extracted with ethyl acetate and partitioned, dried over sodium sulfate, the desiccant was filtered and concentrated under reduced pressure to obtain crude product 28c, which was used directly in the next reaction step.

¹H NMR (400 MHz, DMSO) δ 7.45 (d, J=4.0 Hz, 1H), 7.38-7.35 (m, 3H), 7.21-7.15 (m, 2H), 4.02 (s, 1H).

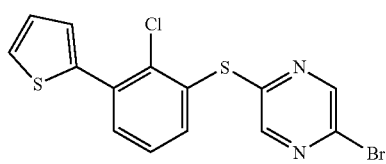

28d 2,5-dibromopyrazine (2.52 g, 10.58 mmol) was dissolved in isopropanol (25 mL), under nitrogen protection, the temperature was raised to 80° C., and a mixture solution of 28c (960 mg, 4.23 mmol)/isopropanol (25 mL)/N,N-diisopropylethylamine (1.1 g, 8.46 mmol) was slowly added dropwise in 1 hour, and continued stirring for 2 hours at 80° C. The reaction was cooled to room temperature, concentrated under reduced pressure, and purified by column to obtain 28d (810 mg, yield 50%).

LCMS m/z [M+H+]: 383.0.

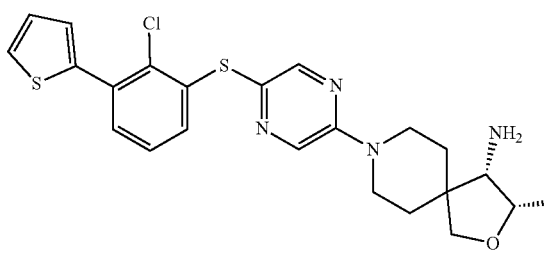

28

28d (810 mg, 2.12 mmol), 1j (620 mg, 2.54 mmol), and potassium phosphate (2.70 g, 12.72 mmol) were added to N—N dimethylformamide (10 mL), displaced with nitrogen, and stirred at 100° C. for 16 hours. Water was added and the solid was precipitated, filtered to obtain the solid, and passed through a reverse-phase column to obtain the target product 28 (150 mg, yield 15%).

¹H NMR (400 MHz, CDCl₃) δ 8.34 (s, 1H), 8.31 (m, 1H), 8.24 (m, 1H), 7.80-7.78 (m, 2H), 7.27 (d, J=8.0 Hz, 2H), 7.19-7.17 (m, 1H), 4.27-4.21 (m, 1H), 3.98-3.97 (m, 2H), 3.84 (d, J=4.0 Hz, 1H), 3.74 (d, J=8.0 Hz, 1H), 3.55-3.44 (m, 2H), 3.04 (d, J=4.0 Hz, 1H), 1.95-1.74 (m, 6H), 1.30 (s, 3H). LCMS m/z [M+H+]: 473.2.

Example 29

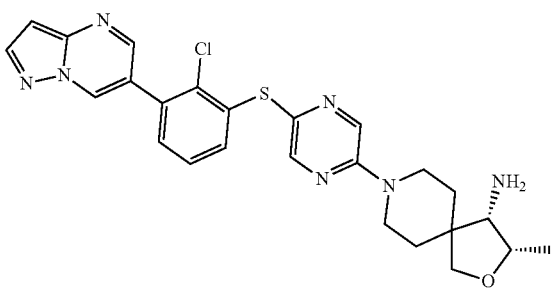

29

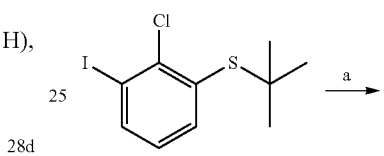

1m

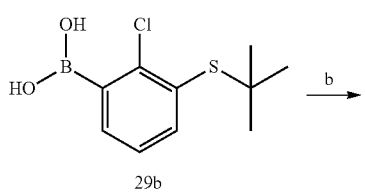

29b

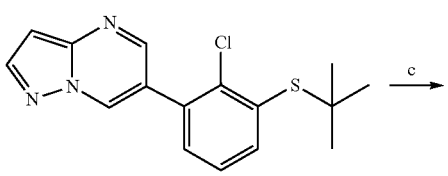

29c

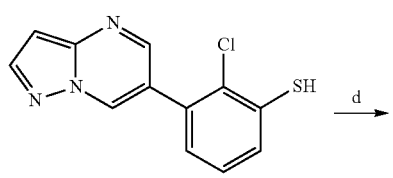

29d

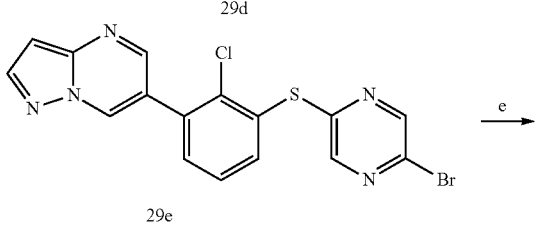

29e

-continued

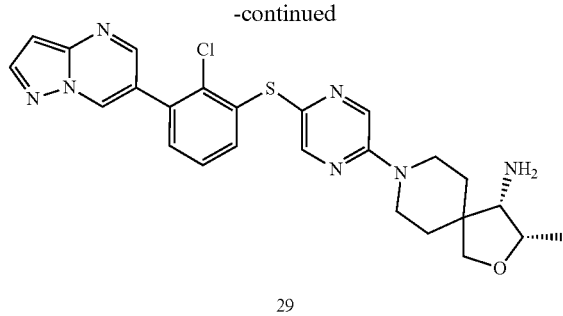

29

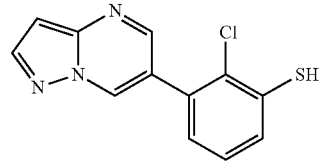

29d 29c (0.82 g, 2.58 mmol) was dissolved in toluene (20 mL), anhydrous aluminum trichloride (1.376 g, 10.32 mmol) was added under an ice-water bath, protected with nitrogen, and stirred at room temperature to react for 4 hours. Quenched with ice water, extracted with ethyl acetate, the organic phase was dried with anhydrous sodium sulfate, filtered and concentrated under reduced pressure to obtain the crude product 29d, which was used directly in the next reaction step.

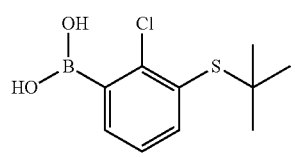

29b

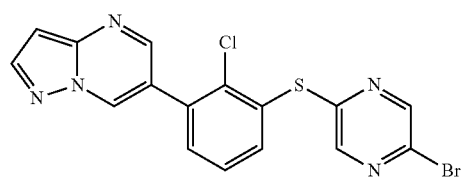

29e 1m (3.0 g, 9.2 mmol) was added to borane tetrahydrofuran complex (19.98 mL, 19.98 mmol), followed by magnesium flakes (0.225 g, 9.2 mmol), and reacted under ultrasonication until the magnesium flakes disappeared. Then, water was slowly added dropwise and the temperature was raised to 100° C. and stirred for 2 hours. The reaction was cooled to room temperature, dilute hydrochloric acid was added, extracted with ethyl acetate, the organic phase was washed once with saturated brine, dried with anhydrous sodium sulfate, filtered, concentrated under reduced pressure, beat with dichloromethane and petroleum ether to obtain a white solid 29b (1.8 g, yield 80%).

$^1$H NMR (400 MHz, CDCl$_3$) δ 7.95 (dd, J=7.5, 1.7 Hz, 1H), 7.76 (dd, J=7.6, 1.8 Hz, 1H), 7.29 (t, J=7.5 Hz, 1H), 5.40 (s, 2H), 1.34 (s, 9H).

2,5-dibromopyrazine (2.455 g, 10.32 mmol) was dissolved in isopropanol (20 mL), under nitrogen protection, the temperature was raised to 80° C., a mixture of 29d (2.58 mmol)/isopropanol (30 mL)/N,N-diisopropylethylamine (1.7 mL, 10.32 mmol) was slowly added dropwise for 2 hours, and continued stirring at 80° C. for 1 hour. Cooled to room temperature, concentrated under reduced pressure, and purified by column to obtain 29e (309 mg, yield 31%).

$^1$H NMR (400 MHz, CDCl$_3$) δ 8.77 (dd, J=2.2, 0.8 Hz, 1H), 8.58 (d, J=2.2 Hz, 1H), 8.48 (d, J=1.4 Hz, 1H), 8.21 (d, J=1.4 Hz, 1H), 8.19 (d, J=2.3 Hz, 1H), 7.75 (dd, J=7.5, 2.0 Hz, 1H), 7.57-7.42 (m, 2H), 6.77 (dd, J=2.3, 0.7 Hz, 1H).

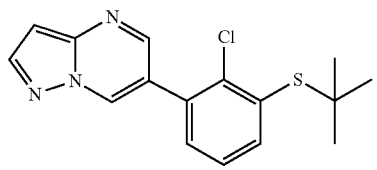

29c

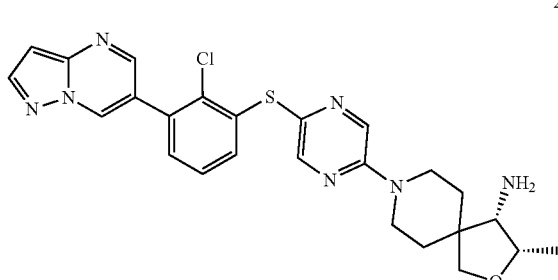

29

29b (0.737 g, 3.02 mmol) was added to dioxane (15 mL), followed by water (5 mL), 6-bromopyrazolo[1,5-A]pyrimidine (0.6 g, 3.02 mmol), tetrakis(triphenylphosphine) palladium (0.349 g, 0.302 mmol), potassium carbonate (1.253 g, 9.06 mmol), heated to 110° C. and stirred for 16 hours under nitrogen protection. Cooled to room temperature, water was added, extracted with ethyl acetate, the organic phase was washed once with saturated brine, dried over anhydrous sodium sulfate, filtered, concentrated under reduced pressure, and passed through the column to obtain 29c (0.82 g, yield 85%).

$^1$H NMR (400 MHz, CDCl$_3$) δ 8.74 (d, J=1.5 Hz, 1H), 8.58 (d, J=2.1 Hz, 1H), 8.17 (d, J=2.3 Hz, 1H), 7.76 (dd, J=7.2, 2.2 Hz, 1H), 7.42-7.32 (m, 2H), 6.75 (d, J=1.9 Hz, 1H), 1.39 (s, 9H).

29e (200 mg, 0.478 mmol), 1j (139 mg, 0.573 mmol), potassium phosphate (406 mg, 1.912 mmol) were added to N—N dimethylformamide (10 mL) and the temperature was raised to 80° C. and stirred for 4 hours under nitrogen protection. Cooled to room temperature, water was added, extracted with dichloromethane, dried over anhydrous sodium sulfate, filtered, concentrated under reduced pressure and passed through the column to obtain the target product 29 (169 mg, yield 68%).

$^1$H NMR (400 MHz, CDCl$_3$) δ 8.74 (d, J=1.4 Hz, 1H), 8.57 (d, J=2.2 Hz, 1H), 8.27 (d, J=1.2 Hz, 1H), 8.21 (d, J=1.1

Hz, 1H), 8.17 (d, J=2.3 Hz, 1H), 7.25-7.13 (m, 2H), 7.04 (dd, J=7.6, 1.8 Hz, 1H), 6.75 (d, J=1.7 Hz, 1H), 4.28-4.15 (m, 1H), 4.08-3.87 (m, 2H), 3.82 (d, J=8.8 Hz, 1H), 3.70 (d, J=8.8 Hz, 1H), 3.52-3.45 (m, 1H), 3.41-3.35 (m, 1H), 3.01 (d, J=4.5 Hz, 1H), 1.94-1.87 (m, 1H), 1.84-1.64 (m, 3H), 1.38 (brs, 2H), 1.24 (d, J=6.4 Hz, 3H). LCMS m/z [M+H$^+$]: 508.3.

Example 30

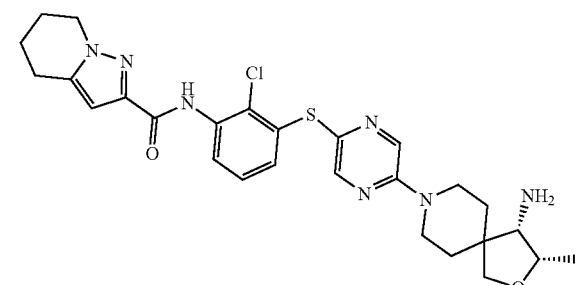

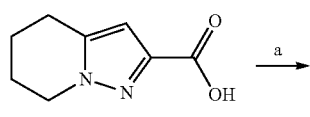

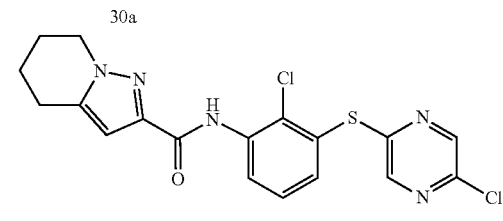

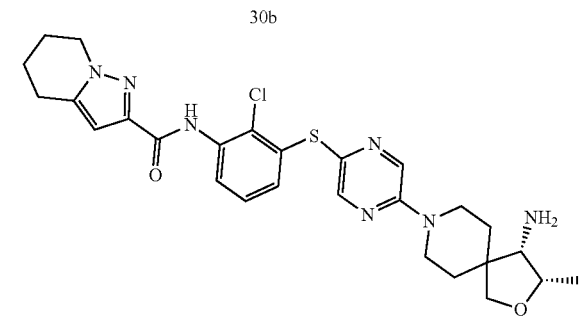

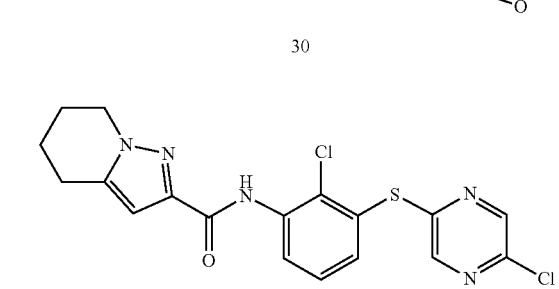

30a (41.5 mg, 0.25 mmol) was dissolved in dichloromethane (3.0 mL), 2 drops of N—N dimethylformamide was added, then oxalyl chloride (1.0 mL) was slowly added in an ice water bath and the reaction was stirred for 4 h at room temperature under nitrogen protection. Concentrated under reduced pressure to obtain acyl chloride. Dichloromethane (3.0 mL), 10b (68.0 mg, 0.25 mmol), N, N-diisopropylethylamine (0.164 mL, 1.0 mmol) were added to acyl chloride and stirred for 2 h at room temperature. Concentrated under reduced pressure and passed through column chromatography to obtain a white solid 30b (21.0 mg, 20% yield).

$^1$H NMR (400 MHz, CDCl$_3$) δ 9.44 (s, 1H), 8.74 (dd, J=8.2, 1.6 Hz, 1H), 8.37 (d, J=1.3 Hz, 1H), 8.04 (d, J=1.3 Hz, 1H), 7.43 (dd, J=7.7, 1.7 Hz, 1H), 7.37 (t, J=7.9 Hz, 1H), 6.61 (s, 1H), 4.19 (t, J=6.2 Hz, 2H), 2.85 (t, J=6.4 Hz, 2H), 2.16-1.98 (m, 2H), 1.97-1.82 (m, 2H).

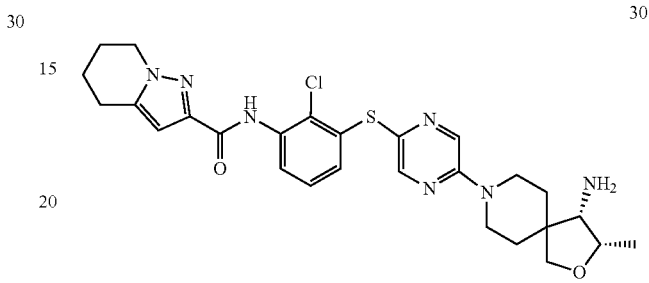

30b (83.0 mg, 0.198 mmol) was dissolved in N—N dimethylformamide (5 mL), followed by 1j (57.8 mg, 0.237 mmol) and potassium phosphate (168.1 mg, 0.792 mmol), and the temperature was raised to 80° C. and stirred for 4 h under nitrogen protection. Cooled to room temperature, water was added, extracted with dichloromethane, dried with anhydrous sodium sulfate, the desiccant was filtered, concentrated under reduced pressure, and the target product 30 (40 mg, 37% yield) was obtained over the column.

$^1$H NMR (400 MHz, CDCl$_3$) δ 9.39 (s, 1H), 8.44 (dd, J=8.3, 1.3 Hz, 1H), 8.19 (d, J=1.3 Hz, 1H), 8.16 (d, J=1.3 Hz, 1H), 7.16 (t, J=8.1 Hz, 1H), 6.79 (dd, J=7.9, 1.4 Hz, 1H), 6.59 (s, 1H), 4.20 (t, J=6.1 Hz, 3H), 4.01-3.85 (m, 2H), 3.82 (d, J=8.8 Hz, 1H), 3.70 (d, J=8.8 Hz, 1H), 3.54-3.28 (m, 2H), 3.01 (d, J=4.3 Hz, 1H), 2.84 (t, J=6.4 Hz, 2H), 2.14-2.01 (m, 2H), 1.97-1.83 (m, 3H), 1.82-1.63 (m, 3H), 1.50-1.27 (m, 1H), 1.25 (d, J=6.4 Hz, 3H), 1.13 (d, J=6.1 Hz, 1H). LCMS m/z [M+H$^+$]: 554.3.

Example 31

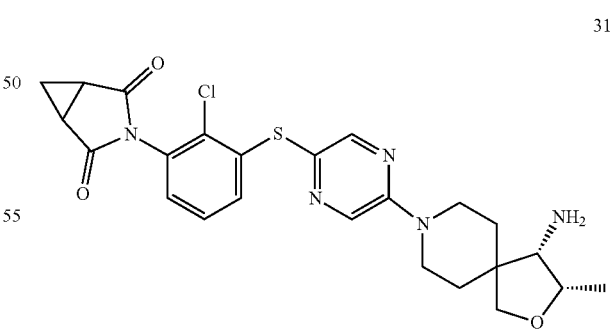

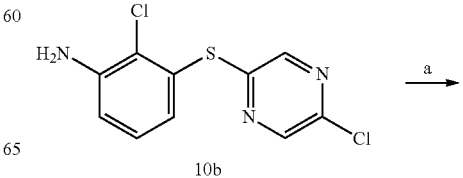

-continued

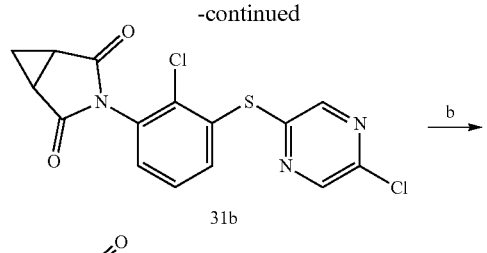

31b

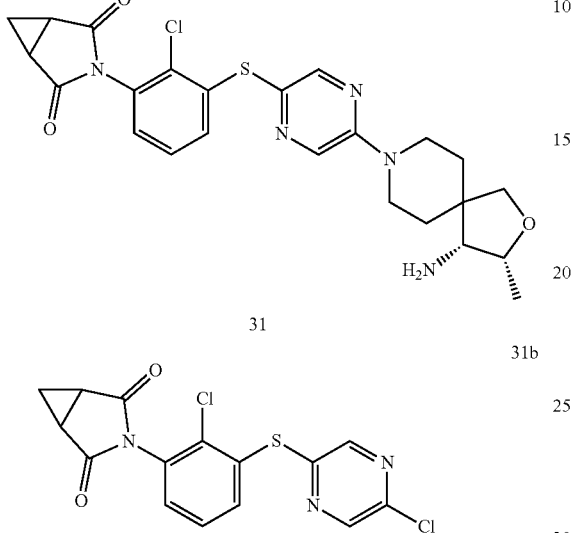

To a solution of 10b (400 mg, 1.48 mmol) in dichloroethane (10 mL), 3-oxabicyclo[3.1.0] hexane-2,4-dione (200 mg, 1.67 mmol) was added, under the protection of nitrogen, the temperature was raised to 100° C. to react for 1.5 hours. Cooled to room temperature, N, N'-carbonyl diimidazole (360 mg, 2.22 mmol) was added, under nitrogen protection, the temperature was raised to 100° C. to react for 4 h. Cooled to room temperature and stirred overnight. Concentrated under reduced pressure and passed through column chromatography to obtain a light yellow solid 31b (300 mg, 46% yield).

$^1$H NMR (400 MHz, CDCl$_3$): δ 8.42 (s, 1H), 8.17 (s, 1H), 7.79-7.76 (m, 1H), 7.48 (t, J=8.0 Hz, 1H), 7.44-7.41 (m, 1H), 2.76-2.70 (m, 2H), 1.94-1.91 (m, 1H), 1.75-1.71 (m, 1H).

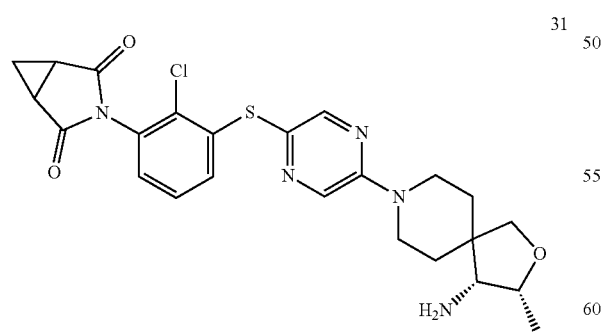

31b (250 mg, 0.68 mmol), 1j (196 mg, 0.81 mmol), potassium phosphate (864 mg, 4.07 mmol) were added to N, N-dimethylformamide (5 mL). Under nitrogen protection, the temperature was raised to 80° C. and stirred for 4 hours. Water was added, extracted with dichloromethane, dried with anhydrous sodium sulfate, the desiccant was filtered, concentrated under reduced pressure, and passed through the column to obtain the target product 31 (50 mg, yield 18%).

$^1$H NMR (400 MHz, CDCl$_3$): δ 8.27 (s, 1H), 8.23 (s, 1H), 7.24 (t, J=8.0 Hz, 1H), 7.14-7.10 (m, 2H), 4.25-4.23 (m, 1H), 4.02-3.95 (m, 2H), 3.87 (d, J=8.0 Hz, 1H), 3.73 (d, J=8.0 Hz, 1H), 3.51-3.40 (m, 2H), 3.06-3.05 (m, 1H), 2.74-2.68 (m, 2H), 1.97-1.95 (m, 2H), 1.81-1.72 (m, 4H), 1.32 (d, J=8.0 Hz, 3H). LCMS m/z [M+H$^+$]: 500.3.

Example 32

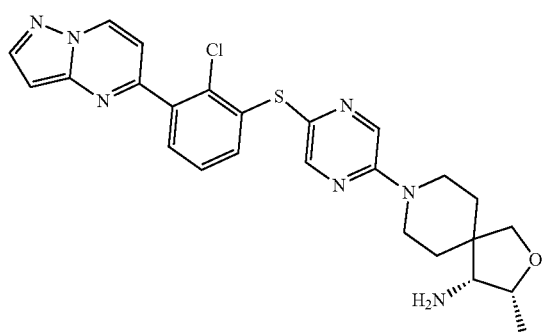

32

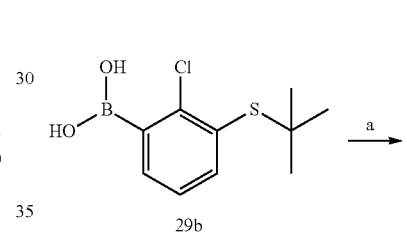

29b

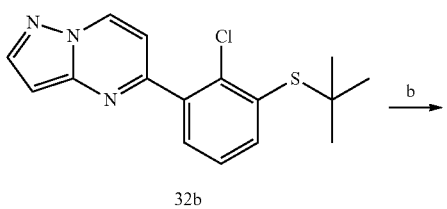

32b

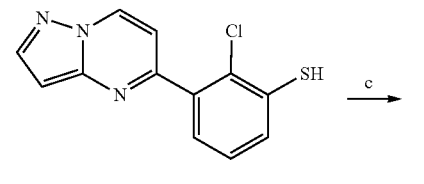

32c

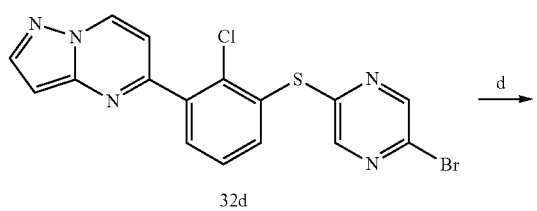

32d

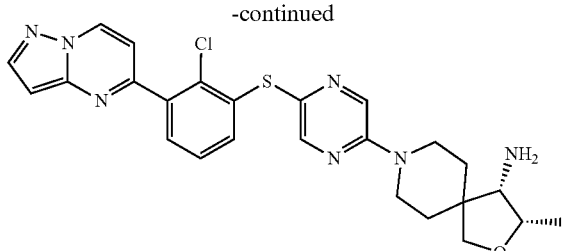

32

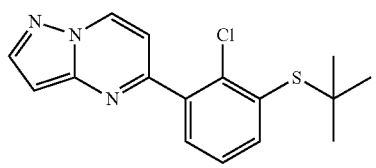

32b 29b (0.584 g, 2.393 mmol) was added to dichloroethane (10 mL), followed by water (10 mL), 5-chloropyrazolo[1,5-a]pyrimidine (0.3676 g, 2.393 mmol), [1,1'-Bis (diphenylphosphino) ferrocenyl]palladium dichloride (0.0875 g, 0.1197 mmol), and sodium carbonate (1.268 g, 11.965 mmol), under nitrogen protection, the temperature was raised to 95° C. and stirred for 16 hours. Cooled to room temperature, water was added, extracted with ethyl acetate, the organic phase was washed with saturated brine once, dried with anhydrous sodium sulfate, the desiccant was filtered, concentrated under reduced pressure, and passed through the column to obtain 32b (0.678 g, yield 89%).

¹H NMR (400 MHz, Chloroform-d) δ 8.71 (d, J=7.2 Hz, 1H), 8.16 (d, J=2.2 Hz, 1H), 7.77 (dd, J=7.7, 1.6 Hz, 1H), 7.62 (dd, J=7.7, 1.6 Hz, 1H), 7.37 (t, J=7.7 Hz, 1H), 7.16 (d, J=7.2 Hz, 1H), 6.78-6.73 (m, 1H), 1.37 (s, 9H).

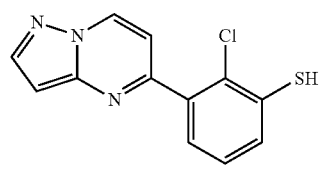

32c 32b (0.68 g, 2.14 mmol) was dissolved in toluene (20 mL), anhydrous aluminum trichloride (1.14 g, 10.32 mmol) was added under an ice-water bath, and under nitrogen protection, the reaction was stirred for 4 hours at room temperature. Quenched with ice water, extracted with ethyl acetate and partitioned, dried with anhydrous sodium sulfate, the desiccant was filtered, and concentrated under reduced pressure to obtain the crude product 32c, which was used directly in the next reaction.

32d 2,5-dibromopyrazine (2.04 g, 8.56 mmol) was dissolved in isopropanol (10 mL), under nitrogen protection, the temperature was raised to 80° C., a mixture solution of 32c (2.14 mmol)/isopropanol (25 mL)/N, N-diisopropylethylamine (1.414 mL, 8.56 mmol) was slowly added dropwise in 2 hours, and continued stirring at 80° C. for 1 hour. Cooled to room temperature, concentrated under reduced pressure, and purified by column to obtain 32d (0.2 g, yield 22%).

¹H NMR (400 MHz, CDCl₃) δ 8.73 (d, J=7.3 Hz, 1H), 8.46 (d, J=1.4 Hz, 1H), 8.19 (d, J=2.3 Hz, 1H), 8.15 (d, J=1.4 Hz, 1H), 7.77 (ddd, J=12.0, 7.7, 1.6 Hz, 2H), 7.48 (t, J=7.7 Hz, 1H), 7.16 (d, J=7.3 Hz, 1H), 6.78 (d, J=2.2 Hz, 1H).

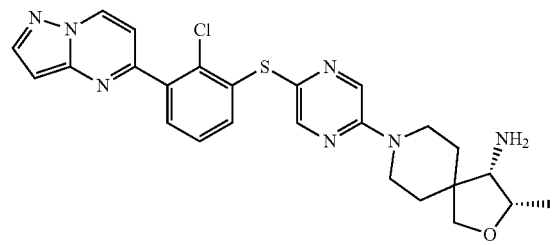

32

32d (200 mg, 0.478 mmol), 1j (139 mg, 0.573 mmol), and potassium phosphate (406 mg, 1.912 mmol) were added to N—N dimethylformamide (10 mL) and stirred at 80° C. for 4 hours under nitrogen protection. Cooled to room temperature, water was added, extracted with dichloromethane, dried over anhydrous sodium sulfate, filtered, concentrated under reduced pressure, and passed through the column to obtain the target product 32 (143 mg, yield 57%).

¹H NMR (400 MHz, CDCl₃) δ 7.45 (dd, J=7.6, 1.6 Hz, 1H), 7.25 (t, J=7.8 Hz, 1H), 7.16 (d, J=7.3 Hz, 1H), 7.09 (dd, J=8.0, 1.6 Hz, 1H), 6.76 (dd, J=2.3, 0.7 Hz, 1H), 4.25-4.15 (m, 1H), 4.04-3.87 (m, 2H), 3.83 (d, J=8.8 Hz, 1H), 3.70 (d, J=8.8 Hz, 1H), 1.96-1.84 (m, 1H), 1.82-1.64 (m, 3H), 1.25 (m, 4H), 1.13 (d, J=6.1 Hz, 1H).

LCMS m/z [M+H⁺]: 508.3.

Example 33

33

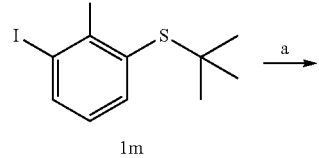

1m

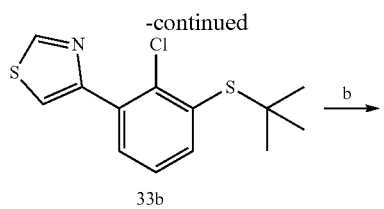

33b

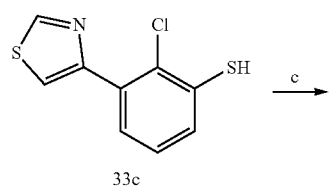

33c

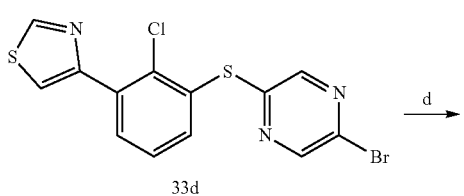

33d

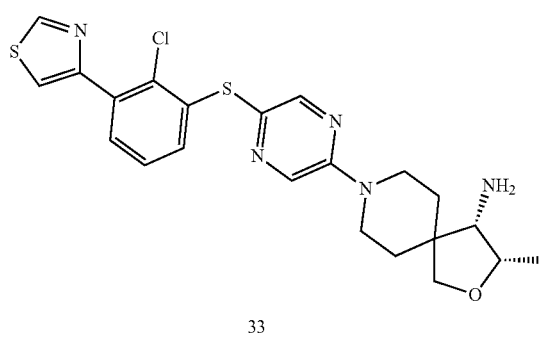

33

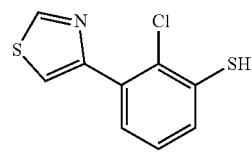

33c 33b (350 mg, 1.23 mmol) was dissolved in acetonitrile (0.5 mL), concentrated hydrochloric acid (12 M, 5 mL) was added, and reacted at 110° C. for 5 hours. After adding water (10 mL), extracted with ethyl acetate (20 mL) twice, washed with saturated brine (20 mL) once, dried with sodium sulfate (5.0 g), filtered, and the filtrate was concentrated under reduced pressure to dryness and it was used directly in the next reaction.

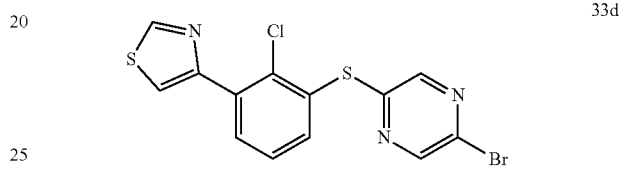

33d 2,5-dibromopyrazine (454 mg, 3.5 mmol) was added to isopropanol (10 mL), protected by nitrogen, the temperature was raised to 80° C., N,N-diisopropylethylamine (671 mg, 2.82 mmol) and 33c in isopropanol were slowly added, continuously added dropwise for 1 hour, and then the temperature was raised to 80° C. overnight. Water (20 mL) was added, extracted with ethyl acetate (20 mL) twice, dried with sodium sulfate (5.0 g), filtered, and the filtrate was concentrated under reduced pressure to dryness. Purified by column chromatography to obtain 33d (120 mg).

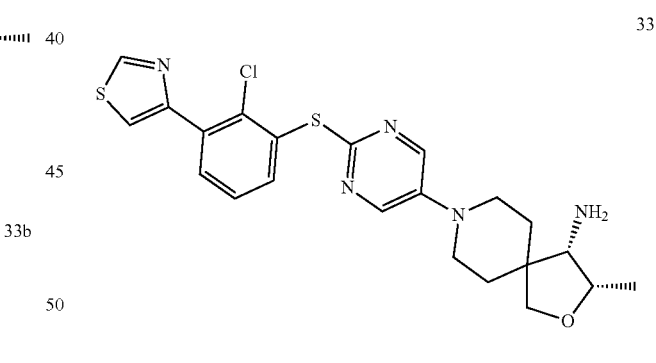

33

To compound 33d (50 mg, 0.13 mmol) and 1j (25.5 mg, 0.15 mmol), N, N-dimethylformamide (2 mL) was added, followed by potassium phosphate (166.5 mg, 0.78 mmol), and heated to 110° C. and reacted for 2 hours. 20 mL of water was added, extracted twice with ethyl acetate (20 mL), washed three times with saturated brine (20 mL), the organic phase was dried with sodium sulfate (5.0 g), spin-dried, passed through a normal phase column and scraped off the plate to obtain 33 (35 mg, 28% yield).

$^1$H NMR (400 MHz, CDCl$_3$) δ 8.92 (s, 1H), 8.29-9.24 (m, 2H), 8.09 (m, 1H), 7.35-6.34 (m, 1H), 7.23-7.19 (m, 1H), 7.06-7.04 (m, 1H), 4.28-4.24 (m, 1H), 4.03-3.98 (m, 2H), 3.92-3.89 (m, 1H), 3.77-3.74 (m, 1H), 3.53-3.52 (m, 1H), 3.41-3.35 (m, 1H), 3.12-3.11 (m, 1H), 2.05-1.97 (m, 2H), 1.80-1.78 (m, 2H), 1.30 (s, 3H). LCMS m/z [M+H]$^+$: 488.4.

Thiazole (300 mg, 3.5 mmol), 1m (1.4 g, 4.23 mmol), 2-(dicyclohexylphosphino)biphenyl (123.5 mg, 0.35 mmol), palladium acetate (158 mg, 0.70 mmol), cesium carbonate (2.27 g, 7.0 mmol) were added to dioxane (10 mL). It was displaced with nitrogen three times, and the reaction was stirred overnight at 110° C. The reaction solution was cooled to room temperature, 50 mL of water was added, and the mixture was extracted three times with ethyl acetate. The organic phases were combined, washed with saturated aqueous sodium chloride solution, dried over anhydrous sodium sulfate, and purified by column to obtain an oily product 33b (350 mg, yield: 35.2%).

Example 34

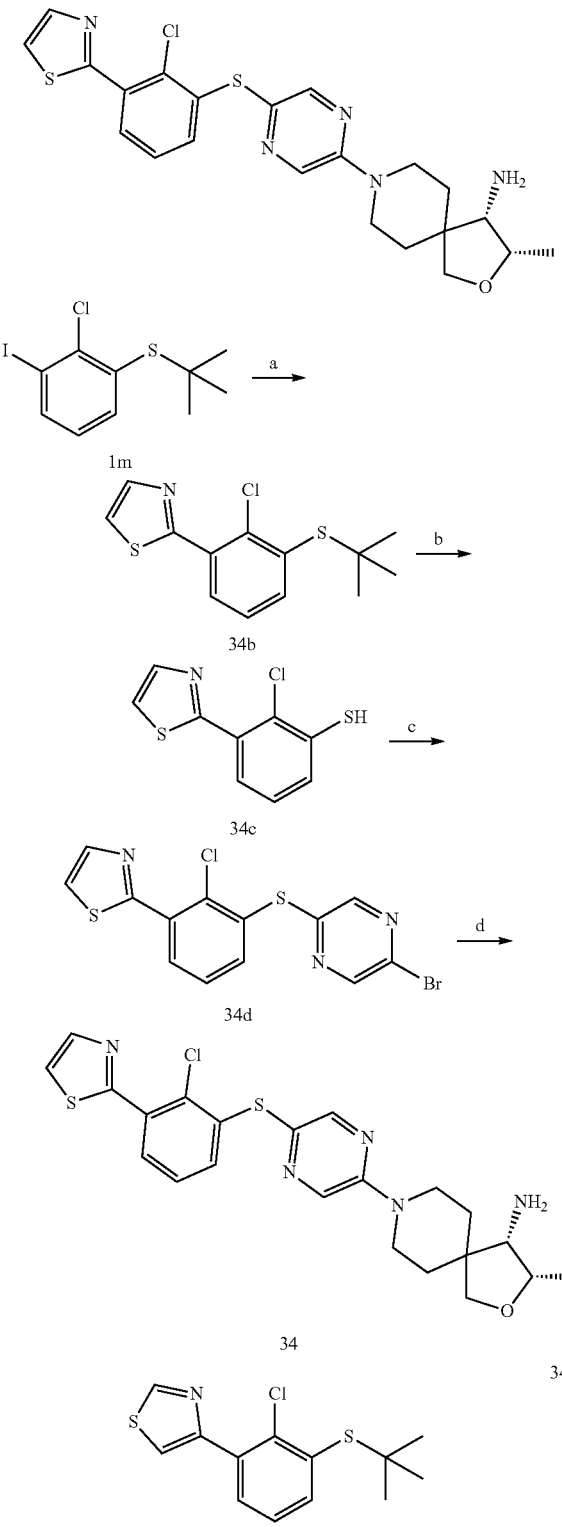

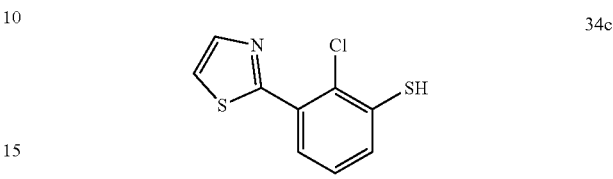

Thiazole (175 mg, 1.8 mmol), 34a (500 mg, 1.5 mmol), cuprous iodide (58 mg, 0.3 mmol), and cesium carbonate (1 g, 3 mmol) were added to dioxane (5 mL). Reacted at 140° C. for 48 hours. The reaction solution was cooled to room temperature, 50 mL of water was added, extracted with ethyl acetate (30 mL) three times, the organic phases were combined, washed once with saturated sodium chloride aqueous solution (50 mL), dried with anhydrous sodium sulfate (5.0 g), and purified by column to obtain 34b (160 mg, yield 37.6%).

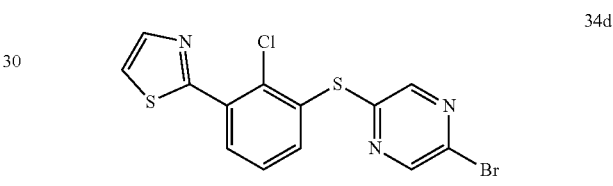

34b (160 mg, 0.56 mmol) was dissolved in acetonitrile (0.5 mL), concentrated hydrochloric acid (12 M, 5 mL) was added, and reacted at 110° C. for 5 hours. After adding water (10 mL), extracted with ethyl acetate (20 mL) twice, washed with saturated brine (20 mL) once, dried with sodium sulfate (5.0 g), filtered, and the filtrate was concentrated under reduced pressure to dryness and it was directly used in the next reaction.

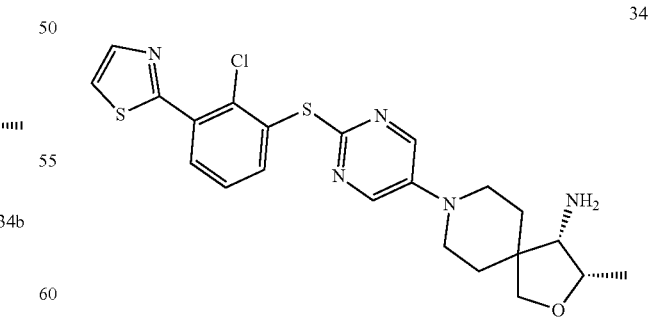

2,5-dibromopyrazine (337.4 mg, 1.4 mmol) was added to isopropanol (10 mL), protected with nitrogen, the temperature was raised to 80° C., N,N-diisopropylethylamine (146 mg, 1.12 mmol) and 34c in isopropanol (2 mL) were slowly added, continuously added dropwise for 1 hour, and then the temperature was raised to 80° C. overnight. The temperature was lowered to room temperature, water (20 mL) was added, extracted with ethyl acetate (20 mL) twice, dried with sodium sulfate (5.0 g), filtered, the filtrate was concentrated under reduced pressure to dryness, and purified by column to obtain 34d (30 mg, yield 13.9%).

N, N-dimethylformamide (2 mL) was added to compound 34d (30 mg, 0.078 mmol) and 1j (20 mg, 0.086 mmol), followed by potassium phosphate (99 mg, 0.47 mmol), and heated to 110° C., reacted for 2 hours. Cooled to room temperature and 20 mL of water was added, extracted twice with ethyl acetate (20 mL), washed three times with saturated brine (20 mL), the organic phase was dried with sodium sulfate (5.0 g), and purified by column to obtain 34 (12 mg, yield 32.5%).

$^1$H NMR (400 MHz, CDCl$_3$) δ 8.15 (s, 1H), 8.10 (s, 1H), 7.89-7.85 (m, 2H), 7.41-7.40 (m, 1H), 7.14-7.10 (m, 1H), 6.97-9.65 (m, 1H), 4.12-4.06 (m, 1H), 3.88-3.79 (m, 2H), 3.73-3.71 (m, 1H), 3.61-3.59 (m, 1H), 3.40-3.25 (m, 2H), 2.92-2.90 (m, 1H), 1.82-1.62 (m, 4H), 1.15 (s, 3H). LCMS m/z [M+H]$^+$: 474.2.

Example 35

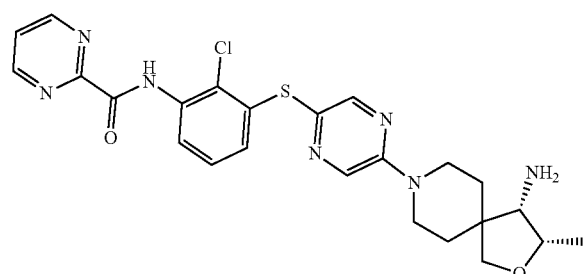

35

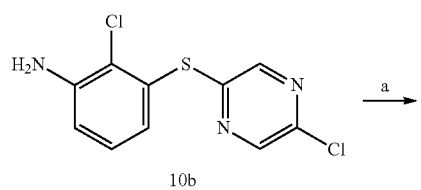

10b

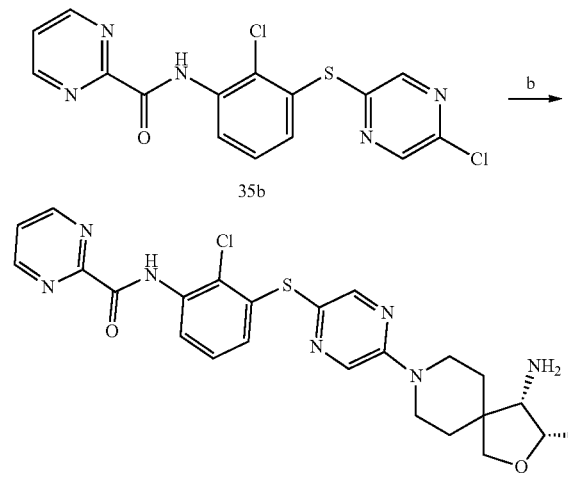

35b

35

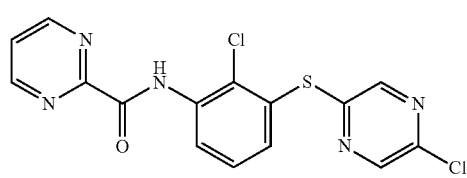

35b

Dichloroethane (5 mL) was added to 10b (50 mg, 0.18 mmol), pyrimidine-2-carboxylic acid (27 mg, 0.22 mmol), and N,N-carbonyldiimidazole (44 mg, 0.27 mmol). Reacted at 130° C. for 48 hours. Cooled to room temperature, water (20 mL) was added, extracted with ethyl acetate (20 mL) twice, washed with saturated brine (20 mL) once, dried with sodium sulfate (5.0 g), filtered, concentrated under reduced pressure to dryness, and purified by column to obtain 35b (90 mg).

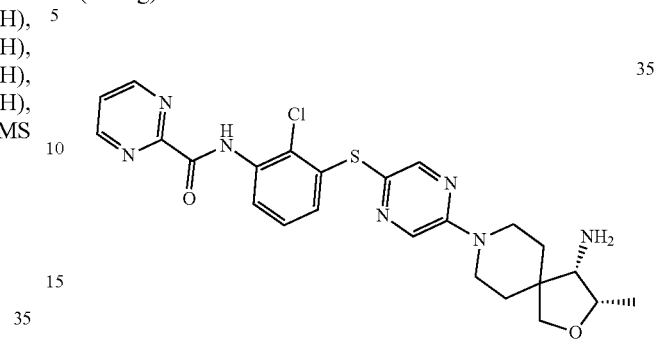

35

To compound 35b (110 mg, 0.29 mmol) and 1j (79 mg, 0.32 mmol), N,N-dimethylformamide (5 mL) was added, then potassium phosphate (370 mg, 1.78 mmol), and heated to 110° C., reacted for 2 hours. Cooled to room temperature, 20 mL of water was added, extracted twice with ethyl acetate (20 mL), washed with saturated brine (20 mL) once, dried with sodium sulfate (5.0 g), filtered, concentrated under reduced pressure to dryness, and purified by column to obtain 35 (30 mg, yield: 20.1%).

$^1$H NMR (400 MHz, CD$_3$OD) δ 8.97-8.96 (m, 2H), 8.29-8.17 (m, 1H), 8.20-8.16 (m, 2H), 7.67-7.65 (m, 1H), 7.21-7.17 (m, 1H), 6.73-6.70 (m, 1H), 4.19-1.13 (m, 1H), 4.05-3.97 (m, 2H), 3.82-3.80 (m, 1H), 3.66-3.64 (m, 1H), 3.41-3.25 (m, 3H), 2.96-2.95 (m, 1H), 1.80-1.57 (m, 4H), 1.15 (s, 3H). LCMS m/z [M+H]$^+$: 512.2.

Example 36

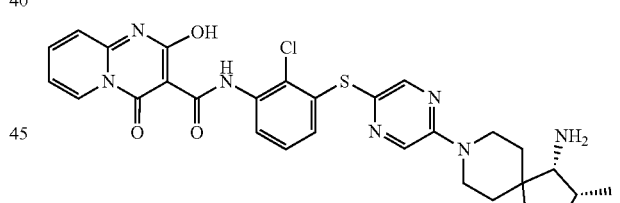

36

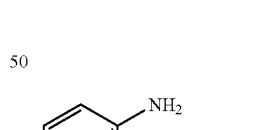

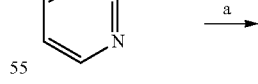

36a

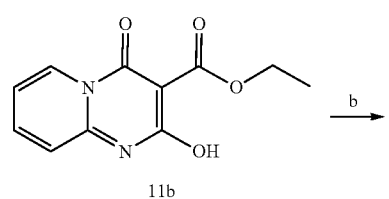

11b

-continued

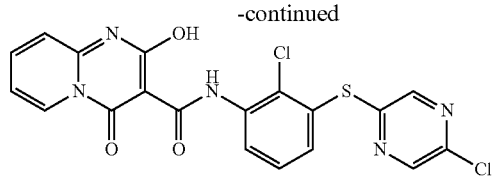

36b

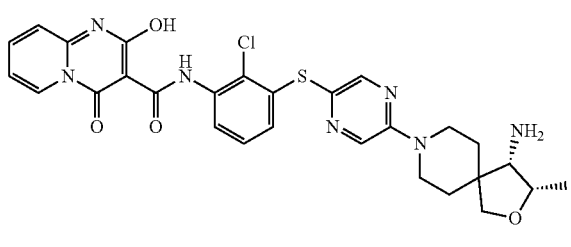

36

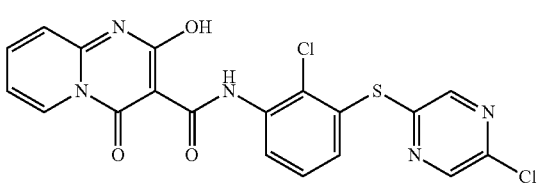

36b

Chlorobenzene (15 ml) was added to 11b (100 mg, 0.41 mmol) and 2-chloro-3-((5-chloropyrazin-2-yl)mercapto)aniline (133 mg, 0.49 mmol). Left at 130° C. overnight. After cooling down, ethyl acetate (15 mL) was added, a solid was precipitated, and 36b (110 mg, yield 49%) was obtained by filtration.

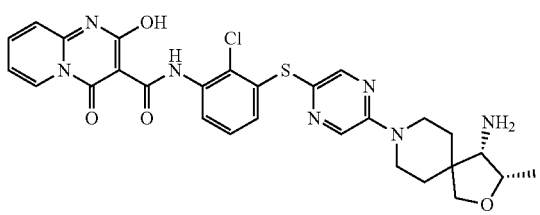

36

To 36b (60 mg, 0.13 mmol) and 1j (26 mg, 0.15 mmol), dimethyl sulfoxide (15 mL) was added, then potassium phosphate (166 mg, 0.78 mmol), and heated to 80° C. to react overnight. Cooled down to room temperature, saturated brine (75 mL) was added, stirred for 30 minutes, and filtered to obtain a solid. After column purification, 36 (60 mg, yield: 76%) was obtained.

$^1$H NMR (400 MHz, DMSO-d$_6$) δ13.96 (s, 1H), 8.61-9.59 (m, 1H), 8.48-8.42 (m, 2H), 8.22-8.21 (m, 1H), 7.55-7.51 (m, 1H), 6.94-6.92 (m, 1H), 6.74-6.71 (m, 1H), 6.47-6.44 (m, 1H), 4.09-4.05 (m, 1H), 3.92-3.84 (m, 2H), 3.68-3.66 (m, 1H), 3.49-3.42 (m, 3H), 2.91-2.90 (m, 1H), 2.02-1.97 (m, 1H), 1.78-1.45 (m, 4H), 1.23 (s, 3H). LCMS m/z [M+H]$^+$: 594.3.

Example 37

37

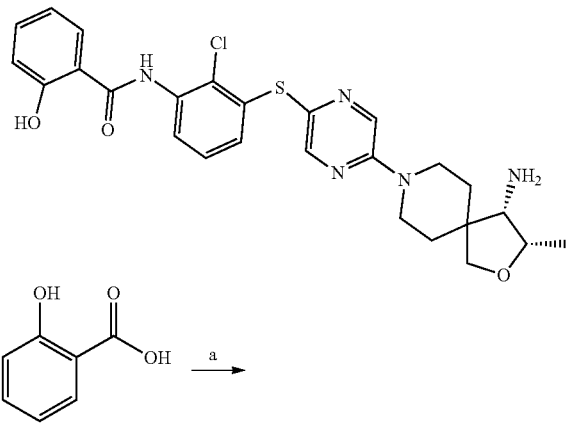

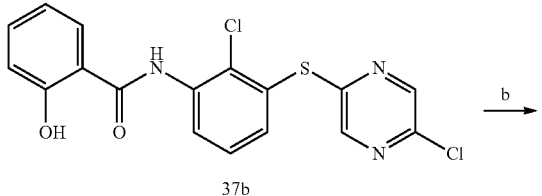

37b

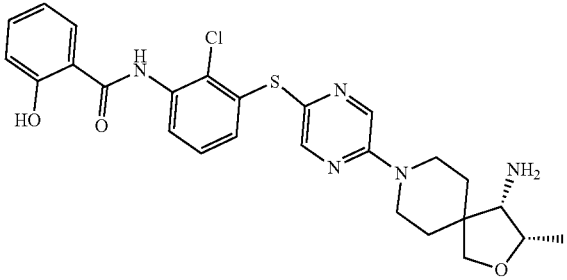

37

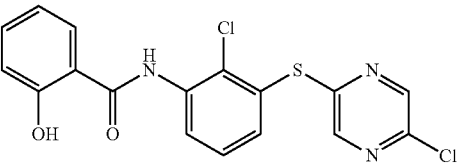

37b 37a (69.0 mg, 0.5 mmol) was added to dry tetrahydrofuran (2.0 mL), oxalyl chloride (0.127 mL, 1.75 mmol) was added dropwise, and the mixture was refluxed under nitrogen for 3 hours. Desolvated under reduced pressure. The obtained oil was dissolved in dry tetrahydrofuran (1.0 mL) and 10b (136.0 mg, 0.5 mmol) in tetrahydrofuran solution (3.0 mL) was slowly added, refluxed under nitrogen for 2 hours, and concentrated on a silica gel column with ethyl acetate/petroleum ether (0-30%) to obtain 37b (175.0 mg, yield 89%).

$^1$H NMR (400 MHz, CDCl$_3$) δ 11.74 (s, 1H), 8.72 (s, 1H), 8.64 (dd, J=8.3, 1.5 Hz, 1H), 8.42 (d, J=1.4 Hz, 1H), 8.17 (d,

J=1.4 Hz, 1H), 7.61 (dd, J=8.1, 1.3 Hz, 1H), 7.58-7.51 (m, 2H), 7.47 (t, J=8.0 Hz, 1H), 7.11 (dd, J=8.4, 0.9 Hz, 1H), 7.05-6.97 (m, 1H).

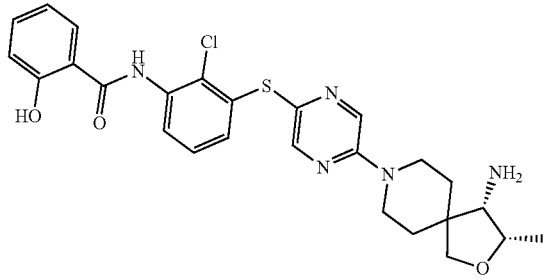

37

The target product 37 was obtained according to the synthesis method of 36.

¹H NMR (400 MHz, DMSO-d₆) δ 8.46 (d, J=1.1 Hz, 1H), 8.38 (dd, J=8.2, 1.2 Hz, 1H), 8.28 (d, J=1.2 Hz, 1H), 7.99 (dd, J=8.0, 1.8 Hz, 1H), 7.47-7.30 (m, 1H), 7.26 (t, J=8.0 Hz, 1H), 6.98 (d, J=8.0 Hz, 1H), 6.93-6.93 (m, 1H), 6.82 (t, J=7.2 Hz, 1H), 6.67 (dd, J=8.0, 1.3 Hz, 1H), 4.21-4.08 (m, 1H), 4.07-3.92 (m, 2H), 3.76 (d, J=8.8 Hz, 1H), 3.57 (d, J=8.8 Hz, 1H), 3.50-3.28 (m, 2H), 3.08 (d, J=5.2 Hz, 1H), 1.89-1.65 (m, 2H), 1.66-1.46 (m, 2H), 1.14 (d, J=6.4 Hz, 3H). LCMS [M+H]⁺: m/z=526.3.

Example 38

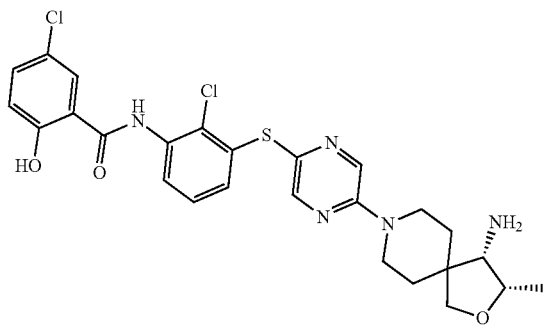

38

The target product 38 was obtained according to the synthesis method of 36.

¹H NMR (400 MHz, DMSO-d₆) δ 8.52-8.38 (m, 2H), 8.27 (d, J=1.2 Hz, 1H), 7.80 (d, J=3.0 Hz, 1H), 7.28-7.09 (m, 2H), 6.74 (d, J=8.9 Hz, 1H), 6.63 (dd, J=7.9, 1.3 Hz, 1H), 4.26-3.98 (m, 3H), 3.84 (d, J=8.9 Hz, 1H), 3.64 (d, J=8.9 Hz, 1H), 3.38-3.18 (m, 3H), 1.87-1.49 (m, 4H), 1.19 (d, J=6.5 Hz, 3H). LCMS [M+H]⁺: m/z=560.2.

Example 39

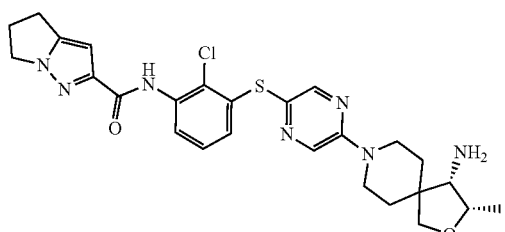

39

The target product 39 was obtained according to the synthesis method of 36.

¹H NMR (400 MHz, DMSO-d₆): δ 9.43 (s, 1H), 8.26 (m, 1H), 8.23 (s, 1H), 8.20 (s, 1H), 7.2 (t, J=8.0 Hz, 1H), 6.82 (m, 1H), 4.26-4.20 (m, 3H), 4.00-3.90 (m, 2H), 3.85 (d, J=8.0 Hz, 1H), 3.73 (d, J=12.0 Hz, 1H), 3.53-3.46 (s, 1H), 3.42-3.36 (s, 1H), 3.03 (d, J=4.0 Hz, 1H), 2.98 (t, J=10.0 Hz, 2H), 2.73-2.66 (m, 2H), 1.95-1.88 (m, 1H), 1.83-1.69 (m, 3H), 1.28 (d, J=8.0 Hz, 3H). LCMS m/z [M+H]⁺: 540.3

Example 40

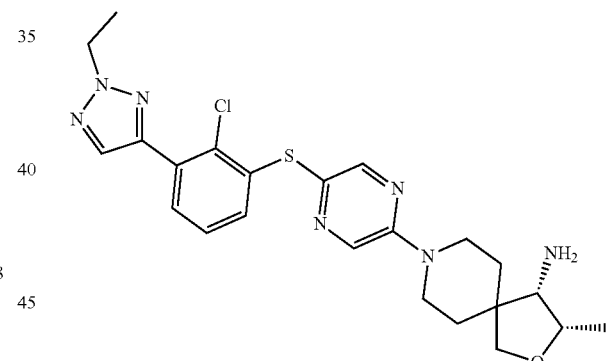

40

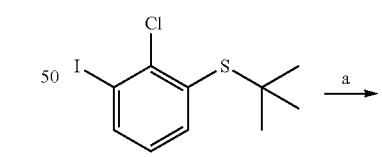

1m

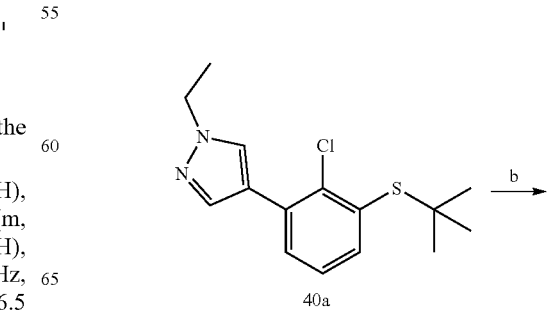

40a

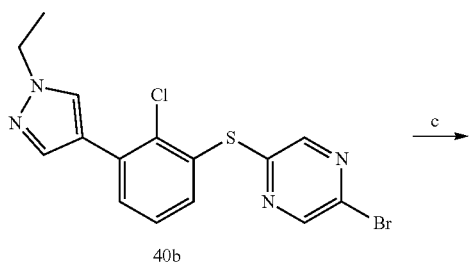

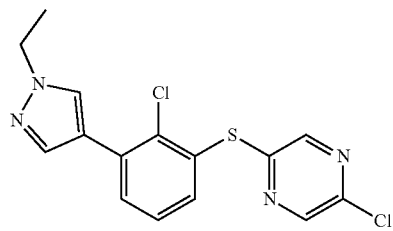

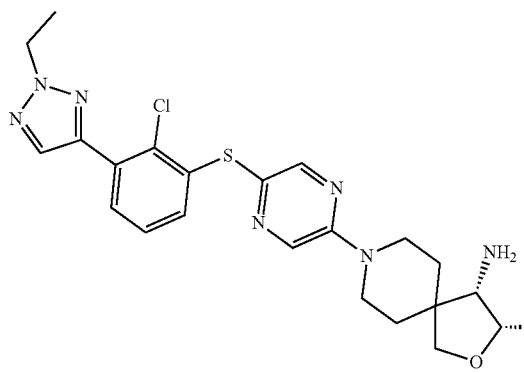

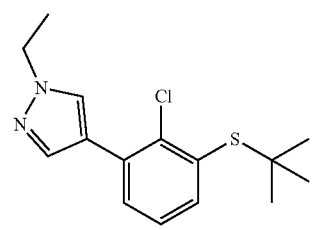

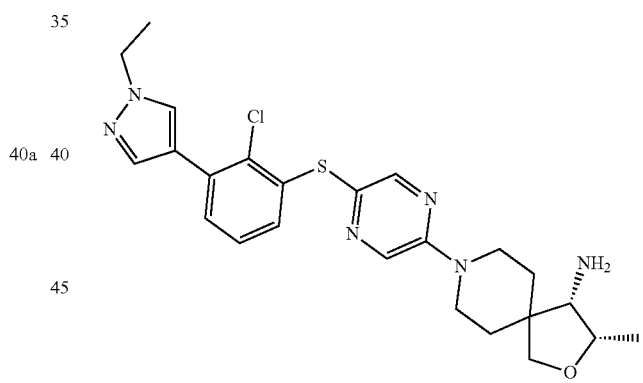

40a (65 mg, 0.22 mmol) was dissolved in acetonitrile (0.5 mL), concentrated hydrochloric acid (12 M, 5 mL) was added, and reacted at 120° C. for 5 hours. Cooled to room temperature, 20 mL of water was added, extracted twice with ethyl acetate (20 mL), washed once with saturated brine (20 mL), dried with sodium sulfate (5.0 g), filtered, and concentrated under reduced pressure to obtain a crude product. The crude product was dissolved in dioxane (5 mL), 2-chloro-5-bromopyrazine (43 mg, 0.22 mmol), 4, 5-bisdiphenylphosphine-9, 9-dimethylxanthene (13 mg, 0.02 mmol), tris(dibenzylideneacetone) dipalladium (10 mg, 0.01 mmol), N, N-diisopropylethylamine (9 mg, 0.7 mmol) were added, reacted at 100° C. for 16 hours under nitrogen protection. 50 mL of water was added, extracted three times with ethyl acetate (50 mL), the organic phases were combined, washed once with saturated aqueous sodium chloride (20 mL), dried with anhydrous sodium sulfate (5.0 g), and purified by column to obtain 40b (55 mg, Yield: 30%).

1m (100 mg, 0.3 mmol), 1-ethyl-1H-pyrazole-4-boronic acid pinacol ester (101.9 mg, 0.45 mmol), tetrakis(triphenylphosphine) palladium (17.68 mg, 0.01 mmol), potassium carbonate (126.7 mg, 0.918 mmol) were added to the mixed solution of toluene (5 mL), water (1 mL), and ethanol (1 mL). The reaction was carried out at 100° C. for 16 hours. The reaction solution was cooled to room temperature, 50 mL of water was added, extracted three times with ethyl acetate (50 mL), the organic phases were combined, washed once with saturated aqueous sodium chloride (20 mL), dried with anhydrous sodium sulfate (5.0 g), concentrated, purified by column to yield 40a (65 mg, 74% yield).

$^1$H NMR (400 MHz, CDCl$_3$): δ 7.85 (s, 1H), 7.81 (s, 1H), 7.61-7.59 (m, 1H), 7.49-7.47 (m, 1H), 7.28-7.24 (m, 1H), 7.06-7.04 (m, 1H), 4.30-4.24 (m, 2H), 1.60-1.56 (m, 3H), 1.40 (s, 9H).

40b (55 mg, 0.15 mmol) and 1j (25.5 mg, 0.15 mmol) were dissolved in N, N-dimethylformamide (2 mL), potassium phosphate (166.5 mg, 0.78 mmol) was added, heated to 110° C., and reacted for 2 hours. Cooled to room temperature, 50 mL water was added, extracted three times with ethyl acetate (50 mL), the organic phases were combined, washed once with saturated sodium chloride aqueous solution (20 mL), dried with anhydrous sodium sulfate (5.0 g), and purified by column to obtain 40 (20 mg, yield 26%).

1H NMR (400 MHz, CDCl$_3$): δ 8.13 (s, 1H), 8.09 (s, 1H), 7.70 (s, 1H), 7.66 (s, 1H), 7.16 (s, 1H), 7.03-6.99 (m, 1H), 6.77-6.75 (m, 1H), 4.16-4.08 (m, 4H), 3.83-3.80 (m, 2H), 3.74-3.72 (m, 1H), 3.61-3.59 (m, 1H), 3.38-3.26 (m, 1H). 4.16-4.08 (m, 4H), 2.92-2.91 (m, 1H), 1.80-1.77 (m, 1H), 1.68-1.61 (m, 1H), 1.46-1.42 (m, 3H), 1.14 (s, 9H). LCMS m/z [M+H]$^+$: 485.3.

Example 41

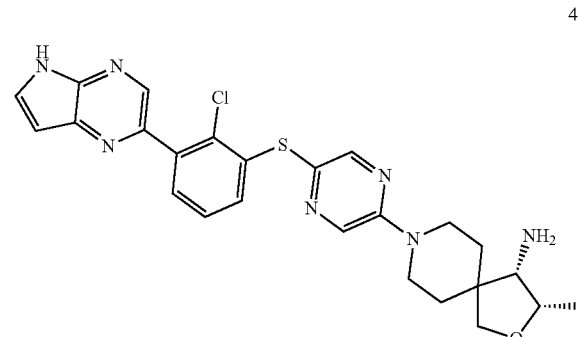

41

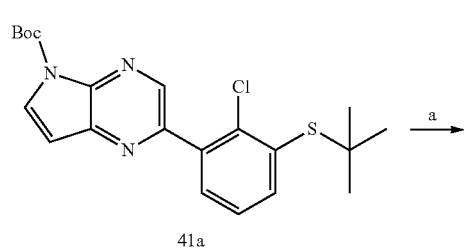

41a

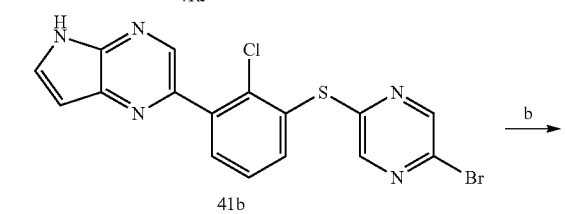

41b

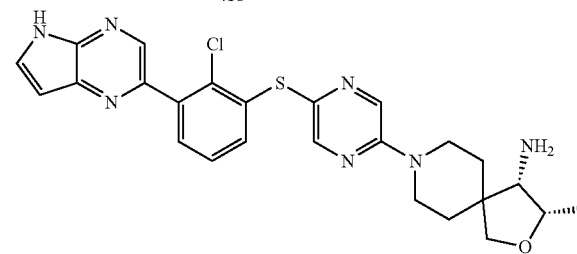

41

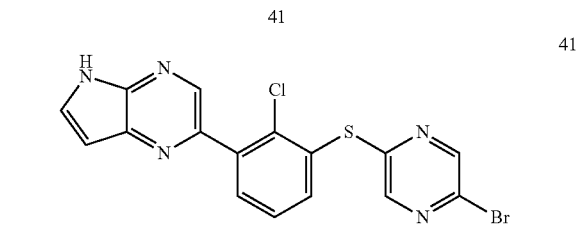

41b 41a (0.83 g, 2.0 mmol) was added to concentrated hydrochloric acid (10 mL) and stirred at reflux until the reaction was complete. Concentrated under reduced pressure to obtain a yellow solid, crude product and N, N-diisopropylethylamine (1.32 mL, 8.0 mmol) were dissolved in isopropanol (20 mL), heated to 80° C., and a solution of 2,5-dibromopyrazine (1.9 g, 8.0 mmol) in isopropanol (15 mL) was added over 2 hours and stirred for one hour. Concentrated and passed through a column (petroleum ether/ethyl acetate: 0-25%) to obtain 41b (0.27 g, yield: 32%).

$^1$H NMR (400 MHz, DMSO-d$_6$): δ 12.27 (s, 1H), 8.78 (d, J=1.4 Hz, 1H), 8.50 (s, 1H), 8.49 (d, J=1.4 Hz, 1H), 8.05-7.94 (m, 1H), 7.84 (dd, J=7.7, 1.6 Hz, 1H), 7.75 (dd, J=7.7, 1.6 Hz, 1H), 7.58 (t, J=7.7 Hz, 1H), 6.73 (dd, J=3.5, 1.7 Hz, 1H).

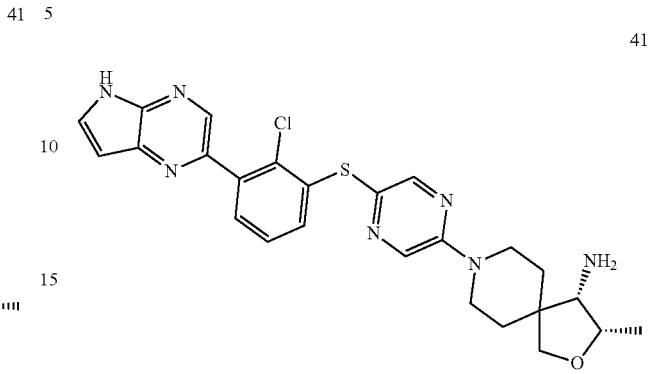

41

N, N-dimethylformamide (5 mL) was added to 41b (0.075 g, 0.179 mmol), 1j (0.048 g, 0.197 mmol), and potassium phosphate (0.152 g, 0.716 mmol), stirred at 70-75° C. for 1 hour. Concentrated through column chromatography (dichloromethane:methanol=100% to 10:1) to obtain 41 (50 mg, yield: 55%).

$^1$H NMR (400 MHz, DMSO-d$_6$): δ 12.26 (s, 1H), 8.50 (s, 1H), 8.47 (s, 1H), 8.33 (s, 1H), 7.99 (d, J=3.1 Hz, 1H), 7.43 (dd, J=7.6, 1.6 Hz, 1H), 7.38 (t, J=7.7 Hz, 1H), 6.97 (dd, J=7.8, 1.7 Hz, 1H), 6.72 (d, J=3.5 Hz, 1H), 4.16-4.05 (m, 1H), 4.01-3.85 (m, 2H), 3.71 (d, J=8.5 Hz, 2H), 3.52 (d, J=8.5 Hz, 1H), 2.95 (d, J=5.1 Hz, 1H), 1.87-1.74 (m, 1H), 1.74-1.63 (m, 1H), 1.63-1.44 (m, 2H), 1.11 (d, J=6.4 Hz, 3H), 1.05 (d, J=10.0 Hz, 2H). LCMS: [M+H]$^+$=508.3.

Example 42

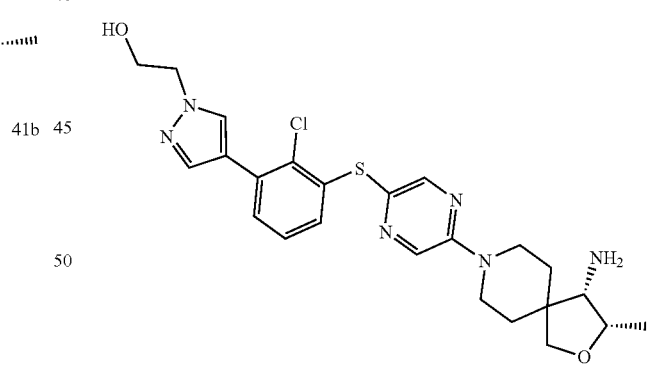

42

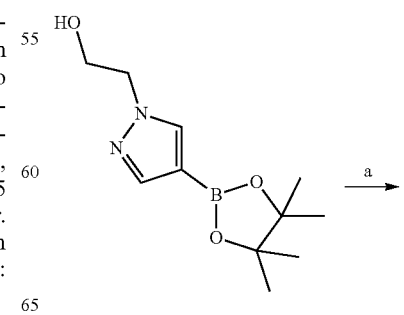

42a

-continued

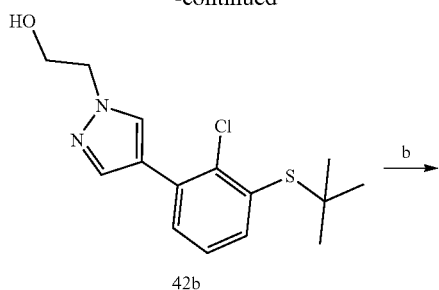

42b

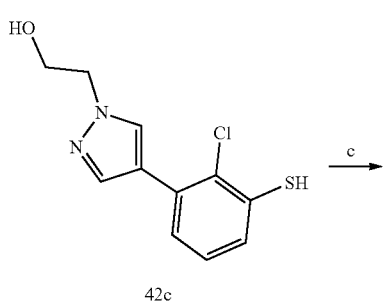

42c

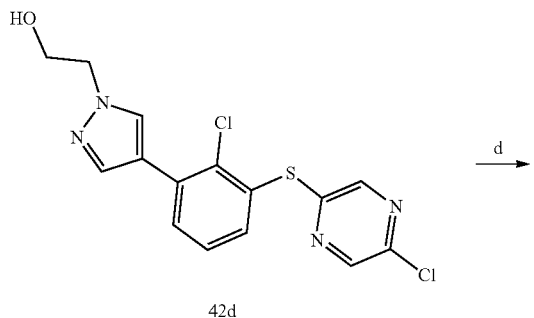

42d

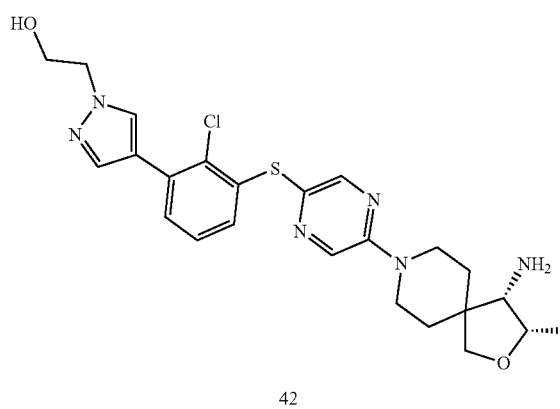

42

1m (326 mg, 1.0 mmol), 42a (238.1 mg, 1.0 mmol), tetrakistriphenylphosphine palladium (115 mg, 0.1 mmol), and potassium carbonate (400 mg, 3.0 mmol) were dissolved in dioxane (10 mL) and water (1 mL), displaced with nitrogen three times and stirred at 110° C. for 16 hours. Concentrated and passed the column (petroleum ether:ethyl acetate=100% to 10:1) to obtain 42b (270 mg, yield: 87.1%).

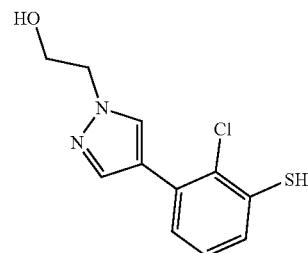

42c

Concentrated hydrochloric acid (5 mL, 12M) was added to 42b (260 mg), displaced with nitrogen three times, and stirred at 80° C. for 2 hours. Cooled to room temperature, quenched the reaction with saturated sodium bicarbonate at 0-10° C., extracted with ethyl acetate (20 mL×6), dried, filtered, and concentrated to obtain 42c, which was used directly in the next step. LCMS m/z [M+H]$^+$: 255.2.

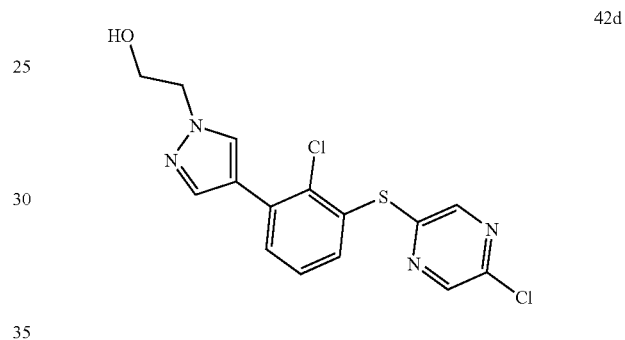

42d 42c (160 mg, 0.8 mmol), 2-chloro-5-bromopyrazine (152 mg, 0.8 mmol), tris(dibenzylideneacetone)dipalladium (36.6 mg, 0.04 mmol), 4,5-bis(diphenylphosphino)-9, 9-dimethylxanthene (46.2 mg, 0.08 mmol), and N, N-diisopropylethylamine (310 mg, 2.4 mmol) were dissolved in dioxane (10 mL), displaced with nitrogen three times, and stirred at 110° C. for 16 hours. Concentrated and passed the column (petroleum ether:ethyl acetate=100% to 10:1) to obtain 42d (180 mg, yield: 77%).

MS m/z [M+H]$^+$: 367.1.

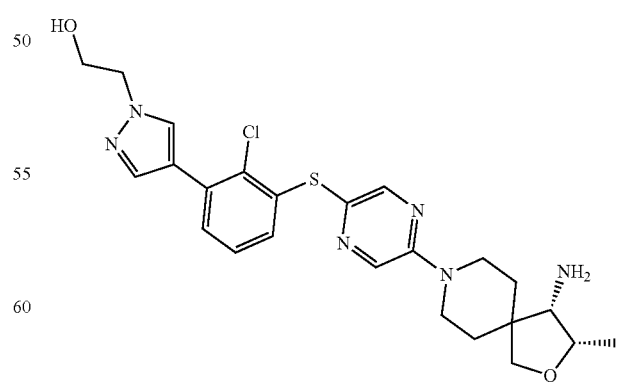

42

Dimethyl sulfoxide (5 mL) was added to 42d (180 mg, 0.49 mmol), 1j (131 mg, 0.54 mmol), and potassium phosphate (636 mg, 3.0 mmol), and stirred at 80-85° C. for 16 hours. Cooled to room temperature, the reaction solution was poured into 10% brine (50 mL), stirred for 5 minutes, extracted with ethyl acetate (50 mL×3), concentrated, and purified by column chromatography (dichloromethane: methanol=100% to 10:1) to obtain 42 (30 mg, yield: 12.2%).

$^1$H NMR (CDCl$_3$, 400 MHz): δ 8.22 (s, 1H), 8.17 (s, 1H), 7.85 (s, 1H), 7.79 (s, 1H), 7.24 (dd, 1H), 7.10 (t, J=8.0 Hz, 1H), 6.84 (dd, 1H), 4.29 (t, J=4.0 Hz, 2H), 4.19-4.16 (m, 1H), 4.04 (t, J=4.0 Hz, 2H), 3.93-3.88 (m, 2H), 3.80 (d, J=12.0 Hz, 1H), 3.72-3.67 (m, 1H), 3.43-3.32 (m, 2H), 2.98 (d, J=4.0 Hz, 1H), 1.85-1.83 (m, 1H), 1.75-1.67 (m, 3H), 1.23 (d, J=8.0 Hz, 3H). LCMS m/z [M+H]$^+$: 501.2.

Example 43

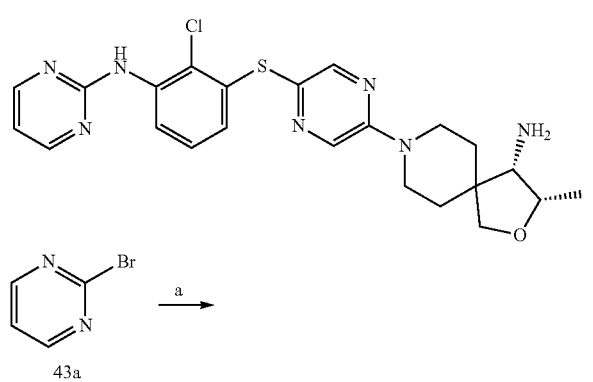

43a

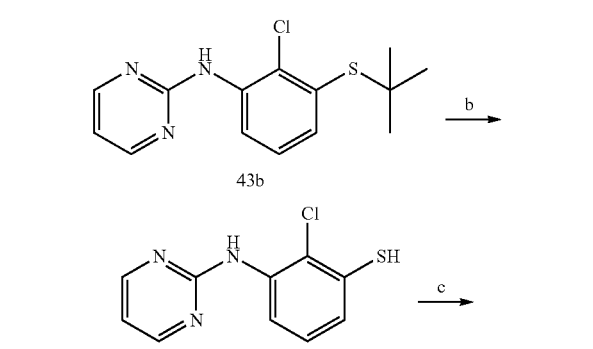

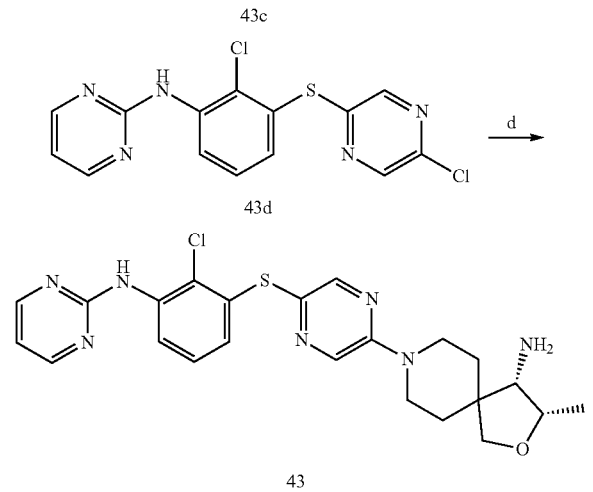

43

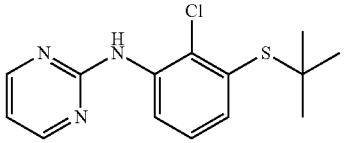

43b 43a (1.59 g, 10 mmol), 11 (2.15 g, 10 mmol), tris(dibenzylideneacetone) dipalladium (228 mg, 0.25 mmol), 4,5-bis(diphenylphosphino)-9,9-Dimethylxanthene (288 mg, 0.5 mmol), and sodium tert-butoxide (1.44 g, 15 mmol) were added to toluene (20 mL), displaced with nitrogen three times, and stirred at 110° C. for 16 hours. Passed through the column (petroleum ether: ethyl acetate=100% to 10:1) to obtain 43b (2.5 g, yield: 85.0%).

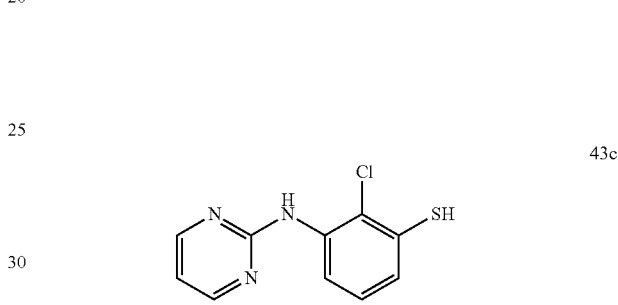

43c

Concentrated hydrochloric acid (5 mL, 12M) was added to 43b (500 mg). It was displaced with nitrogen three times and stirred at 80° C. for 2 hours. Cooled to room temperature, quenched the reaction with saturated sodium bicarbonate at 0-10° C., extracted with ethyl acetate (100 mL×3), dried, filtered, and concentrated to obtain 43c, which was used directly in the next step.

$^1$H NMR (CDCl$_3$, 400 MHz): δ 8.46 (s, 1H), 8.45 (s, 1H), 8.33 (dd, 1H), 7.7 (s, 1H), 7.15 (t, J=8.0 Hz, 1H), 7.02 (dd, 1H), 6.80 (t, J=4.0 Hz, 1H).

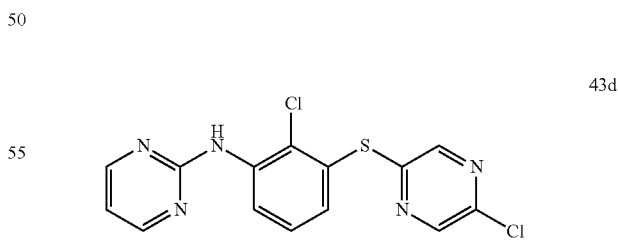

43d

Dioxane (4.5 mL) was added to 43c (237 mg, 1.0 mmol), 2-chloro-5-bromopyrazine (190 mg, 1.0 mmol), tris(dibenzylideneacetone) dipalladium (46 mg, 0.05 mmol), 4,5-bis-diphenylphosphino-9, 9-dimethylxanthene (57 mg, 0.1 mmol), and N, N-diisopropylethylamine (390 mg, 3.0 mmol). It was displaced with nitrogen three times and stirred at 110° C. for 16 hours. Passed the column (petroleum ether:ethyl acetate=100% to 10:1) to obtain 43d (250 mg, yield: 71.4%).

LCMS m/z [M+H]⁺: 350.2.

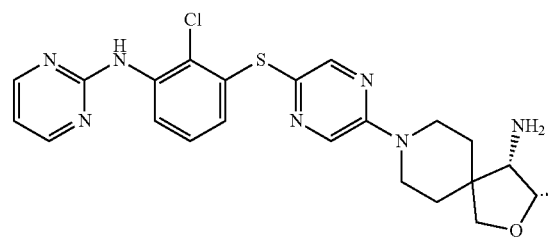

43

Dimethyl sulfoxide (5 mL) was added to 43d (200 mg, 0.57 mmol), 1j (153 mg, 0.63 mmol), and potassium phosphate (726 mg, 6.0 mmol), and stirred at 80-85° C. for 16 hours. The reaction solution was poured into 10% brine (50 mL), stirred for 5 minutes, and extracted with ethyl acetate (50 mL×3). Passed through a normal phase silica gel column with dichloromethane:methanol=100% to 10:1 to obtain 170 mg of solid and passed through a reverse phase column (water/acetonitrile=100% to 60%) to obtain 43 (40 mg yield: 14.5%).

¹H NMR (CDCl₃, 400 MHz): δ 8.47 (s, 1H), 8.46 (s, 1H), 8.43 (d, J=8.0 Hz, 1H), 8.17 (s, 1H), 8.16 (s, 1H), 7.7 (s, 1H), 7.17 (t, J=8.0 Hz, 1H), 6.80 (t, J=4.0 Hz, 1H), 6.73 (d, J=8.0 Hz, 1H), 4.27-4.24 (m, 1H), 4.12-3.95 (m, 3H), 3.75 (d, J=12.0 Hz, 1H), 3.29-3.20 (m, 3H), 2.0-1.98 (m, 1H), 1.90-1.74 (m, 3H), 1.38 (d, J=4.0 Hz, 3H). LCMS m/z [M+H]⁺: 484.3.

Example 44

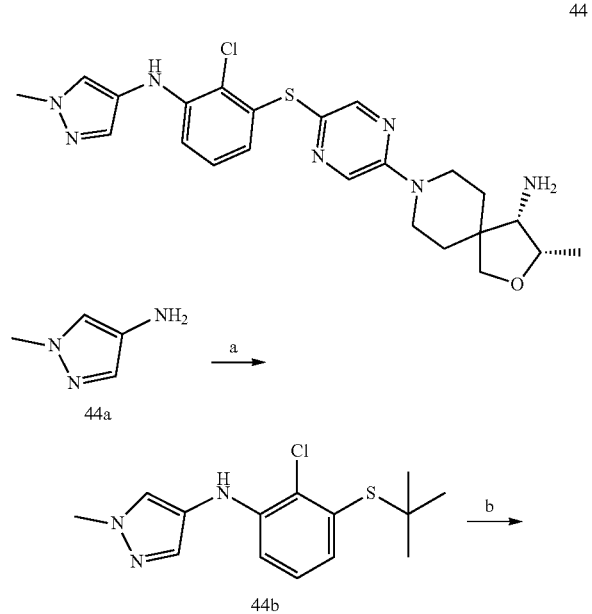

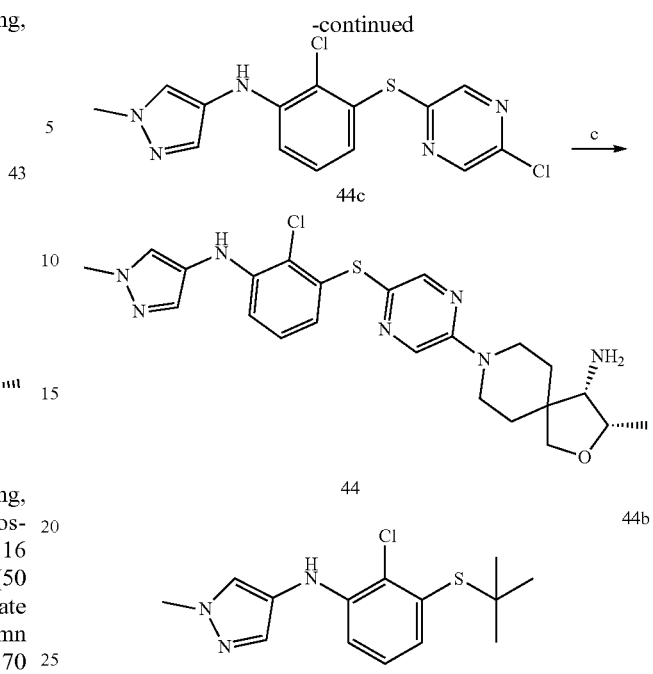

Toluene (3 mL) was added to 1m (100 mg, 0.3 mmol), 44a (45 mg, 0.46 mmol), [1,1'-bis(diphenylphosphino)ferrocene]palladium dichloride (22 mg, 0.03 mmol), and sodium tert-butoxide (59 mg, 0.6 mmol), and reacted at 100° C. for 16 hours. The reaction solution was cooled to room temperature, 50 mL water was added, extracted twice with ethyl acetate (20 mL), washed once with saturated brine (20 mL), dried with sodium sulfate (5.0 g), filtered, concentrated under reduced pressure, and purified by column to obtain 44b (150 mg, 52% yield). 1H NMR (400 MHz, CDCl₃): δ 7.49 (s, 1H), 7.39 (s, 1H), 7.09-7.05 (m, 2H), 6.35-6.33 (m, 1H), 3.94 (m, 3H), 1.39 (m, 9H).

44b (150 mg, 0.50 mmol) was dissolved in acetonitrile (2 mL), concentrated hydrochloric acid (12 M, 6 mL) was added, and reacted at 120° C. for 5 hours. 20 mL of water was added, extracted twice with ethyl acetate (20 mL), washed with saturated brine (20 mL) once, dried with sodium sulfate (5.0 g), filtered, concentrated under reduced pressure to dryness. The crude product was dissolved in dioxane (5 mL), 2-chloro-5-bromopyrazine (99 mg, 0.50 mmol), 4,5-bis(diphenylphosphine)-9, 9-dimethylxanthene (29.3 mg, 0.05 mmol), tris(dibenzylideneacetone) dipalladium (46.5 mg, 0.05 mmol), N, N-diisopropylethylamine (196.7 mg, 1.52 mmol) were added sequentially, protected by nitrogen, and reacted at 100° C. for 16 hours. Cooled to room temperature, water (20 mL) was added, extracted twice with ethyl acetate (20 mL), washed with saturated brine (20 mL) once, dried with sodium sulfate (5.0 g), filtered, concentrated under reduced pressure, and purified by column to obtain 44c (100 mg, yield: 56%).

44

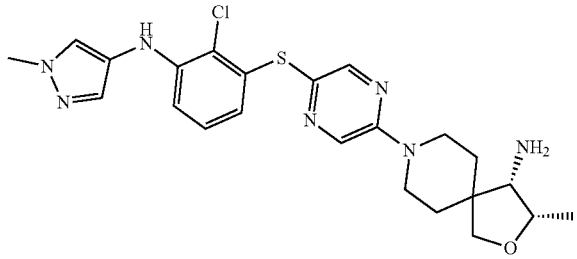

Compound 44c (100 mg, 0.25 mmol) and 1j (74 mg, 0.30 mmol) were added to N, N-dimethylformamide (5 mL), followed by potassium phosphate (322 mg, 1.52 mmol), and heated to 110° C., reacted for 2 hours. Cooled to room temperature, water (20 mL) was added, extracted twice with ethyl acetate (20 mL), washed once with saturated brine (20 mL), dried with sodium sulfate (5.0 g), filtered, concentrated under reduced pressure to dryness, and purified by column to obtain 44 (20 mg, yield 14%).

$^1$H NMR (400 MHz, CDCl$_3$) δ 8.06-8.05 (s, 2H), 7.32 (s, 1H), 7.24 (s, 1H), 6.84-6.80 (s, 1H), 6.54-6.54 (s, 1H), 6.34-6.32 (m, 1H), 4.12-4.06 (m, 1H), 3.79 (m, 3H), 3.72-3.70 (m, 1H), 3.60-3.58 (m, 1H), 3.38-3.19 (m, 3H), 2.91-2.90 (m, 1H), 1.81-1.66 (m, 4H), 1.15 (m, 3H). LCMS m/z [M+H]$^+$: 486.3.

Biological Activity Evaluation

The ability of the compounds of the present invention to selectively inhibit SHP2 activity was evaluated. The inhibitory properties of the compounds of the present invention described herein can be demonstrated by the following experiments.

SHP2 allosteric inhibition experiment

SHP2 is allosterically activated through the activation of a bis-tyrosyl-phosphorylated peptide and Src Homology 2 (SH2) domains. The activation steps followed result in the release of the auto-inhibition interface, which in turn activates the SHP2 protein tyrosine phosphatase (PTP) and can be used for substrate recognition and reaction catalysis. The SHP2 catalytic activity is monitored by a rapid fluorescent mode with the alternative substrate DiFMUP.

The phosphatase reaction was conducted in 384-well black polystyrene plates (Corning, Cat #3575) with flat bottom, low edge and non-binding surface at room temperature and 25 μl final volume of the following buffer condition: 60 mM HEPES, pH 7.2, 75 mM NaCl, 75 mM KCl, 1 mM EDTA, 0.05% P-20, 5 mM DTT.

The following experiments were conducted to monitor the SHP2 inhibition by the compounds (at concentrations of 0.0003-100 μM) in this invention:

Wherein, incubate 0.5 nM SHP2 with 0.5 μM peptide IRS1_pY1172 (dPEG8) pY1222 (sequence: H$_2$N-LN (pY) IDLDLV (dPEG8) LST (pY) ASINFQK-amide) (SEQ ID NO: 1) (WO2016/203406A1). After incubation at 25° C. for 30-60 minutes, the alternative substrate DiFMUP (Invitrogen, cat #D6567) was added to the reaction and incubated at 25° C. for 30 minutes. The reaction was then carefully diluted by adding 5 μL of a 160 μM bpV (Phen) solution (Enzo Life Sciences cat #ALX-270-204). The fluorescence signal was monitored using a microplate reader (VARIOSKAN LUX, Thermo) with excitation and emission wavelengths of 340 nm and 450 nm, respectively. The inhibitory dose-response curve is analyzed using a standardized IC$_{50}$ regression curve based on control-based normalization.

The IC$_{50}$ of the compounds listed in the embodiments of the present invention are listed in Table 1.

TABLE 1

IC$_{50}$ values of compounds inhibiting SHP2

| Example embodiments | Chemical structure | IC$_{50}$ (nM) |
|---|---|---|
| 1 | 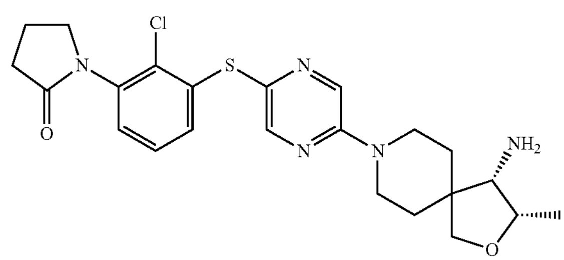 [SMILES: C[C@@H]1OCC2(CCN(c3cnc(Sc4cccc(N5CCCC5=O)c4Cl)cn3)CC2)[C@@H]1N] | 7.69 |
| 2 | 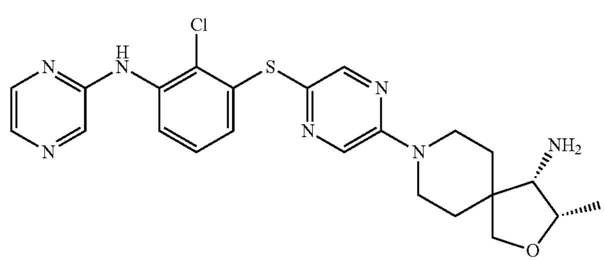 [SMILES: C[C@@H]1OCC2(CCN(c3cnc(Sc4cccc(Nc5cnccn5)c4Cl)cn3)CC2)[C@@H]1N] | 2.71 |

TABLE 1-continued
IC$_{50}$ values of compounds inhibiting SHP2
| Example embodiments | Chemical structure | IC$_{50}$ (nM) |
|---|---|---|
| 3 | 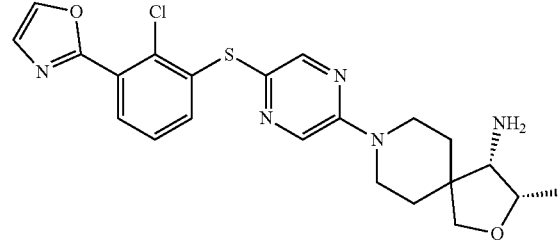 [SMILES: C[C@@H]1OCC2(CCN(c3cnc(Sc4cccc(-c5ncco5)c4Cl)cn3)CC2)[C@@H]1N] | 1.26 |
| 4 | 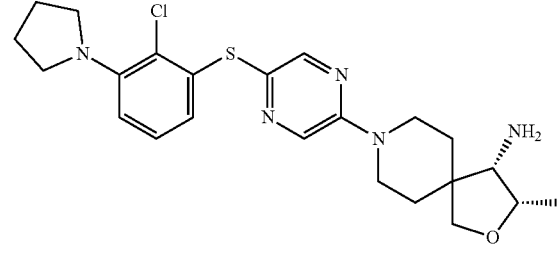 [SMILES: C[C@@H]1OCC2(CCN(c3cnc(Sc4cccc(N5CCCC5)c4Cl)cn3)CC2)[C@@H]1N] | 7.88 |
| 5 | 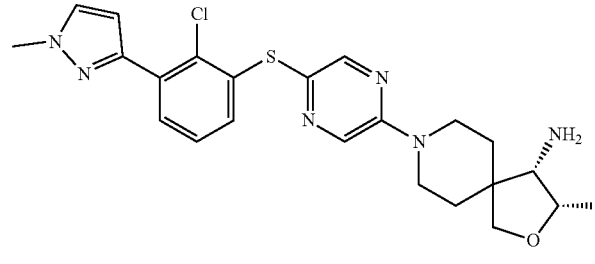 | 2.12 |
| 6 | 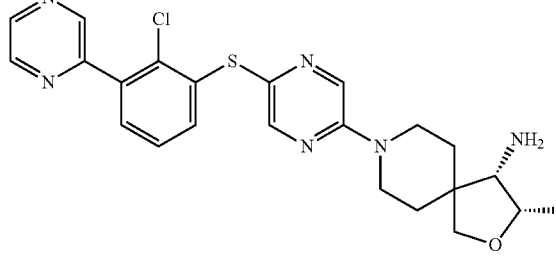 | 1.31 |
| 7 | 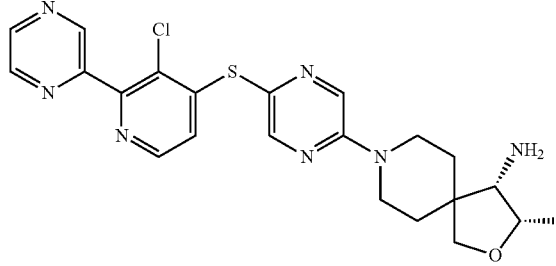 | 41.61 |

TABLE 1-continued

IC₅₀ values of compounds inhibiting SHP2

| Example embodiments | Chemical structure | IC$_{50}$ (nM) |
|---|---|---|
| 8 | 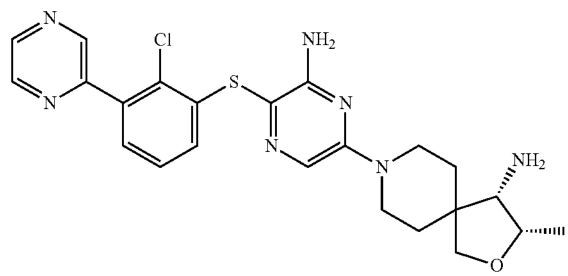 [SMILES: C[C@@H]1OCC2(CCN(c3cnc(Sc4cccc(-c5cnccn5)c4Cl)c(N)n3)CC2)[C@@H]1N] | 5.12 |
| 9 | 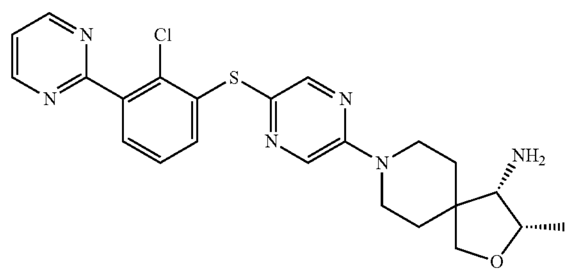 [SMILES: C[C@@H]1OCC2(CCN(c3cnc(Sc4cccc(-c5ncccn5)c4Cl)cn3)CC2)[C@@H]1N] | 6.61 |
| 10 | 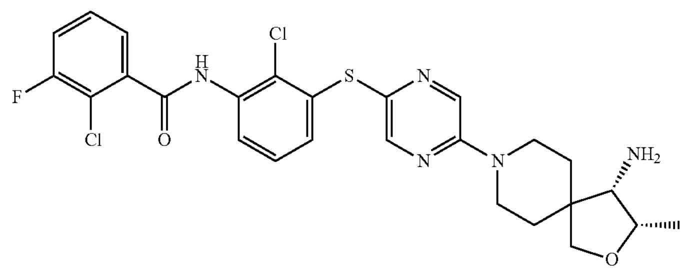 [SMILES: C[C@@H]1OCC2(CCN(c3cnc(Sc4cccc(NC(=O)c5cccc(F)c5Cl)c4Cl)cn3)CC2)[C@@H]1N] | 5.10 |
| 11 | 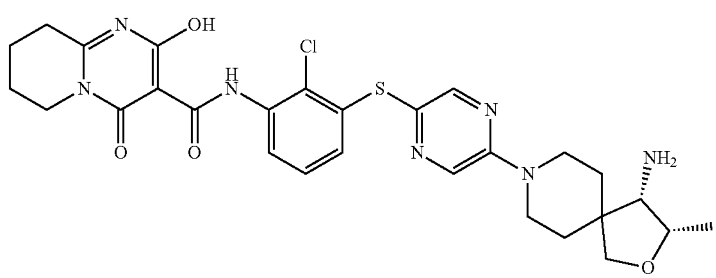 [SMILES: C[C@@H]1OCC2(CCN(c3cnc(Sc4cccc(NC(=O)c5c(O)nc6n(c5=O)CCCC6)c4Cl)cn3)CC2)[C@@H]1N] | 0.31 |
| 12 | 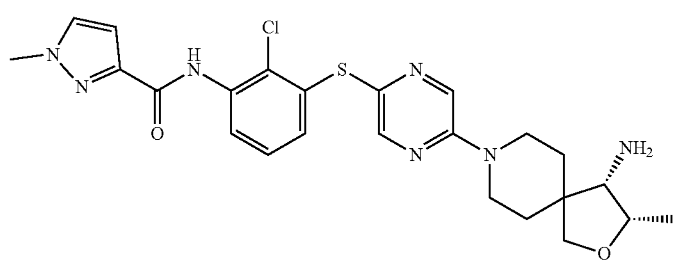 | 3.59 |

TABLE 1-continued

IC$_{50}$ values of compounds inhibiting SHP2

| Example embodiments | Chemical structure | IC$_{50}$ (nM) |
| --- | --- | --- |
| 13 | 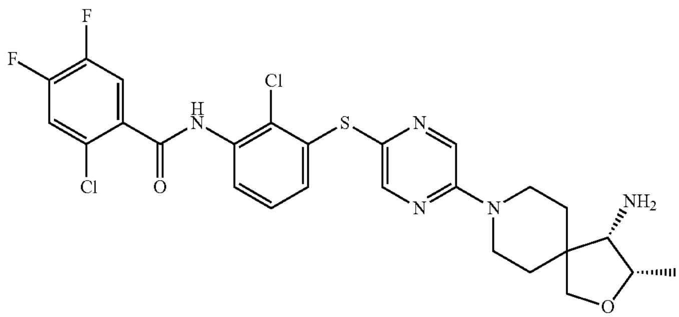 [SMILES: C[C@@H]1OCC2(CCN(c3cnc(Sc4cccc(NC(=O)c5cc(F)c(F)cc5Cl)c4Cl)cn3)CC2)[C@@H]1N] | 5.88 |
| 14 | 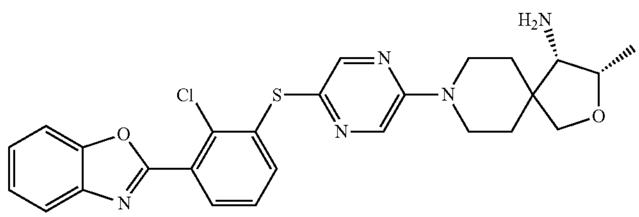 [SMILES: C[C@@H]1OCC2(CCN(c3cnc(Sc4cccc(-c5nc6ccccc6o5)c4Cl)cn3)CC2)[C@@H]1N] | 9.24 |
| 15 | 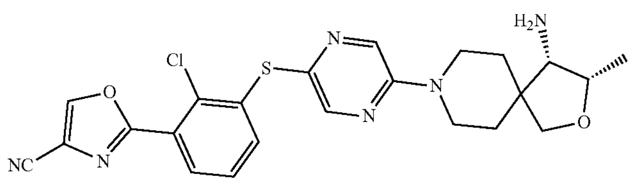 [SMILES: C[C@@H]1OCC2(CCN(c3cnc(Sc4cccc(-c5nc(C#N)co5)c4Cl)cn3)CC2)[C@@H]1N] | 4.06 |
| 16 | 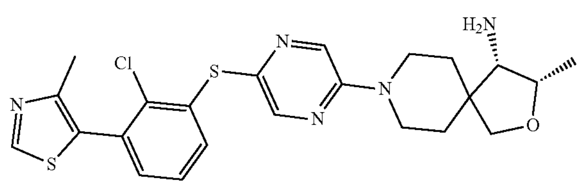 [SMILES: Cc1ncsc1-c1cccc(Sc2cnc(N3CCC4(CC3)CO[C@@H](C)[C@H]4N)cn2)c1Cl] | 4.90 |
| 17 | 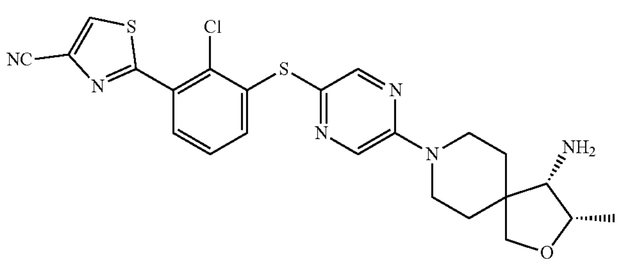 [SMILES: C[C@@H]1OCC2(CCN(c3cnc(Sc4cccc(-c5nc(C#N)cs5)c4Cl)cn3)CC2)[C@@H]1N] | 4.35 |
| 18 | 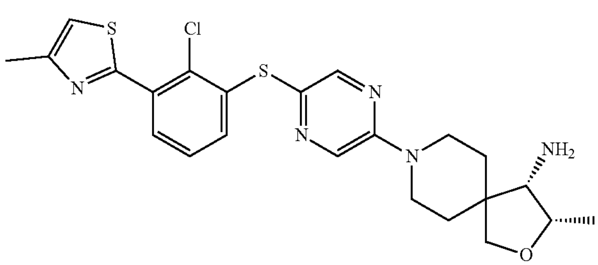 | 7.93 |

TABLE 1-continued

IC₅₀ values of compounds inhibiting SHP2

| Example embodiments | Chemical structure | IC$_{50}$ (nM) |
|---|---|---|
| 19 | 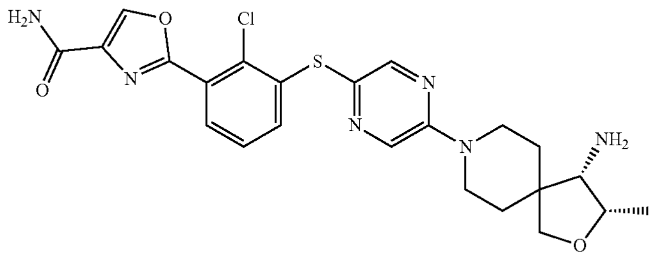 [SMILES: C[C@@H]1OCC2(CCN(c3cnc(Sc4cccc(-c5nc(C(N)=O)co5)c4Cl)cn3)CC2)[C@@H]1N] | 1.95 |
| 20 | 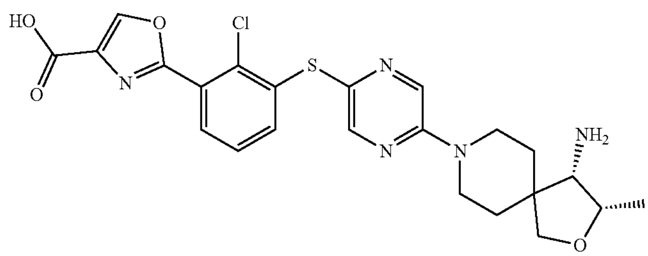 [SMILES: C[C@@H]1OCC2(CCN(c3cnc(Sc4cccc(-c5nc(C(=O)O)co5)c4Cl)cn3)CC2)[C@@H]1N] | 1.27 |
| 21 | 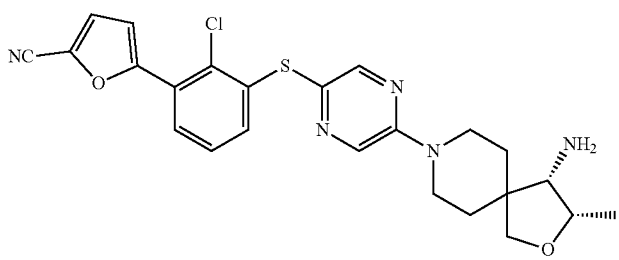 [SMILES: C[C@@H]1OCC2(CCN(c3cnc(Sc4cccc(-c5ccc(C#N)o5)c4Cl)cn3)CC2)[C@@H]1N] | 6.01 |
| 22 | 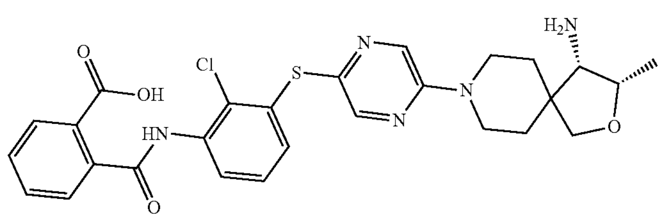 [SMILES: C[C@@H]1OCC2(CCN(c3cnc(Sc4cccc(NC(=O)c5ccccc5C(=O)O)c4Cl)cn3)CC2)[C@@H]1N] | 1.72 |
| 23 | 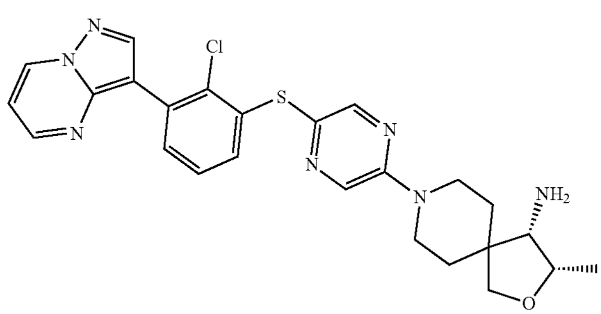 [SMILES: C[C@@H]1OCC2(CCN(c3cnc(Sc4cccc(-c5cnn6cccnc56)c4Cl)cn3)CC2)[C@@H]1N] | 3.28 |

TABLE 1-continued

IC$_{50}$ values of compounds inhibiting SHP2

| Example embodiments | Chemical structure | IC$_{50}$ (nM) |
| --- | --- | --- |
| 24 | 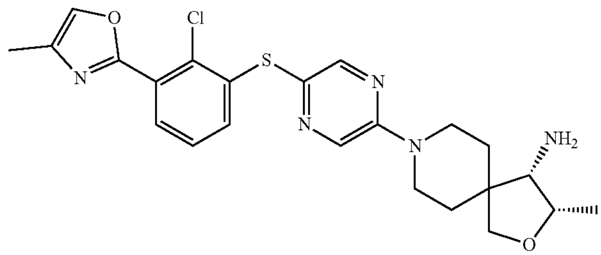 | 2.41 |
| 25 | 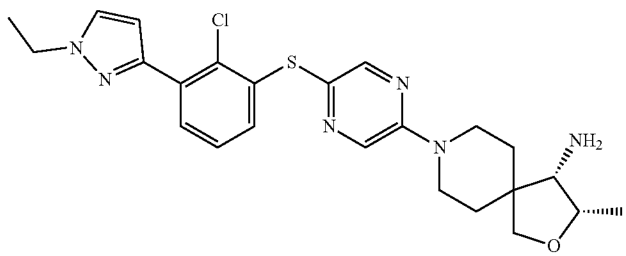 [SMILES: CCn1ccc(-c2cccc(Sc3cnc(N4CCC5(CC4)CO[C@@H](C)[C@H]5N)cn3)c2Cl)n1] | 1.74 |
| 26 | 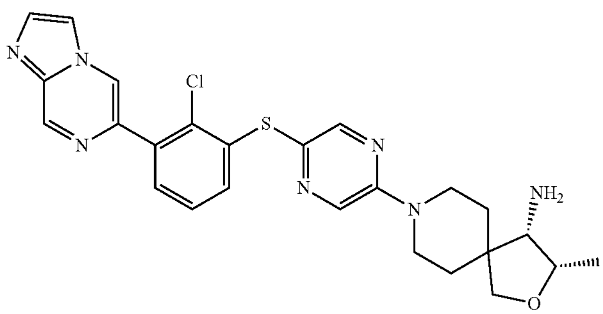 [SMILES: C[C@@H]1OCC2(CCN(c3cnc(Sc4cccc(-c5cn6ccnc6cn5)c4Cl)cn3)CC2)[C@@H]1N] | 6.33 |
| 27 | 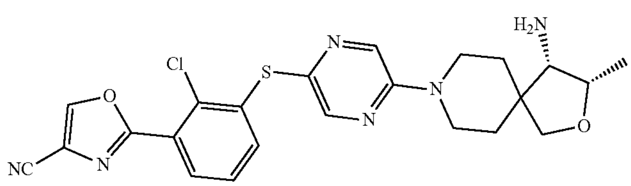 [SMILES: C[C@@H]1OCC2(CCN(c3cnc(Sc4cccc(-c5nc(C#N)co5)c4Cl)cn3)CC2)[C@@H]1N] | 3.51 |
| 28 | 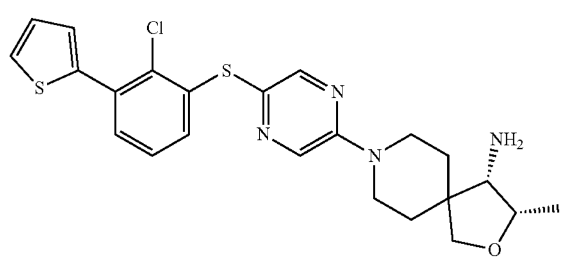 [SMILES: C[C@@H]1OCC2(CCN(c3cnc(Sc4cccc(-c5cccs5)c4Cl)cn3)CC2)[C@@H]1N] | 9.40 |
| 29 | 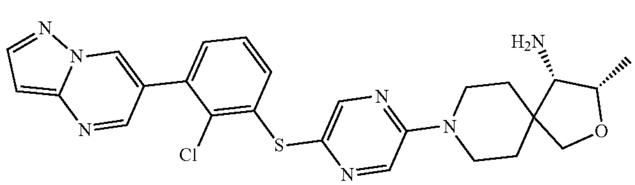 [SMILES: C[C@@H]1OCC2(CCN(c3cnc(Sc4cccc(-c5cnc6ccnn6c5)c4Cl)cn3)CC2)[C@@H]1N] | 6.62 |

TABLE 1-continued
IC$_{50}$ values of compounds inhibiting SHP2
| Example embodiments | Chemical structure | IC$_{50}$ (nM) |
|---|---|---|
| 30 | 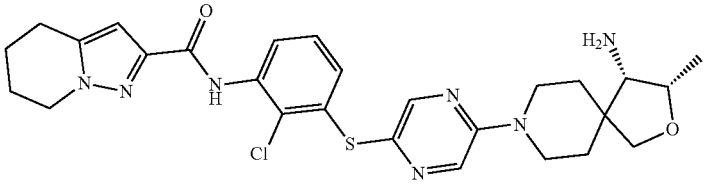 [SMILES: C[C@@H]1OCC2(CCN(c3cnc(Sc4cccc(NC(=O)c5cc6n(n5)CCCC6)c4Cl)cn3)CC2)[C@@H]1N] | 6.45 |
| 31 | 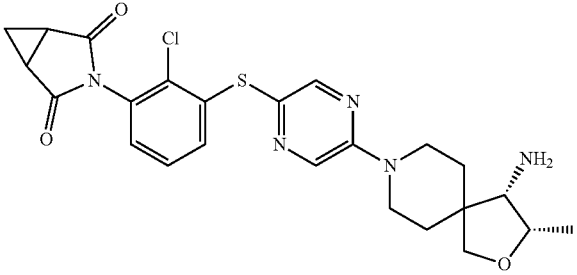 [SMILES: C[C@@H]1OCC2(CCN(c3cnc(Sc4cccc(N5C(=O)C6CC6C5=O)c4Cl)cn3)CC2)[C@@H]1N] | 7.91 |
| 32 | 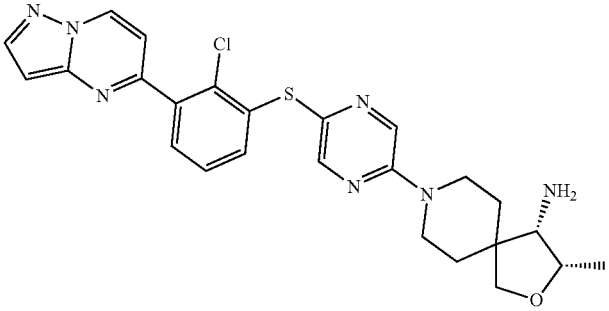 [SMILES: C[C@@H]1OCC2(CCN(c3cnc(Sc4cccc(-c5ccn6nccc6n5)c4Cl)cn3)CC2)[C@@H]1N] | 2.82 |
| 33 | 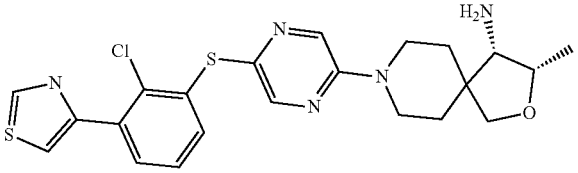 | 2.62 |
| 34 | 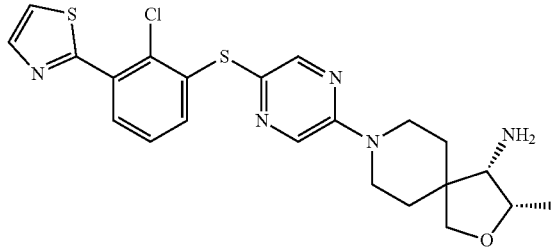 | 5.34 |

TABLE 1-continued

IC₅₀ values of compounds inhibiting SHP2

| Example embodiments | Chemical structure | IC$_{50}$ (nM) |
|---|---|---|
| 35 | 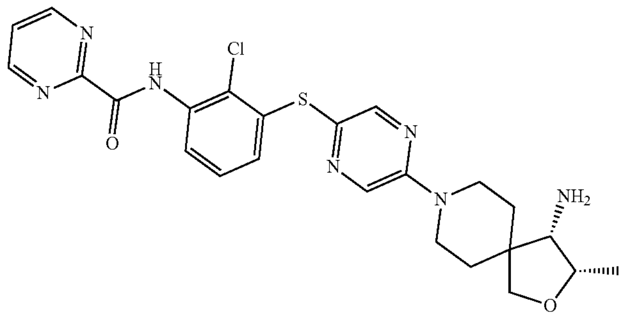 [SMILES: C[C@@H]1OCC2(CCN(c3cnc(Sc4cccc(NC(=O)c5ncccn5)c4Cl)cn3)CC2)[C@@H]1N] | 2.91 |
| 36 | 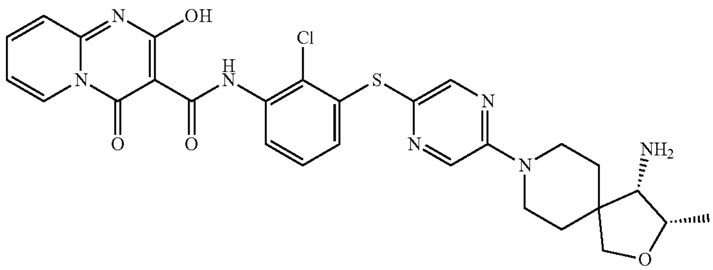 [SMILES: C[C@@H]1OCC2(CCN(c3cnc(Sc4cccc(NC(=O)c5c(O)nc6ccccn6c5=O)c4Cl)cn3)CC2)[C@@H]1N] | 6.42 |
| 37 | 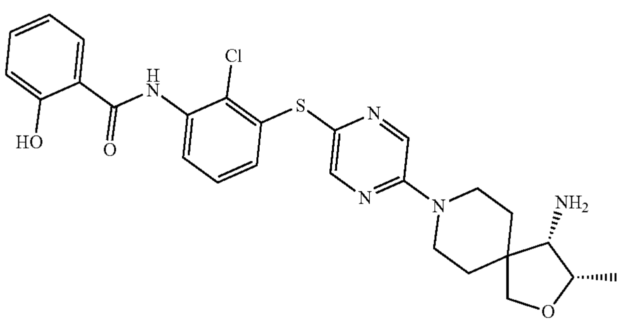 [SMILES: C[C@@H]1OCC2(CCN(c3cnc(Sc4cccc(NC(=O)c5ccccc5O)c4Cl)cn3)CC2)[C@@H]1N] | 9.01 |
| 38 | 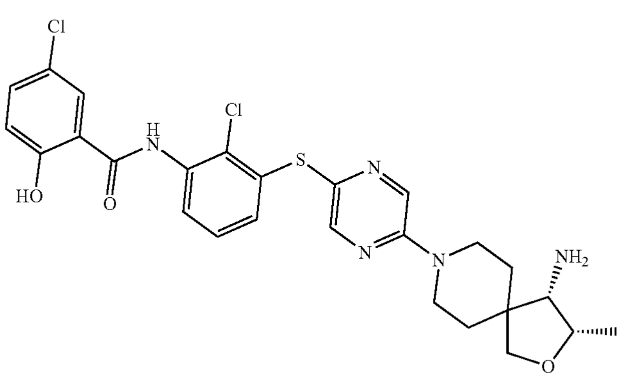 [SMILES: C[C@@H]1OCC2(CCN(c3cnc(Sc4cccc(NC(=O)c5cc(Cl)ccc5O)c4Cl)cn3)CC2)[C@@H]1N] | 9.41 |

TABLE 1-continued

IC$_{50}$ values of compounds inhibiting SHP2

| Example embodiments | Chemical structure | IC$_{50}$ (nM) |
|---|---|---|
| 39 | 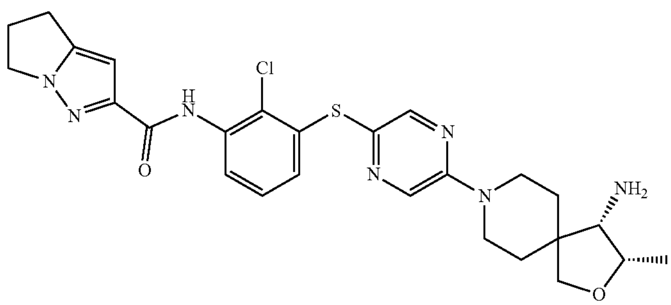 [SMILES: C[C@@H]1OCC2(CCN(c3cnc(Sc4cccc(NC(=O)c5cc6n(n5)CCC6)c4Cl)cn3)CC2)[C@@H]1N] | 8.3 |
| 40 | 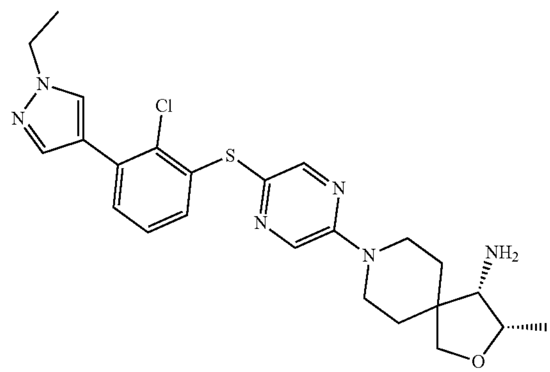 [SMILES: CCn1cc(-c2cccc(Sc3cnc(N4CCC5(CC4)CO[C@@H](C)[C@H]5N)cn3)c2Cl)cn1] | 4.4 |
| 41 | 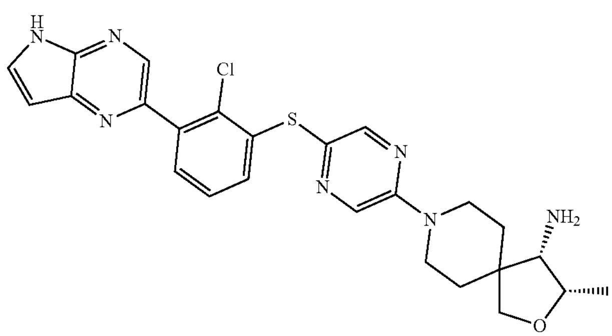 [SMILES: C[C@@H]1OCC2(CCN(c3cnc(Sc4cccc(-c5cnc6[nH]ccc6n5)c4Cl)cn3)CC2)[C@@H]1N] | 6.2 |
| 42 | 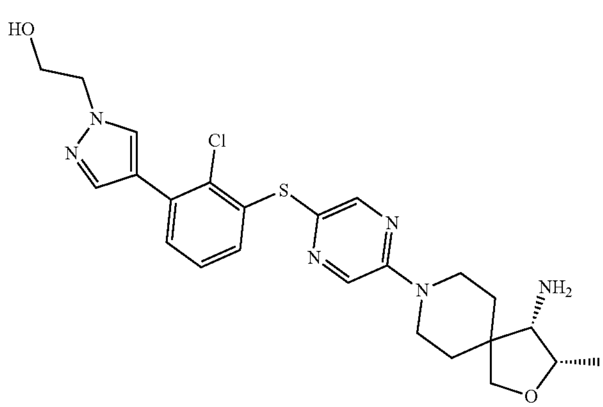 [SMILES: C[C@@H]1OCC2(CCN(c3cnc(Sc4cccc(-c5cnn(CCO)c5)c4Cl)cn3)CC2)[C@@H]1N] | 3.4 |

TABLE 1-continued

IC$_{50}$ values of compounds inhibiting SHP2

| Example embodiments | Chemical structure | IC$_{50}$ (nM) |
|---|---|---|
| 43 | 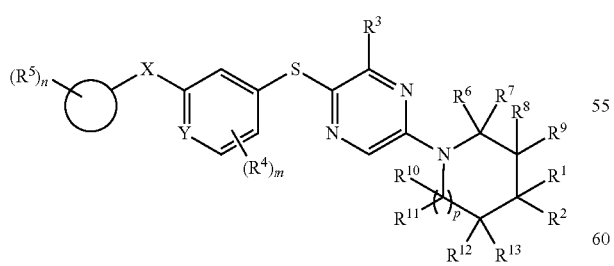 | 7.5 |
| 44 | 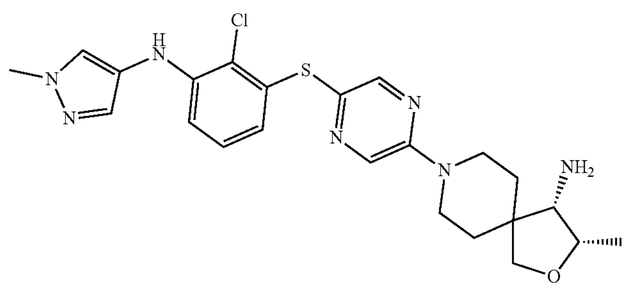 | 7.3 |

By comparing the experimental data in Table 1 with the activity data of the compounds in WO2016/203406A1, it is clear that the novel pyrazine derivatives of the present invention have significantly better SHP2 inhibitory activity relative to the compounds in WO2016/203406A1 (e.g., compound 96 in Table 9).

Specific embodiments of the present invention have been described above. It is to be understood that the present invention is not limited to the specific embodiments described above, and the person skilled in the art may make various variations or modifications within the scope of the claims, which do not affect the substance of the present invention.

The invention claimed is:

1. A compound of formula (I-2) or a pharmaceutically acceptable salt, or solvate thereof, said compound of formula (I-2) having the structure of:

(I)

wherein:
R$^1$ and R$^2$ or together form a 3-8 membered saturated or unsaturated cycloalkyl or heterocyclyl, wherein the 3-8 membered saturated or unsaturated cycloalkyl or heterocyclyl is substituted by 1-3 of —OH, —NH$_2$, —CN, NO$_2$, halogen, C$_1$-C$_{10}$ alkyl, C$_1$-C$_{10}$ alkoxy, C$_1$-C$_{10}$ alkylamino, C$_3$-C$_{12}$ cycloalkyl, C$_6$-C$_{10}$ aryl or 5-10 membered heteroaryl;

R$^3$ is H or D;

X is selected from a chemical bond, —NH—, and —CONH—;

Y is CR$^0$, wherein R$^0$ is selected from H, D, —OH, —CN, halogen, C$_1$-C$_{10}$ alkyl, C$_1$-C$_{10}$ alkoxy, C$_3$-C$_{12}$ cycloalkylamino, C$_1$-C$_{10}$ alkylamino, C$_3$-C$_{12}$ cycloalkyl, 3-8 membered heterocyclyl, halogenated C$_1$-C$_{10}$ alkylamino, C$_6$-C$_{10}$ aryl, and 5-10 membered heteroaryl, wherein said heterocyclyl or heteroaryl contains 1-4 heteroatoms, which heteroatoms are independently selected from S, O, N, and NH;

each R$^4$ is independently selected from H, D, halogen, —CN, —COOH, —CHO, —OH, —NO$_2$, —CONHR$_{14}$, —NHCOR$_{15}$, —NH$_2$, C$_1$-C$_{10}$ alkyl, C$_1$-C$_{10}$ alkylamino, C$_1$-C$_{10}$ alkoxy, C$_3$-C$_{12}$ cycloalkyl, 3-12 membered heterocyclyl, C$_6$-C$_{10}$ aryl, and 5-10 membered heteroaryl; wherein R$^{14}$ and R$^{15}$ are each independently optionally selected from C$_1$-C$_{10}$ alkylamino, C$_3$-C$_{12}$ cycloalkyl, C$_6$-C$_{10}$ aryl, and 5-10 membered heteroaryl;

is selected from C$_6$-C$_{10}$ aryl, 5-10 membered heteroaryl, C$_4$-C$_{12}$ cycloalkyl, 3-12 membered heterocyclyl, C$_6$-C$_{14}$ bridged cyclyl, C$_6$-C$_{14}$ bridged spirocyclyl, C$_6$-C$_{14}$ bridged heterocyclyl, C$_6$-C$_{14}$ spiro heterocyclyl, wherein said 5-10 membered heteroaryl, 3-12 membered heterocyclyl, C$_6$-C$_{14}$ bridged heterocyclyl or spiro heterocyclyl contains 1-3 heteroatoms or groups selected from N, NH, O, S, C (O), and S (O);

each R$^5$ is independently selected from D, halogen, —CN, —COOH, —CHO, —OH, —NO$_2$, aminoacyl, C$_1$-C$_{10}$ alkyl, $C_1$-$C_{10}$ alkylamino, $C_1$-$C_{10}$ alkoxy, —$NH_2$, $C_3$-$C_{12}$ cycloalkyl, 3-12 membered heterocyclyl, $C_6$-$C_{10}$ aryl, and 5-10 membered heteroaryl; or, when n is 2 or 3, two adjacent $R^5$ together may form a 3-6 membered saturated or unsaturated ring optionally substituted by 1-3 members independently selected from the group consisting of —OH, —$NH_2$, —CN, halogen, $C_1$-$C_{10}$ alkyl, and $C_1$-$C_{10}$ alkoxy, $R^6$, $R^7$, $R^8$, $R^9$, $R^{10}$, $R^{11}$, $R^{12}$, and $R^{13}$ are independently selected from H, D, halogen, —CN, —COOH, —CHO, —OH, —$NO_2$, —$NH_2$, $C_1$-$C_{10}$ alkyl, $C_1$-$C_{10}$ alkylamino, $C_1$-$C_{10}$ alkoxy, $C_3$-$C_{12}$ cycloalkyl, $C_3$-$C_{12}$ cycloalkyloxy, 3-12 membered heterocyclyl, $C_6$-$C_{10}$ aryl, and 5-10 membered heteroaryl;

m is 0, 1, 2, or 3;

n is 0, 1, 2, or 3; and p is 0, 1 or 2.

2. The compound according to claim 1 of formula (I-2), or a pharmaceutically acceptable salt or solvate thereof, wherein:

$R^1$ and $R^2$ form a 5-6-membered heterocyclic group, said heterocyclic group containing 1-3 heteroatoms selected from —N—, —NH—, —O—, and —S—, and the 5-6-membered heterocyclic group is optionally substituted by 1-3 substituents independently selected from the group consisting of —OH, —$NH_2$, —CN, $NO_2$, halogen, $C_1$-$C_{10}$ alkyl, $C_1$-$C_{10}$ alkoxy, $C_1$-$C_{10}$ alkylamino, $C_3$-$C_{12}$ cycloalkyl, $C_6$-$C_{10}$ aryl or 5-10 membered heteroaryl.

3. The compound according to claim 1 of formula (I-2), or a pharmaceutically acceptable salt or solvate thereof, said compound of formula (I-2) having the structure of (I-3)

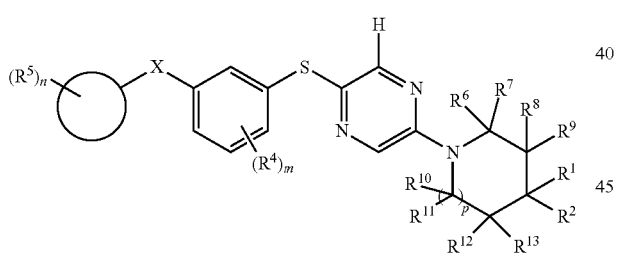

wherein $R^1$ and $R^2$ form a 5-6-membered heterocyclyl, wherein said heterocyclyl contains 1-3 heteroatoms independently selected from —N—, —NH—, —O—, and —S— and said 5-6-membered heterocyclyl is optionally substituted by 1-3 substituents independently selected from the group consisting of halogen, —OH, —$NH_2$, $C_1$-$C_{10}$ alkylamino, $C_1$-$C_{10}$ alkyl, or $C_1$-$C_{10}$ alkoxy; and $R^3$, $R^4$, $R^5$, $R^6$, $R^7$, $R^8$, $R^9$, $R^{10}$, $R^{11}$, $R^{12}$, $R^{13}$, X, m, n, p, and

are defined in formula (I-2).

4. The compound according to claim 1 of formula (I-2), or a pharmaceutically acceptable salt or solvate thereof, said compound of formula (I-2) having the structure of formula (I-4)

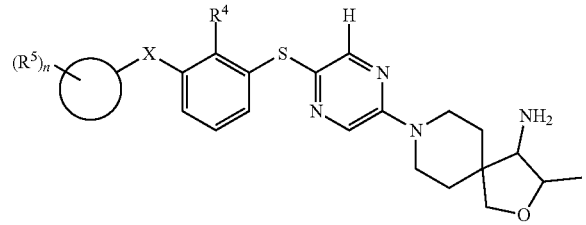

wherein

X is selected from a chemical bond, —NH—, and —CONH—;

$R^4$ is selected from H, D, halogen, —CN, —COOH, —CHO, —OH, —$NO_2$, and —$NH_2$;

each $R^5$ is selected from D, halogen, —CN, —COOH, —CHO, —OH, —$NO_2$, aminoacyl, and —$NH_2$;

n is 0, 1, 2, or 3; and

is defined in formula (I-2).

5. The compound according to claim 4 of formula (I-4), or a pharmaceutically acceptable salt or solvate thereof, wherein:

is selected from phenyl, thienyl, furanyl, pyrimidinyl, pyrazinyl, pyrazolyl, thiazolyl, imidazolyl, oxazolyl, pyrazolopyrimidinyl, imidazopyrazinyl, pyrazolopyrazine, pyridopyrimidinone, benzoxazolyl, pyrrolidinyl, butyrolactamyl, and valerolactamyl;

each $R^5$ is independently selected from D, halogen, —CN, —COOH, —CHO, —OH, —$NO_2$, aminoacyl, $C_1$-$C_{10}$ alkyl, $C_1$-$C_{10}$ alkylamino, $C_1$-$C_{10}$ alkoxy, —$NH_2$, $C_3$-$C_{12}$ cycloalkyl, 3-12 membered heterocyclyl, $C_6$-$C_{10}$ aryl, and 5-10 membered heteroaryl; or, when n is 2 or 3, two adjacent $R^5$ together may form a 3-6 membered saturated or unsaturated ring optionally substituted by 1-3 members independently selected from the group consisting of —OH, —$NH_2$, —CN, halogen, $C_1$-$C_{10}$ alkyl, and $C_1$-$C_{10}$ alkoxy; and n is 0, 1, 2, or 3.

6. A compound, or a pharmaceutically acceptable salt or solvate thereof, selected from the group consisting of:

151
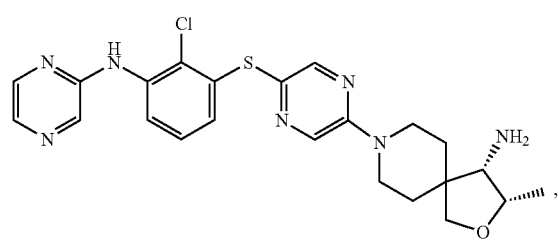
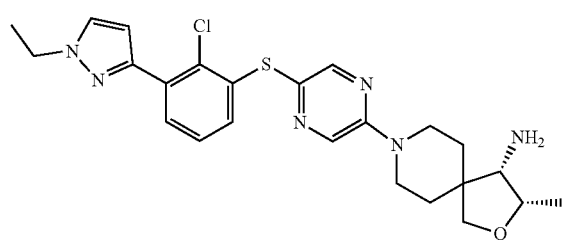
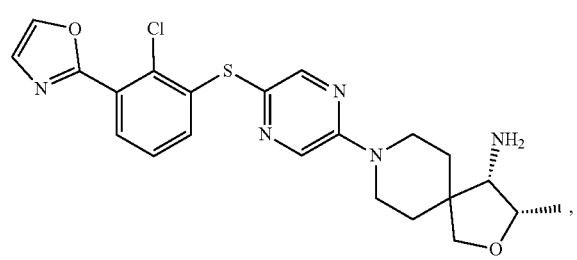
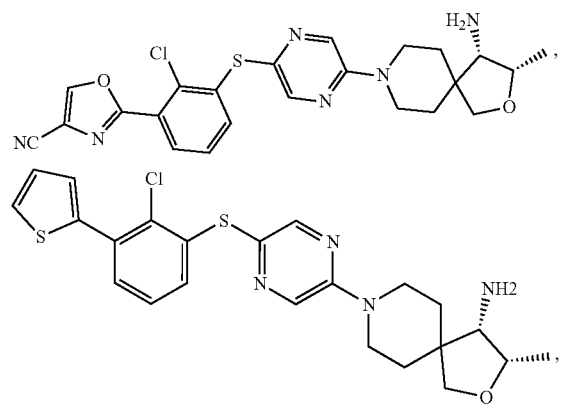
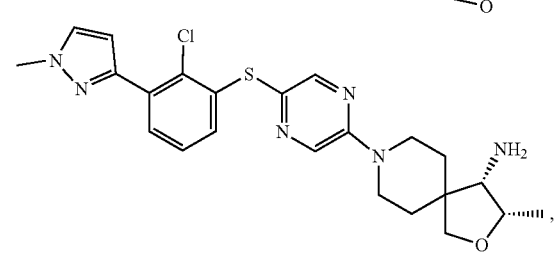
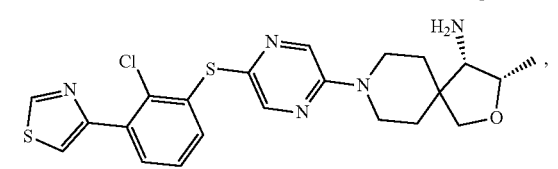
152
-continued
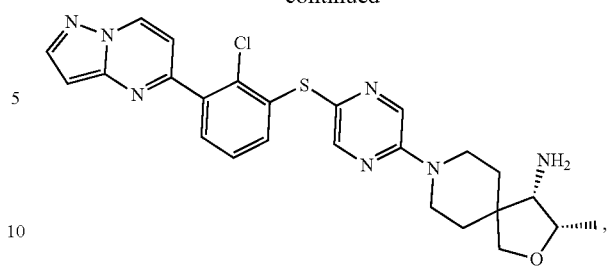
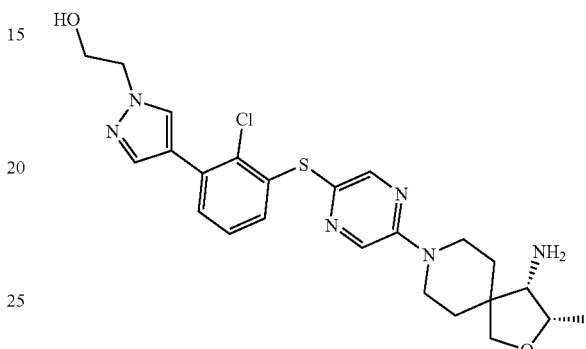
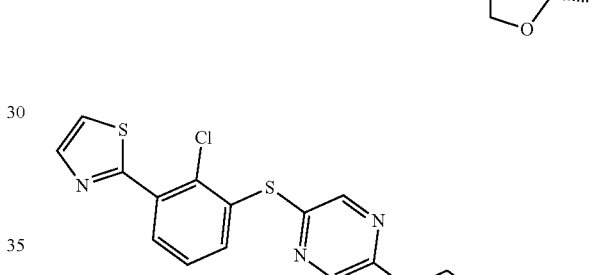
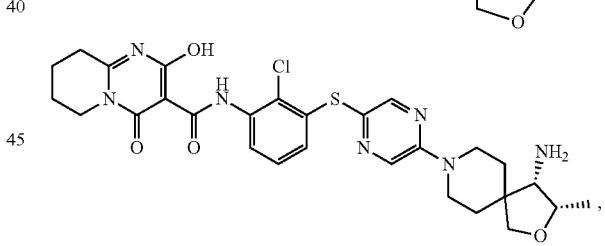
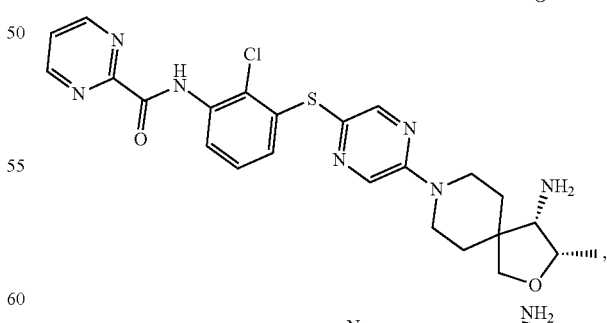
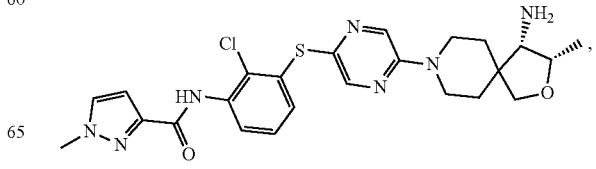

153
-continued

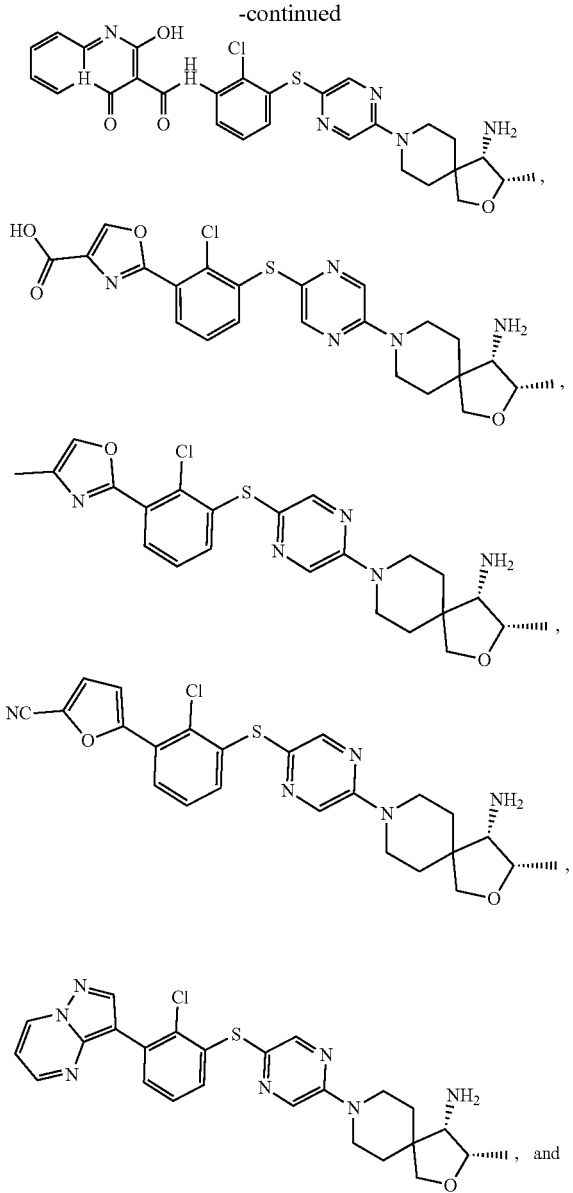

154
-continued

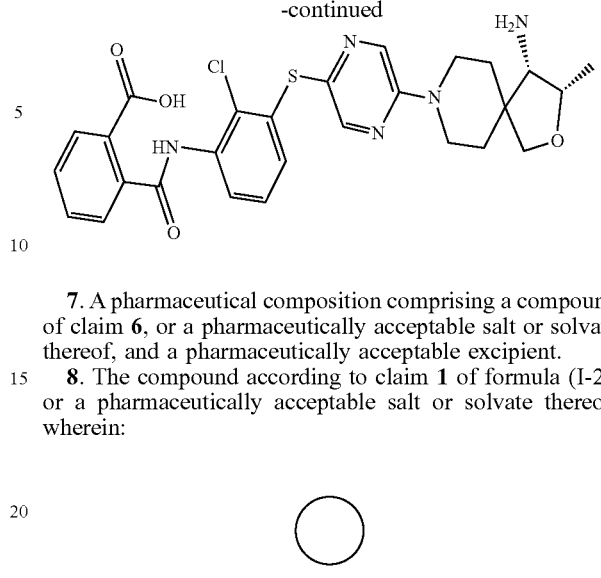

7. A pharmaceutical composition comprising a compound of claim 6, or a pharmaceutically acceptable salt or solvate thereof, and a pharmaceutically acceptable excipient.

8. The compound according to claim 1 of formula (I-2), or a pharmaceutically acceptable salt or solvate thereof, wherein:

is selected from phenyl, thienyl, furanyl, pyrimidinyl, pyrazinyl, pyrazolyl, thiazolyl, imidazolyl, oxazolyl, pyrazolopyrimidinyl, imidazopyrazinyl, pyrazolopyrazine, pyridopyrimidinone, benzoxazolyl, pyrrolidinyl, butyrolactamyl, and valerolactamyl;

each $R^5$ is independently selected from D, halogen, —CN, —COOH, —CHO, —OH, —NO$_2$, aminoacyl, $C_1$-$C_{10}$ alkyl, $C_1$-$C_{10}$ alkylamino, $C_1$-$C_{10}$ alkoxy, —NH$_2$, $C_3$-$C_{12}$ cycloalkyl, 3-12 membered heterocyclyl, $C_6$-$C_{10}$ aryl, and 5-10 membered heteroaryl; or, when n is 2 or 3, two adjacent $R^5$ together may form a 3-6 membered saturated or unsaturated ring optionally substituted by 1-3 members independently selected from the group consisting of —OH, —NH$_2$, —CN, halogen, $C_1$-$C_{10}$ alkyl, and $C_1$-$C_{10}$ alkoxy; and n is 0, 1, 2, or 3.

9. A pharmaceutical composition comprising a compound of claim 8, or a pharmaceutically acceptable salt or solvate thereof, and a pharmaceutically acceptable excipient.

10. A pharmaceutical composition comprising a compound of claim 1, or a pharmaceutically acceptable salt or solvate thereof, and a pharmaceutically acceptable excipient.

\* \* \* \* \*